US010953107B2

(12) United States Patent
Grinstaff et al.

(10) Patent No.: US 10,953,107 B2
(45) Date of Patent: Mar. 23, 2021

(54) POLYPEPTIDE COMPOSITIONS AND METHODS FOR SITE-SPECIFIC TARGETING OF THERAPEUTIC AGENTS

(71) Applicant: Trustees of Boston University, Boston, MA (US)

(72) Inventors: Mark W. Grinstaff, Brookline, MA (US); Christopher Gromisch, Boston, MA (US); Victoria Herrera, Westwood, MA (US); Nelson Ruiz-Opazo, Westwood, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 16/441,208

(22) Filed: Jun. 14, 2019

(65) Prior Publication Data

US 2019/0381186 A1     Dec. 19, 2019

Related U.S. Application Data

(60) Provisional application No. 62/685,377, filed on Jun. 15, 2018.

(51) Int. Cl.
*A61K 47/42* (2017.01)
*A61K 47/64* (2017.01)
*A61K 47/68* (2017.01)
*A61P 35/00* (2006.01)
*A61P 11/00* (2006.01)

(52) U.S. Cl.
CPC .......... *A61K 47/6889* (2017.08); *A61K 47/42* (2013.01); *A61K 47/64* (2017.08); *A61K 47/6803* (2017.08); *A61K 47/6815* (2017.08); *A61K 47/6849* (2017.08); *A61K 47/6859* (2017.08); *A61P 11/00* (2018.01); *A61P 35/00* (2018.01)

(58) Field of Classification Search
CPC ................................ A61K 47/42; A61K 47/64
See application file for complete search history.

(56) References Cited

U.S. PATENT DOCUMENTS 4,867,973 A   9/1989  Goers
5,630,996 A * 5/1997  Reno .................. A61K 51/0497
                                                    424/1.49

(Continued)

FOREIGN PATENT DOCUMENTS

WO    2003/002144 A1    1/2003
WO    2006/055665 A2    5/2006

(Continued)

OTHER PUBLICATIONS

McCarthy (Antiangiogenesis drug promising for metastatic colorectal cancer, The Lancet 2003, 361) (Year: 2003) (Year: 2003).*

(Continued)

*Primary Examiner* — Jeffrey E. Russel
(74) *Attorney, Agent, or Firm* — Nixon Peabody LLP; Ronald I. Eisenstein; Nicole D. Kling

(57) ABSTRACT

Described herein are methods and compositions related to compositions comprising combinations of V/K-type and V/E-type docking peptides and uses thereof, e.g., to deliver therapeutic agents to treat certain conditions such as cancer, infection, or trauma.

25 Claims, 68 Drawing Sheets

Specification includes a Sequence Listing.

(56) References Cited

U.S. PATENT DOCUMENTS

| | | | |
|---|---|---|---|
| 5,939,391 A * | 8/1999 | Tsyrlova | A61K 38/42 514/13.5 |
| 5,969,098 A | 10/1999 | Brittain | |
| 6,576,235 B1 * | 6/2003 | Williams | C12N 9/0048 424/94.4 |
| 7,504,490 B1 | 3/2009 | Weinstock | |
| 7,521,174 B2 * | 4/2009 | Acharya | C12N 5/0006 435/2 |
| 8,067,357 B2 * | 11/2011 | Reutelingsperger | C07K 14/4721 514/1 |
| 8,956,609 B2 | 2/2015 | Herrera et al. | |
| 9,840,553 B2 * | 12/2017 | Perlroth | A61K 38/1866 |
| 2004/0072729 A1 * | 4/2004 | Kwang | A61K 38/42 514/13.4 |
| 2005/0059576 A1 * | 3/2005 | Adamson | A61K 31/7056 424/1.69 |
| 2009/0028852 A1 | 1/2009 | Herrera | |
| 2009/0215680 A1 | 8/2009 | Caboche et al. | |
| 2009/0317836 A1 | 12/2009 | Kuhn | |
| 2011/0300234 A1 * | 12/2011 | Muller | A61K 31/555 424/649 |
| 2013/0022551 A1 | 1/2013 | Ruiz-Opazo et al. | |
| 2013/0177500 A1 | 7/2013 | Ruiz-Opazo et al. | |
| 2015/0037359 A1 * | 2/2015 | Schellenberger | A61P 13/12 424/178.1 |
| 2016/0108124 A1 | 4/2016 | Ruiz-Opazo et al. | |
| 2017/0058036 A1 | 3/2017 | Ruiz-Opazo et al. | |
| 2019/0112576 A1 * | 4/2019 | Germeroth | C12N 5/0636 |

FOREIGN PATENT DOCUMENTS

| | | |
|---|---|---|
| WO | 2007102354 A2 | 9/2007 |
| WO | 2010/114801 A1 | 10/2010 |
| WO | 2012/012750 A1 | 1/2012 |
| WO | 2013/112467 A1 | 8/2013 |

OTHER PUBLICATIONS

Abdollahi et al., "Evading tumor evasion: current concepts and perspectives of anti-angiogenic cancer therapy", Drug Resist Updat 13(1-2) 16-28 (2010).

Bergers et al., "Modes of resistance to anti-angiogenic therapy", Nat Rev Cancer 8(8) 592-603 (2008).

Brown et al., "Tolerance of single, but not multiple, amino acid replacements in antibody VH CDR 2: a means of minimizing B cell wastage from somatic hypermutation?", J Immunol 156(9) 3285-3291 (1996).

Carmeliet et al., "Abnormal blood vessel development and lethality in embryos lacking a single VEGF allele", Nature 380(6573) 435-439 (1996).

Carmeliet et al., "Angiogenesis in life, disease and medicine", Nature 438(7070) 932-936 (2005).

Casset et al., "A peptide mimetic of an anti-CD4 monoclonal antibody by rational design", Biochem Biophys Res Commun 307(1) 198-205 (2003).

Clouthier et al., "Cranial and cardiac neural crest defects in endothelin-A receptor-deficient mice", Development 125(5) 813-824 (1998).

Colman et al., "Effects of amino acid sequence changes on antibody-antigen interactions", Res Immunol 145(1) 33-36 (1994).

Cools-Lartigue et al., "Neutrophil extracellular traps in cancer progression." Cellular and Molecular Life Sciences 71(21):4179-4194 (2014).

Crawford et al., "Chapter 6. Mouse models to investigate anti-cancer effects of VEGF inhibitors", Methods Enzymol 445: 125-139 (2008).

Decano et al., "Dual enothelin-1/VEGFsp receptor (DEspR) roles in adult angiogenesis in despr+/− knockout micr and carotid artery disease rat model", Manuscript submitted to Circulation. (2010).

Decano et al., "Early-life sodium exposure unmasks susceptibility to stroke in hyperlipidemic, hypertensive heterozygous Tg25 rats transgenic for human cholesteryl ester transfer protein", Circulation 119(11) 1501-1509 (2009).

Decano et al., "Molecular imaging of vasa vasorum neovascularization via DEspR-targeted contrast-enhanced ultrasound microimaging in transgenic atherosclerosis rat model", Mol Imaging Biol 13(6) 1096-1106 (2011).

Ebos et al., "Accelerated metastasis after short-term treatment with a potent inhibitor of tumor angiogenesis", Cancer Cell 15(3) 232-239 (2009).

El Kebir et al., "Targeting neutrophil apoptosis for enhancing the resolution of inflammation." Cells 2(2):330-348 (2013).

Fadini et al., "A perspective on NETosis in diabetes and cardiometabolic disorders." Nutrition, Metabolism and Cardiovascular Diseases 26(1):1-8 (2016).

Ferrara et al., "Heterozygous embryonic lethality induced by targeted inactivation of the VEGF gene", Nature 380(6573) 439-442 (1996).

Ferrara et al., "Pathways mediating VEGF-independent tumor angiogenesis", Cytokine Growth Factor Rev 21(1) 21-26 (2010).

Gamicia et al., "Neutrophil extracellular traps in sepsis." Shock 42(4):286-294 (2014).

Gattinoni et al., "Ventilator-induced lung injury: the anatomical and physiological framework." Critical Care Medicine 38(10):S539-S548 (2010).

Gloriosso et al., "Association of ATP1A1 and dear single-nucleotide polymorphism haplotypes with essential hypertension: sex-specific and haplotype-specific effects", Circ Res 100(10) 1522-1529 (2007).

Hanahan et al., "Hallmarks of cancer: the next generation", Cell 144(5) 646-674 (2011).

Herrera et al., "Confirmation of translatability and functionality certifies the dual endothelin1/VEGFsp receptor (DEspR) protein." BMC Molecular Biology 17(1):15 (2016).

Herrera et al., "DEspR roles in tumor vasculo-angiogenesis, invasiveness, CSC-survival and anoikis resistance: a common receptor coordinator' paradigm." PloS One 9(1):e85821 (2014).

Herrera et al., "Embryonic lethality in Dear gene-deficient mice: new player in angiogenesis", Physiol Genomics 23(3) 257-268 (2005).

Herrera et al., "Sex-specific hippocampus-dependent cognitive deficits and increased neuronal autophagy in DEspR haploinsufficiency in mice", Physiol Genomics 35(3) 316-329 (2008).

Lin et al., "Origins of circulating endothelial cells and endothelial outgrowth from blood", J Clin Invest 105(1) 71-77 (2000).

Loges et al., "Mechanisms of resistance to anti-angiogenic therapy and development of third-generation anti-angiogenic drug candidates", Genes Cancer 1(1) 12-25 (2010).

MacCallum et al., "Antibody-antigen interactions: contact analysis and binding site topography", J Mol Biol 262(5) 732-745 (1996).

Michaud et al., "Mechanisms of ventilator-induced lung injury: the clinician's perspective." Critical Care 7(3):209-2010 (2003).

Narasaraju et al., "Neutrophils as Possible Therapeutic Targets in Severe Influenza Pneumonia." Journal of Infectious Pulmonary Diseases 2(2):1-3 (2016).

Paez-Ribes et al., "Antiangiogenic therapy elicits malignant progression of tumors to increased local invasion and distant metastasis", Cancer Cell 15(3) 220-231 (2009).

Paul, "Fundamental Immunology", Third Edition, Raven Press, New York, Chapter 8, 292-295 (1993).

Rudikoff et al., "Single amino acid substitution altering antigen-binding specificity", Proc Natl Acad Sci USA 79(6) 1979-1983 (1982).

Ruiz-Opazo et al., "Molecular characterization of a dual endothelin-1/Angiotensin II receptor", Mol Med 4(2) 96-108 (1998).

Swami et al., "Multipotent tumour endothelial cells", Nature Reviews Cancer 8(11) 2008.

Thalin et al., "NETosis promotes cancer-associated arterial microthrombosis presenting as ischemic stroke with troponin elevation." Thrombosis Research 139:56-64 (2016).

Vajdos et al., "Comprehensive functional maps of the antigen-binding site of an anti-ErbB2 antibody obtained with shotgun scanning mutagenesis", J Mol Biol 320(2) 415-428 (2002).

(56) References Cited

OTHER PUBLICATIONS

Yang et al., "Identification of local and circulating cancer stem cells in human liver cancer", Hepatolofy 47(3) 919-928 (2008).

* cited by examiner

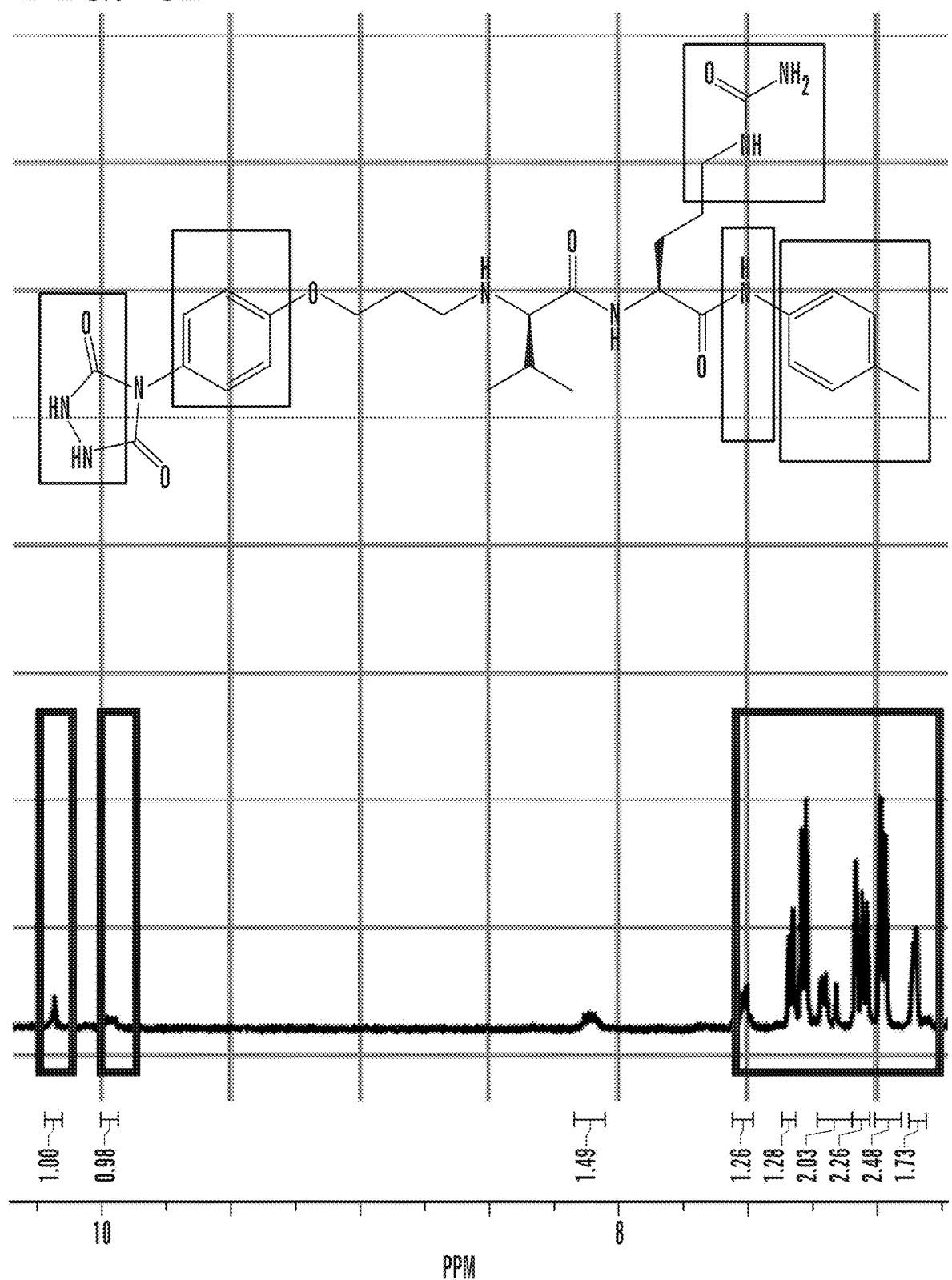
FIG. 6B  1H NMR Structure of Tyrosine Linker

Coiled-coil Wheel Diagram $$\text{Min}_{c(s)} \left\{ \sum_{i,j} [a(r_i, t_j) - \int c(s) L(s, D(s), r_i, t_j) ds]^2 \right\}$$

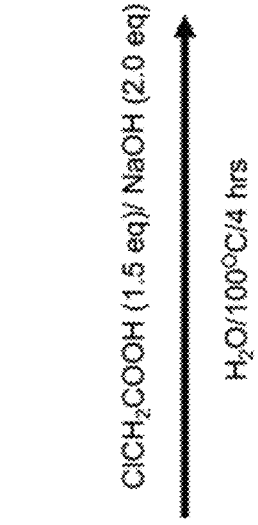
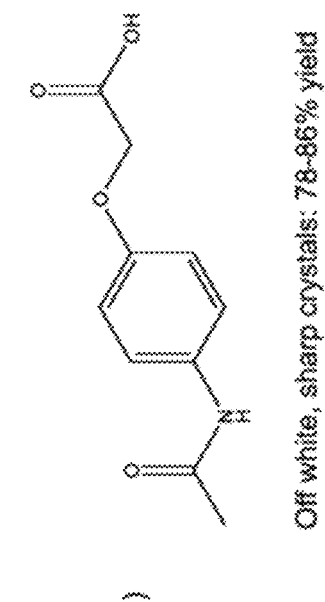
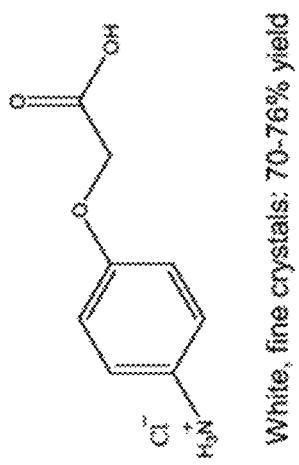
FIG. 22A
FIG. 22B

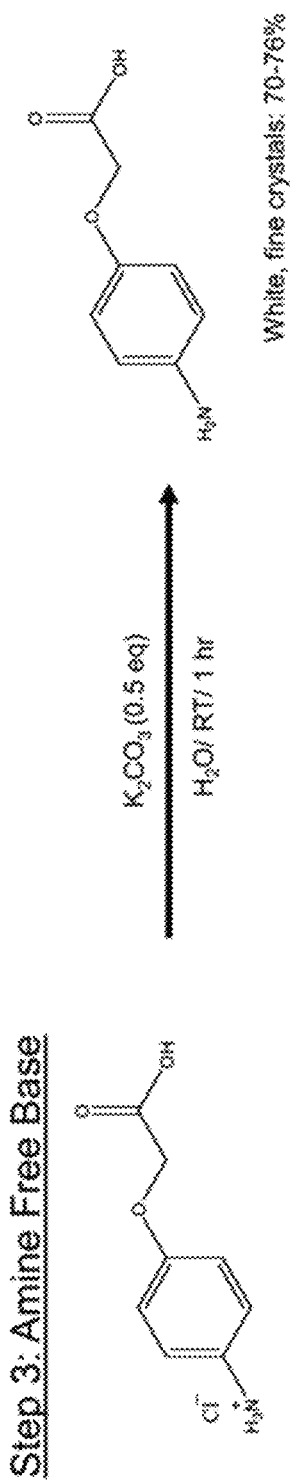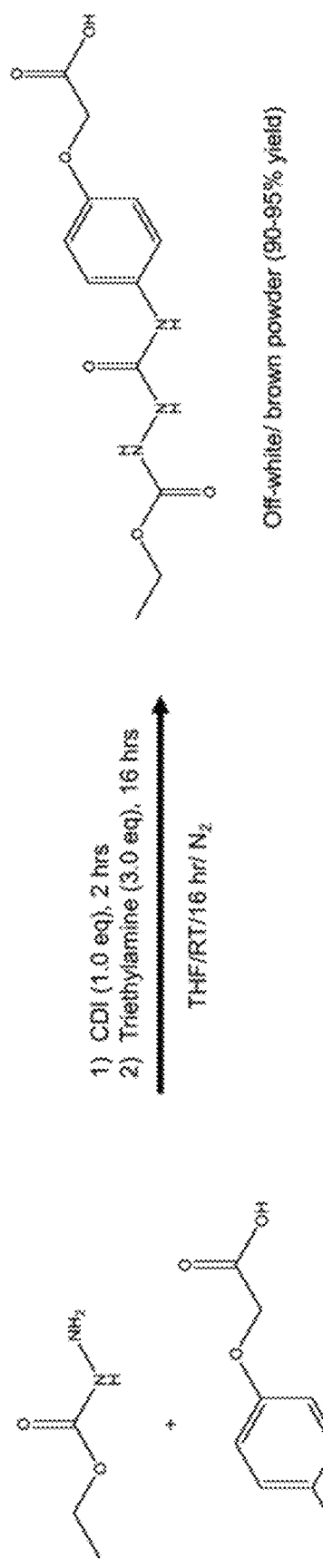
FIG. 22C
FIG. 22D

Step 6: Synthesis of Capthesin B Dipeptide Sequence

Step 7: Addition of "Self-immolative" Sequence

Assay confluence: 20% (starting) – 60% (control, final)
Panc1 DEspR Expression: ~40% (60% confluence)

Assay confluence: 20% (starting) – 60% (control, final)
MIA PaCa2 DEspR Expression: ~60% (60% confluence)

POLYPEPTIDE COMPOSITIONS AND METHODS FOR SITE-SPECIFIC TARGETING OF THERAPEUTIC AGENTS

CROSS-REFERENCE TO RELATED APPLICATIONS

This application claims benefit under 35 U.S.C. § 119(e) of U.S. Provisional Application No. 62/685,377 filed Jun. 15, 2018, the contents of which are incorporated herein by reference in their entirety.

GOVERNMENT SUPPORT

This invention was made with government support under Contract No. T32EB006359 and 1F30CA220843-01A1 awarded by the National Institute of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 13, 2019, is named 701586-092670USPT_SL.txt and is 9 KB in size.

TECHNICAL FIELD

The technology described herein relates to compositions and methods relating to, e.g., targeting therapeutic agents.

BACKGROUND

Antibody drug conjugates (ADCs) are a powerful class of therapeutics for various diseases (e.g., cancer), which combine the specificity of biologics, such as antibodies with small molecule therapeutics (e.g., chemotherapeutics). However, the full potential of this drug class has not been realized in cancer or other diseases because of the poor specificity and unreliable, non-uniform conjugation of the therapeutic to the biologic. Thus, using traditional conjugation methods, ADCs can be limited in their efficacy and therapeutic window. As a result, there is a need for improved ADCs for use in the treatment of diseases such as cancer that are developed with a reliable, uniform conjugation method and designed to increase the ADC efficacy and site-specific targeting.

SUMMARY

The present invention is directed, in part, to the discovery of sets of polypeptides that can each be precisely conjugated to a payload domain (e.g., an antibody and/or a therapeutic agent) and then form supramolecular structures at specific ratios. These polypeptide sets therefore permit site-specific and efficient targeting of an antibody drug conjugate. The methods and compositons described herein are characterized by uniform loading of the payload and/or therapeutic agent to the biologic, high stability, and high specificity for the intended target.

The polypeptide sets described herein comprise specific types and numbers of docking peptides. The inventors have found that certain combinations of docking peptides will not form homo-mers, but given a mixture of two types of docking peptides, the peptides will form tetramers that comprise two of each type of docking peptide. Accordingly, in one aspect of any of the embodiments, described herein is a composition comprising: a first polypeptide component comprising a V/K-type docking peptide; a second polypeptide component comprising a V/K-type docking peptide; a third polypeptide component comprising a V/E-type docking peptide; and a fourth polypeptide component comprising a V/E-type docking peptide. As noted above, the V/K-type docking peptides, will not complex or bind with each other in a pure population and the same is true of a pure population of V/E-type docking peptides. However, when both V/K-type and V/E-type docking peptides are present, a tetramer forms which is comprised of two V/K-type and two V/E type docking peptides.

The docking peptides described herein comprise a general sequence of $(XJJXJJJ)_z$ where X is a hydrophobic amino acid, J is any amino acid, and z is an integer greater than or equal to 1. In some embodiments of any of the aspects, the docking peptides described herein comprise a general sequence of $(XJJXJJJ)_z$ where X is a hydrophobic amino acid, J is any amino acid, and z is an integer greater than or equal to 3. In some embodiments of any of the aspects, the V/K-type docking polypeptide is a basic peptide comprising valine at the 7th position of XJJXJJV (i.e., the V/K-type docking peptide comprises $(XJJXJJV)_z$); and the V/E-type docking polypeptide is an acidic peptide comprising valine at the 5th position of XJJXJJJ (i.e., the V/E-type docking peptide comprises $(XJJXVJJ)_z$.

In one aspect of any of the embodiments, described herein is a composition comprising:
 a. a first polypeptide component comprising a V/K-type docking peptide;
 b. a second polypeptide component comprising a V/K-type docking peptide;
 c. a third polypeptide component comprising a V/E-type docking peptide; and
 d. a fourth polypeptide component comprising a V/E-type docking peptide;
wherein the docking peptides each independently comprise a sequence of $(XJJXJJJ)_z$ where each X is independently a hydrophobic amino acid, each J is independently any amino acid, and z is an integer greater than or equal to 1; and wherein the V/K-type docking polypeptide is a basic peptide comprising valine at the $7^{th}$ position of XJJXJJJ; and wherein the V/E-type docking polypeptide is an acidic peptide comprising valine at the $5^{th}$ position of XJJXJJJ.

In some embodiments of any of the aspects, the z of at least one docking peptide is an integer greater than or equal to 3. In some embodiments of any of the aspects, the z of each docking peptide is an integer greater than or equal to 3. In some embodiments of any of the aspects, the z of at least one docking peptide is 3. In some embodiments of any of the aspects, the z of at each docking peptide is 3.

In some embodiments of any of the aspects, each docking peptide comprises leucine at the $1^{st}$ position of XJJXJJJ and an isoleucine at the $4^{th}$ position of XJJXJJJ. In some embodiments of any of the aspects, the XJJXJJJ of the V/K-type docking peptide is LKKIJJV. In some embodiments of any of the aspects, the z of the V/E-type docking peptide is greater than 1 and at least 1 iteration of XJJXJJJ comprises tyrosine at the sixth position. In some embodiments of any of the aspects, at least one of the V/E-type docking peptides comprises an amino acid sequence of LEEIJJJ. In some embodiments of any of the aspects, at least one of the V/E-type docking peptides comprises an amino acid sequence of LEEIXJX.

In some embodiments of any of the aspects, at least one docking peptide comprises an amino acid sequence selected from the group consisting of SEQ ID NOs: 1-4 or 6; or any combination thereof.

In some embodiments of any of the aspects, the first, second, third, and fourth docking peptides form a tetrameric-coiled coil structure.

In some embodiments of any of the aspects, at least one of the polypeptide components further comprise a targeting domain. In some embodiments of any of the aspects, the targeting domain comprises an aptamer, antibody reagent, or antigen-binding portion thereof, polypeptide reagent, or a small molecule. In some embodiments of any of the aspects, each antibody reagent is a Fab or ScFv. In some embodiments of any of the aspects, the antibody reagent is a monoclonal antibody or a bispecific monoclonal antibody. In some embodiments of any of the aspects, the antibody reagent is a humanized antibody.

In some embodiments of any of the aspects, the targeting domain specifically binds to a target selected from the group consisting of: circulating cancer cells, metastatic cancer cells, tumor-leukocyte aggregates, tumor-platelet aggregates, leukocytes, circulating pathogens, microthrombi, macrothrombi, atherosclerotic plaques, epithelial cells, leukocyte-platelet aggregates, pathogen-leukocyte aggregates, neutrophil extracellular traps (NETs), and circulating nucleic acids. In some embodiments of any of the aspects, the target is selected from the group consisting of: dual endothelin1/VEGFsignal peptide receptor (DEspR), G protein-coupled receptor 87 (GPR87), ErbB family receptors, transforming growth factor beta (TGF-β) family receptors, cluster of differentiation 52 (CD52), programmed death-ligand 1 (PD-L1), vascular endothelial growth factor receptor 1 (VEGFR1), vascular endothelial growth factor receptor 2 (VEGFR2), vascular endothelial growth factor receptor3 (VEGFR3), Platelet-derived growth factor receptor beta (PDGFRβ), abelson murine leukemia viral oncogene (ABL), cluster of differentiation 19 (CD19), cluster of differentiation 3 (CD3), mitogen-activated protein kinase kinase (MEK), programmed cell death protein 1 (PD-1), and cluster of differentiation 20 (CD20). In some embodiments of any of the aspects, the target of the targeting domain is an intravascular target.

In some embodiments of any of the aspects, at least one of the polypeptide components further comprises a payload domain. In some embodiments of any of the aspects, the payload domain comprises a small molecule, enzyme, or polypeptide (e.g., antibody reagent). In some embodiments of any of the aspects, the payload domain comprises a chemotherapeutic agent. In some embodiments of any of the aspects, the chemotherapeutic agent is selected from the group consisting of: mertansine; emtansine; ravtansine; ansamitocin; soravtansine; maytansine; paclitaxel; gemcitabine; fluorouracil; irinotecan; leucovorin; oxaliplatin; capecitabine; cisplatin; docetaxel; and any derivative thereof.

In some embodiments of any of the aspects, at least one docking peptide is located at the C-terminus of the respective polypeptide component. In some embodiments of any of the aspects, each docking peptide is located at the C-terminus of the respective polypeptide component.

In some embodiments of any of the aspects, at least one polypeptide component further comprises a polypeptide linker between the docking peptide and the payload and/or targeting domain of the polypeptide component. In some embodiments of any of the aspects, the polypeptide linker is a cleavable linker. In some embodiments of any of the aspects, the polypeptide linker comprises at least one of:
 a. an amino acid crosslinker;
 b. a lysosomally cleaved sequence; or
 c. a self-immolative sequence.

In some embodiments of any of the aspects, the polypeptide linker comprises a capthepsin B cleavage site. In some embodiments of any of the aspects, the cleavable linker comprises an ester, a thioester, a hydrazine, a hydrazine, a disulfide, or a protease linker. In some embodiments of any of the aspects, the polypeptide linker comprises a non-cleavable linker. In some embodiments of any of the aspects, the non-cleavable linker is selected from the group consisting of: a 4-phenyl-urazole; an amide; a carbamate; urea; thiourea; and a triazole linker.

In some embodiments of any of the aspects, the ratio of payload domain molecules to targeting domain molecules is from 2:6 to 6:2. In some embodiments of any of the aspects, the ratio of payload domain molecules to targeting domain molecules is from 1:3 to 3:1. In some embodiments of any of the aspects, the ratio of payload domain molecules to targeting domain molecules is 1:3, 1:1, 1:2, 2:1, 3:1, 4:1, 5:2, or 6:2. In some embodiments of any of the aspects, the ratio of payload domain molecules to targeting domain molecules is greater than 6:2.

In one aspect of any of the embodiments, described herein is a method of treating a disease, the method comprising: administering the composition described herein to a subject in need thereof, wherein the payload domain comprises a therapeutic agent. In some embodiments of any of the aspects, the disease is cancer, infection, or trauma. In one aspect, described herein is a method of treating cancer, the method comprising: administering the composition described herein to a subject in need thereof, wherein the payload domain comprises a chemotherapeutic agent.

In some embodiments of any of the aspects, the cancer is selected from the group consisting of: pancreatic cancer, cancer of the digestive system; hepatic carcinoma; liver cancer; colon cancer; esophageal cancer; gastric cancer; hepatoma; kidney or renal cancer; oral cavity cancer; prostate cancer; rectal cancer; stomach cancer; basal cell carcinoma, biliary tract cancer; lung cancer; brain cancer, breast cancer, bladder cancer; cervical cancer; endometrial cancer; uterine cancer; cancer of the urinary system; leukemia; lymphoma; and leukemic and solid tumor metastatic cancers. In some embodiments of any of the aspects, the disease is selected from the group consisting of: myocardial infarction, stroke, disseminated intravascular coagulation, hypercoagulation, atherosclerosis, acute respiratory distress syndrome, infant respiratory distress syndrome, Crohn's disease, ulcerative colitis, rheumatoid arthritis, Celiac disease, type 1 diabetes, lupus, and multiple sclerosis.

In one aspect of any of the embodiments, described herein is a method of inducing cytotoxicity of a cancer cell, the method comprising: contacting the cancer cell with a composition described herein. In some embodiments of any of the aspects, the cancer cell is a pancreatic cancer cell.

In one aspect of any of the embodiments, described herein is a method of delivering a payload agent to a cell, the method comprising: contacting a population of cells and/or a subject with a composition described herein, wherein at least one polypeptide component comprises a targeting domain and at least one polypeptide component comprises a payload domain; whereby the payload domain is delivered to a cell expressing the target of the targeting domain.

BRIEF DESCRIPTION OF THE DRAWINGS

FIG. 6A shows (from left to right) the tyrosine linker structure with tyrosine reactive handle, cathepsin cleavable sequence, self-releasing group, and mertansine shown. FIG. 6B shows 1H NMR of tyrosine linker with pertinent chemical shifts (in ppm) shown for the PTAD amides, PABC amide, Cirtulline urea group, and aromatic hydrogens. FIG. 6C depicts the structure of an exemplary tripeptide spacer, e.g., the structure of KADCYLA ADC (K-ADC) linker with lysine linker (SMCC) and mertansine.

FIG. 14A demonstrates that circular dichroism shows that receiving peptide and docking peptide do not self-assemble, but equimolar receiving and docking spontaneously form a coiled contract. FIG. 14B demonstrates that the structure is relatively stable to thermal denaturation, with less than 20% unfolding at 90° C.; folding is entirely reversible, ensuring the structure that is formed is a discrete, specific structure. FIG. 14C demonstrates combined thermal/chemical denaturation on pre-formed species showed resistance to unfolding, with unfolding less than 50% observed at 6 M guanidinium chloride and 90° C., suggesting a highly stable species for in vivo application. $\Delta G_{folding}$ based on analysis of unfolding of peptide V/E+V/K at varying concentrations of guanidinium chloride at 90° C., demonstrating the high stability of this peptide structure. FIG. 14D demonstrates resistance to unfolding at low pH was assessed, showing minimal shift (unfolding <20%) at pH 3, with repeat thermal denaturation not destabilizing tetramer formation. demonstrates that combination of guandinium chloride (a chaotropic agent) and thermal denaturation does not fully denature the tetrameric helical structure, demonstrating the high stability of the heterotetrameric peptide structure. Helical structure, a surrogate for the percent unfolding of the species, is measured by circular dichroism at 222 nm.

FIG. 15A gives an example of how speed-dependent gradients allow for measurement of equilibrium to determine particle size and interactions. Depicted are Peptide V/K (SEQ ID NO: 28) and V/E (SEQ ID NO: 27). FIG. 15B shows structural analysis by sedimentation equilibrium analytical ultracentrifugation. FIG. 15C shows the sedimentation of the V/E (top), V/K (middle) and V/E-V/K (bottom) peptides.

FIG. 22A-22J shows the synthesis of an exemplary linker. FIG. 22A shows ether synthesis for the synthesis of the Tyrosine reactive urazole. FIG. 22B shows acyl deprotection for the synthesis of the Tyrosine reactive urazole. FIG. 22C shows amine-free base synthesis for the synthesis of the Tyrosine reactive urazole. FIG. 22D shows semicarbazate synthesis for the synthesis of the Tyrosine reactive urazole. FIG. 22E shows urazole cyclization for the synthesis of the Tyrosine reactive urazole. FIG. 22F shows the synthesis of the Capthesin B dipeptide sequence. FIG. 22G demonstrates the addition of the "self immolative" sequence. FIG. 22H shows preparation of the ADC drug linker by attachment of activated mertansine. FIG. 22I shows removal of the Fmoc Group from the ADC drug linker. FIG. 22J shows addition of a PTAD group to the ADC linker.

FIG. 27 demonstrates binding characterization of normal cells. H6c7: 7c5-AFC: 24.6+0.6%; 7c5-488: 52.3+1.4%. HUVEC Cells: 7c5-488: 0.0+0.0%; 7c5-AFC: 0.0+0.0%. KV-2 Cells: 7c5-488: 0.0+0.0%; 7c5-AFC: 0.0+0.0%. BJ Fibroblasts Cells: 7c5-488: 6.1%+1.5%; 7c5-AFC: 17.2%+2.9%.

DETAILED DESCRIPTION

Figure 1:
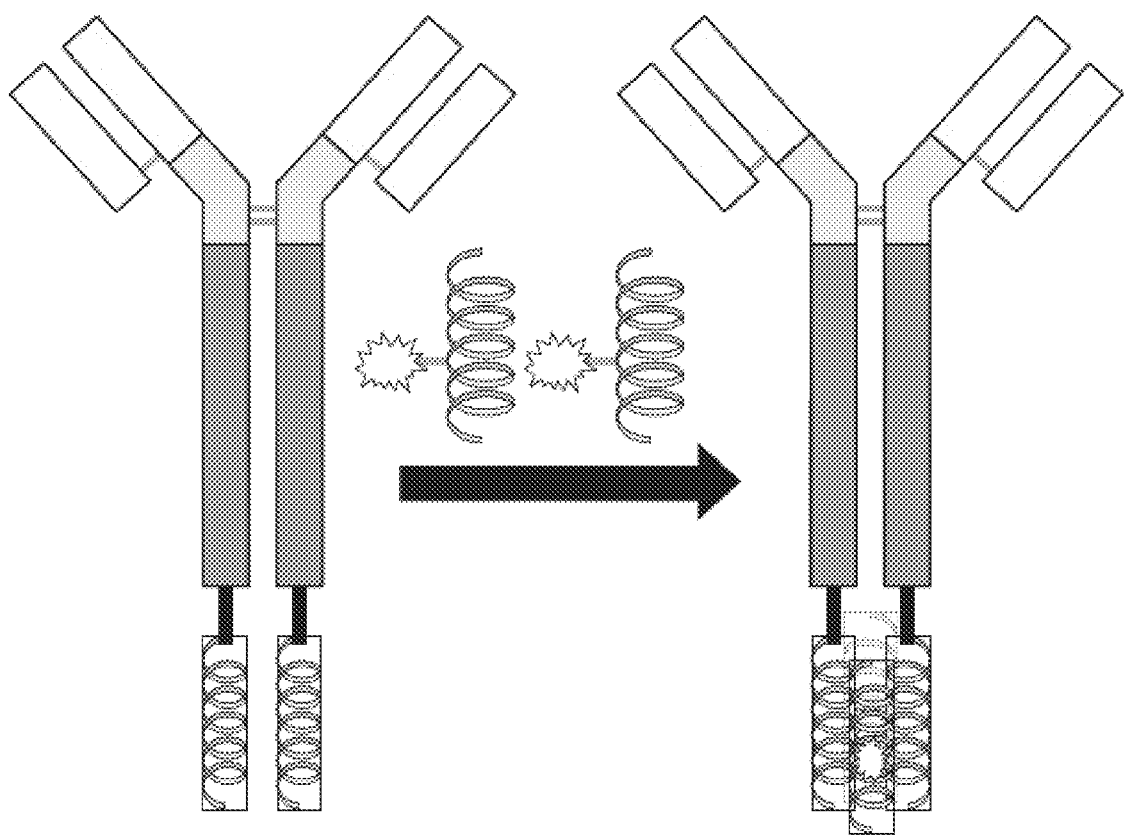
FIG. 1 demonstrates an exemplary conjugation method. Two C-terminal receiving sequences on a monoclonal antibody react with two drug (spiked bubble)-loaded docking sequences to form a tetrameric structure.

Briefly, the methods and compositions described herein relate, in part, to the discovery of a pair of polypeptide sequences (referred to herein as "docking peptides") that do not form homo-mers, but rather specifically form hetero tetramers. These docking peptides can be conjugated to payload domains (e.g., comprising a therapeutic agent and/or an antibody), permitting exquisitely precise control of the ratio of different payloads in the final composition. Accordingly, the methods and compositions described herein relate, at least in some embodiments to improved antibody drug conjugates (ADCs) and/or novel frameworks for the construction of ADCs.

In one aspect of any of the embodiments, the composition comprises: (a) a first polypeptide component comprising a V/K-type docking peptide; (b) a second polypeptide component comprising a V/K-type docking peptide; (c) a third polypeptide component comprising a V/E-type docking peptide; and (d) a fourth polypeptide component comprising a V/E-type docking peptide.

Each polypeptide component comprises at least one polypeptide/peptide sequence and optionally additional domains and elements, wherein the sequences, domains, and elements are interconnected by covalent bonds. The first, second, third, and fourth polypeptide components form a quarternary structure due to, e.g., hydrogen bonding between the docking peptides as explained elsewhere herein.

As used herein, the term "docking peptide," refers to a peptide sequence as specified herein. In some embodiments of any of the aspects, a docking peptide can be conjugated to a linker and/or a payload domain (e.g., a drug or agent) and/or a targeting domain as described herein. As defined herein, a docking peptide comprises a sequence of $(XJJXJJJ)_z$ where each X is independently a hydrophobic amino acid, each J is independently any amino acid, and z is an integer greater than or equal to 1. In some embodiments of any of the aspects z is an integer selected from the range of 1 to 10. In some embodiments of any of the aspects z is an integer selected from the range of 3 to 10. In some embodiments of any of the aspects z is 3. In some embodiments of any of the aspects, a docking peptide comprises a sequence of $(XOOXJJJ)_z$ where each X is independently a hydrophobic amino acid, each J is independently any amino acid, each O is independently a charged amino acid, and z is an integer greater than or equal to 1. In some embodiments of any of the aspects, a docking peptide comprises a sequence of $(XOOXJJJ)_z$ where each X is independently a hydrophobic amino acid, each J is independently any amino acid, each O is independently glutamic acid or lysine, and z is an integer greater than or equal to 1. In some embodiments of any of the aspects, each docking peptide comprises leucine at the $1^{st}$ position of $(XJJXJJJ)_z$ (e.g., comprises $(LJJXJJJ)_z$) and/or comprises a leucine at the $4^{th}$ position of XJJXJJJ (e.g., comprises $(XJJUJJJ)_z$) (or comprises $(LJJUJJJ)_z$). In some embodiments of any of the aspects, each docking peptide comprises an isoleucine at the $1^{st}$ position of $(XJJXJJJ)_z$ (e.g., comprises $(IJJXJJJ)_z$) and/or comprises an isoleucine at the $4^{th}$ position of XJJXJJJ (e.g., comprises $(XJJIJJJ)_z$) (or comprises $(IJJIJJJ)_z$).

In some embodiments of any of the aspects, each docking peptide comprises $(LOOXJJJ)_z$, $(XOOLJJJ)_z$ or $(LOOLJJJ)_z$ where each X is independently a hydrophobic amino acid, each J is independently any amino acid, each O is independently a charged amino acid, and z is an integer greater than or equal to 1. In some embodiments of any of the aspects, each docking peptide comprises $(LOOXJJJ)_z$, $(XOOLJJJ)_z$ or $(LOOLJJJ)_z$ where each X is independently a hydrophobic amino acid, each J is independently any amino acid, each O is independently glutamic acid or lysine, and z is an integer greater than or equal to 1.

In some embodiments of any of the aspects, each docking peptide comprises $(IOOXJJJ)_z$, $(XOOIJJJ)_z$ or $(IOOIJJJ)_z$ where each X is independently a hydrophobic amino acid, each J is independently any amino acid, each O is independently a charged amino acid, and z is an integer greater than or equal to 1. In some embodiments of any of the aspects, each docking peptide comprises $(IOOXJJJ)_z$, $(XOOIJJJ)_z$ or $(IOOIJJJ)_z$ where each X is independently a hydrophobic amino acid, each J is independently any amino acid, each O is independently glutamic acid or lysine, and z is an integer greater than or equal to 1.

In some embodiments of any of the aspects, each docking peptide comprises $(LOOIJJJ)_z$ or $(IOOLJJJ)_z$ where each X is independently a hydrophobic amino acid, each J is independently any amino acid, each O is independently a charged amino acid, and z is an integer greater than or equal to 1. In some embodiments of any of the aspects, each docking peptide comprises $(IOOLJJJ)_z$, or $(LOOIJJJ)_z$ where each X is independently a hydrophobic amino acid, each J is independently any amino acid, each O is independently glutamic acid or lysine, and z is an integer greater than or equal to 1.

In some embodiments of any of the aspects, the V/K-type docking polypeptide is a basic peptide comprising valine at the 7th position of $(XJJXJJJ)_z$ (e.g., comprises $(XJJXJJV)_z$); and the V/E-type docking polypeptide is an acidic peptide comprising valine at the 5th position of $(XJJXJJJ)_z$, (e.g., comprises $(XJJXVJJ)_z$) where each X is independently a hydrophobic amino acid, each J is independently any amino acid, and z is an integer greater than or equal to 1.

Figure 14A:
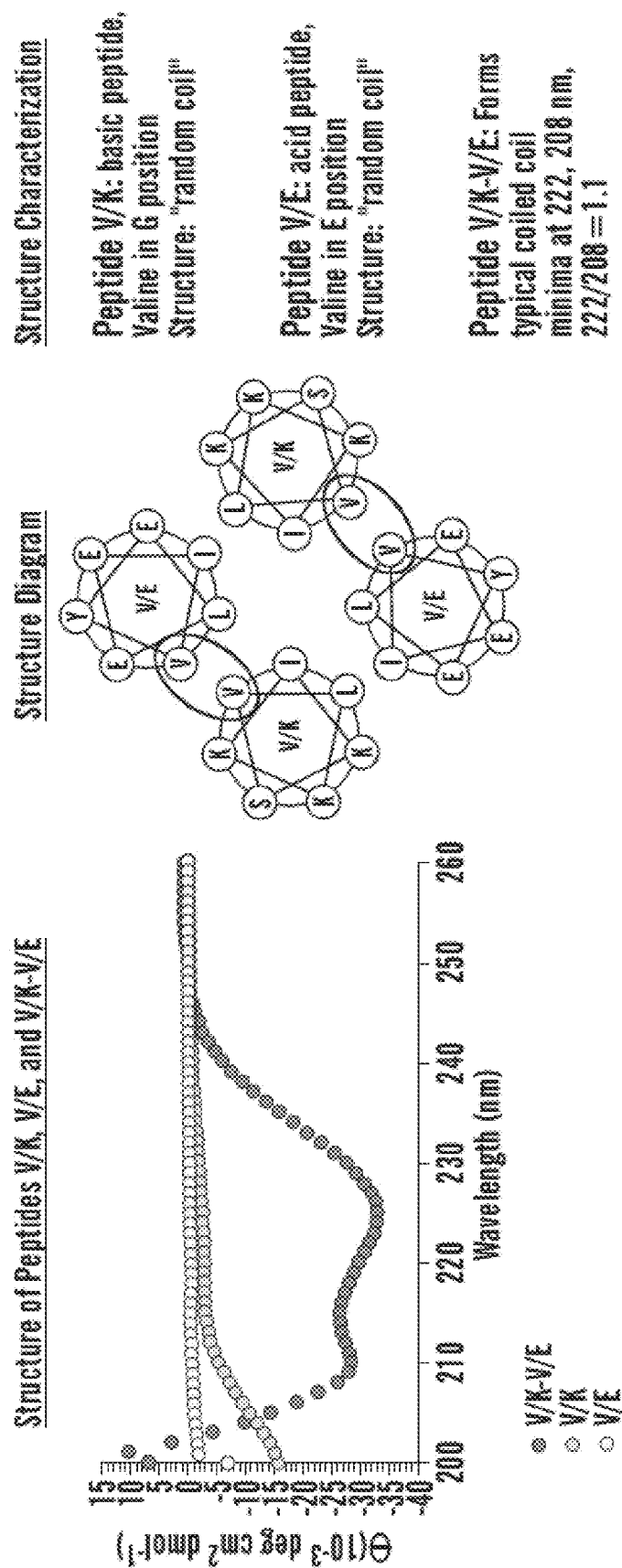
FIGS. 14A-14D demonstrate CD Structure of Peptide V/K and V/E. Depicted is the evaluation of specificity and structural assembly.
Figure 14B:
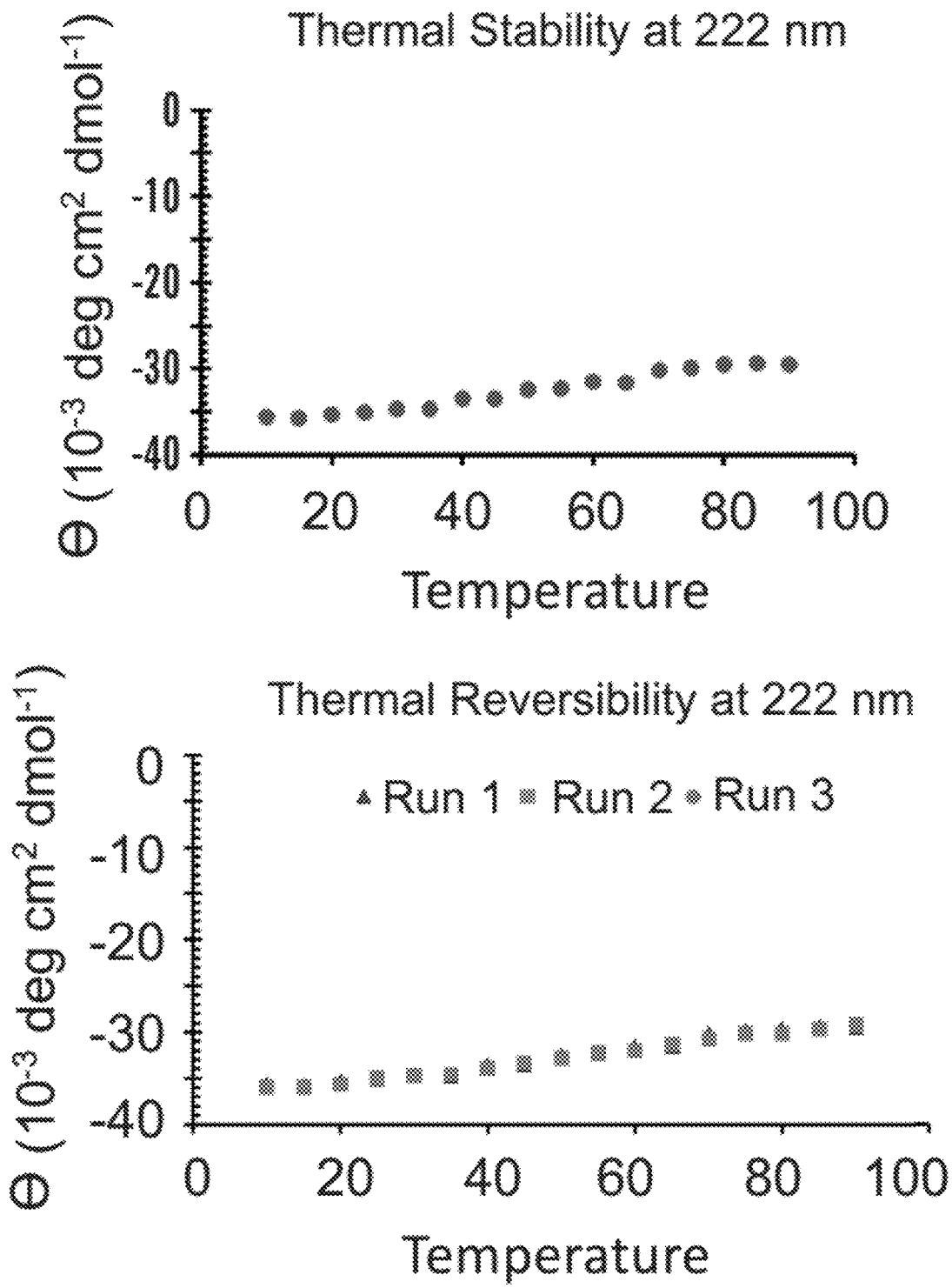
Figure 14C:
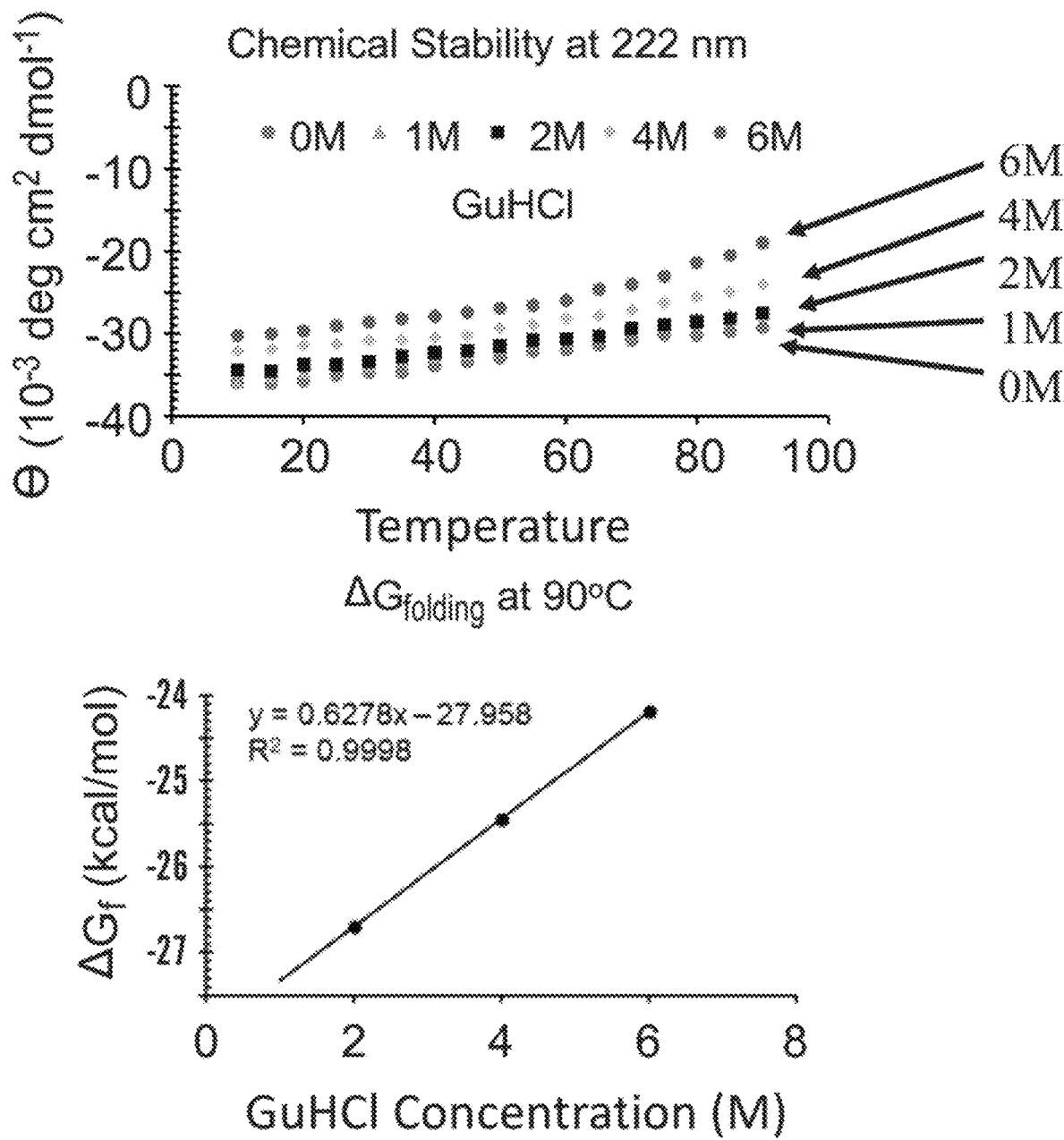
Figure 14D:
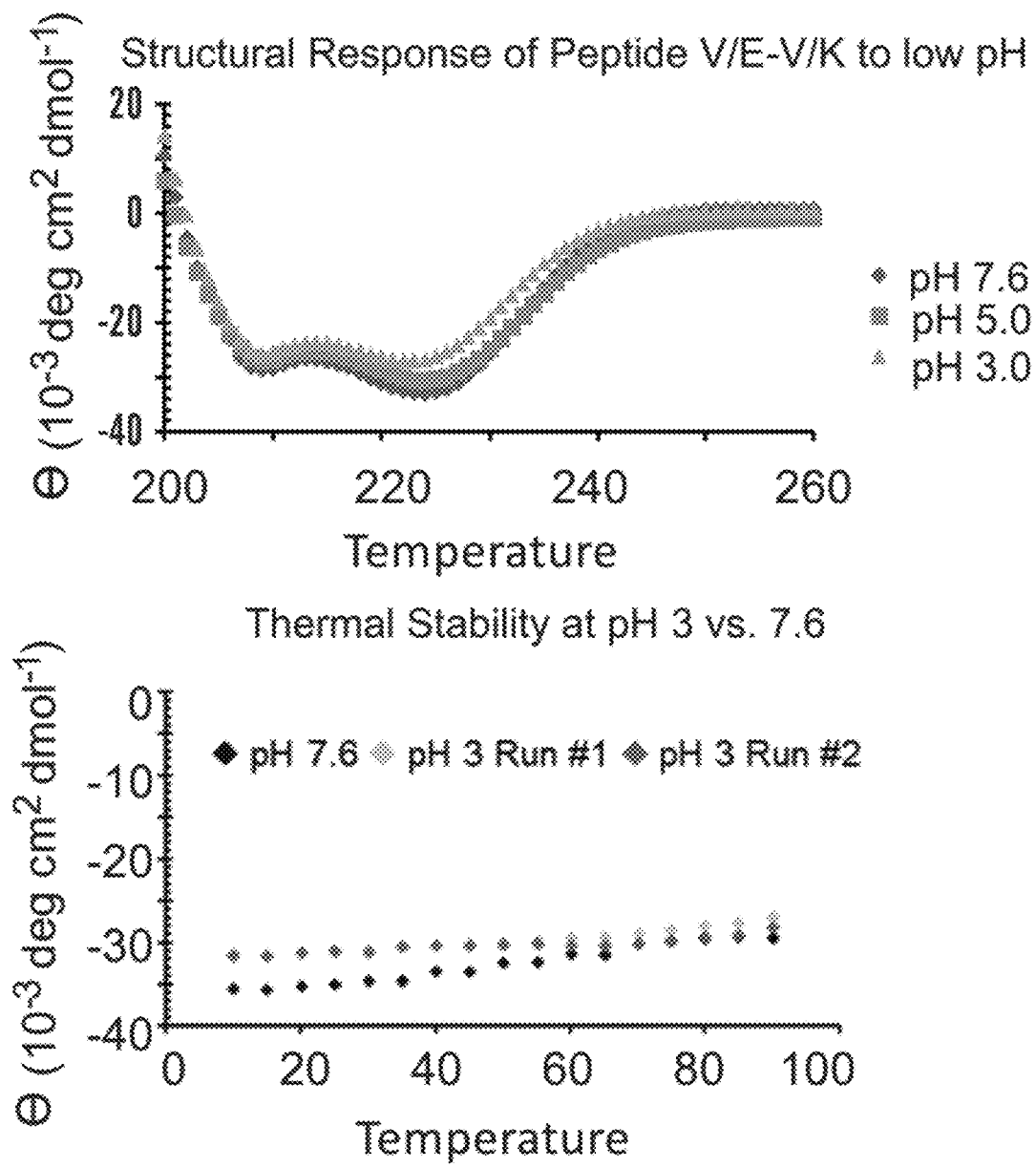

Illustrative diagrams of V/K and V/E-type docking peptides are depicted in FIG. 14A. In the working examples, a "docking sequence" and a "receiving sequence" or "receiving peptide" are described. In the working examples, the "receiving sequence (or peptide)" terminology is used to refer to a type of docking peptide that is directly conjugated to the C-terminus of an antibody reagent. It is noted that in the context of the polypeptide compositions described herein, the term "docking peptide" as used herein is inclusive of both of the V/E- or V/K-type polypeptides. The use of "receiving sequence (or peptide)" in the working example is simply to differentiate the two types of docking peptides and their disparate cargoes in those specific embodiments.

In some embodiments of any of the aspects the V/K-type docking polypeptide is a basic peptide comprising $(XOOXJJV)_z$; and/or the V/E-type docking polypeptide is an acidic peptide comprising $(XOOXVJJ)_z$ where each X is independently a hydrophobic amino acid, each O is independently a charged amino acid, each J is independently any amino acid, and z is an integer greater than or equal to 1. In some embodiments of any of the aspects the V/K-type docking polypeptide is a basic peptide comprising $(XOOXJJV)_z$; and/or the V/E-type docking polypeptide is an acidic peptide comprising $(XOOXVJJ)_z$ where each X is independently a hydrophobic amino acid, each O is independently glutamic acid or lysine, each J is independently any amino acid, and z is an integer greater than or equal to 1.

In some embodiments of any of the aspects the V/K-type docking polypeptide is a basic peptide comprising $(LJJXJJV)_z$, $(LJJLJJV)_z$, or $(XJJLJJV)_z$; and/or the V/E-type docking polypeptide is an acidic peptide comprising $(LJJXVJJ)_z$, $(XJJLVJJ)_z$, $(LJJLVJJ)_z$ where each X is independently a hydrophobic amino acid, each J is independently any amino acid, and z is an integer greater than or equal to 1. In some embodiments of any of the aspects the V/K-type docking polypeptide is a basic peptide comprising $(IJJXJJV)_z$, $(IJJIJJV)_z$, or $(XJJIJJV)_z$; and/or the V/E-type docking polypeptide is an acidic peptide comprising $(IJJXVJJ)_z$, $(XJJIVJJ)_z$, $(IJJIVJJ)_z$ where each X is independently a hydrophobic amino acid, each J is independently any amino acid, and z is an integer greater than or equal to 1. In some embodiments of any of the aspects the V/K-type docking polypeptide is a basic peptide comprising (IJJLJJV)$_z$ or (UJIJJV)$_z$; and/or the V/E-type docking polypeptide is an acidic peptide comprising (IJJLVJJ)$_z$ or (LJJIVJJ)$_z$ where each X is independently a hydrophobic amino acid, each J is independently any amino acid, and z is an integer greater than or equal to 1.

In some embodiments of any of the aspects the V/K-type docking polypeptide is a basic peptide comprising (LOOXJJV)$_z$, (LOOLJJV)$_z$, or (XOOLJJV)$_z$; and/or the V/E-type docking polypeptide is an acidic peptide comprising (LOOXVJJ)$_z$, (XOOLVJJ)$_z$, (LOOLVJJ)$_z$ where each X is independently a hydrophobic amino acid, each O is independently a charged amino acid, each J is independently any amino acid, and z is an integer greater than or equal to 1. In some embodiments of any of the aspects the V/K-type docking polypeptide is a basic peptide comprising (LOOXJJV)$_z$, (LOOLJJV)$_z$, or (XOOLJJV)$_z$; and/or the V/E-type docking polypeptide is an acidic peptide comprising (LOOXVJJ)$_z$, (XOOLVJJ)$_z$, (LOOLVJJ)$_z$ where each X is independently a hydrophobic amino acid, each O is independently glutamic acid or lysine, each J is independently any amino acid, and z is an integer greater than or equal to 1.

In some embodiments of any of the aspects the V/K-type docking polypeptide is a basic peptide comprising (LKKXJJV)$_z$ (SEQ ID NO: 9), (LKKLJJV)$_z$ (SEQ ID NO: 10), or (XKKLJJV)$_z$ (SEQ ID NO: 11); and/or the V/E-type docking polypeptide is an acidic peptide comprising (LKKXVJJ)$_z$ (SEQ ID NO: 12), (XKKLVJJ)$_z$ (SEQ ID NO: 13), (LKKLVJJ)$_z$ (SEQ ID NO: 14) where each X is independently a hydrophobic amino acid, each J is independently any amino acid, and z is an integer greater than or equal to 1. In some embodiments of any of the aspects the V/K-type docking polypeptide is a basic peptide comprising (LKKXJJV)$_z$ (SEQ ID NO: 9), (LKKLJJV)$_z$ (SEQ ID NO: 10), or (XKKLJJV)$_z$ (SEQ ID NO: 11); and/or the V/E-type docking polypeptide is an acidic peptide comprising (LKKXVJJ)$_z$ (SEQ ID NO: 12), (XKKLVJJ)$_z$ (SEQ ID NO: 13), (LKKLVJJ)$_z$ (SEQ ID NO: 14) where each X is independently a hydrophobic amino acid, each J is independently any amino acid, and z is an integer greater than or equal to 1.

In some embodiments of any of the aspects the V/K-type docking polypeptide is a basic peptide comprising (LOOIJJV)$_z$ or (IOOLJJV)$_z$ and/or the V/E-type docking polypeptide is an acidic peptide comprising (LOOIVJJ)$_z$ or (IOOLVJJ)$_z$ where each X is independently a hydrophobic amino acid, each O is independently a charged amino acid, each J is independently any amino acid, and z is an integer greater than or equal to 1. In some embodiments of any of the aspects the V/K-type docking polypeptide is a basic peptide comprising (LOOIJJV)$_z$ or (IOOLJJV)$_z$; and/or the V/E-type docking polypeptide is an acidic peptide comprising (LOOIVJJ)$_z$ or (IOOLVJJ)$_z$ where each X is independently a hydrophobic amino acid, each O is independently glutamic acid or lysine, each J is independently any amino acid, and z is an integer greater than or equal to 1.

In some embodiments of any of the aspects the V/K-type docking polypeptide is a basic peptide comprising (LKKIJJV)$_z$ (SEQ ID NO: 15) or (IKKUJV)$_z$ (SEQ ID NO: 16) and/or the V/E-type docking polypeptide is an acidic peptide comprising (LKKIVJJ)$_z$ (SEQ ID NO: 17) or (IKKLVJJ)$_z$ (SEQ ID NO: 18) where each X is independently a hydrophobic amino acid, each J is independently any amino acid, and z is an integer greater than or equal to 1. In some embodiments of any of the aspects the V/K-type docking polypeptide is a basic peptide comprising (LKKIJJV)$_z$ (SEQ ID NO: 15) or (IKKLJJV)$_z$ (SEQ ID NO: 16); and/or the V/E-type docking polypeptide is an acidic peptide comprising (LKKIVJJ)$_z$ (SEQ ID NO: 17) or (IKKLVJJ)$_z$ (SEQ ID NO: 18) where each X is independently a hydrophobic amino acid, each J is independently any amino acid, and z is an integer greater than or equal to 1.

In some embodiments of any of the aspects, a V/K-type docking polypeptide is a basic peptide comprising LKKIJJV, where position 1 is leucine, position 4 is isoleucine, and positions 2 and 3 are lysine, such that the V/K-type docking peptide comprises a sequence of (LKKIJJV) repeated z times. In some embodiments of any of the aspects, the V/E-type docking polypeptide is an acidic peptide comprising LEEIXJJ, where position 1 is leucine, position 4 is isoleucine, and positions 2 and 3 are glutamic acid. In some embodiments of any of the aspects, the V/E-type docking polypeptide is an acidic peptide comprising LEEIXJJ, where position 1 is leucine, position 4 is isoleucine, and positions 2 and 3 are glutamic acid, and position 5 is a hydrophobic amino acid. In some embodiments of any of the aspects, the V/E-type docking polypeptide is an acidic peptide comprising LEEIXJJ, where position 1 is leucine, position 4 is isoleucine, and positions 2 and 3 are glutamic acid, position 5 is a hydrophobic amino acid, and position 6 is tyrosine in at least one repeat of LEEIXJJ.

In some embodiments of any of the aspects, where z is greater than 1, each iteration of XJJXJJJ in a single docking peptide can differ, e.g., the J and X residues are selected independently from each other both within a single iteration of XJJXJJJ and between iterations.

In some embodiments of any of the aspects, a V/K-type docking peptide can comprise, consist of, or consist essentially of SEQ ID NO:1 or SEQ ID NO: 4. In some embodiments of any of the aspects, a V/K-type docking peptide can comprise, consist of, or consist essentially of one, two, three, four, or more repeats of SEQ ID NO: 4. In some embodiments of any of the aspects, a V/K docking peptide can comprise, consist of, or consist essentially of four repeats of SEQ ID NO: 4. In some embodiments of any of the aspects, a V/E-type docking peptide can comprise, consist of, or consist essentially of SEQ ID NO:2, 3, or 6. In some embodiments of any of the aspects, a V/E-type docking peptide can comprise, consist of, or consist essentially of one, two, three, four, or more repeats of SEQ ID NO: 3 or 6. In some embodiments of any of the aspects, a V/E-type docking peptide can comprise, consist of, or consist essentially of four repeats of SEQ ID NO: 3 or 6. In some embodiments of any of the aspects, at least one docking peptide of the composition comprises an amino acid sequence selected from the group consisting of SEQ ID NOs: 1-6; or any combination thereof.

The sequences of the docking peptides can be the same or used in any combination. For example, the V/K-type docking peptides can comprise the amino acid sequence of SEQ ID NO: 4, and the V/E-type docking peptides can comprise the amino acid sequence of SEQ ID NO: 3 or 6. The following table provides examples of the sequences and combinations of sequences that are possible for each polypeptide of the composition described herein as indicated by the x.

```
(Receiving peptide or V/K peptide)        SEQ ID NO: 1
MK(LKKIKSV)4VGER (V/K peptide)                             SEQ ID NO: 4
LKKIKSV (Docking peptide or V/E peptide)          SEQ ID NO: 2
MK(LEEIVSE)2LEEIVTELEEIVSEVGER (V/E peptide)                             SEQ ID NO: 3
LEEIVYE (V/E peptide)                             SEQ ID NO: 6
LEEIVSE
```

| V/E-type docking polypeptide | V/K-type docking polypeptide | |
|---|---|---|
| | SEQ ID NO: 1 | SEQ ID NO: 4 |
| SEQ ID NO: 2 | X | x |
| SEQ ID NO: 3 or 6 | X | x |

In some embodiments of any of the aspects, a docking peptide consists or consists essentially of a sequence specified herein.

The term "hydrophobic amino acid" refers to an amino acid that tends to aggregate in an aqueous solution and exclude water molecules. Non-limiting examples of amino acids with hydrophobic side chains include, glycine (G), alanine (A), valine (V), leucine (L), isoleucine (I), phenylalanine (F), tryptophan (W), and methionine (M). The hydrophobic amino acids of the docking peptides described herein, allow for stabilization of the tetrameric coiled coil structure.

As noted above, the V/K-type docking peptides, will not complex or bind with each other in a pure population and the same is true of a pure population of V/E-type docking peptides. However, when both V/K-type and VIE-type docking peptides are present, a tetramer forms which is comprised of two V/K-type and two V/E type docking peptides. In some embodiments of any of the aspects, the first, second, third, and fourth docking peptides form a tetrameric-coiled coil structure. The polypeptide composition described herein relies, at least in part, on the stability of hydrophobic amino acids to form a tetrameric coiled coil structure. Coiled coil structures are known and described in the art. See, for example, Hu, J. C., O'Shea, E. K., Kim, P. S. & Sauer, R. T. Science. 250, 1400-3 (1990); Harbury, P. B., Zhang, T., Kim, P. S. & Alber, T. Science 262, 1401-7 (1993); incorporated herein by reference in their entirety.

In some embodiments of any of the aspects, the composition further comprises additional docking peptides.

The compositions described herein comprise a first, second, third, and fourth polypeptide component. Each polypeptide component comprises a docking peptide and can optionally comprise additional polypeptide sequences or other moieties (e.g., payload and/or targeting domains). In some embodiments of any of the aspects, the docking peptide of a polypeptide is located at the C-terminus of the polypeptide component. In some embodiments of any of the aspects, the polypeptide component consists of or consists essentially of a docking peptide.

Additional polypeptides can be added, independently, to each of the polypeptide component described herein for the purification, labeling, or isolation of an antibody drug conjugate. For example, an additional polypeptide can be added to the antibody drug conjugate with the amino acid sequence comprising SEQ ID NO: 5. In some embodiments of any of the aspects, any of the polypeptide components can comprise a payload or targeting domain.

In some embodiments of any of the aspects, a targeting domain is a domain or moiety which binds to a target, e.g., a target molecule found or expressed on a target cell type or target tissue. As used herein, the term "target" refers to a biological molecule (e.g., peptide, polypeptide, protein, lipid, carbohydrate) to which a domain or moiety can selectively bind. The target can be, for example, an intracellular target (e.g., an intracellular protein target) or a cell surface target (e.g., a membrane protein, a receptor protein) or an extracellular matrix (e.g., collagen). In some embodiments of any of the aspects, a target is a cell surface target, such as a cell surface protein. By binding to a particular target, the targeting domain localizes the entire composition comprising the four polypeptide components to the target molecule.

In some embodiments of any of the aspects, the targeting domain targets (i.e., binds specifically to) an intravascular target. As used herein, the term "intravascular target" refers to any cell, protein, receptor, small molecule, or the like that is associated with the vascular system. By way of non-limiting example, cancer cells begin to promote angiogenesis and abnormal growth by establishing a vascular network within the tumor. This process enhances the growth and metastis potential of the tumor, leading to significant clinical symptoms of the disease. Thus, biomarkers for cancer cells are typically associated with proteins and signaling molecules that are pro-angiogenic. The signaling pathways for cancer cell mediated angiogenesis, and thus the identity of cancer cell markers, are well known in the art. See for example, Nishida et al. *Vas Health Risk Manag* (2006); Rajabi and Mousa, *Biomedicines* (2017); Lamszus *Clin. Cancer Research*. (2003); Vigneron et al. *Biomed Research Inst*. (2005); Gross et al. *PNAS* (1989); Knochelmann et al. *Front Immunol*. (2018); which are incorporated herein by reference in their entireties. Intravascular targets described herein are not limited, simply to cancer. Non-limiting examples of additional diseases that may require intravascular targeting by the therapeutic agents and/or the compositions described herein include infection, acute respiratory disease syndrome (ARDS), arthritis, inflammatory diseases, lupus, myocardial infarction, stroke, disseminated intravascular coagulation, hyper-coagulation, infant respiratory distress syndrome, Crohn's disease, ulcerative colitis, retinopathies, psoriasis, endometriosis, atherosclerosis, Celiac disease, type 1 diabetes, lupus, multiple sclerosis, and those described by Felmeden et al *European Heart Journal* (2003); Young Yoo and Kwon *Mediators Inflamm*. (2013); Holmes et al. *Major Infectious Diseases*, 3$^{rd}$ edition (2017); Lederberg et al. *Emerging Infections: Microbial Threats to Health in the United States*. (1992), which are incorporated herein by reference in their entireties.

Non-limiting examples of intravascular targets include but are not limited to circulating cancer cell units, circulating tumor cells, metastatic cells, tumor-leukocyte aggregates, tumor-platelet aggregates, tumor-cell clusters; circulating pathogens (e.g., viruses, bacteria, fungi, ameba, etc); microor macro-thrombi circulating or attached to a blood vessel wall; leukocyte-platelet aggregates; pathogen-leukocyte aggregates; neutrophil extracellular traps (NETs); circulating T-cells or neutrophils attacking "self" (e.g., graft vs host disease, autoimmune disease, chronic inflammation); circulating nucleic acids (such as DNA, RNA, histone-bound DNA, microRNAs, and the like from the host or pathogens.

In some embodiments of any of the aspects, the targeting domain binds specifically to a vascular target (e.g., such as all stages of atherosclerotic plaques, neovessels, denuded sites, and the like). In some embodiments of any of the aspects, the targeting domain binds specifically to a tissue target (e.g., solid tumors, metastatic tumors, scar tissue, leukocyte infiltrates, infiltrated NETs (neutrophil extracellular traps) and the like). In some embodiments of any of the aspects, the targeting domain binds specifically to an airway target (e.g., epithelia, pathogens, leukocytes in airway).

In some embodiments of any of the aspects, the targeting domain binds specifically to a receptor, extracellular matrix protein, extracellular protein, ion channel, transporter, peptide, polypeptide, nucleic acid, or microorganism. In some embodiments of any of the aspects, the targeting domain binds specifically to dual endothelin1/VEGFsignal peptide receptor (DEspR), G protein-coupled receptor 87 (GPR87), ErbB family receptors, transforming growth factor beta (TGF-β) family receptors, cluster of differentiation 52 (CD52), programmed death-ligand 1 (PD-L1), vascular endothelial growth factor receptor 1 (VEGFR1), vascular endothelial growth factor receptor 2 (VEGFR2), vascular endothelial growth factor receptor3 (VEGFR3), platelet-derived growth factor receptor beta (PDGFRβ), abelson murine leukemia viral oncogene (ABL), cluster of differentiation 19 (CD19), cluster of differentiation 3 (CD3), mitogen-activated protein kinase kinase (MEK), programmed cell death protein 1 (PD-1), and/or cluster of differentiation 20 (CD20).

In some embodiments of any of the aspects, a targeting domain can comprise an aptamer, antibody reagent, or antigen-binding portion thereof, polypeptide reagent, or a small molecule. In some embodiments of any of the aspects, each an antibody reagent described herein is a Fab or ScFv. In some embodiments of any of the aspects, the antibody reagent described herein is a monoclonal antibody or a bispecific monoclonal antibody. Antibody reagents that are therapeutic and/or specific for any particular target antigen are readily selected by one of skill in the art from known antibody reagents, e.g. from FDA-approved therapeutic antibody reagents and/or commercially available antibody reagents which are listed in catalogs according to their target specificity.

In some embodiments of any of the aspects, an antibody reagent or antigen-binding fragment thereof (e.g., of a targeting domain) can be an anti-DEspR antibody reagent or antigen-binding fragment thereof. For example, an anti-DEspR antibody is described in WO 2012/012750 A1, which is incorporated herein by reference in its entirety.

A DEspR binding protein, antibody, or antigen-binding portion thereof, can be part of a larger immunoadhesion molecule or composition of molecules, formed by covalent or noncovalent association of the antibody antigen-binding portion with one or more other proteins or peptides. Examples of such immunoadhesion molecules include use of the streptavidin core region to make a tetrameric scFv molecule (Kipriyanov et al. (1995) Human Antibod. Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab').sub.2 fragments, can be prepared from whole antibodies using conventional techniques, such as papain or pepsin digestion, respectively, of whole antibodies. Moreover, antibodies, antigen-binding portions thereof, and immunoadhesion molecules can be obtained using standard recombinant DNA techniques. A target binding protein, such as an antigen-binding portion of an antibody may also be part of a dual variable domain (DVD-Ig).

In some embodiments of any of the aspects, at least one of the polypeptide components described herein further comprises a payload domain. As used herein, the "payload domain" or "payload agent" are used interchangeably to describe a portion of a polypeptide component described herein that comprises an agent, small molecule, compound, chemical, polypeptide, virus, nucleic acid, and/or any other moiety known in the art. In some embodiments of any of the aspects, the payload can be a modulator (e.g., agonist or inhibitor) of a desired molecule or activity. In some embodiments of any of the aspects, the payload is a therapeutic payload. The payload domain can comprise multiple agents or therapeutics, e.g., a single composition can comprise one type of payload domain or multiple distinct payload domains. In some embodiments of any of the aspects, a composition as described herein comprises a single type of payload domain (e.g., only one therapeutic agent is found in any payload domain present in the composition). In some embodiments of any of the aspects, a composition as described herein comprises a at least two distinct types of payload domain (e.g., at least two different therapeutic agents are found in the payload domains present in the composition). In some embodiments of any of the aspects, the payload agent can be released from the composition described herein and bind to a specific target (e.g., a receptor expressed by a cancer cell). The payload can be, for example, a small molecule, a nucleic acid (e.g., miRNA), a polypeptide, a gene editing system, a vector (e.g., a viral vector), etc.

In some embodiments of any of the aspects, at least one polypeptide component comprises a targeting domain and at least one polypeptide component comprises a payload agent. In some embodiments of any of the aspects, at least one polypeptide component comprises a targeting domain and at least one polypeptide component comprises a payload agent, whereby the payload agent is delivered to a cell expressing the target of the targeting domain. In various embodiments of the compositions described herein, 1-4 of the polypeptide components can comprise a payload domain, and/or 1-4 of the polypeptide components can comprise a targeting domain. In some embodiments of any of the aspects, an individual polypeptide component can comprise only a payload domain or a targeting domain. In some embodiments of any of the aspects, an individual polypeptide component can comprise both a payload domain and a targeting domain. In some embodiments of any of the aspects, polypeptide components comprising a V/K-type docking peptide further comprise one of a payload domain or a targeting domain, while polypeptide components comprising a V/E-type docking peptide further comprise the domain type not comprised by the V/K-type docking peptide polypeptide components.

In some embodiments of any of the aspects, the ratio of payload domain molecules to targeting domain molecules is from 1:3 to 3:1, 1:1, 1:3, 1:2, 2:1, 3:1, 4:1, 5:2, 6:2, or greater than 6:2.

In some embodiments of any of the aspects, the agent is a chemotherapeutic agent or anti-cancer therapy. In some embodiments of any of the aspects, the chemotherapeutic agent is selected from the group consisting of: mertansine; emtansine; ravtansine; ansamitocin; soravtansine; maytansine; paclitaxel; gemcitabine; fluorouracil; irinotecan; leucovorin; oxaliplatin; capecitabine; cisplatin; docetaxel; and any derivative thereof.

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included herein.

As used herein, a "chemotherapeutic agent" is a chemical compound or small molecule useful in the treatment of cancer. Examples of chemotherapeutic agents include, but are not limited to mertansine; emtansine; ravtansine; ansamitocin; soravtansine; maytansine; paclitaxel; gemcitabine; fluorouracil; irinotecan; leucovorin; oxaliplatin; capecitabine; cisplatin; docetaxel; and any derivative thereof. Additional non-limiting examples of chemotherapeutics that can be used include: alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. *Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYK-ERB); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. Other chemotherapeutic agents that can be used with compositions and methods described herein include, brentuximab vedontin (ADCETRIS®; Seattle Genetic), and ado-trastuzumab emtansine (KADCYLA®; Genentech) and those disclosed in US Publication No. 20080171040 or US Publication No. 20080305044, which are incorporated herein by reference in their entirety.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Agents useful in the treatment of cancer also include growth inhibitory agents. A "growth inhibitory agent" as used herein refers to a compound or composition which inhibits growth of a cell in vitro and/or in vivo. Thus, the growth inhibitory agent can be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

In some embodiments of any of the aspects, at least one docking peptide is located at the C-terminus of the respective polypeptide component.

In some embodiments of any of the aspects, one or more of the polypeptide components can further comprises a polypeptide linker between the docking peptide and the payload and/or targeting domain of the polypeptide component.

As used herein, the term "linker" generally refers to a molecular entity that can directly or indirectly connect at two parts of a composition, e.g., the docking peptide to the payload domain. In some embodiments of any of the aspects, the linker can directly or indirectly connect to one or more agents. The linker can be attached to the N- or C-terminal of the docking peptide. Further, the linker can be linked directly or via another linker (e.g., a peptide of one, two, three, four, five, six, seven, eight, nine, ten or more amino acids) to the polypeptides described herein.

Linkers can be configured according to a specific need, e.g., based on at least one of the following characteristics. In some embodiments of any of the aspects, linkers can be configured to have a sufficient length and flexibility such that it can allow for a cleavage at a target site. In some embodiments of any of the aspects, linkers can be configured to allow multimerization of at least two payloads or polypeptides. In some embodiments of any of the aspects, linkers can be configured to facilitate expression and purification of the antibody drug conjugates described herein. In some embodiments of any of the aspects, a linker can be configured to have any length in a form of a peptide, peptidomimetic, an aptamer, a protein, a nucleic acid (e.g., DNA or RNA), or any combinations thereof. In some embodiments of any of the aspects, a linker can be a chemical linker of any length. In some embodiments of any of the aspects, chemical linker can comprise a direct bond or an atom such as oxygen or sulfur, a unit such as NH, C(O), C(O)NH, SO, $SO_2$, $SO_2NH$, or a chain of atoms, such as substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{12}$ aryl, substituted or unsubstituted $C_5$-$C_{12}$ heteroaryl, substituted or unsubstituted $C_5$-$C_{12}$ heterocyclyl, substituted or unsubstituted $C_3$-$C_{12}$ cycloalkyl, where one or more methylenes can be interrupted or terminated by O, S, S(O), $SO_2$, NH, or C(O). In some embodiments of any of the aspects, the chemical linker can be a polymer chain (branched or linear). The linker can be of any shape. In some embodiments of any of the aspects, the linkers can be linear. In some embodiments of any of the aspects, the linkers can be folded. In some embodiments of any of the aspects, the linkers can be branched. For branched linkers, each branch of a microbe surface-binding domain can comprise at least one microbe surface-binding domain. In some embodiments of any of the aspects, the linker adopts the shape of the physical substrate.

In some embodiments of any of the aspects, the linker can further comprise a detectable label. In some embodiments of any of the aspects, the detectable label can be a chromogenic or fluorescent label so that when the polypeptide composition binds to the target molecule or antigen, the enzyme can interact with the detectable label to induce a color change. Examples of such labels can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-deoxyglucopyranoside, and any other art-recognized label. Such embodiments can act as an indicator for the presence of an antigen.

In some embodiments of any of the aspects, the polypeptide linker is a non-cleavable linker. In some embodiments of any of the aspects, the non-cleavable linker is a 4-phenylurazole, an amide, a carbamate, urea, thiourea, and/or a triazole linker.

In some embodiments of any of the aspects, the polypeptide linker is a cleavable linker. Cleavable linkers can rely on the endosomal and lysosomal pathways in various cell types to release the payload or agent described herein. In some embodiments of any of the aspects, the cleavable linker is an ester, thioester, or hydrazone linker. Cleavable linkers can be, for example, peptide linkers, dipeptide linkers, hydrazones, or disulfide linkers. Thus, upon antigen binding, the cleavage of the linker permits the release of the payload in a site-specific manner.

Figure 20:
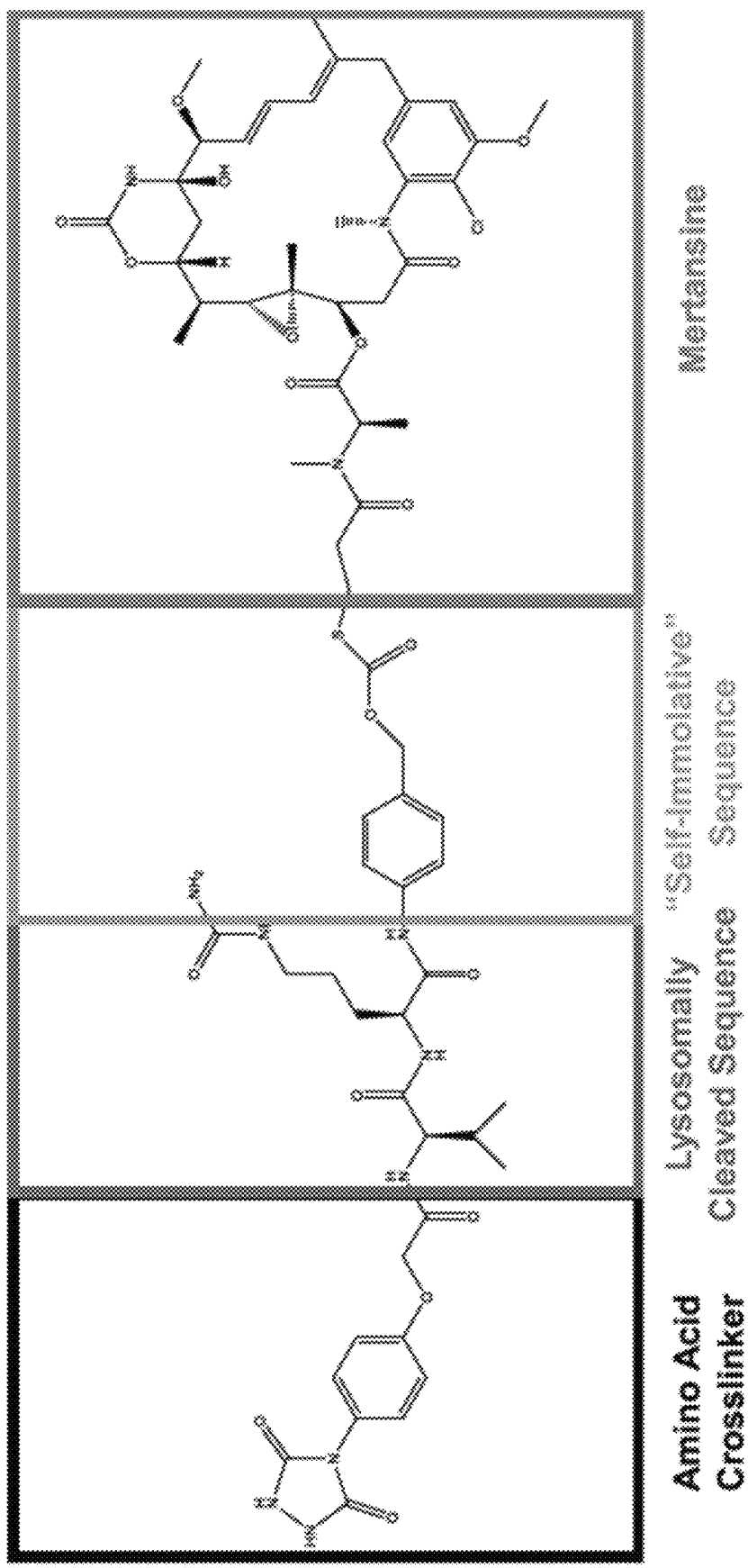
FIG. 20 shows an exemplary ADC drug linker structure comprising (1) an amino acid crosslinker, (2) a lysosomally cleaved sequence, (3) a "self-immolative sequence, and (4) mertansine.

In some embodiments of any of the aspects, the polypeptide linker comprises at least one of: an amino acid cross-linker; a lysosomally cleaved sequence; and/or a self-immolative sequence. For example, the structure of one embodiment of the linker is shown in FIG. 20. In some embodiments of any of the aspects, the linker can have the structure of Formula I

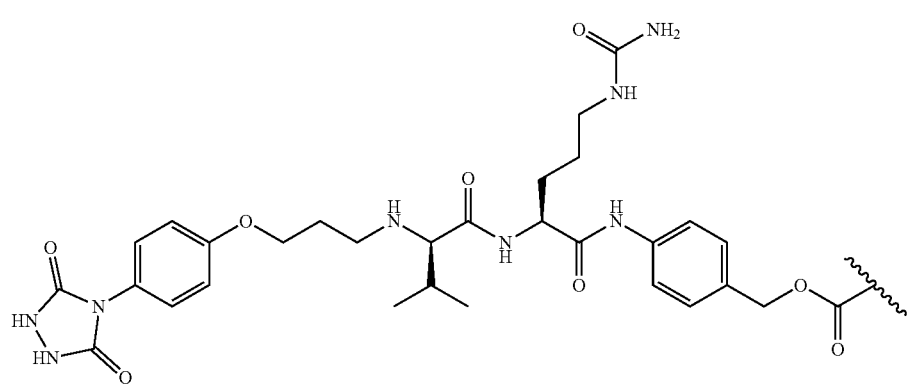

Formula I

In some embodiments of any of the aspects, a linker can be a dipeptide, tripeptide, tetrapeptide, pentapeptide, or longer peptide. In some embodiments of any of the aspects, a linker can be a tripeptide comprising asp, val, and citrulline. In some embodiments of any of the aspects, a linker can be a non-peptide linker, e.g., the linker can comprise disulfide, hydrazine, triazole, amide, ester, carbonate, carbamate, and/or S-thiocarbonate linkers between 4-phenyl urazole and the payload or targeting domain.

As used herein, an "amino acid crosslinker" is the portion of the linker that allows for crosslinking of the peptides described herein to the C-terminus of the antibody reagent. The N-terminus of the linker can comprise the amino acid crosslinker. In some embodiments of any of the aspects, the amino acid crosslinker comprises a tyrosine reactive urazole. As used herein, the "lysosomally cleaved sequence" is a peptide sequence that is cleaved by an enzyme (e.g., capthepsin B). As used herein, a "self-immolative sequence" refers to a portion of the linker that is a spacer between the dipeptide and the payload or agent. Upon cleavage of the lysosomally cleaved sequence, the C-terminal self-immolative sequence allows for the release of the payload. The self-immolative spacer allows for free payload release after degradation of the N-terminal portion of the linker. Further examples of self-immoative chemistry can be found, for example, in Blencowe et al. *Polymer Chemistry*, (2011) and U.S. Pat. No. 7,989,434 B2, which are incorporated herein by reference in their entirety. In some embodiments of any of the aspects, the agent described herein is conjugated to the self-immolative sequence.

Figure 21:
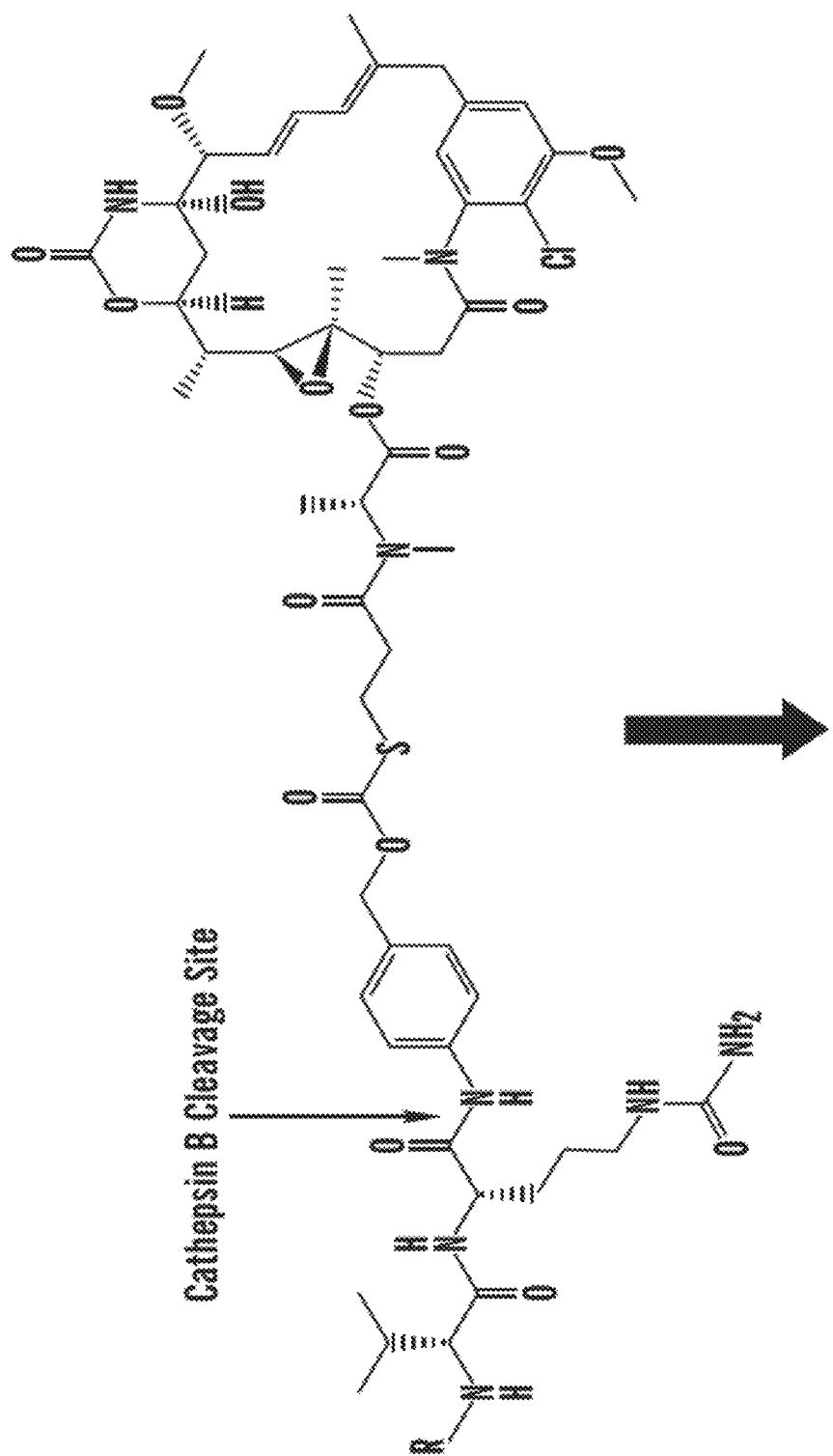
FIG. 21 demonstrates ADC linker functionality.
Figure 21:
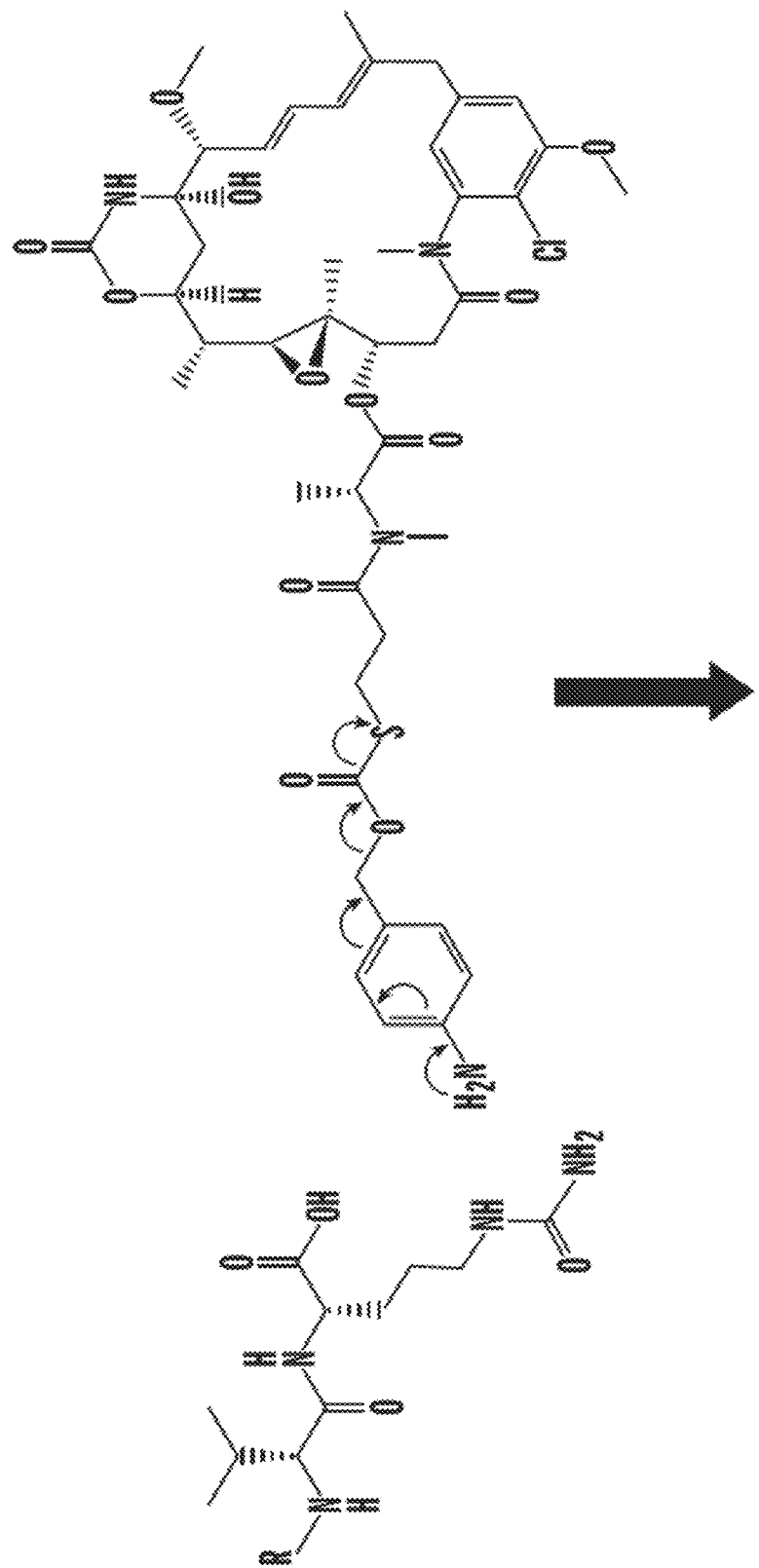
Figure 21:
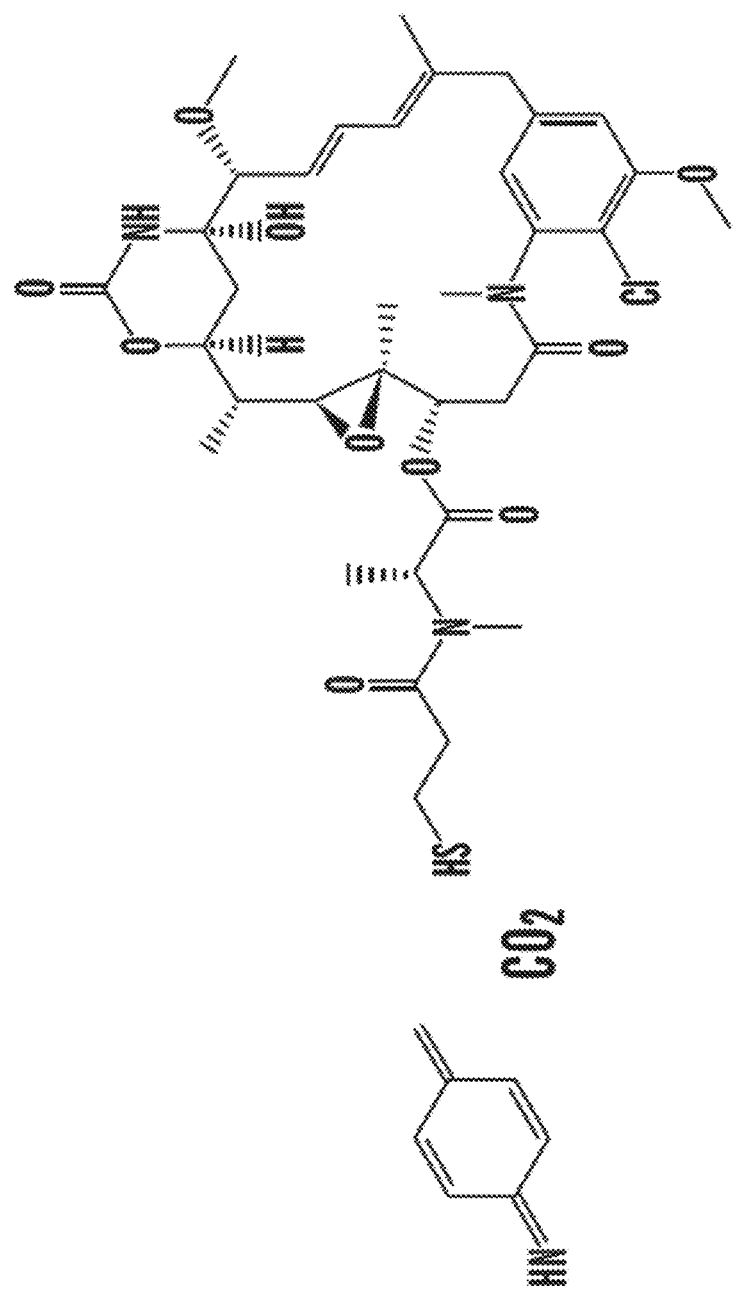

In some embodiments of any of the aspects, polypeptide linker comprises a capthepsin B cleavage site. One example of a capthepsin B cleavage site is shown in FIG. 21 indicated by the labeled arrow. In some embodiments of any of the aspects, the linker can comprise the structure of Formula II.

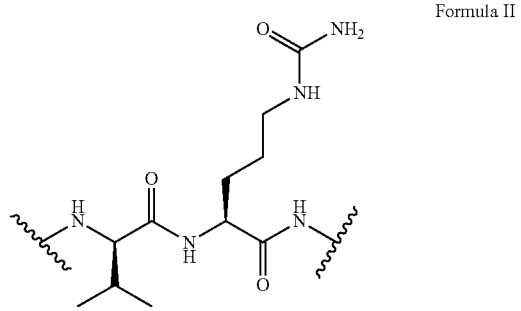 [SMILES: *NC(=O)[C@H](CCCNC(N)=O)NC(=O)[C@H](N*)C(C)C]

Formula II

Capthepsin B is a protein synthesized in the rough endoplasmic reticulum that functions as a lysosomal cysteine protease capable of cleaving peptides. Capthepsin B is also found to be upregulated in cancer cells. Therefore, a capthepsin cleavage site can further improve the site-specificity of the polpeptides and compositions described herein.

As used herein, the term "inducible" refers to a composition that is substantially inactive until an inducing agent is provided. By way of example only, the peptides and compositions described herein can be inducible (e.g., can be designed with a linker that is cleaved by a particular cleaving agent or enzyme).

In some embodiments of any of the aspects, the docking peptides and/or polypeptide components described herein have an amino acid sequence of at least 7 amino acids. In some embodiments of any of the aspects, the peptides described herein have an amino acid sequence at least about 7, at least about 10, at least about 15, at least about 20, at least about 30, at least about 40, at least about 50, at least about 60, at least about 70, at least about 80, at least about 90, at least about 100, at least about 200, at least about 300, at least about 400, at least about 500, amino acid residues or more.

In another aspect of any of the embodiments, described herein is a method of treating a disease, the method comprising: administering the composition described herein to a subject in need thereof. In some embodiments of any of the aspects, the payload domain comprises a therapeutic agent, e.g., an agent known to be therapeutic for that disease. Known therapeutic agents are easily identified by one of ordinary skill in the art, e.g., by identifying FDA-approved therapeutics. In some embodiments of any of the aspects, the targeting domain can specifically bind to a diseased cell target.

In some embodiments of any of the aspects, the disease is cancer, infection, or trauma. In some embodiments of any of the aspects, the disease is myocardial infarction, stroke, disseminated intravascular coagulation, hyper-coagulation, atherosclerosis, acute respiratory distress syndrome, infant respiratory distress syndrome, Crohn's disease, ulcerative colitis, rheumatoid arthritis, Celiac disease, type 1 diabetes, lupus, and multiple sclerosis.

In another aspect of any of the embodiments, described herein is a method of treating cancer, the method comprising: administering the composition described herein to a subject in need thereof, wherein the payload domain comprises a chemotherapeutic agent. In some embodiments of any of the aspects, the targeting domain can specifically bind to a cancer cell target.

In some embodiments of any of the aspects, the cancer is selected from the group consisting of: pancreatic cancer, cancer of the digestive system; hepatic carcinoma; liver cancer; colon cancer; esophageal cancer; gastric cancer; hepatoma; kidney or renal cancer; oral cavity cancer; prostate cancer; rectal cancer; stomach cancer; basal cell carcinoma, biliary tract cancer; lung cancer; brain cancer, breast cancer, bladder cancer; cervical cancer; endometrial cancer; uterine cancer; and cancer of the urinary system, leukemias, lymphomas, leukemic and solid tumor metastatic cancers.

In another aspect of any of the embodiments, described herein is a method of inducing cytotoxicity of a target cell, the method comprising: contacting the cell with the composition described herein, wherein the payload domain comprises a chemotherapeutic agent, cytotoxic agent, and/or growth inhibitory agent. In some embodiments of any of the aspects, the targeting domain can specifically bind to a target molecule on the target cell.

In another aspect of any of the embodiments, described herein is a method of inducing cytotoxicity of a cancer cell, the method comprising: contacting the cancer cell with the composition described herein, wherein the payload domain comprises a chemotherapeutic agent, cytotoxic agent, and/or growth inhibitory agent. In some embodiments of any of the aspects, the targeting domain can specifically bind to a cancer cell target.

As used herein, the terms "cytotoxicity" or "cytotoxic" refers to the quality of an agent or composition to induce cellular necrosis, apoptosis, death, lysis, or reduce cell viability. Chemotherapeutics and the compositions described herein can induce cytotoxicity through a variety of signaling pathways. For example, microtubule destabilization is one method of causing cytotoxicity of a cancer cell. The microtubules are responsible for maintaining the cellular cytoskeleton and intracellular transport. Tubulin inhibitors (e.g., mertansine) inhibit the assembly of microtubule by binding to the tubulin proteins at a rhizoxin binding site and destabilizing the cellular cytoplasm.

In some embodiments of any of the aspects, the cancer cell is a pancreatic cancer cell. As used herein, a "pancreatic cancer cell" is a cell that is derived from pancreatic cancer tissues. The pancreatic cancer cells can be directly from a subject (e.g., a mammal) or available commercial and cultured in vitro. Non-limiting examples of pancreatic cancer cells include Panc1 cells and MIA PaCa2 cells.

In another aspect of any of the embodiments, described herein is a method of delivering a payload agent to a cell, the method comprises: contacting a population of cells and/or a subject with the composition described herein. The payload agent can be targeted to the desired cell type by including a targeting domain specific for the desired cell type.

In some embodiments of any of the aspects, the compositions described herein are formulated as pharmaceutical composition. Thus, methods of delivering and administering pharmaceutical compositions known in the art can be applied to the compositions described herein. As used herein, the term "pharmaceutical composition" can include any material or substance that, when combined with an active ingredient (e.g., mertansine), allows the ingredient to retain biological activity and is non-reactive with the subject's immune system. Examples include, but are not limited to, any of the standard pharmaceutical carriers such as a phosphate buffered saline solution, emulsions such as oil/water emulsion, and various types of wetting agents. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The term "pharmaceutically acceptable carrier" excludes tissue culture media. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Non-limiting examples of pharmaceutical carriers include particle or polymer-based vehicles such as nanoparticles, microparticles, polymer microspheres, or polymer-drug conjugates.

In some embodiments of any of the aspects, the pharmaceutical composition is a liquid dosage form or solid dosage form. Liquid dosage forms for oral administration include, but are not limited to, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

In addition, pharmaceutically acceptable emulsions, microemulsions, solutions, suspensions, syrups and elixirs can be used. Pharmaceutical compositions include formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

The term "effective amount" is used interchangeably with the term "therapeutically effective amount" or "amount sufficient" and refers to the amount of the compositions described herein of a pharmaceutical composition, at dosages and for periods of time necessary to achieve the desired therapeutic result, for example, to "attenuate", reduce or stop at least one symptom of a disease (e.g., cancer). For example, an effective amount using the methods as disclosed herein would be considered as the amount sufficient to reduce one or more symptoms of cancer by at least 10%.

An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from cancer. Accordingly, the term "effective amount" or "therapeutically effective amount" as used herein refers to the amount of the compositions described herein in a pharmaceutical composition to alleviate at least one symptom of a disease. Stated another way, "therapeutically effective amount" of a cytotoxic composition as disclosed herein is the amount of an agonist which exerts a beneficial effect on, for example, the symptoms of the disease (e.g., cancer). The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify agonist as disclosed herein which will achieve the goal of reduction in the severity of cancer or at least one related symptom thereof.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animals. Generally, the compositions are administered so that a compound of the disclosure herein is used or given at a dose from 1 μg/kg to 1000 mg/kg; 1 μg/kg to 500 mg/kg; 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compositions described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

In some embodiments of any of the aspects, the polypeptide composition described herein is administered continuously (e.g., at constant levels over a period of time). Continuous administration of an agent can be achieved, e.g., by epidermal patches, continuous release formulations, or on-body injectors.

The composition can be administered as a single bolus or multiple boluses, as a continuous infusion, or a combination thereof. For example, the composition can be administered as a single bolus initially, and then administered as a continuous infusion following the bolus. The rate of the infusion can be any desired rate. Some contemplated infusion rates include from 1 μg/kg/min to 100 mg/kg/min, or from 1 μg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the composition is administered via infusion at a rate sufficient to safely maintain a sufficient effective plasma concentration of compound in the bloodstream.

The compositions described herein can be co-administered with other agents or therapeutics. As used herein, the phrase "co-administering" or to "co-administer" means the administration of an inhibitor described herein and another compound, e.g., a therapeutic agent, separately, simultaneously, and/or sequentially over a period of time as determined by a qualified care giver.

"Unit dosage form" as the term is used herein refers to a dosage for suitable one administration. By way of example a unit dosage form can be an amount of therapeutic disposed in a delivery device, e.g., a syringe or intravenous drip bag. In some embodiments of any of the aspects, a unit dosage form is administered in a single administration. In some embodiments of any of the aspects, more than one-unit dosage form can be administered simultaneously.

The dosage of the compositions as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

In some embodiments of any of the aspects, the compositions described herein are used as a monotherapy. In some embodiments of any of the aspects, the compositions described herein can be used in combination with other known agents and therapies used for the treatment of a disease (e.g., cancer). Administered "in combination," as used herein, means that two (or more) different treatments are delivered to the subject during the course of the subject's affliction with the disorder, e.g., the two or more treatments are delivered after the subject has been diagnosed with the disorder (e.g., cancer) and before the disorder has been cured or eliminated or treatment has ceased for other reasons. In some embodiments of any of the aspects, the delivery of one treatment is still occurring when the delivery of the second begins, so that there is overlap in terms of administration. This is sometimes referred to herein as "simultaneous" or "concurrent delivery."

In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments of any of the aspects, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The compositions described herein and the at least one additional therapy can be administered simultaneously, in the same or in separate compositions, or sequentially. For sequential administration, the composition described herein can be administered first, and the additional agent can be administered second, or the order of administration can be reversed. The compositions described herein and/or other therapeutic agents, procedures or modalities can be administered during periods of active disorder, or during a period of remission or less active disease. The compositions described herein can be administered before another treatment, concurrently with the treatment, post-treatment, or during remission of the disorder.

When administered in combination, compositions described herein and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect.

In some embodiments of any of the aspects, the composition is administered by direct injection, subcutaneous injection, muscular injection, oral, or nasal administration. In some embodiments of any of the aspects, the administering of the composition or pharmaceutical composition provided herein reduces tumor growth or proliferation in a subject.

The terms "administered" and "subjected" are used interchangeably in the context of treatment of a disease or disorder. In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered orally. In some embodiments of any of the aspects, the agents or compositions provided herein are directly injected into the portal vein. For example, injection into the portal vein can limit systemic side effects of the agent or pharmaceutical composition. In some embodiments of any of the aspects, the compositions provided herein are implanted into the portal vein for sustained release. In some embodiments of any of the aspects, the compositions are administered via an injection port.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. Without limitations, oral administration can be in the form of solutions, suspensions, tablets, pills, capsules, sustained-release formulations, oral rinses, powders and the like.

Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, described herein is an composition or pharmaceutical composition that is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm & Haas, Spring House, Pa. USA).

The efficacy of a composition as described herein, e.g., for the treatment of cancer, can be determined by the skilled practitioner. However, a treatment is considered "effective treatment," as the term is used herein, if one or more of the signs or symptoms of a disease (e.g., cancer) are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., tumor size or growth, white blood cell count, etc. Efficacy can also be measured by a failure of an individual to worsen as assessed by hospitalization, or need for medical interventions (i.e., progression of the symptoms). Methods of measuring these indicators are known to those of skill in the art and/or are described herein.

Efficacy can be assessed in animal models of a condition described herein, for example, a mouse model or an appropriate animal model of pancreatic cancer as the case may be. When using an experimental animal model, efficacy of treatment is evidenced when a statistically significant change in a marker is observed, e.g., tumor growth.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by werner Luttmann, published by Elsevier, 2006; Janeway's Immunobiology, Kenneth Murphy, Allan Mowat, Casey weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "administering" or "delivering" refers to the placement of a therapeutic or composition as disclosed herein into a subject by a method or route which results in at least partial delivery of the agent at a desired site. The compositions comprising agents as disclosed herein can be administered by any appropriate route which results in an effective treatment in the subject.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female.

A subject can be one who has been previously diagnosed with or identified as suffering from or having a condition in need of treatment (e.g., pancreatic cancer or another type of cancer, among others) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

As used herein, the term "cancer" refers to a hyperproliferation of cells that exhibit a loss of normal cellular control that results in unregulated growth, lack of differentiation, local tissue invasion, and metastasis. The methods and compositions described herein can be used for the treatment of solid tumors (e.g., pancreatic cancers) or non-solid tumors, such as leukemia, blood cell cancers, and the like. Solid tumors can be found in bones, muscles, the brain, or organs, and can be sarcomas or carinomas. Where the technology described herein can overcome barriers of tumor treatment, including, but not limited to barriers to treatment or inhibition of metastases, it is contemplated that aspects of the technology described herein can be used to treat all types of solid and non-solid tumor cancers, including cancers not listed in the instant specification. The compositions and methods described herein, without limitation, include methods of treating cancer, methods of inhibiting metastases, and methods of inducing an anti-tumor immune response.

As used herein, the term "contacting" when used in reference to a cell or organ, encompasses both introducing or administering the composition described herein, an agent, surface, hormone, etc. to the cell, tissue, or organ in a manner that permits physical contact of the cell with the agent, surface, hormone etc., and/or introducing an element, such as a genetic construct or vector, that permits the expression of a payload (e.g., an agent, such as a miRNA, polypeptide, or other expression product in the cell).

The term "pharmaceutically acceptable" can refer to compounds and compositions which can be administered to a subject (e.g., a mammal or a human) without undue toxicity.

As used herein, the term "pharmaceutical composition" or "pharmaceutically acceptable carrier" are used interchangeably and can include any material or substance that, when combined with an active ingredient, allows the ingredient to retain biological activity and is non-reactive with the subject's immune system. Examples include, but are not limited to, any of the standard pharmaceutical carriers such as a phosphate buffered saline solution, emulsions such as oil/water emulsion, and various types of wetting agents. The term "pharmaceutically acceptable carriers" excludes tissue culture media. Non limiting examples of pharmaceutical carriers include particle or polymer-based vehicles such as nanoparticles, microparticles, polymer microspheres, or polymer-drug conjugates.

As used herein, an "appropriate control" refers to an untreated, otherwise identical cell or population (e.g., a subject who was not administered the composition described herein, or was administered by only a subset of agents provided herein, as compared to a non-control cell).

As used herein, a "reference level" can refer to one or more parameters or markers as measured for a normal, otherwise unaffected cell population or tissue (e.g., a biological sample obtained from a healthy subject, or a biological sample obtained from the subject at a prior time point, or a biological sample that has not yet been contacted with an agent as described herein). For measuring or monitoring therapeutic efficacy, a level determined prior to treatment or earlier in treatment can also provide a reference level for a given parameter or value.

As used herein, the term "modulates" refers to an effect including increasing or decreasing a given parameter as those terms are defined herein.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level. For example, increasing activity can refer to activating a receptor or a signaling pathway (e.g., apoptotic pathway).

The terms "decrease", "reduced", "reduction", or "inhibit" are all used herein to mean a decrease or lessening of a property, level, or other parameter by a statistically significant amount. In some embodiments of any of the aspects, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The term "statistically significant" or "significantly" refers to statistical significance and generally means a two standard deviation (2SD) or greater difference.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues provided herein are preferred to be in the "L" isomeric form. However, residues in the "D" isomeric form may be substituted for any L-amino acid residue provided the desired properties of the polypeptide are retained.

The term "homology" as used herein refers to sequence similarity between two peptides or between two nucleic acid molecules. Homology can be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology refers to a function of the number of identical or similar amino acids at positions shared by the compared sequences. A sequence which is "unrelated" or "non-homologous" shares less than 40% identity. Determination of homologs of the genes or peptides described herein may be easily ascertained by the skilled artisan.

The sequences provided here can be modified, comprise conservative amino acid substitutions, or have additional amino acids that can improve targeting or efficacy of the composition described herein. In some embodiments of any of the aspects, the first polypeptide has an amino acid sequence with at least 99% homology to the second polypeptide. In some embodiments of any of the aspects, the third polypeptide has an amino acid sequence with at least 99% homology to the fourth polypeptide. In some embodiments of any of the aspects, the first polypeptide has an amino acid sequence that is non-homologous to the second polypeptide. In some embodiments of any of the aspects, the third polypeptide has an amino acid sequence that is non-homologous to the fourth polypeptide. In some embodiments of any of the aspects, the first or second polypeptide has an amino acid sequence that is non-homologous to the third and/or fourth polypeptides.

The term "conservative substitution," when describing a polypeptide, refers to a change in the amino acid composition of the polypeptide that does not substantially alter the polypeptide's activity, fore examples, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, *Proteins*, W. H. Freeman and Company (1984).) In addition, individual substitutions, deletions or additions that alter, add or delete a single amino acid or a small percentage of amino acids in an encoded sequence are also "conservative substitutions." Insertions or deletions are typically in the range of about 1 to 5 amino acids.

Conservative substitutions that permit the formation of the tetrameric coiled coil structure described herein can be used. For example, directed evolution can be used to subject the polypeptides described herein to random mutagenesis and the resulting polypeptides are screened for desired qualities (e.g, using circular dichroism or binding assays). These methods are known in the art. See Wang et al. *Cell*, Volume 160, Issue 4, 2015, Pages 785-797; or Daugherty et al. *Protein Engineering*, Design and Selection, Volume 11, Issue 9, 1998, Pages 825-832.

As used herein the term, "aptamer" refers to single-stranded nucleic acids that are capable of binding to cells and target molecules. Nucleic acid aptamers include RNA, DNA, and/or synthetic nucleic acid analogs (e.g., PNA) capable of specifically binding target molecules. Aptamers are an attractive alternative to antibodies for cell selection because of their high level of specificity and affinity for cell surface markers. As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites).

The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The term "antibody" or "antibody reagent" broadly refers to any immunoglobulin (Ig) molecule or compositions of Igs and/or immunologically active portions of immunoglobulin molecules (i.e., molecules that contain an antigen binding site that immunospecifically bind an antigen) comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below, and include but are not limited to a variety of forms, including full length antibodies and antigen-binding portions thereof; including, for example, an immunoglobulin molecule, a monoclonal antibody, a chimeric antibody, a CDR-grafted antibody, a human antibody, a humanized antibody, a single chain antibody, a Fab, a F(ab'), a F(ab')2, a Fv antibody, fragments produced by a Fab expression library, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., *Eur. J. Immunol.* 17, 105 (1987)) and single chains (e.g., Huston et al., *Proc. Natl. Acad. Sci.* U.S.A., 85, 5879-5883 (1988) and Bird et al., Science 242, 423-426 (1988), which are incorporated herein by reference) and/or antigen-binding fragments of any of the above (See, generally, Hood et al., *Immunology*, Benjamin, N.Y., 2ND ed. (1984), Harlow and Lane, Antibodies. *A Laboratory Manual*, Cold Spring Harbor Laboratory (1988) and Hunkapiller and Hood, *Nature,* 323, 15-16 (1986), which are incorporated herein by reference). Antibodies also refer to immunoglobulin molecules and immunologically active portions of immunoglobulin molecules, i.e., molecules that contain antigen or target binding sites or "antigen-binding fragments." The antibody or immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art. Furthermore, in humans, the light chain can be a kappa chain or a lambda chain.

In a full-length antibody, each heavy chain is comprised of a heavy chain variable domain (abbreviated herein as HCVR or VH) and a heavy chain constant region. The heavy chain constant region is comprised of three domains: CH1, CH2, and CH3. Each light chain is comprised of a light chain variable domain (abbreviated herein LCVR as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. This structure is well-known to those skilled in the art. The chains are usually linked to one another via disulfide bonds.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain, and a CH3 domain, and optionally comprises a CH4 domain. Replacements of amino acid residues in the Fc portion to alter antibody effector function are known in the art (U.S. Pat. Nos. 5,648,260 and 5,624,821). The Fc portion of an antibody mediates several important effector functions, for example, cytokine induction, ADCC, phagocytosis, complement dependent cytotoxicity (CDC), and half-life/clearance rate of antibody and antigen-antibody complexes. In some cases, these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

The term "antigen-binding portion" of an antibody refers to one or more fragments of an antibody that retain the ability to specifically bind to an antigen (e.g., DEspR). Antigen-binding functions of an antibody can be performed by fragments of a full-length antibody. Such antibody fragment embodiments may also be incorporated in bispecific, dual specific, or multi-specific formats such as a dual variable domain (DVD-Ig) format; specifically binding to two or more different antigens (e.g., DEspR and a different antigen molecule). Examples of binding fragments encompassed within the term "antigen-binding portion" of an antibody include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature, 341: 544-546; PCT Publication No. WO 90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, for example, Bird et al. (1988) Science 242: 423-426; and Huston et al. (1988) Proc. Natl. Acad. Sci. USA 85: 5879-

5883). Such single chain antibodies are also intended to be encompassed within the term "antigen-binding portion" of an antibody.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al. (1993) Proc. Natl. Acad. Sci. USA 90: 6444-6448; Poljak (1994) Structure 2: 1121-1123); Kontermann and Dubel eds., Antibody Engineering, Springer-Verlag, N.Y. (2001), p. 790 (ISBN 3-540-41354-5). As used herein, a "bispecific antibody" refers to an antibody that can simultaneously bind to two different types of antigen.

In addition, single chain antibodies also include "linear antibodies" comprising a pair of tandem Fv segments (VH-CH1-VH-CH1) which, together with complementary light chain polypeptides, form a pair of antigen binding regions (Zapata et al. (1995) Protein Eng. 8(10): 1057-1062; and U.S. Pat. No. 5,641,870). An immunoglobulin constant (C) domain refers to a heavy (CH) or light (CL) chain constant domain. Murine and human IgG heavy chain and light chain constant domain amino acid sequences are known in the art.

In some embodiments of any of the aspects, the antibody reagent is a humanized antibody.

The term "humanized antibody" refers to antibodies that comprise heavy and light chain variable domain sequences from a non-human species (e.g., a mouse) but in which at least a portion of the VH and/or VL sequence has been altered to be more "human-like", i.e., more similar to human germline variable sequences. Accordingly, "humanized" antibodies are a form of a chimeric antibody, that are engineered or designed to comprise minimal sequence derived from non-human immunoglobulin. For the most part, humanized antibodies are human immunoglobulins (recipient or acceptor antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992). As used herein, a "composite human antibody" or "deimmunized antibody" are specific types of engineered or humanized antibodies designed to reduce or eliminate T cell epitopes from the variable domains.

One type of humanized antibody is a CDR-grafted antibody, in which human CDR sequences are introduced into non-human VH and VL sequences to replace the corresponding nonhuman CDR sequences. Also "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab').sub.2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments of any of the aspects, a humanized antibody contains both the light chain as well as at least the variable domain of a heavy chain. The antibody also may include the CH1, hinge, CH2, CH3, and CH4 regions of the heavy chain. In some embodiments of any of the aspects, a humanized antibody only contains a humanized light chain In some embodiments of any of the aspects, a humanized antibody only contains a humanized heavy chain. In specific embodiments, a humanized antibody only contains a humanized variable domain of a light chain and/or humanized heavy chain. A humanized antibody may be selected from any class of immunoglobulins, including IgM, IgG, IgD, IgA and IgE, and any isotype including without limitation IgG1, IgG2, IgG3, and IgG4. The humanized antibody may comprise sequences from more than one class or isotype, and particular constant domains may be selected to optimize desired effector functions using techniques well known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In an exemplary embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

A "human antibody," "non-engineered human antibody," or "fully human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 14:309-314 (1996): Sheets et al. Proc. Natl. Acad. Sci. 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous mouse immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody can be prepared via immortalization of human B lymphocytes producing an antibody directed against a target antigen (such B lymphocytes can be recovered from an individual or can have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

As described herein, an "antigen" is a molecule that is bound by a binding site on a polypeptide agent, such as a binding protein, an antibody or antibody fragment, or antigen-binding fragment thereof. Typically, antigens are bound by antibody ligands and are capable of raising an antibody response in vivo. An antigen can be a polypeptide, protein, nucleic acid or other molecule. In the case of conventional antibodies and fragments thereof, the antibody binding site as defined by the variable loops (L1, L2, L3 and H1, H2, H3) is capable of binding to the antigen. The term "antigenic determinant" refers to an epitope on the antigen recognized by an antigen-binding molecule, and more particularly, by the antigen-binding site of said molecule.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by a binding protein. An epitope may be determined by obtaining an X-ray crystal structure of an antibody:antigen complex and determining which residues on the antigen (e.g., DEspR) are within a specified distance of residues on the antibody of interest, wherein the specified distance is, 5 Å or less, e.g., 5 Å, 4 Å, 3 Å, 2 Å, 1 Å or any distance in between. In some embodiments of any of the aspects, an "epitope" can be formed on a polypeptide (e.g., DEspR) both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In some embodiments of any of the aspects, an epitope comprises of 8 or more contiguous or non-contiguous amino acid residues in the target sequence (e.g, DEspR) in which at least 50%, 70% or 85% of the residues are within the specified distance of the antibody or binding protein in the X-ray crystal structure.

The terms "specificity" or "specific for" refers to the number of different types of antigens or antigenic determinants to which a binding protein, antibody or antibody fragment, or antigen-binding portion thereof as described herein can bind. The specificity of a binding protein, antibody or antibody fragment, or antigen-binding portion thereof can be determined based on affinity and/or avidity. The affinity, represented by the equilibrium constant for the dissociation ($K_D$) of an antigen with an antigen-binding protein, is a measure of the binding strength between an antigenic determinant and an antigen-binding site on the antigen-binding protein, such as a binding protein, antibody or antibody fragment, or antigen-binding portion thereof: the lesser the value of the $K_D$, the stronger the binding strength between an antigenic determinant and the antigen-binding molecule. Alternatively, the affinity can also be expressed as the affinity constant ($K_A$), which is $1/K_D$). As will be clear to the skilled person, affinity can be determined in a manner known per se, depending on the specific antigen of interest. Accordingly, a binding protein, antibody or antibody fragment, or antigen-binding portion thereof as defined herein is said to be "specific for" a first target or antigen compared to a second target or antigen when it binds to the first antigen with an affinity (as described above, and suitably expressed, for example as a $K_D$ value) that is at least 10 times, such as at least 100 times, and preferably at least 1000 times, and up to 10000 times or more better than the affinity with which said amino acid sequence or polypeptide binds to another target or polypeptide.

Accordingly, as used herein, "binds specifically" or "selectively binds" or "specifically binds" or "specific binding" in reference to the interaction of an antibody, or antibody fragment thereof, or a binding protein described herein, means that the interaction is dependent upon the presence of a particular structure (e.g., an antigenic determinant or epitope or target) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In certain embodiments, a binding protein or antibody or antigen-binding fragment thereof that specifically binds to an antigen binds to that antigen with a $K_D$ greater than $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M. In other embodiments, a binding protein or antibody or antigen binding fragment thereof that specifically binds to an antigen binds to that antigen with a $K_D$ between $10^{-6}$ and $10^{-7}$ M, 10 and $10^{-8}$ M, 10 and $10^{-9}$ M, $10^{-6}$ and $10^{-10}$ M, $10^{-6}$ and $10^{-11}$ M, $10^6$ and $10^{-12}$ M, $10^{-6}$ and $10^{-13}$ M, $10^{-6}$ and $10^{-14}$ M, $10^{-9}$ and $10^{-10}$ M, $10^{-9}$ and $10^{-11}$ M, $10^{-9}$ and $10^{-12}$ M, $10^{-9}$ and $10^{-13}$ M, $10^{-9}$ and $10^{-14}$ M. In some embodiments of any of the aspects, a binding protein or antibody or antigen-binding fragment thereof binds to an epitope, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. In certain embodiments, a binding protein or antibody or antigen-binding fragment thereof is said to "specifically bind" an antigen when it preferentially recognizes its target antigen in a complex mixture of proteins and/or macromolecules. Binding proteins, antibodies or antigen-binding fragments that bind to the same or similar epitopes will likely cross-compete (one prevents the binding or modulating effect of the other). Cross-competition, however, can occur even without epitope overlap, e.g., if epitopes are adjacent in three-dimensional space and/or due to steric hindrance.

Avidity is the measure of the strength of binding between an antigen-binding molecule (such as a binding protein, antibody or antibody fragment, or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as a binding protein, antibody or antibody fragment, or antigen-binding portion thereof described herein) will bind to their cognate or specific antigen with a dissociation constant ($K_D$ of $10^{-5}$ to $10^{-12}$ moles/liter or less, and preferably $10^{-7}$ to $10^{12}$ moles/liter or less and more preferably $10^{-8}$ to $10^{12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on a binding protein, antibody or antibody fragment, or antigen-binding portion thereof described herein will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

The term "$K_D$" (also "Kd"), as used herein, is intended to refer to the "equilibrium dissociation constant", and refers to the value obtained in a titration measurement at equilibrium, or by dividing the dissociation rate constant (Koff) by the association rate constant (Kon). The association rate constant (Kon), the dissociation rate constant (Koff), and the equilibrium dissociation constant (K are used to represent the binding affinity of a binding protein to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "antibody fragment," or "antigen-binding fragment" as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

An antibody having a "biological characteristic" or "functional characteristic" of a designated antibody is one which possesses one or more of the biological properties of that antibody which distinguish it from other antibodies that bind to the same antigen, including, for example, binding to a particular epitope, an EC50 value, IC50 value or $K_D$ values, as defined elsewhere herein.

In order to screen for antibodies that bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In certain embodiments, the antibody will be purified (1) to greater than 95% by weight of antibody as determined by, for example, the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

The term "antibody conjugate" refers to a binding protein or antibody or antigen-binding fragment thereof as described herein chemically linked to a second chemical moiety, such as a therapeutic or cytotoxic agent. The terms "antibody drug conjugate" or "antibody-drug conjugate," as used herein, refer to an antibody conjugated to a non-proteinaceous agent, typically a chemotherapeutic agent, e.g., a cytotoxic agent, a cytostatic agent, a toxin, or a radioactive agent. A linker molecule can be used to conjugate the drug to the antibody. A wide variety of linkers and drugs useful in ADC technology are known in the art and can be used in embodiments described herein. (See, for example, US20090028856; US2009/0274713; US2007/0031402; WO2005/084390; WO2009/099728; U.S. Pat. Nos. 5,208,020; 5,416,064; 5,475,092; 5,585,499; 6,436,931; 6,372,738; and 6,340,701, all incorporated herein by reference in their entireties). By combining the unique targeting of monoclonal antibodies or fragments thereof with the cancer-killing ability of cytotoxic drugs, antibody drug conjugates allow sensitive and increased discrimination between healthy and diseased tissue.

The term "agent" is used herein to denote a chemical compound, a mixture of chemical compounds, a biological macromolecule, or an extract made from biological materials. In some embodiments of any of the aspects, the therapeutic or cytotoxic agents include, but are not limited to, anti-cancer therapies as discussed herein (e.g., mertansine), as well as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, a binding protein conjugate or antibody conjugate may be a detectably labeled antibody, which is used as the detection antibody.

In some embodiments of any of the aspects, the agent is a small molecule. As used herein, the term "small molecule" refers to a organic or inorganic molecule, either natural (i.e., found in nature) or non-natural (i.e., not found in nature), which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" $J.$ $Am.$ $Chem.$ $Soc.$ 120:8565, 1998; incorporated herein by reference). In certain other preferred embodiments, natural-product-like small molecules are utilized.

As used herein, a "compound" refers to any chemical, test chemical, drug, new chemical entity (NCE) or other moiety. For example, a compound can be any foreign chemical not normally present in a subject such as mammals including humans. A compound can also be an endogenous chemical that is normally present and synthesized in biological systems, such as mammals, including humans.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those provided herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise explained, all technical and scientific terms used herein have the same meaning as commonly understood by one of ordinary skill in the art to which this disclosure belongs.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A composition comprising:
   a. a first polypeptide component comprising a V/K-type docking peptide;
   b. a second polypeptide component comprising a V/K-type docking peptide;
   c. a third polypeptide component comprising a V/E-type docking peptide; and
   d. a fourth polypeptide component comprising a V/E-type docking peptide;
   wherein the docking peptides each independently comprise a sequence of $(XJJXJJJ)_z$ where each X is independently a hydrophobic amino acid, each J is independently any amino acid, and z is an integer greater than or equal to 1; and
   wherein the V/K-type docking polypeptide is a basic peptide comprising valine at the $7^{th}$ position of XJJXJJJ; and
   wherein the V/E-type docking polypeptide is an acidic peptide comprising valine at the $5^{th}$ position of XJJXJJJ.
2. The composition of paragraph 1, wherein the z of at least one docking peptide is an integer greater than or equal to 3.
3. The composition of any of paragraphs 1-2, wherein the z of each docking peptide is an integer greater than or equal to 3.
4. The composition of any of paragraphs 1-3, wherein the z of at least one docking peptide is 3.
5. The composition of any of paragraphs 1-4, wherein the z of at each docking peptide is 3.
6. The composition of any of paragraphs 1-5, wherein each docking peptide comprises leucine at the $1^{st}$ position of XJJXJJJ and an isoleucine at the $4^{th}$ position of XJJXJJJ.
7. The composition of any of paragraphs 1-6, wherein the XJJXJJJ of the V/K-type docking peptide is LKKIJJV.
8. The composition of any of paragraphs 1-7, wherein the z of the V/E-type docking peptide is greater than 1 and at least 1 iteration of XJJXJJJ comprises tyrosine at the sixth position.
9. The composition of any of paragraphs 1-8, wherein at least one of the V/E-type docking peptides comprises an amino acid sequence of LEEIJJJ.
10. The composition of any of paragraphs 1-9, wherein at least one of the V/E-type docking peptides comprises an amino acid sequence of LEEIXJX.
11. The composition of any of paragraphs 1-10 wherein at least one docking peptide comprises an amino acid sequence selected from the group consisting of SEQ ID NOs: 1-4 or 6; or any combination thereof
12. The composition of any one of paragraphs 1-11, wherein the first, second, third, and fourth docking peptides form a tetrameric-coiled coil structure.
13. The composition of any one of paragraphs 1-12, wherein at least one of the polypeptide components further comprise a targeting domain.
14. The composition of paragraph 13, wherein the targeting domain comprises an aptamer, antibody reagent, or antigen-binding portion thereof, polypeptide reagent, or a small molecule.
15. The composition of paragraph 14, wherein each antibody reagent is a Fab or ScFv.
16. The composition of paragraph 14, wherein the antibody reagent is a monoclonal antibody or a bispecific monoclonal antibody.
17. The composition of any one of paragraph 14-16, wherein the antibody reagent is a humanized antibody.
18. The composition of any one of paragraphs 13-17, wherein the targeting domain specifically binds to a target selected from the group consisting of: circulating cancer cells, metastatic cancer cells, tumor-leukocyte aggregates, tumor-platelet aggregates, leukocytes, circulating pathogens, microthrombi, macrothrombi, atherosclerotic plaques, epithelial cells, leukocyte-platelet aggregates, pathogen-leukocyte aggregates, neutrophil extracellular traps (NETs), and circulating nucleic acids.
19. The composition of paragraph 18, wherein the target is selected from the group consisting of: dual endothelin1/VEGFsignal peptide receptor (DEspR), G protein-coupled receptor 87 (GPR87), ErbB family receptors, transforming growth factor beta (TGF-β) family receptors, cluster of differentiation 52 (CD52), programmed death-ligand 1 (PD-L1), vascular endothelial growth factor receptor 1 (VEGFR1), vascular endothelial growth factor receptor 2 (VEGFR2), vascular endothelial growth factor receptor3 (VEGFR3), Platelet-derived growth factor receptor beta (PDGFRβ), abelson murine leukemia viral oncogene (ABL), cluster of differentiation 19 (CD19), cluster of differentiation 3 (CD3), mitogen-activated protein kinase kinase (MEK), programmed cell death protein 1 (PD-1), and cluster of differentiation 20 (CD20).
20. The composition of any of paragraphs 13-19, wherein the target of the targeting domain is an intravascular target.
21. The composition of any one of paragraphs 1-20, wherein at least one of the polypeptide components further comprises a payload domain.
22. The composition of paragraph 21, wherein the payload domain comprises a small molecule, enzyme, or polypeptide.
23. The composition of paragraph 21 or paragraph 22, wherein the payload domain comprises a chemotherapeutic agent.
24. The composition of paragraph 23, wherein the chemotherapeutic agent is selected from the group consisting of: mertansine; emtansine; ravtansine; ansamitocin; soravtansine; maytansine; paclitaxel; gemcitabine; fluorouracil; irinotecan; leucovorin; oxaliplatin; capecitabine; cisplatin; docetaxel; and any derivative thereof
25. The composition of any one of paragraphs 1-24, wherein at least one docking peptide is located at the C-terminus of the respective polypeptide component.

26. The composition of any one of paragraphs 1-25, wherein at least one polypeptide component further comprises a polypeptide linker between the docking peptide and the payload and/or targeting domain of the polypeptide component.
27. The composition of paragraph 26, wherein the polypeptide linker is a cleavable linker.
28. The composition of paragraph 26 or paragraph 27, wherein the polypeptide linker comprises at least one of:
   a. an amino acid crosslinker;
   b. a lysosomally cleaved sequence; or
   c. a self-immolative sequence.
29. The composition of any one of paragraphs 26-28, wherein the polypeptide linker comprises a capthepsin B cleavage site.
30. The compositions of any of paragraphs 26-29, wherein the cleavable linker comprises an ester, a thioester, a hydrazine, a hydrazine, a disulfide, or a protease linker.
31. The composition of any one of paragraphs 26-30, wherein the polypeptide linker comprises a non-cleavable linker.
32. The composition of paragraph 31, wherein the non-cleavable linker is selected from the group consisting of: a 4-phenyl-urazole; an amide; a carbamate; urea; thiourea; and a triazole linker.
33. A method of treating a disease, the method comprising: administering the composition of any one of paragraphs 1-32 to a subject in need thereof, wherein the payload domain comprises a therapeutic agent.
34. The method of paragraph 33, wherein the disease is cancer, infection, or trauma.
35. The method of paragraph 34, wherein the cancer is selected from the group consisting of: pancreatic cancer, cancer of the digestive system; hepatic carcinoma; liver cancer; colon cancer; esophageal cancer; gastric cancer; hepatoma; kidney or renal cancer; oral cavity cancer; prostate cancer; rectal cancer; stomach cancer; basal cell carcinoma, biliary tract cancer; lung cancer; brain cancer, breast cancer, bladder cancer; cervical cancer; endometrial cancer; uterine cancer; cancer of the urinary system; leukemia; lymphoma; and leukemic and solid tumor metastatic cancers.
36. The method of paragraph 33, wherein the disease is selected from the group consisting of: myocardial infarction, stroke, disseminated intravascular coagulation, hyper-coagulation, atherosclerosis, acute respiratory distress syndrome, infant respiratory distress syndrome, Crohn's disease, ulcerative colitis, rheumatoid arthritis, Celiac disease, type 1 diabetes, lupus, and multiple sclerosis.
37. A method of treating cancer, the method comprising: administering the composition of any one of paragraphs 21-32 to a subject in need thereof, wherein the payload domain comprises a chemotherapeutic agent.
38. The method of paragraph 37, wherein the cancer is selected from the group consisting of: pancreatic cancer, cancer of the digestive system; hepatic carcinoma; liver cancer; colon cancer; esophageal cancer; gastric cancer; hepatoma; kidney or renal cancer; oral cavity cancer; prostate cancer; rectal cancer; stomach cancer; basal cell carcinoma, biliary tract cancer; lung cancer; brain cancer, breast cancer, bladder cancer; cervical cancer; endometrial cancer; uterine cancer; cancer of the urinary system; leukemia; lymphoma; and leukemic and solid tumor metastatic cancers.
39. A method of inducing cytotoxicity of a cancer cell, the method comprising: contacting the cancer cell with the composition of any one of paragraphs 21-32.
40. The method of paragraph 39, wherein the cancer cell is a pancreatic cancer cell.
41. A method of delivering a payload agent to a cell, the method comprising: contacting a population of cells and/or a subject with a composition of any one of paragraphs 1-32, wherein at least one polypeptide component comprises a targeting domain and at least one polypeptide component comprises a payload domain; whereby the payload domain is delivered to a cell expressing the target of the targeting domain.
42. The method or compositions of any of paragraphs 1-41, wherein the ratio of payload domain molecules to targeting domain molecules is from 2:6 to 6:2.
43. The method or composition of paragraph 42, wherein the ratio of payload domain molecules to targeting domain molecules is from 1:3 to 3:1.
44. The method or composition of paragraph 42, wherein the ratio of payload domain molecules to targeting domain molecules is 1:3, 1:1, 1:2, 2:1, 3:1, 4:1, 5:2, or 6:2.
45. The method or compositions of any of paragraphs 1-41, wherein the ratio of payload domain molecules to targeting domain molecules is greater than 6:2.
46. The use of the composition of any one of paragraphs 1-32 to treat a disease, wherein the payload domain comprises a therapeutic agent, the use comprising administering the composition to a subject in need of treatment for the disease.
47. The use of paragraph 46, wherein the disease is cancer, infection, or trauma.
48. The use of paragraph 47, wherein the cancer is selected from the group consisting of: pancreatic cancer, cancer of the digestive system; hepatic carcinoma; liver cancer; colon cancer; esophageal cancer; gastric cancer; hepatoma; kidney or renal cancer; oral cavity cancer; prostate cancer; rectal cancer; stomach cancer; basal cell carcinoma, biliary tract cancer; lung cancer; brain cancer, breast cancer, bladder cancer; cervical cancer; endometrial cancer; uterine cancer; cancer of the urinary system; leukemia; lymphoma; and leukemic and solid tumor metastatic cancers.
49. The use of paragraph 46, wherein the disease is selected from the group consisting of: myocardial infarction, stroke, disseminated intravascular coagulation, hyper-coagulation, atherosclerosis, acute respiratory distress syndrome, infant respiratory distress syndrome, Crohn's disease, ulcerative colitis, rheumatoid arthritis, Celiac disease, type 1 diabetes, lupus, and multiple sclerosis.
50. The use of the composition of any one of paragraphs 21-32 to treat a cancer, wherein the payload domain comprises a chemotherapeutic agent, the use comprising administering the composition to a subject in need of treatment for the cancer.
51. The use of paragraph 50, wherein the cancer is selected from the group consisting of: pancreatic cancer, cancer of the digestive system; hepatic carcinoma; liver cancer; colon cancer; esophageal cancer; gastric cancer; hepatoma; kidney or renal cancer; oral cavity cancer; prostate cancer; rectal cancer; stomach cancer; basal cell carcinoma, biliary tract cancer; lung cancer; brain cancer, breast cancer, bladder cancer; cervical cancer; endometrial cancer; uterine cancer; cancer of the urinary system; leukemia; lymphoma; and leukemic and solid tumor metastatic cancers.

52. The use of any of paragraphs 46-51, wherein the ratio of payload domain molecules to targeting domain molecules is from 2:6 to 6:2.
53. The use of paragraph 52, wherein the ratio of payload domain molecules to targeting domain molecules is from 1:3 to 3:1.
54. The use of paragraph 52, wherein the ratio of payload domain molecules to targeting domain molecules is 1:3, 1:1, 1:2, 2:1, 3:1, 4:1, 5:2, or 6:2.
55. The use of any of paragraphs 46-51, wherein the ratio of payload domain molecules to targeting domain molecules is greater than 6:2.

EXAMPLES

Example 1: Self-Assembly Linkers and Uses Thereof

Neutrophil extracellular traps (NETs) are extracellular fibrillary structures of chromatin filaments coated with histones, proteases and granular and cytosolic proteins released by neutrophils as an antimicrobial mechanism that 'traps' and kills bacteria. Cumulative research reveals that NETs' antimicrobial killing properties can also induce tissue injury when dysregulated. Hence, NETs are increasingly recognized as a culprit-driver in the pathogenesis of multiple major diseases—acute respiratory distress syndromes (ARDS), acute coronary syndromes (ACS), multi-organ failure (MOF) in ARDS, and sepsis—where durable breakthrough therapies are lacking, despite significant research. Regardless of the disease, the fact that NETs are the common culprit in diverse and pathogenically disparate diseases argues the importance and high-value priority of targeting NETs.

To not be bound by a particular theory, it was hypothesized that successful neutralization and dismantlement of intravascular NETs will stop NET-driven endothelial injury at pulmonary vascular-alveolar barrier injury sites in acute respiratory distress syndrome (ARDS). To overcome the concomitant biological and biophysical barriers to dismantling NETs and neutralizing NET-driven tissue injury, a multi-pronged therapeutic is needed. A novel therapeutic was developed herein that comprises: 1) a highly specific, humanized hinge-stabilized S228P IgG4 antibody that targets the dual endothelin1/signal peptide$^{VEGF}$ receptor (DEspR) detected on NETosing neutrophils—anti-DEspR-humab; and, 2) DNase1 conjugated to a tripeptide linker that is cleaved by cathepsin G (cg). Release of the DNase1 by cathepsin G cleavage at the NET site will facilitate NET dismantlement and serve as a substrate decoy for cathepsin G reactivity, thus minimizing its direct endothelial injury activity. This targeted enzymatic bioconjugate is enabled by a novel method of stoichiometric, site-specific conjugation to antibodies—i.e., the NanoZip which utilizes the supramolecular assembly of coiled coils (SMACC) to achieve selective, specific coupling of two DNase1 enzymes to the C-terminus of an antibody.

The aims of the experimental research provided herein is as follows:

Aim 1.
Preparation of a polypeptide-antibody therapeutic that can target DESPR1 (DESPRnase1) and evaluate structural stability and dose-dependent release of DNase1 by cathepsin G in basal plasma conditions, and in the presence of low pH and high ROS milieus present in ARDS.

Aim 2.
Determine DESPRnase1 targets and binds to DEspR$^+$ NETs, dismantles DEspR$^+$ NETs without complement activation, and/or serves as substrate-decoys to attenuate NETs' cathepsin G-induced injury of human endothelial cells ex vivo. The bio[nano]conjugate provided herein is a breakthrough therapeutic to dismantle NETs and stop the vicious cycle of endothelial injury in ARDS. Notably, efficacy in ARDS will open the door to potential applications in ACS and other indications.

The methods and compositions provided herein advance a humanized monoclonal antibody as a first-in class therapy against pancreatic ductal adenocarcinoma (PDAC). The antibody selectively targets the unique dual endothelin1/signal peptide$^{VEGF}$ receptor (DEspR) that is highly expressed on cancer stem-like cells (CSCs) and non-CSC tumor cells within the tumor niche—DEspR-humab.

Aim 1 characterizes the role of tumor targets (e.g., DEspR) in tumor cell survival by investigating the mechanism of cell death (necroptosis vs. apoptosis and Apaf1 and BIRC3) from receptor binding by the polypeptide-antibody therapeutic, the role of cellular stress in directing cell death, and the role of nuclear shuttling of the receptor in cancer cells. These studies provide a fundamental understanding of DEspR-humab mechanism of action.

Aim 2 develops a novel controlled site-specific method for conjugation of two drugs to DEspR-humab and evaluates the in vitro efficacy of the DEspR-humab and an antibody drug conjugate (ADC) of DEspR-humab and mertansine, a potent microtubule-targeted cytotoxic agent, in a Panc-1 and Panc-1 derived CSCs. The in vivo data provided herein show that DEspR-humab treatment alone outperforms gemcitabine, thus providing support and motivation for the proposed studies.

Specific Aims
Multi-Functional Targeted Bio-Conjugate Platform to Dismantle Neutrophil Extracellular Traps (NETs)

Clinical Need.
Neutrophil extracellular traps (NETs) are extracellular fibrillary structures of chromatin filaments coated with histones, proteases and granular and cytosolic proteins released by neutrophils as an antimicrobial mechanism that 'traps' and kills bacteria.[1-3] While mechanisms and types of NETosis are still being unraveled, the intact NETs structure is key to its antimicrobial action.[4] However, cumulative research reveals that NETs antimicrobial killing properties can also induce tissue injury when dysregulated.[1] Not surprising, NETs are increasingly recognized as a culprit-driver in the pathogenesis of multiple major diseases—acute respiratory distress syndromes (ARDS), acute coronary syndromes (ACS), multi-organ failure (MOF) in ARDS, and sepsis[1,2]—where durable breakthrough therapies are lacking, despite significant research.

Technological Need.
Regardless of the disease, the fact that NETs are the common culprit in diverse and pathogenically disparate diseases argues the importance and high-value priority of targeting NETs. We hypothesize that successful neutralization and dismantlement of intravascular NETs will stop NET-driven endothelial injury at pulmonary vascular-alveolar barrier injury sites in acute respiratory distress syndrome (ARDS). To overcome the concomitant biological and biophysical barriers to dismantling NETs and neutralizing NET-driven tissue injury, a multi-pronged therapeutic is needed. Studies show that deoxyribonuclease I (DNase1) can dismantle NETs, but "DNase1 alone" therapies are insufficient to resolve NETs-mediated pathologies or tissue injury in patients[5,6] and animal models,[7,8] indicating the need for targeted multi-pronged therapies. While PAD4 inhibitors or deficiency prevent NETosis,[7] they cannot block ongoing active NETs-driven tissue injury.

Solution.

The targeted delivery of DNase1 and concurrent sequestration of NET proteases, such as cathepsin G, can dismantle the NET-scaffold and downregulate the pathogenic action of neutrophil proteases, respectively. This unique antibody conjugate defines a new platform technology that can address NET-mediated tissue injuries in sites other than the vasculature. To accomplish this goal, a novel therapeutic is developed that comprises: 1) a highly specific, humanized hinge-stabilized S228P IgG4 antibody that targets the dual endothelin1/signal peptide$^{VEGF}$ receptor (DEspR)[9] detected on NETosing neutrophils (FIG. 2)—anti-DEspR-humab; and, 2) DNase1 conjugated to a tripeptide linker that is cleaved by cathepsin G (cg). Release of the DNase1 by cathepsin G cleavage at the NET site will facilitate NET dismantlement and serve as a substrate decoy for cathepsin G reactivity, thus minimizing its direct endothelial injury activity. This technological advance in targeted enzymatic bioconjugates is enabled by a novel method of stoichiometric, site-specific conjugation to antibodies—i.e., the NanoZip which utilizes the supramolecular assembly of coiled coils (SMACC) to achieve selective, specific coupling of two DNase1 enzymes to the C-terminus of an antibody. The specific aims are:

Aim 1.

Preparation of the humab-cg-peptide-DNase1 that targets DESPR1 therapeutic prototype (DESPRnase1) and evaluate structural stability and dose-dependent release of DNase1 by cathepsin G in basal plasma conditions, and in the presence of low pH and high ROS milieus present in ARDS.

Aim 2.

Determining DESPRnase1 targeting and binding properties to DEspR$^+$ NETs, dismantles DEspR$^+$ NETs without complement activation, and/or serves as substrate-decoys to attenuate NETs' cathepsin G-induced injury of human endothelial cells ex vivo.

Major Milestones.

Go:

DESPRnase1 binds and dismantle NETs significantly better than naked DNase1.

No Go:

DESPRnase1 induces complement activation.

No Go:

DESPRnase1 worsens NETs-mediated endothelial injury.

Impact.

A novel bio[nano]conjugate is provided herein as a breakthrough therapeutic to dismantle NETs—thus breaking the vicious cycle of NET-induced endothelial injury-NETosis in ARDS, and opens the door for several therapeutic applications for ACS, as well as prevent NETs-mediated thrombosis in multi-organ failure in ARDS, sepsis, and trauma. More importantly, the prototype DESPRnase1 serves as a modular platform wherein the targeting antibody, payload, or cleavage linker can be modified to address disease-specific therapeutic needs, thus further broadening the impact of this innovative, high-risk bioengineering proposal. Finally, successful completion of this proposal will provide a NET targeting prototype for testing in an ARDS±MOF in vivo model to advance its translation to the clinic.

Research Strategy

A. Significance.

Cumulative data in multiple diseases in different organ systems implicate neutrophil extracellular traps (NETs) in the progression of disease, as well as in the feed forward mechanisms of end-stage life-threatening pathogenesis in acute respiratory distress syndrome (ARDS), acute coronary syndromes (ACS), multi-organ failure (MOF) in ARDS, sepsis, cancer, trauma.[1-3] Despite significant preclinical research[8,10,11] and clinical trials,[5,12,13] there is no FDA-approved curative-intent therapeutic for NETs-driven pathology or tissue injury.

The successful design and evaluation of the DESPRnase1, and its proof-of-concept of dismantling NETs provide a solid basis to drive this research towards a much needed targeted therapy for NET-driven endothelial injuries. Beyond a therapeutic, the stepwise validation of the design and efficacious multifunctionality of the DESPRnase1 provide a foundational paradigm for approaching NETs. In the future, refining the design to include different release mechanisms (e.g., neutrophil elastase and not just cathepsin G), and different payloads (e.g., thrombolytics, and not just DNase1) expand the projected impact. Moreover, efficacy in neutralizing intravascular NETs will showcase one example of an approach to target NETs within tissues.

The DESPRnase1 is a true breakthrough technology as it is designed to address the underlying biophysical properties of NETs which obstruct the dismantling of DNA/chromatin-mesh scaffold, and hinder the neutralization of the neutrophil proteases activity within NETs. The fact that NETs remain impervious to hypoxia or ROS causes NETs-driven pathologies a conundrum because neutrophil cell death does not stop NETosis, but actually becomes a part of it—as in suicidal NETosis. In fact, hypoxia and ROS can stimulate more NETosis. Hence, efficacy of the DESPRnase1 in low pH and/or high ROS conditions will expand the potential impact.

B. Innovation.

There are multiple levels of innovation provided herein. 1$^{st}$: The therapeutic approach to NET-driven pathologies is novel, and as a therapeutic platform it can be modified for other medical applications. 2$^{nd}$: The integration of a) the target's biophysical properties (DNA mesh-scaffold), b) the target's pathophysiological actions (multiple proteases), and c) the target's microenvironment (low pH, hi-ROS) into the design of a single multifunctional therapeutic is novel and highlights the rationale behind transdisciplinary nanomedicine approaches. 3$^{rd}$: The supramolecular assembled coiled-coil strategy and the use of recombinant DNA technology to attain the ability to conjugate proteins (150 kDa targeting antibody, 30.1 kDa DNase1 payload) with a protease cleavable linker at 4° C. is novel. 4$^{th}$: The targeting of DEspR$^+$ NETs, but sparing of DEspR(−) quiescent neutrophils via the anti-DEspR mAb is novel.

C. Background.

Coiled Coil Structures Provide a Novel Method to Site-Specifically Label the Antibody C-Terminus.

This approach (FIG. 1) relies on two types of peptide sequences: a C-terminal receiving sequence and a drug carrying docking sequence. Separately, they cannot form an organized structure, but in 1:1 molar ratios, they spontaneously form an organized, tetrameric-coiled coil structure. This system will allow selective and reliable conjugation with minimal impact on antigen binding.

Circular Dichroism (CD) and Isothermal Titration Calorimetry (ITC) Data Confirm nanoZip Formation for <0.74 kDa Payload as a Prelude to Design of Novel nanoZip for 30-Fold Larger DNase1 Payload.

Figure 2A:
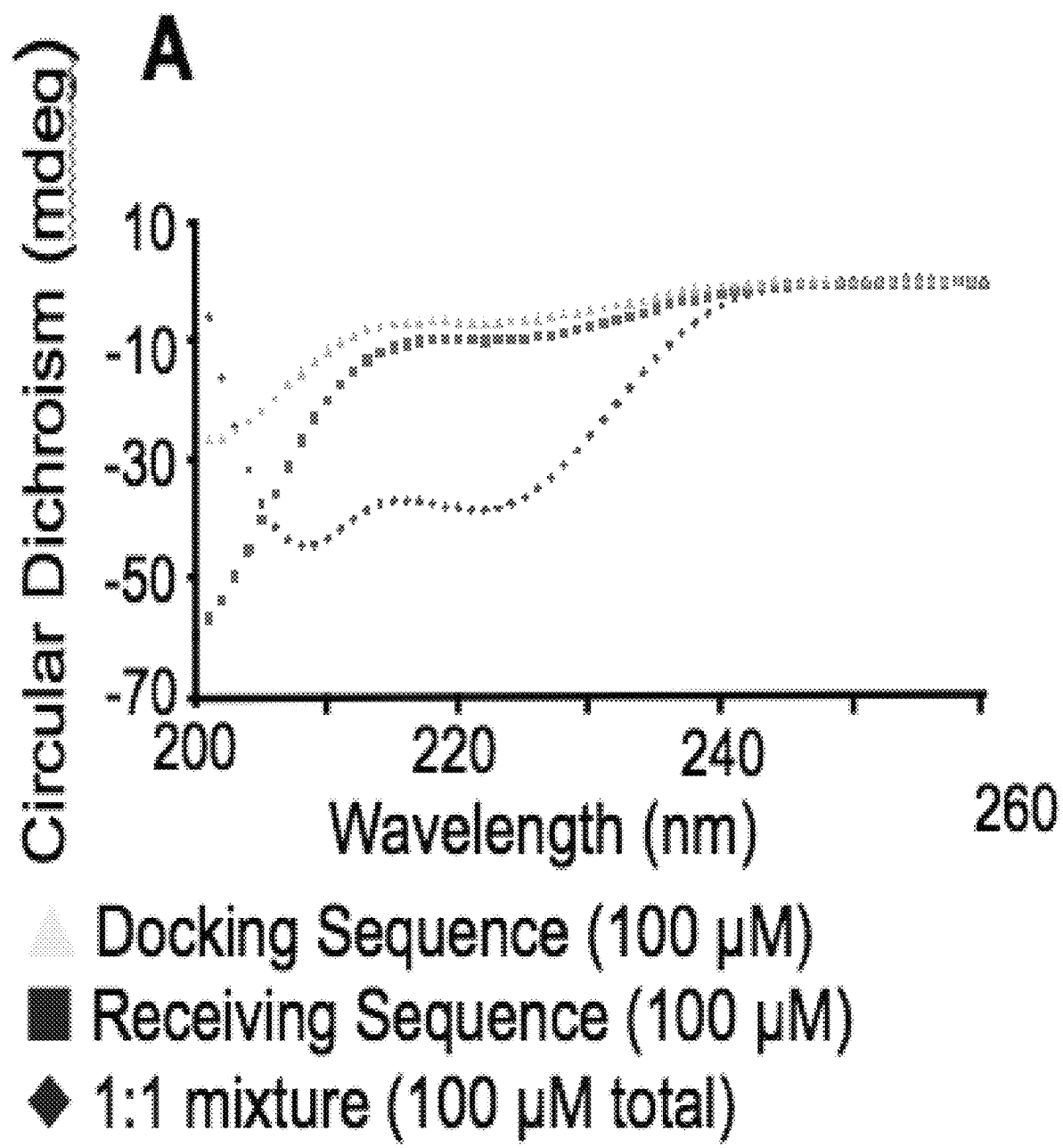
FIG. 2A demonstrates that circular dichroism shows that receiving peptide and docking peptide do not self-assemble, but equimolar receiving and docking spontaneously form a coiled contract.
Figure 2B:
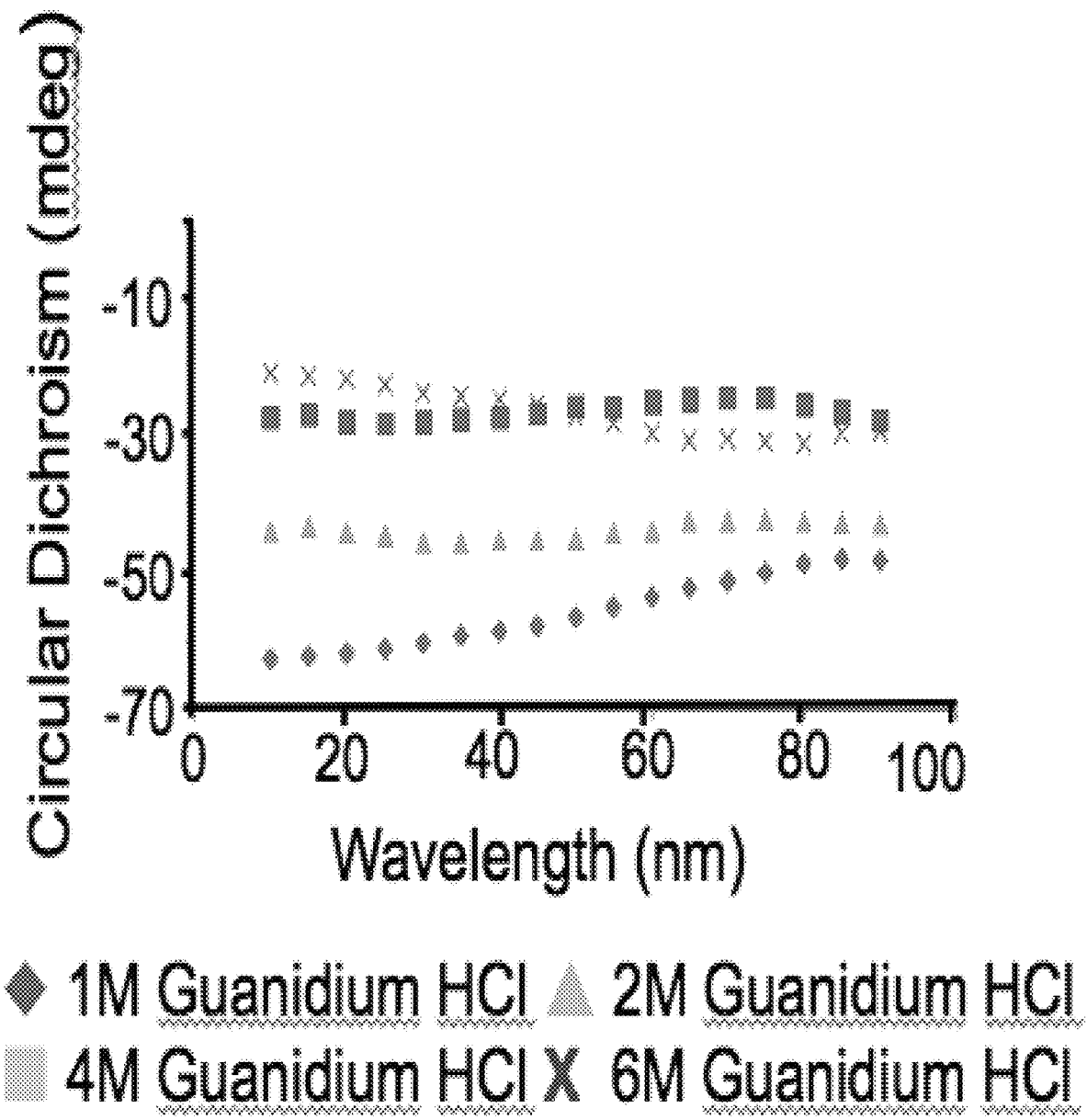
FIG. 2B demonstrates that thermal studies with increasing guanidium chloride concentrations (1M-6M) showed no change in structure and high stability by monitoring CD at 222 nm.
Figure 2C:
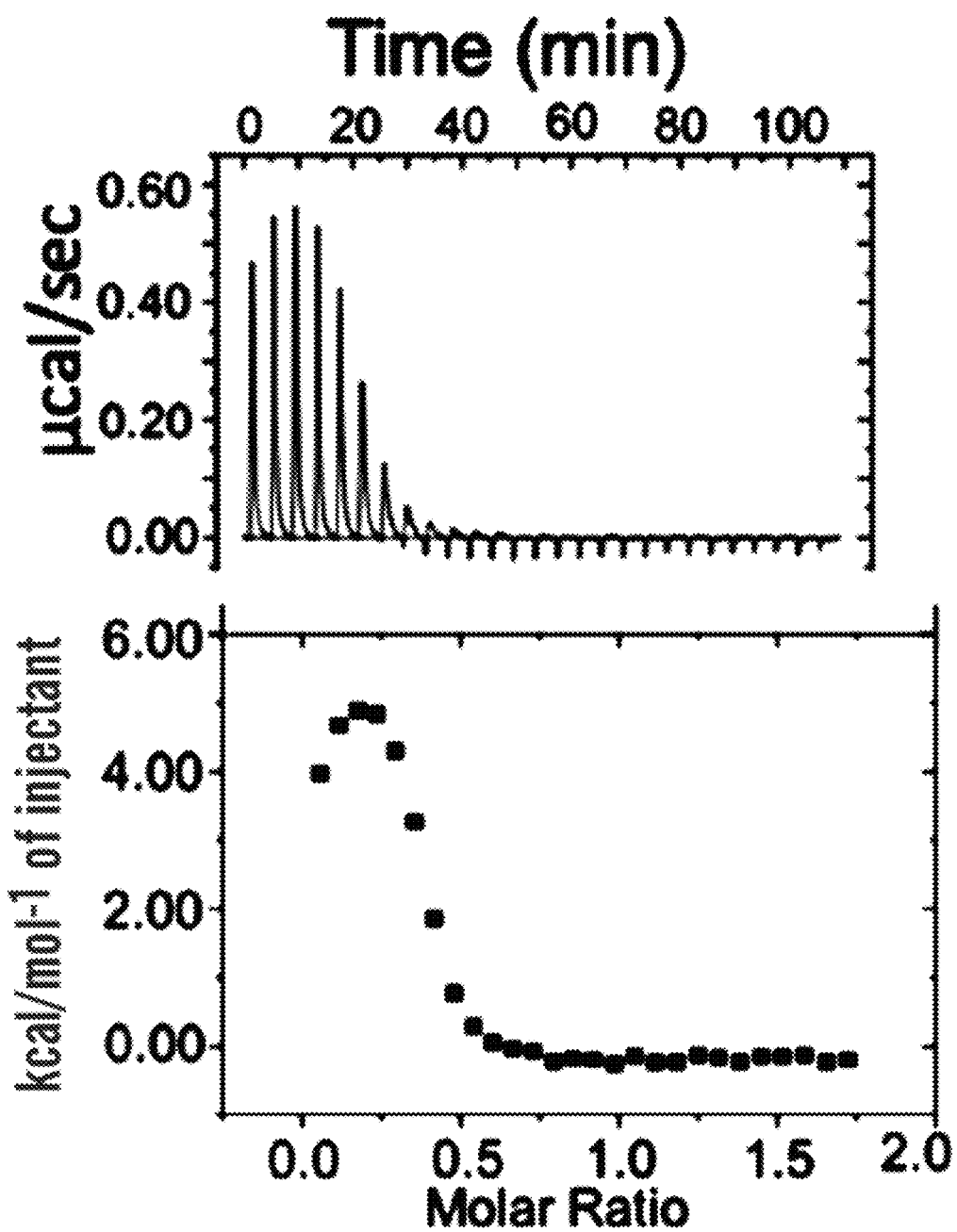
FIG. 2C demonstrates the ITC trace showing interaction between docking peptide with receiving peptide (Ka=6.2×10-8 M).

We designed and prepared peptide sequences that form a tetrameric coiled coil,[14,15] but discourage self-interaction (positively charged amino acids in docking, negatively charged in receiving). Several sequences were evaluated for specificity and structural assembly; the receiving peptide: MK(LKKIKSV)$_4$VGER (SEQ ID NO: 1) and docking peptide: MK(LEEIVSE)$_2$LEEIVTELEEIVSEVGER (SEQ ID NO: 2) were selected as optimal by circular dichroism (CD) and isothermal titration calorimetry (ITC) (FIGS. 2A-2C).

These data support the development of a unique nanoZip structure for coupling DNase1 to the anti-DEspR-humab, hu6g8, and its subsequent evaluation.

D. Approach.

Aim 1.

Preparation of the polypeptide-antibody therapeutic that can target DESPR1 (DESPRnase1) and evaluate structural stability and dose-dependent release of DNase1 by cathepsin G in basal plasma conditions, and in the presence of low pH and high ROS milieus present in ARDS.

The use of reliable $F_c$ specific conjugation via the coiled-coil can minimally affect antibody binding. Furthermore, it is contemplated that DESPRnase1 is stable in the presence of low pH and high ROS milieus, and release DNase1 when in the presence of cathepsin G (cg).

Outcome.

Successful completion of Aim 1 provides a NET therapeutic DESPRnase1 that will is used in Aim 2 to evaluate ex vivo multi-functionalities relevant to intravascular NET-mediated endothelial injury and prothrombotic nidus formation.

Design Rationale and Justification for Components

To neutralize NETs-driven endothelial injury, the concomitant biophysical and biological properties of existing NETs must be addressed together. Given the shortcomings of multiple approaches to current NETs-neutralization leading to the insight that NETs are best prevented rather than resolved,[7] a new therapy was design herein that possesses the following advantages:

(1) Targeting the intravascular NETs sites. A humanized anti-DEspR-mab was selected with a hinge-stabilized IgG4/kappa Fc region to avoid Fab arm exchange in vivo and ensuing loss of targeting. Additionally, this avoids immune effector functions of IgG1 mAbs (ADCC, CDC), which can worsen endothelial injury. Importantly, the antibody binds to activated neutrophils and NETs, and inhibits the extended survival of activated neutrophils. Thus, inhibition of activated neutrophils to preempt NETosis is accomplished, in addition to the targeting moiety function for the DESPRnase1. We propose that DESPRnase1 will digest the 'naked' DNA in between nucleosomes (DNase1 hypersensitive sites), as well as the DNA wrapped around histones in the nucleosomes at DARNS (DNase1 annotated regions of nucleosome stability) sites.[16]

(2) Delivering DNase1. The recombinant human DNase1 (30.1 kDa) was selected because it is FDA-approved and used as an aerosol therapeutic to decrease the sputum viscosity in cystic fibrosis patients.[17]

(3) Releasing DNase1 from the antibody carrier. A tripeptide linker sensitive to cleavage by cathepsin G was selected since cathepsin G is a neutrophil serine protease consistently present in NETs, along with neutrophil elastase and proteinase-3. Hence DNase1 will be released upon docking of DESPRnase1 onto NETs via antibody targeting. Moreover, as cathepsin G directly injures the endothelium and enhances thrombosis, engaging cathepsin G via a substrate decoy function of the DESPRnase1 can add endothelial protection and anti-thrombotic functional advantages.

(4) Connecting the DNase1-Cathepsin G sensitive tripeptide linker to the anti-DEspR-mab using a novel NanoZip supramolecular assembled coiled-coil (SMACC) structure. NanoZip coupling (illustrated in FIGS. 1 and 3) will allow site-directed, stoichiometric, uniform loading of two DNase1 onto the targeting antibody without negatively impacting antigen recognition or destabilizing the antibody targeting function and DNase1 activity. This cannot be accomplished by any currently used commercial methods. The latter depend on conjugation to tyrosines or lysines—both amino acids are present in the heavy and light chain variable region CDRs of our antibody, hence traditional conjugation would inhibit target-binding. Furthermore, assembly by this technique uses mild conjugation methods (4° C. in aqueous buffer), which minimally affect protein stability and functionality of both targeting antibody and DNase1 payload. Self-assembly of coiled coil structures is highly sequence specific, and the NanoZip recognition is accomplished by the high specificity of docking sequences to antibody bound receiving sequences, without self-interaction between docking or receiving sequences.

1. Preparation of the Antibody-DNase1 Therapeutic.

Figure 3:
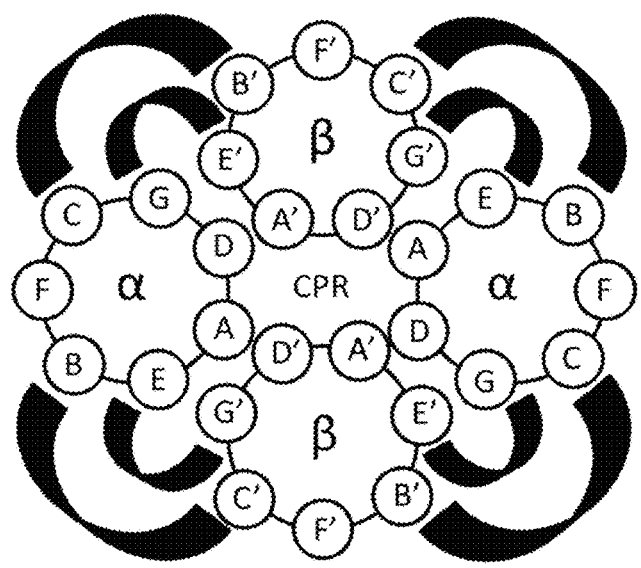
FIG. 3 shows a diagram showing the interaction of coiled coil tetramer pairings.

DESPRnase1, a novel antibody enzyme conjugate, was developed stepwise with validation at each step as follows: structural optimization of NanoZip coils for the humanized antibody; preparation of the cathepsin-G cleavable tripeptide linker; and, preparation of the anti-DEspR-humab-cg-peptide-DNase1 (DESPRnase1).

a. NanoZip Construct Assembly. A small library of peptide sequences will be prepared that meet the conditions for coiled coil tetrameric assembly: 1) peptide sequences have four repeating heptads, ABCDEFG, where A and D are hydrophobic amino acids and B, C, and F are hydrophilic; and, 2) position A is always a leucine and position D is always an isoleucine (FIG. 3). To prevent homodimerization and encourage heterodimerization, a set of peptides (receiving sequence) were developed where the B and C positions have a positively charged amino acid, lysine, while a separate set (docking sequence) has the negatively charged amino acid, glutamic acid, in the B and C positions. After these constraints, the G position of the receiving sequence can all be made positively charged, lysine, and the E position is varied with different hydrophobic amino acids to improve tetrameric interaction. The docking sequences will have a hydrophobic amino acid in the G position, and a negatively charged amino acid, glutamic acid, in the E position.

Figure 4:
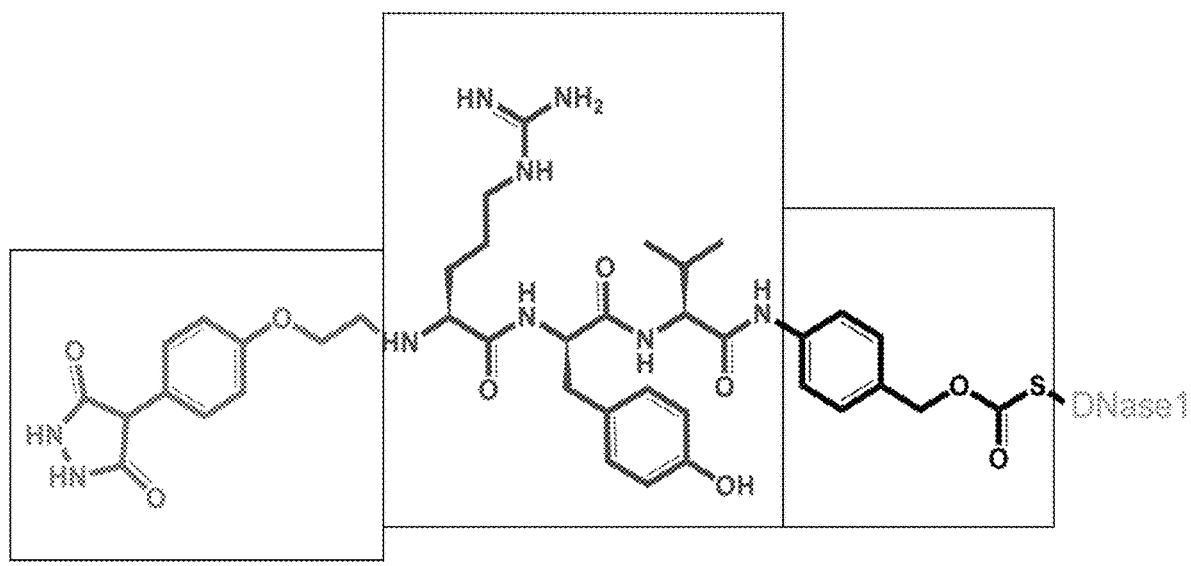
FIG. 4 demonstrates the structure of an exemplary ripeptide spacer. N-terminal tyrosine reactive handle (left box) attaches linker to antibody. Tripeptide sequences (middle box) of Arg-Tyr-Val is highly specific to Cathepsin G and will allow release of free DNase1 after cleavage and release of PABC spacer (right box).

In total, ten different peptide sequences can be synthesized and analyzed for homodimerization and heterodimerization by CD in stoichiometric ratios via a temperature sweep and a titration with guanidium chloride. Strength of interaction, measured as $K_d$, can be determined for each pairing using isothermal titration calorimetry (ITC).

b. Structure Determination of Optimal SMACC components. Optimal packing of the SMACC structures entail minimization of antibody strain by keeping the suprahelical diameter close to the bond distance between heavy chains. The structure of each heteromeric structure will be assessed with 2D NMR (in collaboration with Dr. McKnight) and x-ray crystallography. Lyophilized paired peptides can be dissolved in 500 μL of 100 mM KCl, 50 mM KPO$_4$ in 90% H$_2$O/10% D$_2$O buffer solution (pH 6.7), with a final concentration of 1.0 mM of each peptide, using 4,4-dimethyl-4-silapentane-1-sulfonic acid (DSS) as an internal $^1$H reference. Initial $^1$H-NMR can be performed on the complex at 500 MHz, and COSY (correlation spectroscopy) can be performed to get initial constraints for structural analysis. Natural abundance 2D $^1$H-$^{15}$N-HSQC spectra will be acquired followed by 2D $^1$H-$^1$H homonuclear TOCSY (Total Correlation Spectroscopy) and NOESY (Nuclear Overhausen Effect Spectroscopy) experiments to allow for side-chain assignments and to provide further structural restraint information. Crystallization of the tetrameric SMACC structures can be accomplished by high-throughput screening of solvent conditions using crystallization kits, Crystallization Cryo Kit for Proteins and Crystallization Kit for Proteins for Automatic Screening (Sigma). Crystallography experiments can be performed using a Bruker AXS X8 Proteum-R instrument, including a kappa four circle goniometer, MICROSTAR rotating anode X-ray source and PLATINUM135 CCD area detector for single crystal X-ray diffraction. Structural data will be complemented with NMR data and through molecular replacement with known tetrameric structures and predicted constraints from CCBuilder modeling software.

c. Preparation of tripeptide-DNAse1 Linker. Cathepsin G specificity cleaves the sequence Arginine-Tyrosine-Valine. This short sequence will be synthesized as follows (FIG. 4). Briefly, 9-fluorenylmethoxycarbonyl (Fmoc) protected L-arginine can be coupled to L-tyrosine using N,N'-dicyclohexylcarbodiimide and 2,3,4,5,6-pentafluorophenol; the purified dipeptide will be coupled with L-valine through the same coupling procedure. A releasable p-aminobenzyl alcohol is added to the C-terminus of the tripeptide using 2-ethoxy-1-ethoxycarbonyl-1,2,dihydroquinoline (EEDQ). The Fmoc protection group will be removed using triethylamine, and a tyrosine reactive handle, 4-(4 (Prop-2-yn-1-yloxy)phenyl)-1,2,4-triazolidine-3,5-dione (PTAD), is attached by selective catalytic hydroamination: tetrakis(diethylamino)titanium IV catalyst and 2,6 diisopropylphenol, followed by selective reduction with zinc chloride and sodium cyanoborohydride. DNase1 can be selectively reduced by mercapoethanol in the presence of 4 mM $Ca^{2+}$, reducing only one disulfide bond and retaining DNase1 activity.[18] The exposed cysteines will be reacted with nitrophenol chloroformate to produce an activated S-thiocarbonate. Coupling of the linker to DNase1 can be achieved by stoichiometric addition in the presence of triethylamine. Purity, and structural confirmation of the product can be determined by HPLC analysis, NMR, and high resolution mass spec analysis.

d. Preparation of DESPRnase1. Inclusion of the appropriate receiving sequence (e.g., GGGGSMK(LKKIKSG)$_4$VGER (SEQ ID NO: 19)) into the C-terminus of anti-DEspR-humab can be achieved by recombinant methods, through the use of a CRO (LakePharma Inc). Conjugation of DNase1 will be achieved in three steps: 1) activation of the tyrosine linker; 2) coupling of the linker to the docking peptide; and, 3) supramolecular assembly of the SMACC. The tripeptide linker will be activated by reacting one equivalent of the linker with one equivalent of 1,3-dibromo-5,5,-dimethylhydantin in DMF. The activated linker in DMF will be added dropwise to a Tris buffered saline (TBS) solution (pH 7) of the docking sequence at 37° C. Conjugated peptides will be purified by dialysis followed by HPLC to select only conjugated sequences. Circular Dichroism will be performed to determine if heating and cooling has any effect on ability of peptides to self-assemble relevant to downstream steps and use of the DESPRnase1 in vivo. The purified, DNase1-loaded peptide will then be added to the targeting antibody moiety, anti-DEspR-humab containing the receiving sequences, at 4° C. in pH 7 TBS, purified by (MW 30.1 kDa), and analyzed by HPLC.

2. Validation of the DESPRnase1 Therapeutic.

This can then be validated as follows: in vitro evaluation of DNase1 release from the construct in the presence of cathepsin G and validation of DNase1 functionality following release; in vitro stability of DESPRnase1, and evaluation of DESPRnase1 binding to target DEspR epitope.

a. In vitro evaluation of DNase1 release from the construct in the presence of cathepsin G and validation of DNase1 functionality following release. Kinetic release of DNase1 can be evaluated via cathepsin G digestion of the linker on the DESPRnase1. Cathepsin G, lyophilized from leukocytes (Sigma), in varying physiological concentrations (0.01 to 10 μg/mL) will be added to vials of DESPRnase1 at 100 mM in TBS, pH 7.0; release of DNase1 will be assessed by time course analysis of 50 μL aliquots taken at the following times: 0 seconds, 15 seconds, 30 seconds, 1 minute, 3 minutes, 10 minutes, and 30 minutes, and analyzed by HPLC for free DNase1. Next, the activity of the released DNase1 will be compared to native DNase1 using a fluorometric DNase Alert Substrate Kit (Integrated DNA Technologies).

b. Evaluation of DESPRnase1 stability in low pH [permissive hypercapnia] and oxidative stress conditions. The stability of the conjugated DNase1 will be assessed by incubation of the DESPRnase1 in human plasma, at 37° C. at different levels of pH and oxidative stress in static conditions, simulating the pathophysiological conditions in ARDS patients. The pH range 7.0-7.4 can also be compare, and DESPRnase1 can be stable at pH 7.2, the minimum pH level for permissive hypercapnia in ARDS patients in order to minimize ventilator-induced lung injury.[19] DESPRnase1 stability in oxidative stress conditions can be tested and induced by $H_2O_2$ (0.1-0.6 mM). This is relevant to reactive oxygen species (ROS) oxidative stress conditions present in pulmonary endothelial-alveolar injury sites in ARDS patients. DNase1 concentration will be determined by collecting 50 μL of the solution and analyzed by HPLC. Stability will be assessed at 0.5, 1, 3, 7, 14, 30, 45, 60, and 90 days. Success will be measured by DESPRnase1 levels >30 days human plasma (degradation <1% by 30 days). Stabilility in oxidative stress conditions is a prerequisite for in vivo efficacy as DESPRnase1 stability determines the ability for targeted delivery of DNase1 to NETs at pulmonary endothelial injury sites and in systemic prothrombotic nidus sites relevant to the progression of ARDS to multi-organ failure.

c. Evaluation of DESPRnase1 binding to target epitope. The effect of DNase1 conjugation on antigen binding can be assessed by ELISA, using an antigenic peptide comprising the epitope on human DEspR that is recognized by humanized anti-DEspR-mab. Corning 96-well plates will be coated with 10 μg/mL of the antigenic peptide spanning the DEspR epitope to which humanized anti-DEspR-mab is known to bind to. Wells will be treated with varying concentration of 'naked' humanized anti-DEspR-mab and DESPRnase1 (0.1 to 10 μg/mL). Binding will be assessed with a secondary anti-human IgG $F_c$ (Sigma) antibody, followed by TMB substrate colorimetric detection. Successful conjugation without impeding DEspR-targeting will have <5-10% difference in binding from native antibody. Binding affinity will also be assessed in low pH conditions and oxidative stress conditions as described above.

Aim 2.

Determine DESPRnase1 Targeting and Binding Properties to DEspR NETs, Dismantles DEspR NETs without Complement Activation, and/or Serves as Substrate-Decoys to Attenuate NETs' Cathepsin G-Induced Injury of Human Endothelial Cells Ex Vivo.

Goal.

The goal of the following experiments is that DESPRnase1 will: 1) bind human $DEspR^+$ NETs in equal affinity under basal and ARDS-like stress conditions; 2) release DNase1 that exhibits comparable activity to native DNase1; and, 3) reduce cathepsin G induced pulmonary endothelial injury compared to untreated control.

Outcome.

Successful completion of Aim 2 provides a DESPRnase1 for testing in an in vivo rat model of LPS-induced ARDS with multi-organ failure progression.

a. Ex vivo targeting: Determine whether DESPRnase1 targets and binds to human DEspR+ NETs in basal and ARDS-like stress conditions: low pH and increased reactive oxygen species (ROS). A competitive binding assay using fluorescence activated cell sorting (FACS) analysis under shear conditions (rotational shaker) can be used to compare DESPRnase1 binding to the native antibody—humanized anti-DEspR-mab. Commercially available human neutrophils (huPMNs) will be used for these assays. HuPMNs (200,000 per test point) will be activated with LPS (0.1, 1, 10 μg/mL×30 minutes), then incubated with 10 μg/mL anti-DEspR-mab$^{AF594}$, with 0.01, 0.03, 0.1, 0.3, 1, and 3 and 10 μg/mL of DESPRnase1 at 0° C. in 200 μL 2% heat-inactivated FBS in Hank's Buffered Saline (Ab buffer). Cells will then be washed with 0° C. antibody buffer and filtered; mean fluorescence will be measured by LSR II SORP (BD) FACS. The background can be subtracted and compared to control DEspR-mab$^{AF594}$ alone. Success can be measured by binding of DESPRnase1 within 95% of the native antibody. This defines binding in basal conditions. The optimal condition will then be repeated in low pH 7.2 (permissive hypercapnia level) vs pH 7.4, and elevated ROS conditions ($H_2O_2$ 0.1-0.6 mM) as described above.

b. Ex vivo efficacy: Determine if DESPRnase1 dismantles NETs in rotational shear conditions in basal and ARDS-like stress conditions ex vivo. Activity will be assessed by comparing digestion of NET-DNA scaffolds by cathepsin G release of DNase1 vs control, unconjugated DNase1 using induced human-NETs. First, NETs will be induced using LPS at different concentrations, as described above, for 30 minutes (vital NETosis or early NETs) or 3-4 hours incubation to suicidal NETosis (late NETs). After confirmation of conditions with maximum early NETs and late NETs formation, we will then assess dose-dependent ex vivo efficacy of DESPRnase1 to dismantle both types of NETs over a range of antibody concentrations (0.01-30 μg/mL) to reflect projected in vivo circulating DESPRnase1 levels. We will compare baseline NETs levels with post DESPRnase1 treatment levels measured on FACS analysis of NETs markers: Sytox green for extruded DNA, citH3 for citrullinated Histone 3, and a NET-neutrophil protease component (cathepsin G or elastase) gated for neutrophils and NETs on FSC and SSC. We will determine if DEspRnase1 does not trigger complement activation by ELISA detection of the terminal complex of the activated complement cascade, C5b-9.

c. Ex vivo decoy functionality. Determine if DESPRnase1 functions as a cathepsin-G decoy that reduces cathepsin G induced pulmonary endothelial injury. This putative substrate decoy function of DESPRnase1 is an additional advantage as upregulated cathepsin G activity directly leads to endothelial injury. Moreover cathepsin G in intravascular NETs is protected from endogenous inhibitors and thus no counter measures are available to date.[22] In order to test this novel functionality, we will grow human endothelial cells on tissue-culture 96 well plate (Corning 3603). Cells will be labeled for viable (NucBlue stain) and dead (propidium iodide, 1 μg/mL) prior to experiment. The DESPRnase1 will be added to endothelial cells (range 0.01-30 μg/mL, concentration based on antibody) to reflect projected in vivo circulating drug levels, mixed and equilibrated for five minutes; cells will then be treated with cathepsin G (1 μg/mL), and returned to 37° C. cell incubator. Fluorescence imaging will be recorded using Nexcelom Celigo Microwell Plate Imager; total cell count, viable cells, and dead cells will be recorded at times: 0 hrs, 2 hrs, 4 hrs, 8 hrs, 16 hrs, 24 hrs, from addition of cathepsin G (cg), with capture of blue and red fluorescence channels and bright field images. Results will be compared to non-DESPRnase1 treated cells.

Rigorous Experimental Design and Statistical Analysis for Aims 1 and 2

When evaluating all results, predetermined and appropriate statistical methods can be used to establish significance. All data for the CD, ITC, antigen binding, DNase1 release, and functional characterization of DESPRnase1 can be conducted in triplicate or greater and expressed as a mean±standard deviation. Continuous variables are typically compared across groups using one-way analysis of variance (ANOVA). The level of significance will be preset at a p-value of 0.05.

Research Strategy (A) Significance

1. Pancreatic ductal adenocarcinoma (PDAC) is the most lethal common cancer in the United States: in 2017 there will be around 54,000 new cases and 43,000 patient deaths.' The high mortality of PDAC is related to late disease presentation and aggressiveness; nearly 52% of patients present with metastatic disease at the time of diagnosis.[1] Current treatments only marginally improve survival, with the most efficacious treatment, gemcitabine and nab-paclitaxel, having a median survival of 12.2 months.[18] Failure of current PDAC treatments is attributed to the inefficacy of systemic chemotherapeutics and the development of resistance.[19]

2. Dual Endothelin1/Signal Peptide$^{VEGF}$ receptor (DEspR). DEspR is a receptor involved in developmental and pathogenic angiogenesis, the regulation of survival of cancer stem cells (CSC), and the inhibition of activated neutrophils: the dual endothelin1/vascular endothelial growth factor (VEGF) signal peptide receptor (DEspR).[13,17,20] Cumulative research implicates CSCs in chemo-radiotherapy resistant metastatic cancer, therefore it is critical to inhibit CSCs and the supportive niche that allows them to survive, metastasize, and evade immune surveillance.[7-10] This unmet need is most glaring in PDAC.[21,22] Published data confirms that DEspR is a crucial survival gene of PDAC CSCs, tumor cells, and the supportive CSC niche[13,17]. Provided herein are methods and compositions to investigate the mechanism of regulation of DEspR inhibition within cancer cells.

Figure 5:
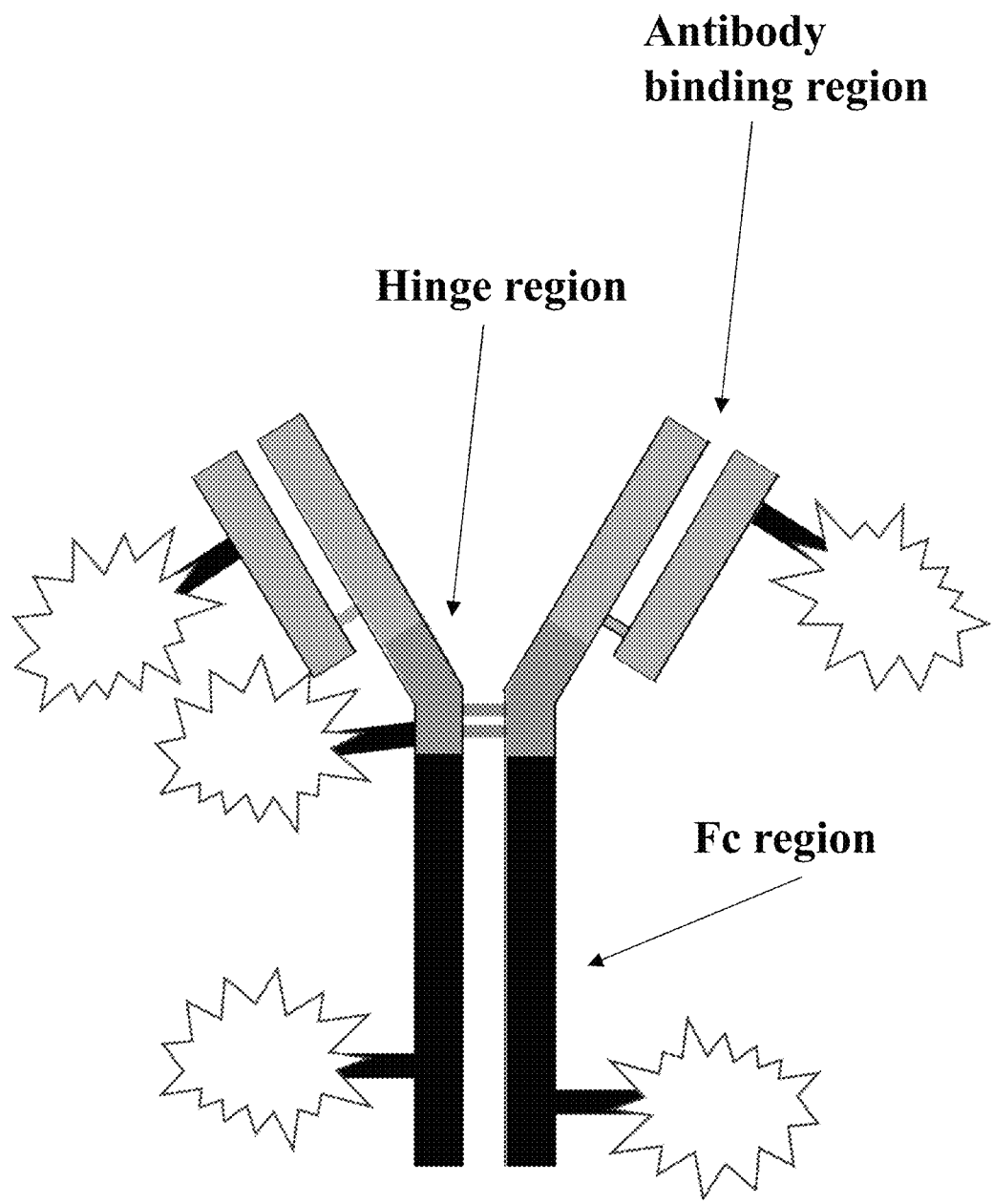
FIG. 5 demonstrates a conventional ADC conjugation with non-specific, tuneable conjugation that gives undesirable drug loading; it may adversely affect the hinge region and antibody-binding region. Ideal conjugation is in the Fc region.

3. Antibody Drug Conjugates (ADCs). ADCs are a powerful class, which combine the high specificity of biologics with the high cytotoxicity of chemotherapeutics.[23,24] However, the full potential of this drug class has not been realized in cancer because of the following limitations: poor antigen specificity and unreliable conjugation methods.[24-26] Only two anti-cancer ADCs have received FDA approval: brentuximab vedontin (ADCETRIS®; Seattle Genetic), and ado-trastuzumab emtansine (KADCYLA®; Genentech); both rely on unreliable conjugation that significantly limits the efficacy and therapeutic window of the antibody.[27-30] (FIG. 5) Currently, there are few antigens with the necessary specificity, and no conjugation techniques that can capitalize on the full potential of this class. DEspR, is highly tumor specific. Thus, the use of the ADC provided herein generates a novel, reliable, and site-specific protein conjugation method, supramolecular assembly (SMA) of coiled coils[31-39], to produce an optimal ADC. This approach allows site-specific conjugation in the $F_c$ region (considered optimal)[28,29] and uniform loading of two mertansine molecules (highly potent microtubule inhibitor, optimal drug loading)[28]. Conjugation using coiled coils has been successful in numerous applications[40-43], my method will expand on these successes to give: 1) a reliable conjugation method for ADCs; and, 2) a maximally potent ADC for PDAC treatment.

(B) Approach

Aim 1: Characterize DEspR-Humab Induction of Necroptosis and/or Apoptosis in PDAC-CSCs and Non-CSC Tumor Cells Under Different Tumor-Specific Stress Conditions.

Justification/Rationale.

Aside from concomitant inhibition of angiogenesis,[13] the mechanism by which DEspR inhibition exerts its potent effect in PDAC is unknown, and the focus of this aim. Specifically, the following can be investigated: 1) the key regulators in DEspR cell death induction; 2) the impact of cellular stress (low pH, oxidative stress, and hypoxia) presentation in the tumor microenvironment on the preference of cell death with DEspR inhibition; and, 3) the trafficking mechanism of DEspR bound to the antibody to the nucleus, Research Design.

1a. Investigating Cell Death via DEspR Inhibition. The mechanisms of DEspR-humab internalization-induced apoptosis and necroptosis can be studied. Specifically, experiments can determine the following: 1) the time-course of Caspase3-specific activation (Cell Event caspase3/7 Green activation) for apoptosis and separately; and, 2) the time-course of lysosomal membrane permeability (LMP), an early marker of necroptosis,[45] by LysoTracker Green, and nuclear membrane permeability by LIVE/DEAD Fixable Blue for apoptosis, both along with the time course of DespR-humab$^{AF568RED}$ intracellular trafficking by live cell imaging. Isotype IgG4$^{AF488}$ serve as mock-treated controls. The number of apoptosis+ or necroptosis+ cells across 50 cells can be quantified in at least 3 independent experiments comparing treated, non-treated, and mock-treated Panc1 cells. Correlation with cell morphology changes consistent with apoptosis (nuclear condensation, cell blebbing)[46] and necroptosis (cell and nuclear swelling)[47] will be assessed. To confirm these findings, experiments can be conducted to determine the concomitant nuclear translocation of RIP1 for necroptosis and Apaf1 for apoptosis, and their colocalization with DEspR in fixed cell immunocytostaining at 15 min, 30 min, 1, 2, and 6 hrs comparing DespR-humab$^{AF568}$-treated, non-treated and mock-treated cells as described above. Levels of phosphorylated$^{S727*}$STAT3—the activator of both BIRC3 and Apaf1[48,49], signaling protein increase upon DEspR-human-activation by its ligand, SP$^{VEGF}$ will also be determined.[17]

1b. Role of Cellular Stress in Directing DespR Mediated Cell Death. Cells will be pre-treated in the following conditions: pH 6.5 media (lactic acid), reactive oxygen environment (100 μM hydrogen peroxide), and hypoxic conditions (2% 02 balance, Hypoxia Incubator Chamber (StemCell). Following incubation for 1 hour, cells will be assessed for apoptosis and necroptosis as done in Aim 1a.

Aim 2: Determine the Binding, Internalization, Stability and Enhanced CSC/Tumor Cell Killing of Mertansine-DEspR-Humab Vs Conventional Mertansine Linked ADC and Native DEspR-Humab.

Justification/Rationale.

DEspR-humab is an ideal candidate for ADC modification as it is: 1) tumor selective; 2) internalized and retained in PDAC; and, 3) lysosomally degraded (allows use of lysosomally cleavable linkers). A novel ADC (mer2-DEspR-humab) is provided herein that combines DEspR-human specificity with mertansine, a potent microtubule inhibitor capable of killing PDAC cells,[56] using site-specific conjugation. Specifically, the supramolecular assembly of coiled coil structure tetramers are used for controlled and site-specific drug conjugation at the C-terminus. This technique (FIG. 1) relies on two types of peptide sequences: a C-terminal receiving sequence and a drug carrying docking sequence. Separately, they cannot form an organized structure, but in 1:1 molar ratios, they spontaneously form an organized, tetrameric-coiled coil structure. This system was designed to allow selective and reliable conjugation to minimally effect antigen binding[26]. The mer2-DEspR-humab synthesized can be compared to an ADC prepared under the same conditions as Kadcyla, the only FDA approved ADC for solid tumors. Successful completion of this aim provides: 1) in vitro data on efficacy, safety, and stability of a novel ADC for PDAC (currently no FDA approved ADC for PDAC); 2) in vitro information on a novel method of site-specific conjugation, which can replace current techniques for protein conjugation and solve current limitations of ADCs; 3) provide a comparison of my novel method to current methods to currently approved ADC preparatory techniques; 4) PK experiments to evaluate in vivo stability; and, 5) ADCs for future in vivo efficacy and safety experiments.

Experimental Data.

Figure 6A:
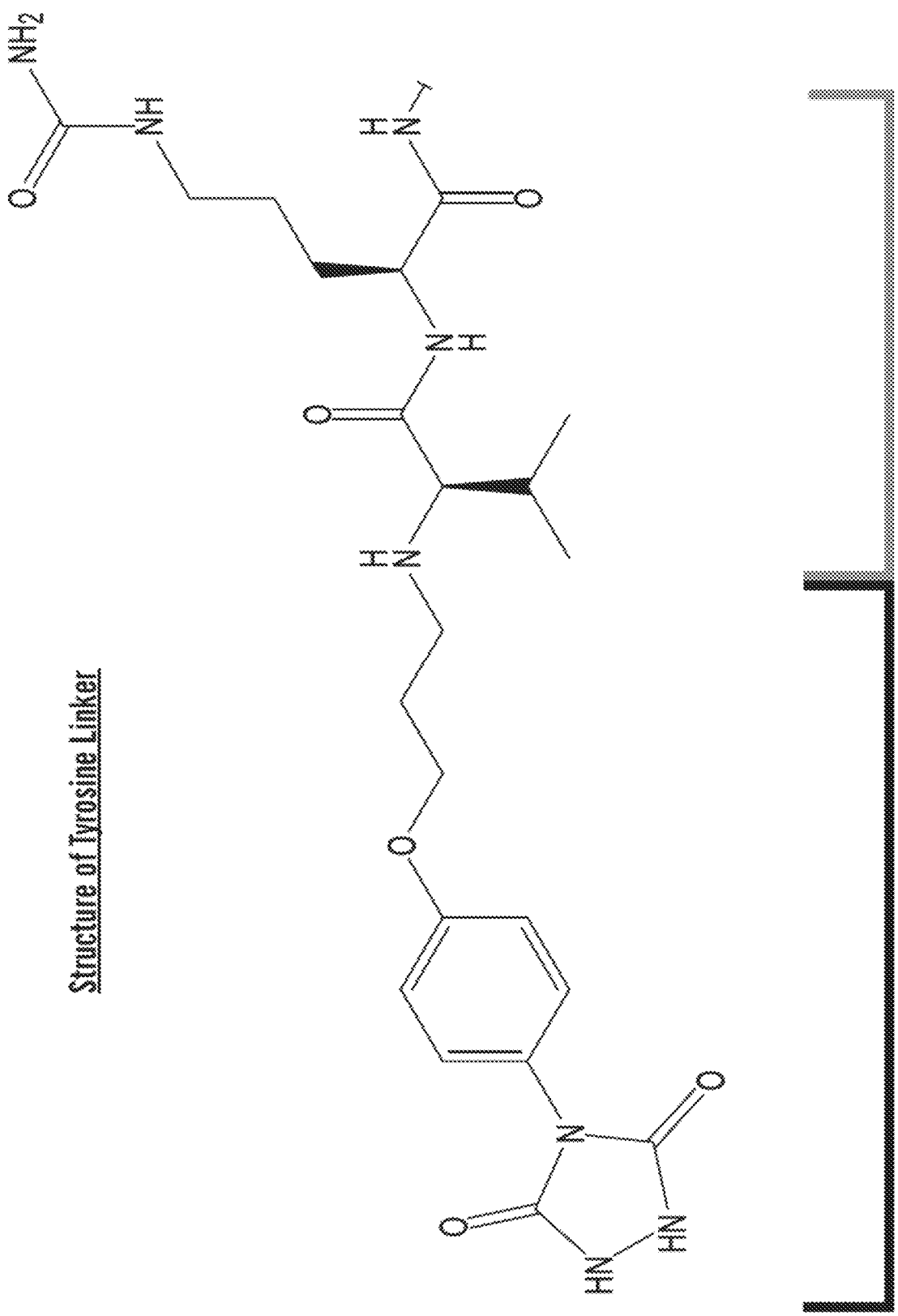
FIG. 6A-6C shows exemplary linker synthesis.
Figure 6A:
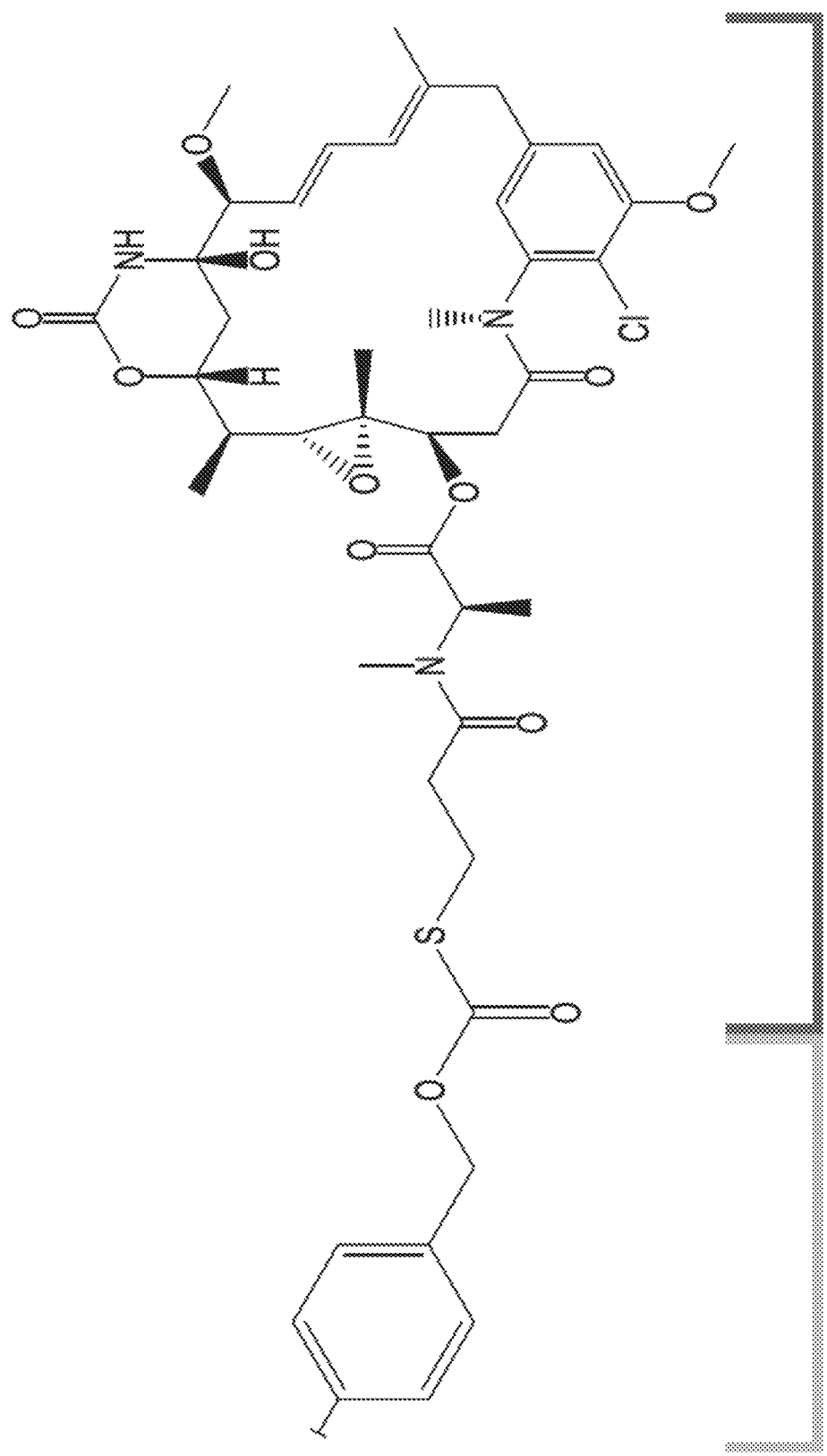
Figure 6B:
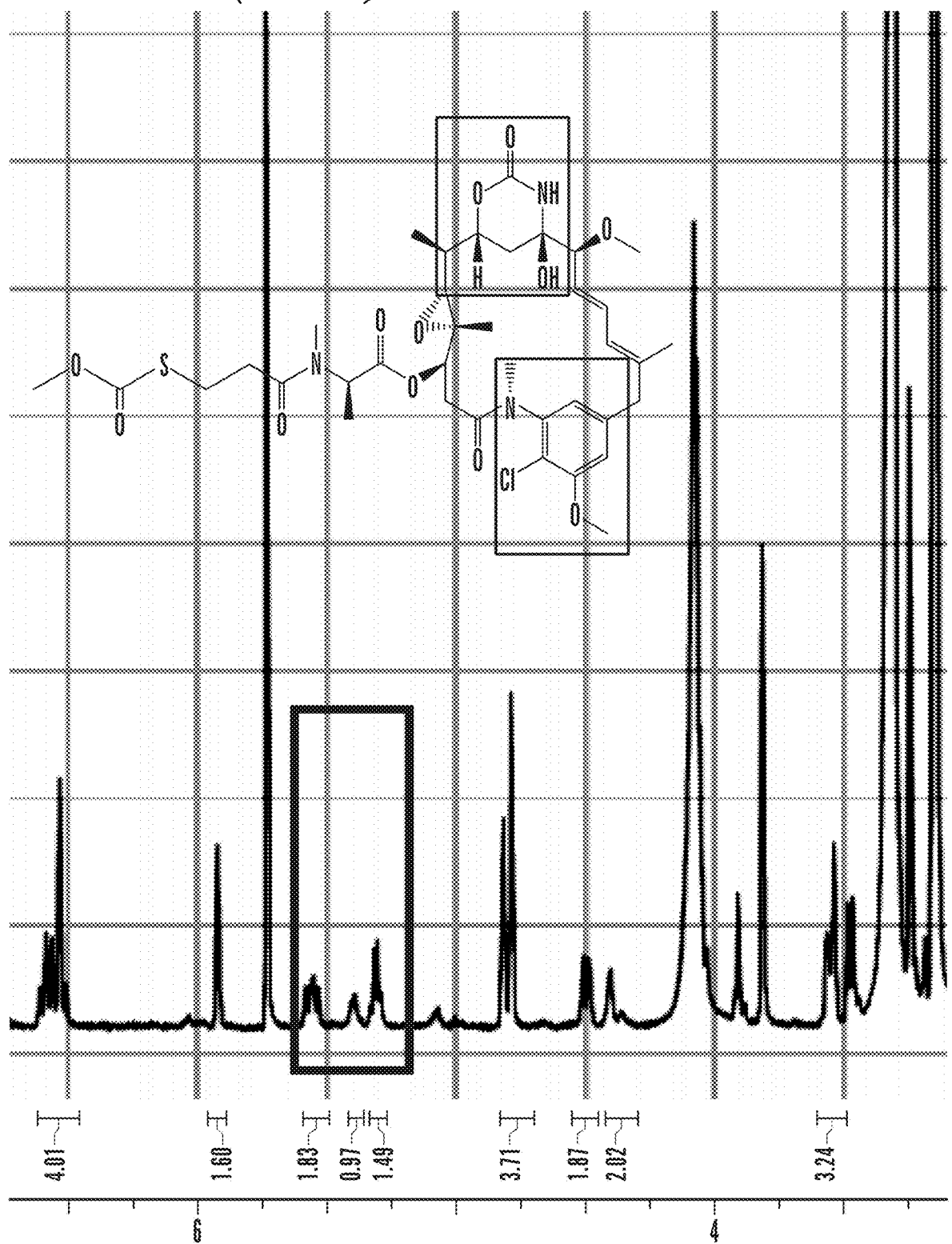
Figure 6B:
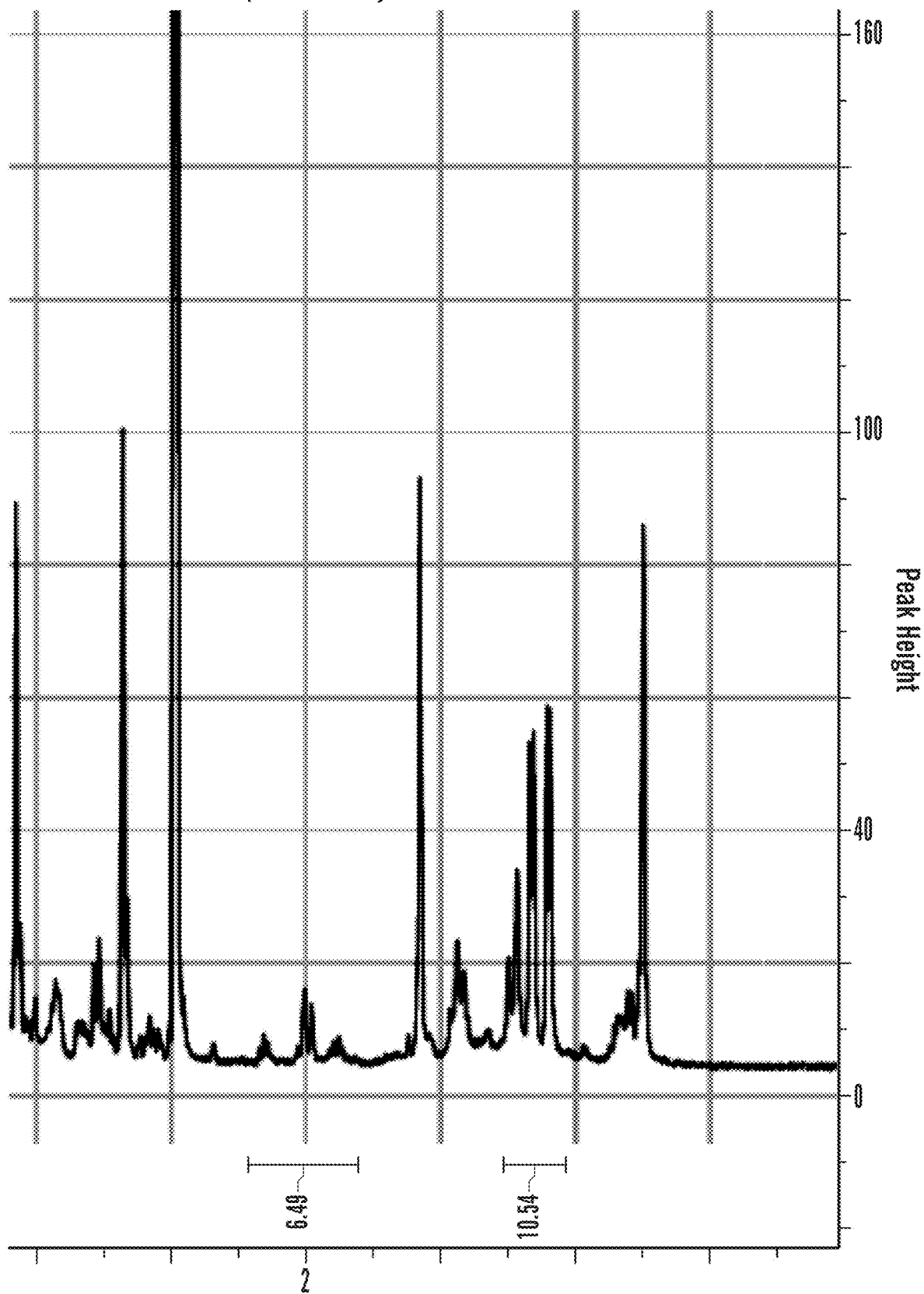
Figure 6C:
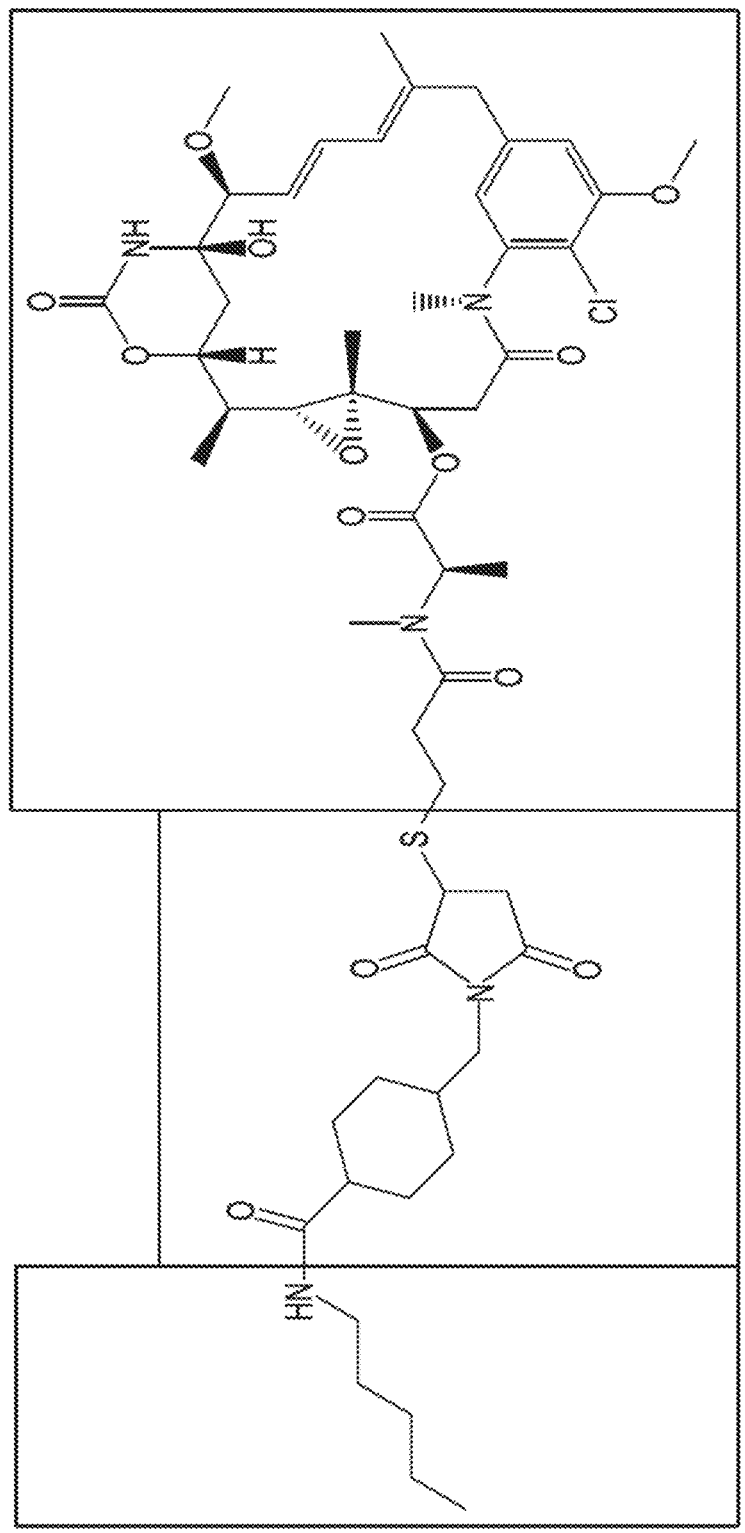

The peptide sequences that form a tetrameric coiled coil (repeating ABCDEFG heptad) were designed and tested (FIG. 3),[33,34] but discourage self-interaction (positively charged amino acids in docking, negatively charged in receiving). Several sequences were evaluated for specificity and structural assembly; the receiving peptide: MK(LKKIKSV)$_4$VGER (SEQ ID NO: 1) and docking peptide: MK(LEEIVSE)$_2$LEEIVTELEEIVSEVGER (SEQ ID NO: 2) were selected as optimal by circular dichroism (CD) and isothermal titration calorimetry (ITC) (FIG. 2A-2C). The proposed mer2-DEspR-humab linker was synthesized (FIG. 6A, FIG. 6C) and confirmed by $^1$H NMR after column purification and dialysis (FIG. 6B).

Briefly, 9-fluorenylmethoxycarbonyl protected L-valine was coupled to L-citruline to afford a cathepsin cleavable dipeptide sequence (yield 84%). A releasable p-aminobenzyl alcohol was then added to the C-terminus of the dipeptide using 2-ethoxy-1-ethoxycarbonyl-1,2,dihydroquinoline (EEDQ) (yield 83%). Fmoc was removed, and 4-(4 (Prop-2-yn-1-yloxy)phenyl)-1,2,4-triazolidine-3,5-dione (PTAD) was attached via a catalytic hydroamination step with a tetrakis(diethylamino)titanium IV catalyst and 2,6 diisopropylbenzene (yield 35%) Mertansine was converted to an intermediary S-thiocarbonate via reaction with nitrophenol chloroformate (yield 98%). The S-thiocarbonate mertansine was reacted with the PTAD linker in the presence of triethylamine to form the final linker (yield 68%). The Kadcyla-based ADC (K-ADC) can be prepared by publish protocols.[57]

Research Design.

2a. Preparation of Mer2-DEspR-Humab.

Preparation of mer2-DEspR-humab can be achieved by: 1) inclusion of the receiving peptide into the C-terminus of our antibody, using the same recombinant methods to prepare DEspR-humab; 2) conjugation of the tyrosine linker to the docking peptide via a) activation of the linker with 1 equivalent of 1,3-dibromo-5,5,-dimethylhydantin in DMF, b) dropwise addition of DMF solution to peptide in Tris buffered saline (TBS) (pH 7) at 37° C., followed by, c) dialysis and purification by HPLC (peaks observed with drug absorbance at 233 nm and antibody absorbance at 280 nm) (heat doesn't affect self-assembly); and, 3) addition of purified drug-loaded docking peptide to the antibody at 4° C. in pH 7 TBS, purified by (MW 30 K), and analyzed by HPLC observing drug absorbance (233 nm) and antibody absorbance (280 nm).

2b. In Vitro Experiments.

The prepared mer2-DEspR-humab can be compared in its effect on antigen binding, engagement of DEspR positive cells (cytotoxicity in PDAC), non-specific killing (early drug release) in DEspR negative cells to a K-ADC and the native antibody. The stability of mertansine loading can also be assessed between both ADCs via HPLC analysis.

Binding Assays.

The effect of drug loading on antigen binding can be assessed between ADCs and native antibody by ELISA. Corning 96-well plates will be coated with 10 µg/ml of a DEspR-humab binding antigenic peptide. Wells will be treated from 0.01 to 10 µg/mL of mer2-DEspR-humab and K-ADC, and binding will be assessed with a secondary anti-IgG $F_c$ (Sigma) antibody, with TMB substrate detection. Successful ADC conjugation will have <5% difference in binding from DEspR-humab and mer2-DEspR-mab ≥ K-ADC.

Competition Binding Assays.

To further study how conjugation effects binding, ADCs can be compared to the native antibody by competitive binding using fluorescence activated cell sorting (FACS) analysis. Panc1 and Panc 1 CSC cells (200,000 cells) will be incubated with 10 µg/mL DEspR-humab$^{AF568}$, with 0.01 to 10 µg/mL of either ADC for 30 minutes at 0° C. in 200 µl 2% FBS in Hank's Buffered Saline (Ab buffer). Cells will then be washed with 0° C. Ab buffer and filtered; mean fluorescence will be measured by LSR II SORP (BD) FACS. The background will be subtracted and compared to control DEspR-humab$^{AF5684}$. Success can be measured by binding of mer2-DEspR-mab within 95% of the native antibody and ≥ADC1.

Cytotoxicity Assays.

In vitro efficacy can be assessed across three well characterized, commercial human PDAC cell lines: Panc1, MIA PaCa-2, and Capan-1 (ATCC) representing three different KRAS mutants, KRAS$^{G12D}$, KRAS$^{G12C}$ and KRAS$^{G12C}$ respectively. Both non-CSC cells and CSC cells can be used from these cell lines[13,17] to assess the efficacy of each ADC vs. the native antibody. Cell viability can be assessed using a direct cell counting with Celigo fluorescence imaging in a 96-well format; cells will be treated from 0.01 to 10 µg/mL (dynamic range of antibody) of native antibody, mer2-DEspR-mab, or K-ADC. Total cell count can be measured by positive nuclear stain (NucBlue ThermoFisher), and cell death can be assessed by propidium iodide (sigma) or Caspase 3/7 (ThermoFisher) positivity. Bystander killing can be assessed by FACS analysis, using DEspR-humab$^{AF568}$ and LIVE/DEAD® Fixable Violet stain. Bystander killing is defined by % dead cells/% dead DEspR+ cells; >1 indicates bystander killing effects of DEspR(−) cancer cells. Success can be assessed by mer2-DEspR-humab cytotoxicity ≥antibody toxicity+mertansine toxicity and >ADC1 toxicity.

2c. Safety Assays.

It can be assessed whether mer2-DEspR-humab induces cytotoxicity in DEspR negative cells. Three clinically relevant cell lines will be selected: human endothelial cells (HUVECs); normal pancreatic cells (hTERT-HPNE), as DEspR is not present in the non-cancerous pancreas; and, 3) human Kupffer cells, non-specific uptake by these cells in implicated in ADC toxicity.[27,28] Cytotoxicity will be assessed using Celigo for healthy/dead cells as outlined in Aim 2c. Success can be assessed by mer2-DEspR-mab cytotoxicity <110% DEspR-mab toxicity and <ADC1 cytotoxicity.

2d. Plasma Stability.

Stability of the mer2-DEspR-humab and K-ADC can be assessed to determine the improvement when using the conjugation method. Mer2-DEspR-humab or K-ADC will be incubated in rat plasma (RNU) or human plasma, at 37° C. Mertansine concentration will be determined by collecting 50 µL of the solution, diluting with methanol (0.1 mL, 0° C.) and then centrifugation, followed by HPLC for analysis of the supernatant. Stability of mer2-DEspR-humab and the K-ADC can be assessed at 0.5, 1, 3, and 7, 14, and 30 days. Success can be measured by mer2-DEspR-mab stability >14 days in rat and human plasma (degradation <1% by 14 days) and mer2-DEspR-mab stability ≥ADC1 stability.

2e. PK Analysis.

To support the in vitro plasma studies, a PK study can be conducted, comparing the mer2-DEspR-humab to DEspR-humab. The study can assess both the elimination of the antibody vs. the ADC, as well as mertansine accumulation and elimination. Six treatment groups will be assessed: 1, 3, 15 mg/kg ADC; 1, 3, 15 mg/kg antibody; n=3 RNU rats per cohort. RNU rats will be injected with 2 million Panc1 CSCs, after 3 weeks rats will be randomized to their treatment and will receive a single i.v. bolus injection. Plasma can be collected at 5 min, 15 min, 30 min, 1 hr, 8 hrs, 1 day, 3 days, 7 days, and 14 days. Total antibody content can be assessed by Western blot; ADC vs antibody can be distinguished by HPLC following extraction, and total mertansine will be measured by HPLC following extraction. In addition, the liver, heart, lung, spleen, kidney, and brain can be homogenized and total mertansine can be assessed following extraction and HPLC.

Statistics.

For binding assays, all 6 runs can be made per condition, with results reported as averages±standard deviation, and comparisons made by one-way ANOVA with Tukey post-hoc. Stability data can have 10 runs per condition, and can be reported as percent mertansine release (frequency± standard deviation), and comparisons made by one-way ANOVA. Cytotoxicity and safety data can typically have 6 runs per condition, and be reported as averages±standard deviation, and comparisons made by one-way ANOVA with Tukey post-hoc. PK samples can be analyzed in triplicate per cohort, plotted using PK Solver software, as done previously for DEspR-humab, in a two compartment system of i.v. bolus, and $t_{1/2}\beta$ reported for each group.

Outcome.

mer2-DEspR-humab, through the use of a more controlled, site-specific conjugation, can show equivalent binding (equal to or within 5% of native antibody, DEspR-humab), better stability (based on studies of conjugation in vitro)[25-27], similar stability to the native antibody in vivo (based on reported data on site-specific conjugation)[25-27], greater efficacy in PDAC cells (due to uniform loading of drug), and improved safety (due to better stability) compared to K-ADC, which was prepared using a less chemically controlled method of conjugation. The safe conditions of this method (4° C., TBS) minimally affect binding. Since ideal ADC drug loading is 2, and uneven drug loading limits efficacy[26,28], mer2-DEspR-humab achieves greater potency without increased toxicity relative to DEspR-humab or K-ADC. Successful completion provides a new method to optimize ADC synthesis and in vivo characterization of the mer2-DEspR-humab.

LITERATURE CITED FOR EXAMPLE 1

1. Papayannopoulos, V. Neutrophil extracellular traps in immunity and disease. *Nat. Rev. Immunol.* (2017). doi: 10.1038/nri.2017.105
2. Mitsios, A., Arampatzioglou, A., Arelaki, S., Mitroulis, I. & Ritis, K. NETopathies? Unraveling the Dark Side of Old Diseases through Neutrophils. *Front. Immunol.* 7, 678 (2016).
3. Jorch, S. K. & Kubes, P. An emerging role for neutrophil extracellular traps in noninfectious disease. *Nat. Med.* 23, 279-287 (2017).
4. Brinkmann, V. et al. Neutrophil Extracellular Traps Kill Bacteria. *Science* (80-.). 303, 1532-1535 (2004).
5. Davis, J. C. et al. Recombinant human Dnase I (rhDNase) in patients with lupus nephritis. *Lupus* 8, 68-76 (1999).
6. Shah, P. L. et al. In vivo effects of recombinant human DNase I on sputum in patients with cystic fibrosis. *Thorax* 51, 119-25 (1996).
7. Kolaczkowska, E. et al. Molecular mechanisms of NET formation and degradation revealed by intravital imaging in the liver vasculature. *Nat. Commun.* 6, 6673 (2015).
8. Verthelyi, D., Dybdal, N., Elias, K. A. & Klinman, D. M. DNAse treatment does not improve the survival of lupus prone (NZB6NZW)F1 mice. *Lupus* 7, 223-230 (1998).
9. Herrera, V. L. M. et al. Confirmation of translatability and functionality certifies the dual endothelin1/VEGFsp receptor (DEspR) protein. *BMC Mol. Biol.* 17, 15 (2016).
10. Macanovic, M. et al. The treatment of systemic lupus erythematosus (SLE) in NZB/W F1 hybrid mice; studies with recombinant murine DNase and with dexamethasone. *Clin. Exp. Immunol.* 106, 243-52 (1996).
11. Knight, J. S. et al. Peptidylarginine deiminase inhibition disrupts NET formation and protects against kidney, skin and vascular disease in lupus-prone MRL/lpr mice. *Ann. Rheum. Dis.* 74, 2199-2206 (2015).
12. van Bijnen, S., Wouters, D., van Mierlo, G. J. & Muus, P. Neutrophil Extracellular Trap Formation In PNH Patients With and Without a History Of Thrombosis—Effects Of Eculizumab. *Blood* 122, (2013).
13. Patel, S. et al. Nitric oxide donors release extracellular traps from human neutrophils by augmenting free radical generation. *Nitric Oxide* 22, 226-234 (2010).
14. Harbury, P. B., Zhang, T., Kim, P. S. & Alber, T. A switch between two-, three-, and four-stranded coiled coils in GCN4 leucine zipper mutants. *Science* 262, 1401-7 (1993).
15. Hu, J. C., O'Shea, E. K., Kim, P. S. & Sauer, R. T. Sequence requirements for coiled-coils: analysis with lambda repressor-GCN4 leucine zipper fusions. *Science* 250, 1400-3 (1990).
16. Winter, D. R., Song, L., Mukherjee, S., Furey, T. S. & Crawford, G. E. DNase-seq predicts regions of rotational nucleosome stability across diverse human cell types. *Genome Res.* 23, 1118-1129 (2013).
17. Shah, P. L., Scott, S. F., Geddes, D. M. & Hodson, M. E. Two years experience with recombinant human DNase I in the treatment of pulmonary disease in cystic fibrosis. *Respir. Med.* 89, 499-502 (1995).
18. Price, P. A., Stein, W. H. & Moore, S. Effect of divalent cations on the reduction and re-formation of the disulfide bonds of deoxyribonuclease. *J. Biol. Chem.* 244, 929-32 (1969).
19. Ragaller, M. & Richter, T. Acute lung injury and acute respiratory distress syndrome. *J. Emerg. Trauma. Shock* 3, 43-51 (2010).
20. Liang, J. & Liu, B. ROS-responsive drug delivery systems. *Bioeng. Transl. Med.* 1, 239-251 (2016).
21. Liao, T. H., Ting, R. S. & Yeung, J. E. Reactivity of tyrosine in bovine pancreatic deoxyribonuclease with p-nitrobenzenesulfonyl fluoride. *J. Biol. Chem.* 257, 5637-44 (1982).
22. Owen, C. A., Campbell, M. A., Sannes, P. L., Boukedes, S. S. & Campbell, E. J. Cell surface-bound elastase and cathepsin G on human neutrophils: a novel, non-oxidative mechanism by which neutrophils focus and preserve catalytic activity of serine proteinases. *J. Cell Biol.* 131, 775-89 (1995).

Example 2: Development of a Novel Antibody Drug Conjugate for the Treatment of Pancreatic Adenocarcinoma There are currently many challenges in the treatment of pancreatic cancer. First, pancreatic cancer is the most lethal common tumor. The median survival upon diagnosis with pancreatic cancer, is less than 1 year in advanced stages. 53% of pancreatic cancer cases are in distant stage cancers. Thus, the clinical challenges of pancreatic cancer include late presentation of the disease and poor detection. Second, on a cellular level, pancreatic cancer cells have widespread alterations in KRAS, p53, cdk2a, and Smad4/DPC4 signalling that are difficult to target due to frequent mutations in these genes or proteins. Third, there can be biophysical barriers to treating a pancreatic tumor such as tumor desmoplasia, high oncotic pressure, and poor perfusion. Surgery is currently the only treatment. However, some first line chemotherapeutics can be used, such as FOLFIRINOX® (FOL—folinic acid (leucovorin), F—fluorouracil (5-FU), IRIN—irinotecan, and OX oxaliplatin) and GEMZAR® (Gemcitabine) in combination with ABRAXANE® (Protein-bound paclitaxel).

The limitations to the current regimens of targeted therapy include, but are not limited to, a lack of improvement in late-stage disease outcomes, frequent KRAS mutations, and poor drug delivery. Table 1 shows several drugs, drug targets, and corresponding overall survival (OS) and progression-free survival (PFS) rate. The table highlights the dire need for improved therapeutics for the treatment of cancer such as pancreatic cancer.

TABLE 1

Limitations of Current Targeted Therapeutics for the Treatment of Pancreatic Cancer

| Target | Drug | OS | PFS |
| --- | --- | --- | --- |
| EGFR | Cetuximab | 6.3 vs. 5.9 mo | 3.4 vs 3.0 mo |
|  | Erlotinib | 6.2 vs. 5.9 mo | 3.8 vs. 3.6 mo |
|  | Nimotuzumab | 8.6 vs. 6.0 mo | 5.3 vs. 3.6 mo |
| IGFR | Cixutumumab | 7.0 vs. 6.7 mo | 3.6 vs 3.6 mo |
| Ras | Tipifarnib Salirasib | 6.4 vs. 6.1 mo | 3.7 vs 3.6 mo |
| MEK 1/2 | Selumetinib | 5.4 vs 5.0 mo | 2.1 vs. 2.2 mo |
|  | Trametinib | 8.4 vs. 6.7 mo | 4.0 vs. 3.8 mo |
| MEK 1/2 + AKT | Selumetinib + MK-2206 | 3.9 vs. 6.7 mo | 1.9 vs. 2.0 mo |

Antibody Drug Conjugates as Combination Targeted Therapy

Figure 7:
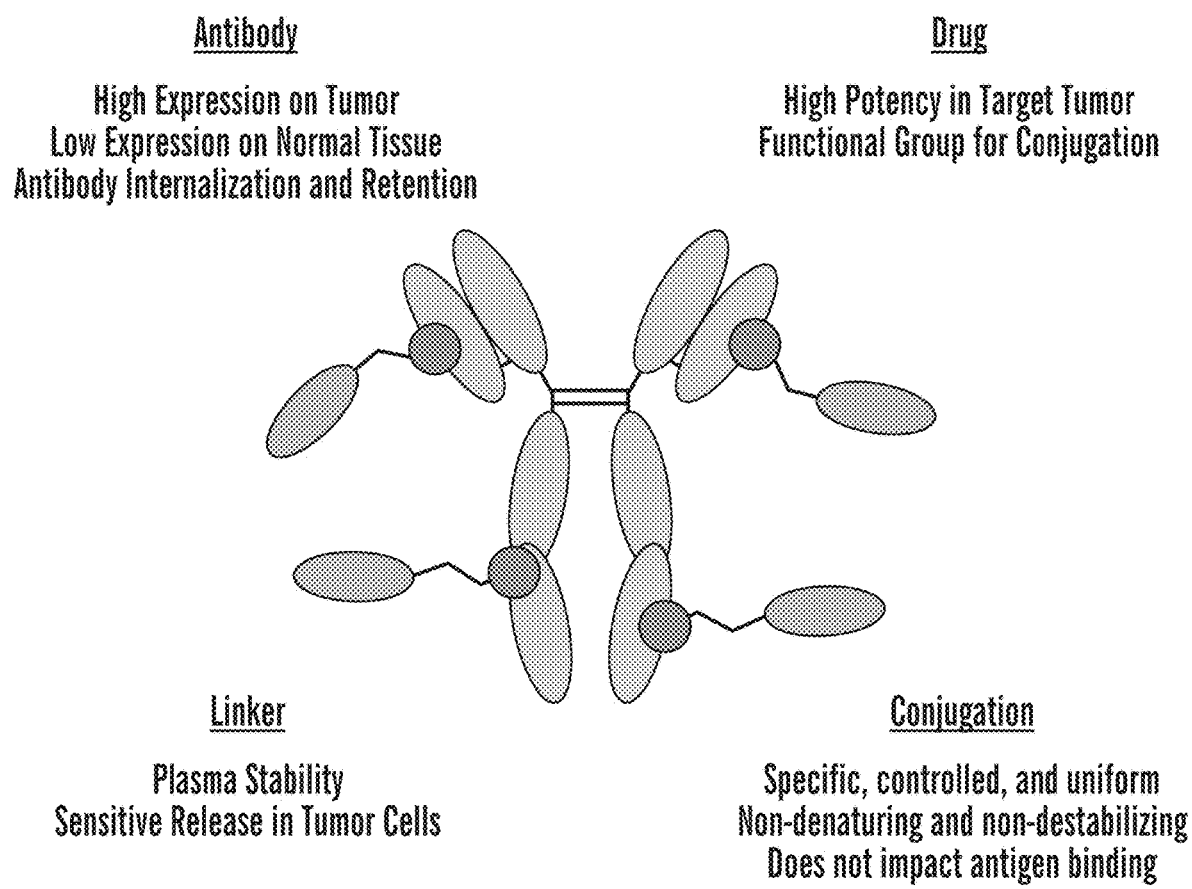
FIG. 7 demonstrates an example of Antibody Drug Conjugates (ADC) as combination targeted therapy.

The current challenge of treating cancers such as pancreatic cancers is discovering effective, targeted therapies. The goal is to develop a unique anti-pancreatic cancer antibody drug conjugate (ADC) that will improve drug delivery and augment biologic therapy (FIG. 7).

ADC Development Criteria

There are some known ADC parameters such as (1) Linkers: Dipeptide linkers are most effective; and (2) Drug payload: Auristatins, Calicheamicins, and Maytansines used in FDA approved ADCs. However, there are also unknown ADC parameters that can be addressed herein such as: (1) definine an effective antigenic target for pancreatic cancer; and (2) establishing an effective drug conjugation method. The current challenges with ADCs is that a suitable target needs to be determined along with an ideal conjugation method for the drug payload.

Project Aims

Aim #1: Investigated a Novel Pancreatic Specific Target for ADC Development

Rationale: Highly specific tumor target for pancreatic cancer to minimize off-target drug delivery. Key Features include: High tumor expression, low normal tissue expression, and internalization and retention of antibody receptor complex Aim #2: Developed a Site-Specific, Uniform Method of Drug Conjugation for Tunable ADC Development Goal: Developed a site-specific, tunable method of protein conjugation. Key features include: high specificity, complete or near complete conversion from antibody to ADC, high stability of binding, tunable to different drug linkers, uniform drug loading.

Aim #3: Synthesized a Tunable Drug Linker

Aim #4: Synthesized an ADC-Targeting Pancreatic Cancer

Aim #2: Ideal Conjugation Method for ADC

Current ADCs on the market have non-uniform loading, hinge-loading, ADR is >4, and have loading in the binding region of the antibody.

Figure 8:
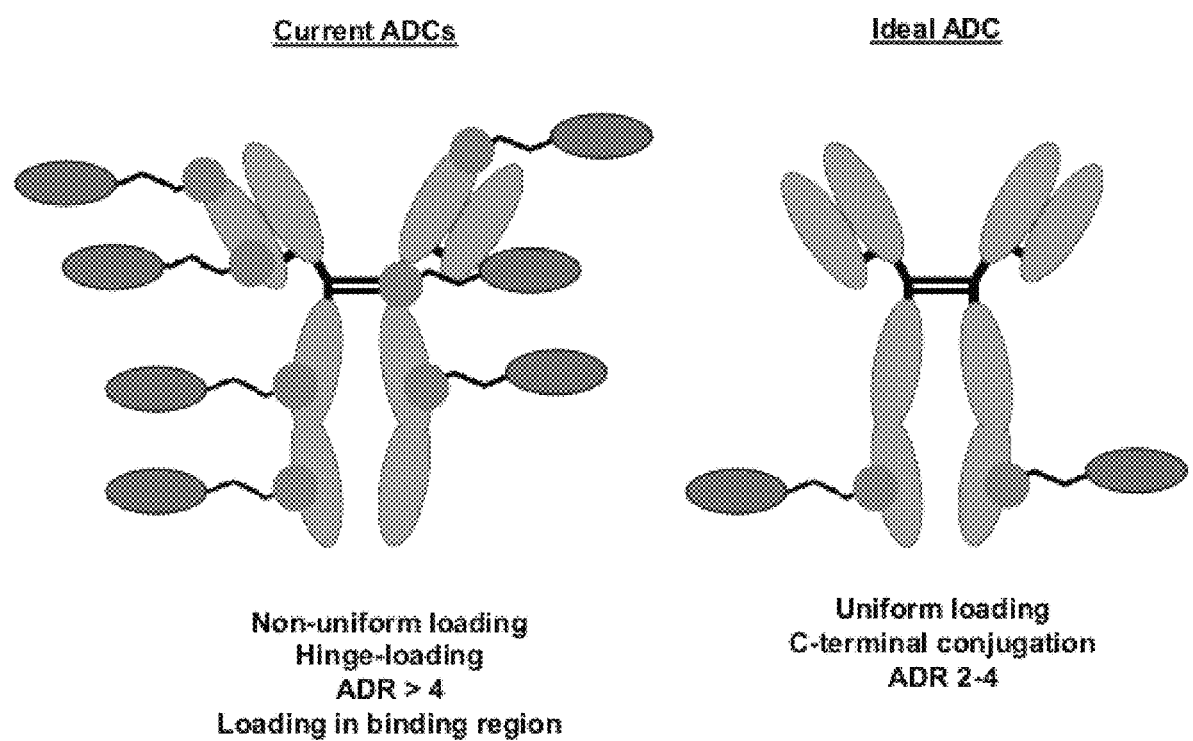
FIG. 8 demonstrates current ADC preparations, which produce non-uniform, unfavorable conjugation (left) to ideal ADC conjugation, which is tuneable and site-specific.

The ideal ADC has the following properties: high stability and specificity; uniform, controlled drug loading (e.g., ADR: 2-4 drugs/ADC); C-terminal conjugation, minimal impact on antigen binding; minimal impact on antibody stability; and is minimally immunogenic (FIG. 8).

Aim #2: Drug Loading System: Supramolecular Conjugation

Figure 9:
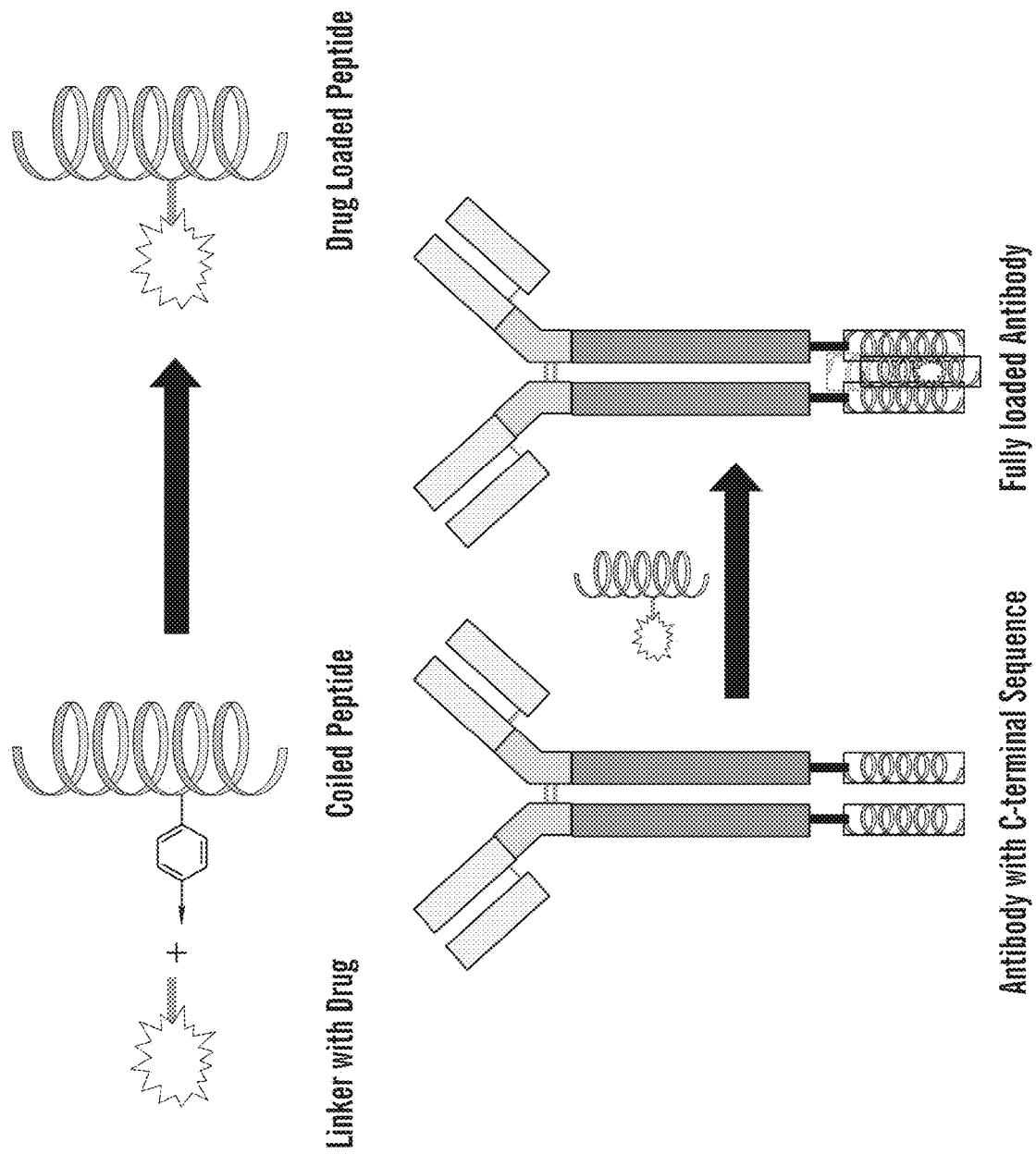
FIG. 9 demonstrates an exemplary conjugation method. Two C-terminal receiving sequences on a monoclonal antibody react with two drug-loaded docking sequences to form a tetrameric structure.

Specific drug loading can be accomplished using supramolecular assembly. This is designed with two sets of peptides—a drug-loaded peptide and a C-terminal complement peptide (FIG. 9). This design allows for the formation of a high specificity "peptide velcro" bond to ensure that the ADC is uniform, can have specific loading of 2 drugs/antibody, and has C-terminal loading to minimize effects on binding/stability.

Aim #2: Development of Drug Loading System

Figure 10:
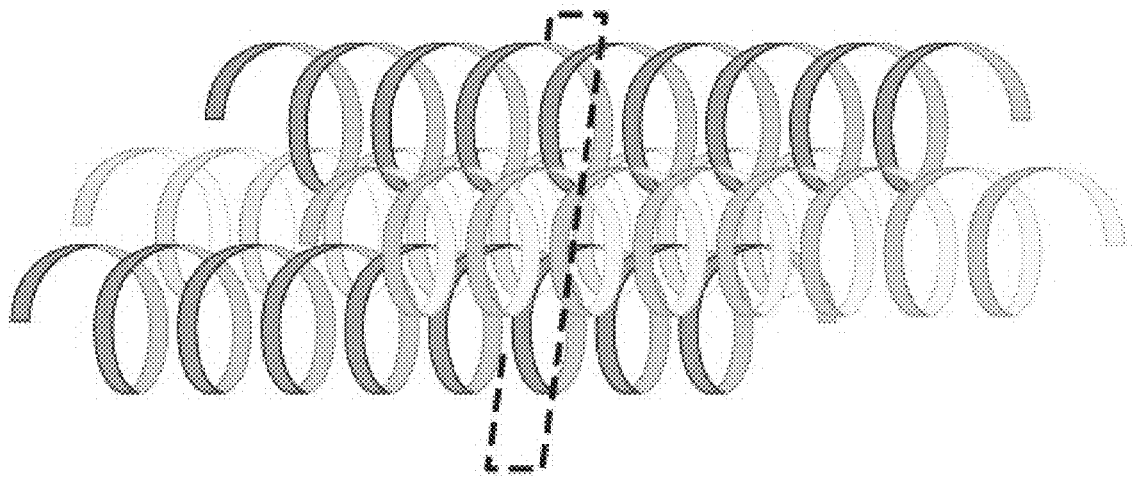
FIG. 10 shows a diagram showing the interaction of coiled coil tetramer pairings.
Figure 10:
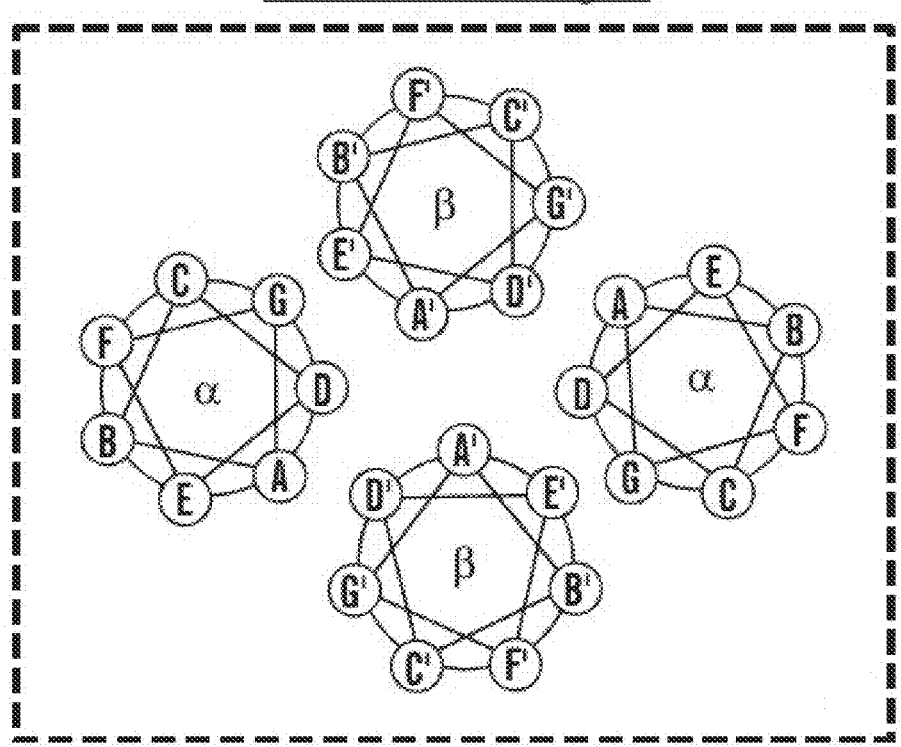

Coiled coils are a common structure in supramolecular assembly. They consist of a peptide structure of repeating heptad (XJJXJJJ) where each X is independently a hydrophobic amino acid and each J is independently any amino acid. Positions 1 and 4 (A and D) determine oligomeric state/orientation. Leucine and Isoleucine (A and D) are known to form parallel coiled coil tetramers (FIG. 10).

The design criteria for the drug loading system were as follows:

(1) Tetrameric structure—greater strength/heptad than dimers, timers; hides hydrophobic residues (immunogenic).

(2) Non-self interacting—peptides are either negatively charged (glutamic acid) or positively charted (lysine) on outside (B/C) residues.

(3) High strength—inclusion of hydrophobic interaction (G/E'); β-branched (isoleucine, valine) or unbranched (leucine) to determine ideal packing.

Figure 11:
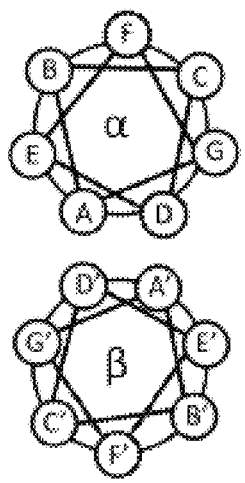
FIG. 11 depicts diagrams of the formation of hetero tetramers.
Figure 11:
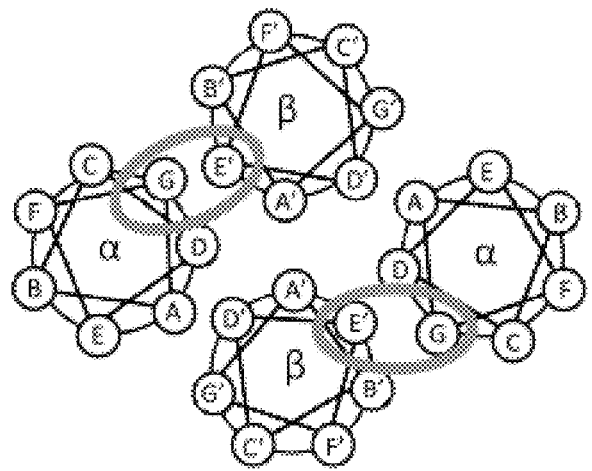

(4) Bio-orthogonal Tyrosine at F' position (FIG. 11).

The criteria for optimal design outcomes include but were not limited to the following:

(1) Both peptides do not self-interact (monomer only); (2) peptides form a stable, single tetrameric structure (ABAB orientation), ideally based on A and D amino acid position; and (3) interaction is highly stable (e.g., G/E' has optimal amino acid pairing).

Aim #2: Structural Analysis by Circular Dichroism (CD)

Circular dichroism can be used to estimate protein secondary structure. Examples of this method can be found in Brahms, S.; Brahms, J. Re-drawn by Greenfield, N. *Nature Protocols*. (2006), which is incorporated herein by reference in its entirety.

Aim #2: CD Structure of Peptide L/K and L/E

Figure 12:
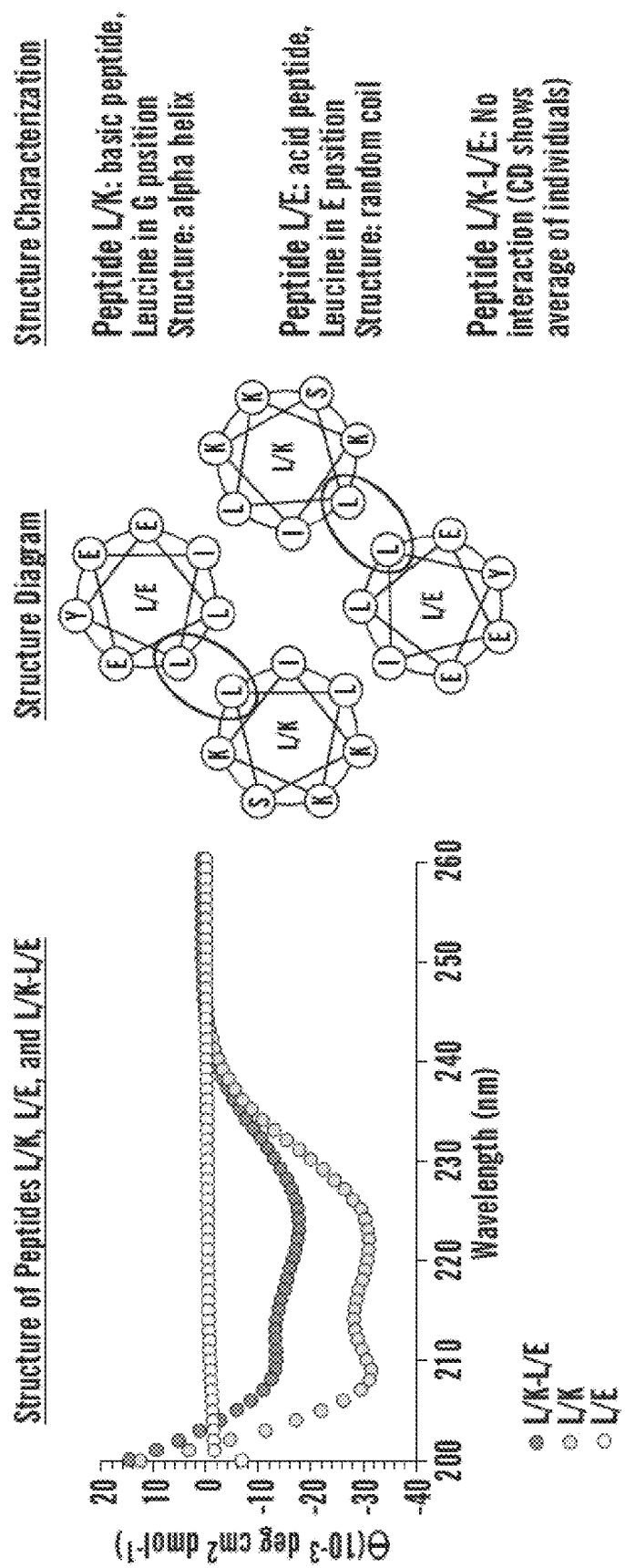
FIG. 12 demonstrates CD Structure of Peptide L/K and L/E.

FIG. 12 shows the structure of peptides L/K, L/E, and L/K-L/E and structure characterization.

Aim #2: CD Structure of Peptide I/K and L/E

Figure 13:
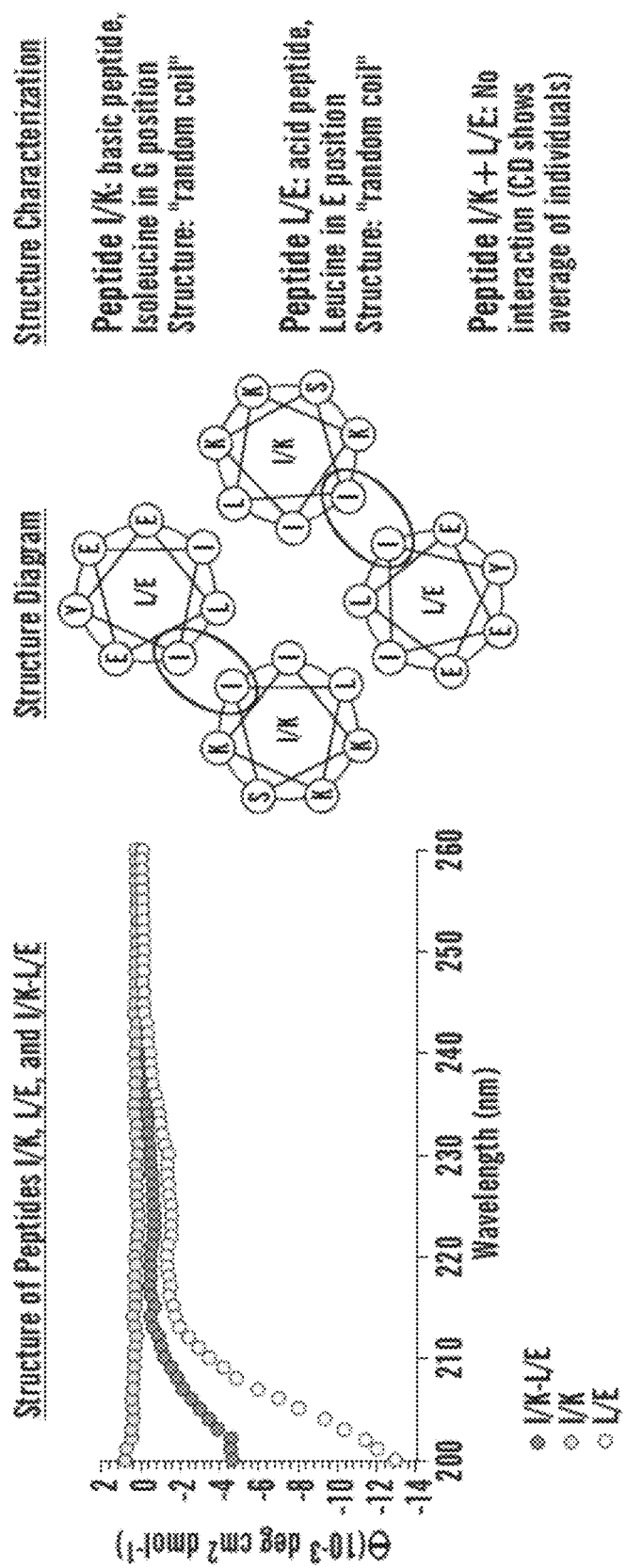
FIG. 13 demonstrates CD Structure of Peptide I/K and L/E.

FIG. 13 shows the structure of peptides I/K, L/E, and I/K-L/E and structure characterization.

Aim #2: CD Structure of Peptide V/K and V/E

FIG. 14 shows the structure of peptides V/K, V/E, and V/K-V/E and structure characterization.

Aim #2: Valine G/E Interaction is Permissive for Coiled Coil

The results from FIGS. 12-14 shows that the Valine-Valine G/E interaction is optimal, the size of hydrophobic group matters. These results also show that Leucine/Isoleucine disrupt heterohelix formation in G position and that Leucine/Isoleucine produce non-ideal packing in E position.

Aim #2: Structural Analysis by Velocity Sedimentation Analytical Ultracentrifugation Protein sedimentation by centrifugation force can be completed to determine the physical properties of protein (mass, shape), as this can affect the rate of sedimentation. Measuring physical properties of protein solution can be completed to determine the protein oligomeric state. Examples of this method can be found on the world wide web at http <www.coriolis-pharma.com> under the section called "AUC Service: Protein aggregation analysis by SV-AUC (Sedimentation Velocity Analytical Ultracentrifugation)", which is incorporated herein by reference in its entirety.

Aim #2: Peptide V/E-V/K Forms a Tetrameric Structure

Figure 15A:
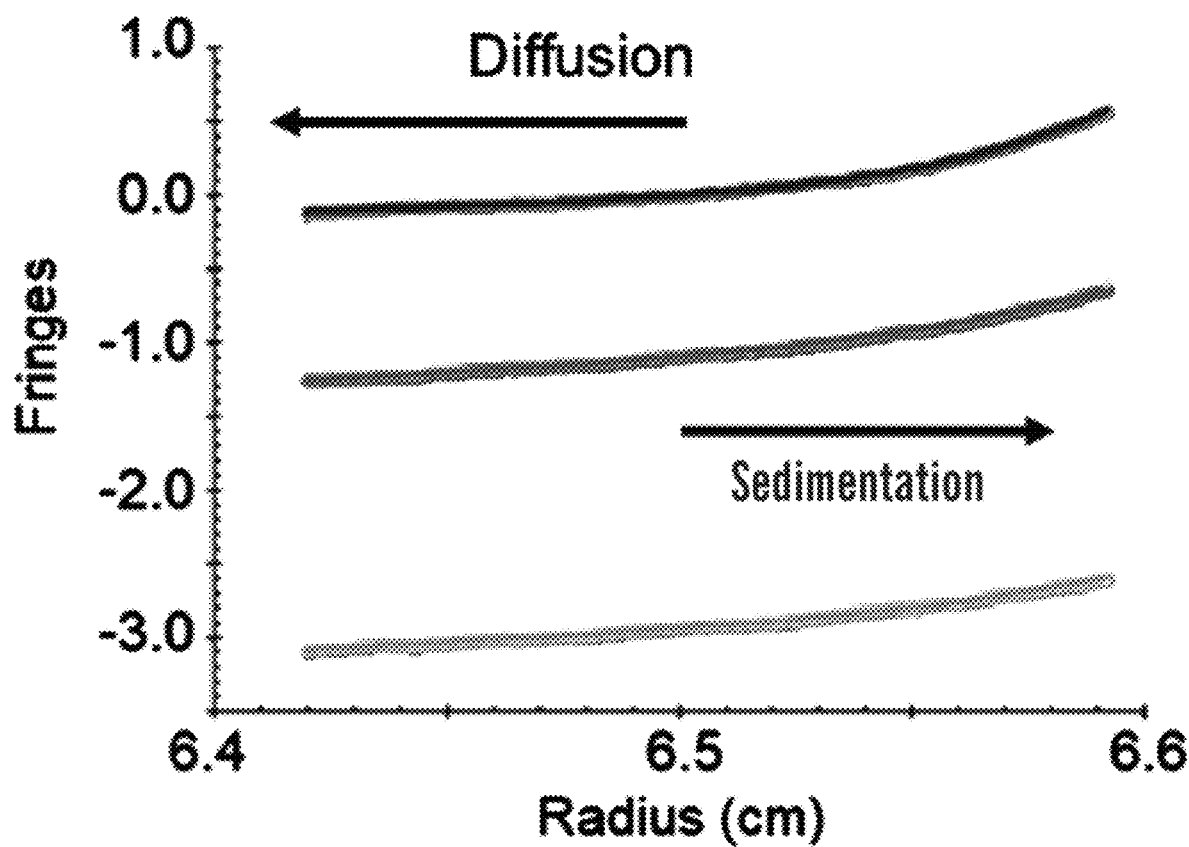
FIG. 15A-15C shows that peptide V/E+V/K Forms a tetrameric structure.
Figure 15B:
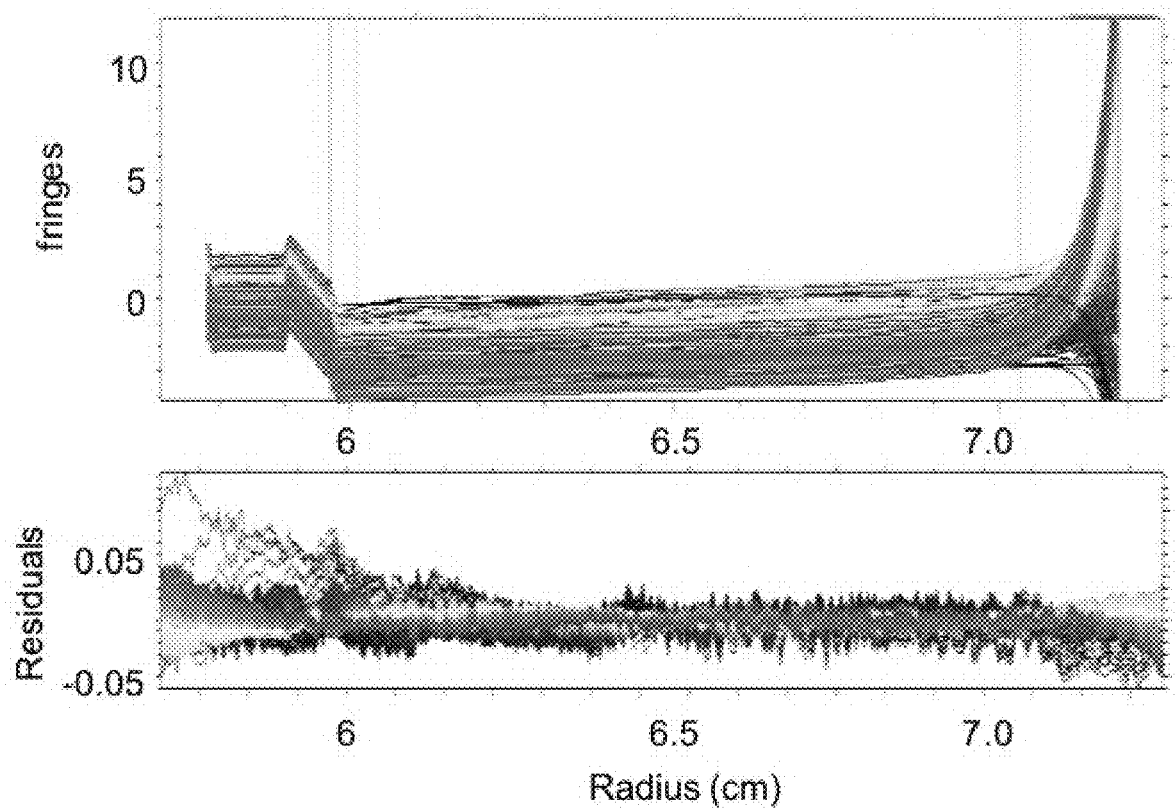
Figure 15C:
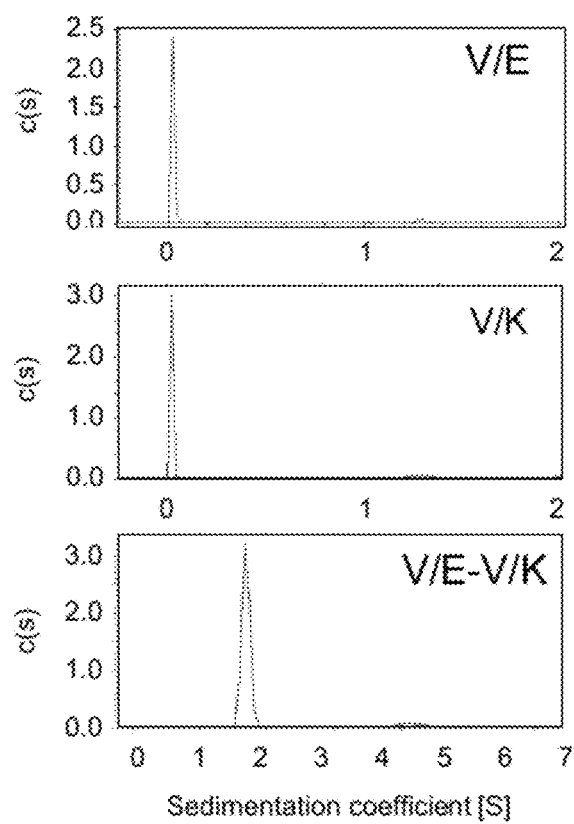
Figure 16:
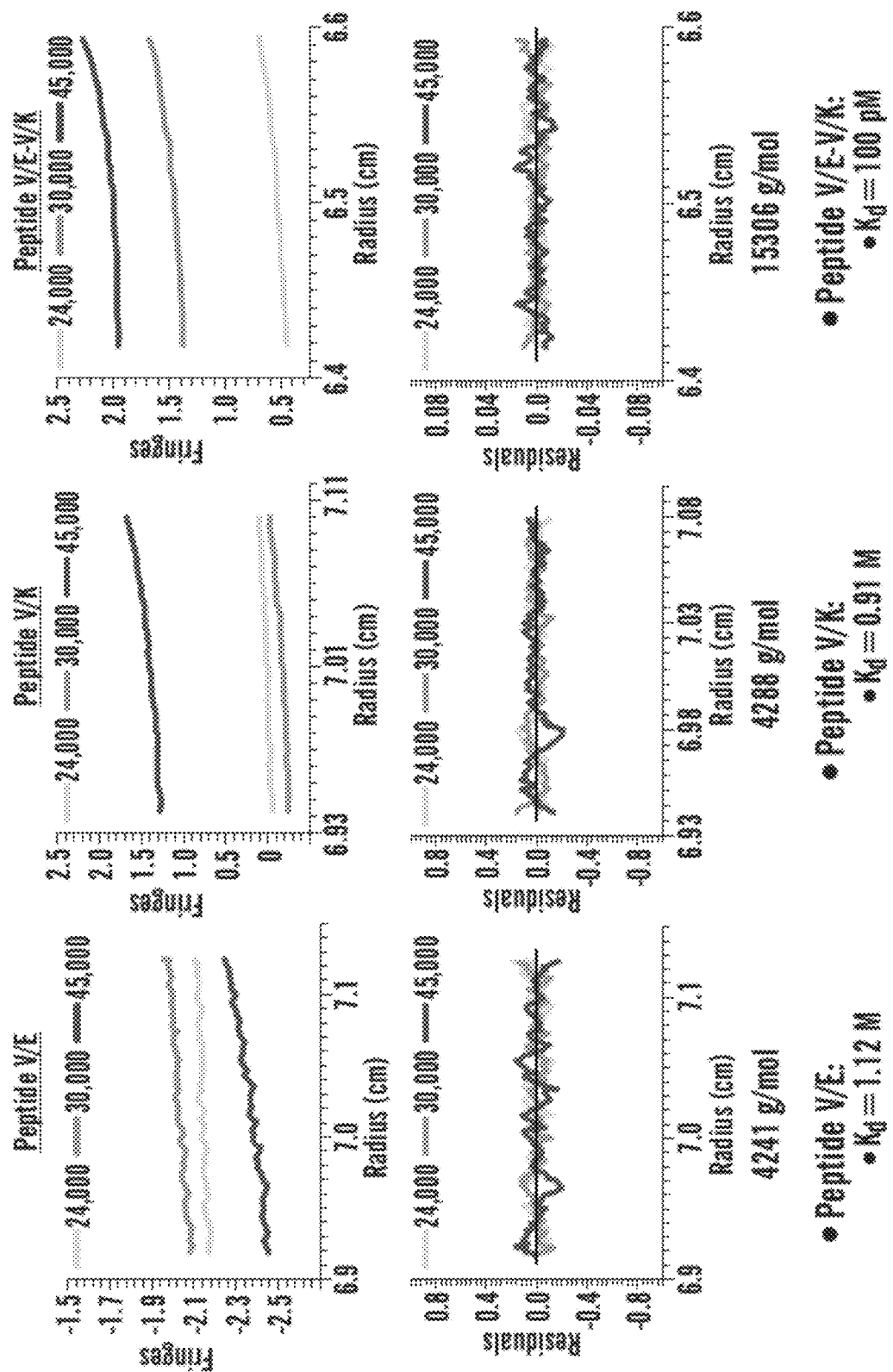
FIG. 16 demonstrates CD Structure of alternative targets Peptide L/K and L/E, demonstrating importance of fifth position valine in basic peptides (i.e. peptides with lysine in $2^{nd}$ and $3^{rd}$ position). Depicted are Peptide L/K (SEQ ID NO: 24) and L/E (SEQ ID NO: 23).

Using the protein sedimentation method shown in FIG. 15A-15C, peptide V/E-V/K are shown to form a tetrameric structure. The Kd of the peptides are shown in FIG. 16. For example, peptide V/E has a Kd of 1.12 Molar (M). Peptide V/K has a Kd of 0.91 M. Peptide V/E-V/K has a Kd of 100 picoMolar (pM).

Aim #2: Peptide V/E+V/K Forms a Highly Stable Complex

Figure 17:
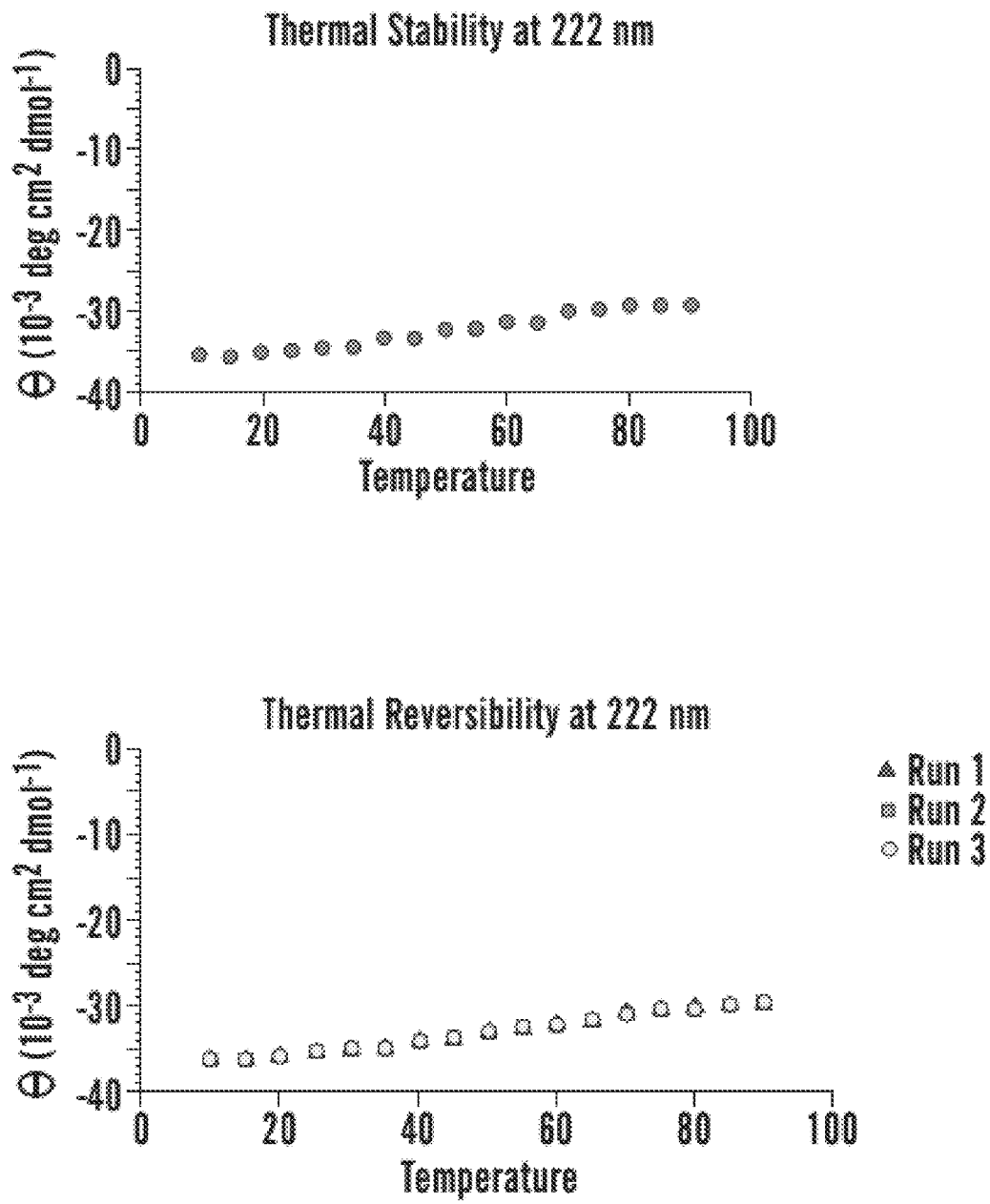
FIG. 17 demonstrates CD Structure of Peptide I/K and L/E demonstrating importance of fifth position valine in basic peptides (i.e. peptides with lysine in $2^{nd}$ and $3^{rd}$ position). Depicted are Peptide I/K (SEQ ID NO: 26) and L/E (SEQ ID NO: 25).
Figure 17:
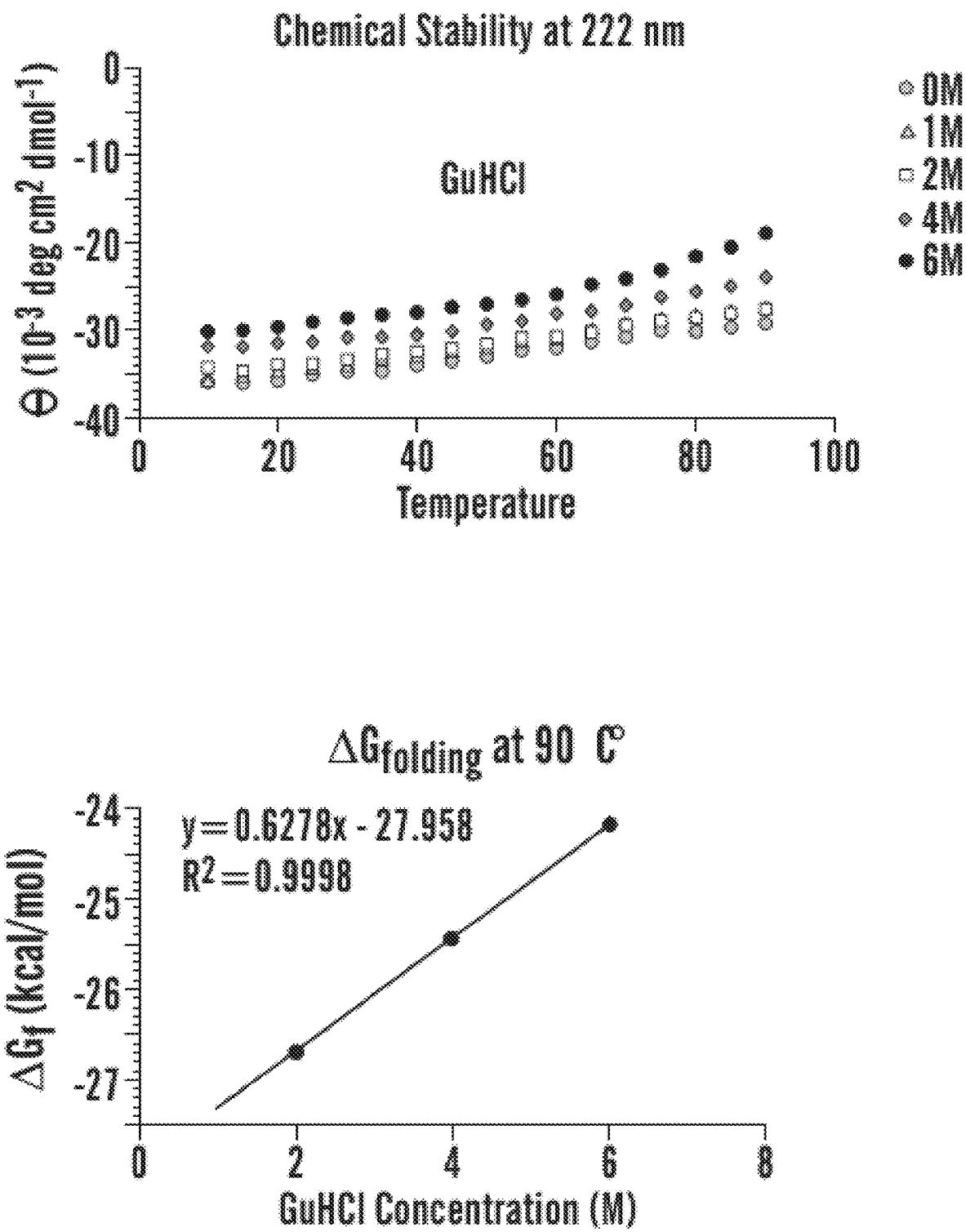
Figure 17:
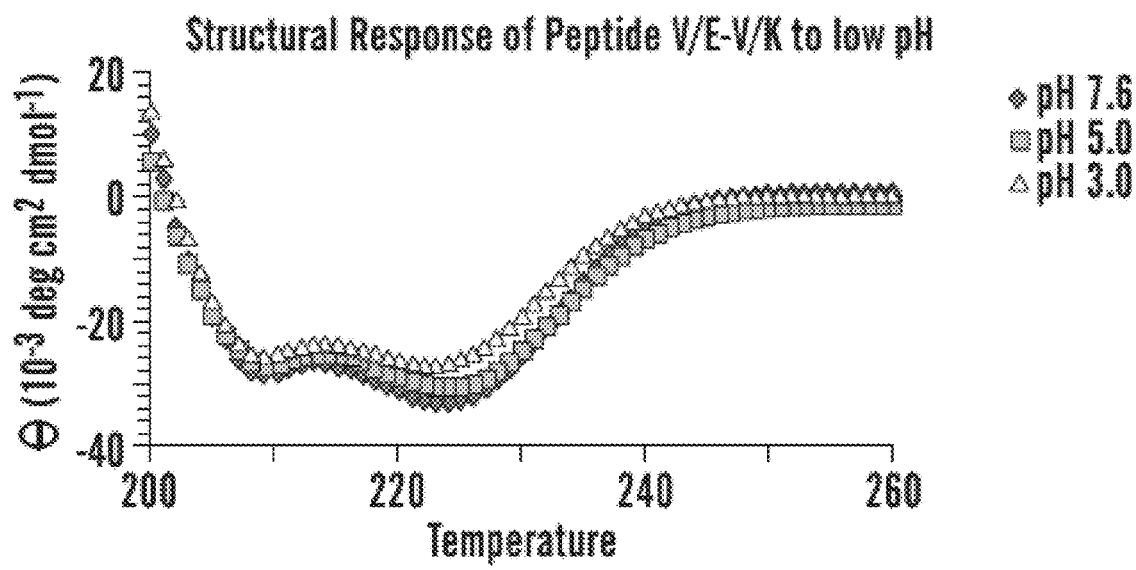
Figure 17:
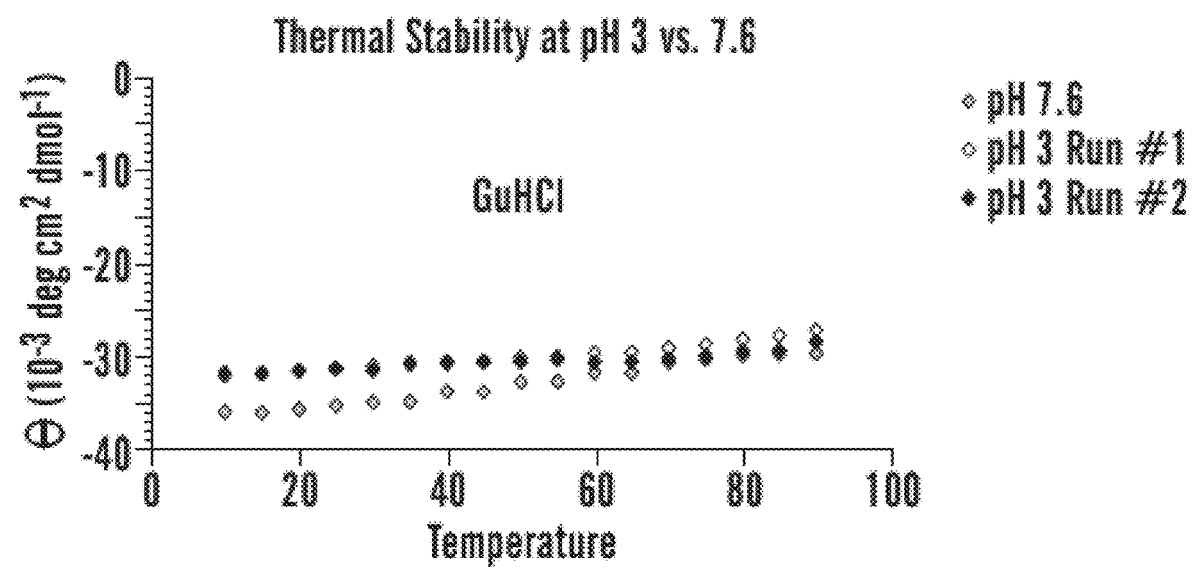

V/E and V/K peptides also form a highly stable complex. The thermal stability was tested at 222 nm are results are shown along with the structural response of peptide V/E-V/K in various pH levels (e.g., 7.6, 5.0, and 3.0) in FIG. 17.

Aim #3: Synthesized Tunable Drug Linker

Goal: Synthesize an ADC drug linker. Key features of the drug linker include (1) low nanomolar to high picomolar potency and (2) a method to link drug to the antibody.

Aim #3: Mertansine as a Potent Microtubule Inhibitor

Figure 18:
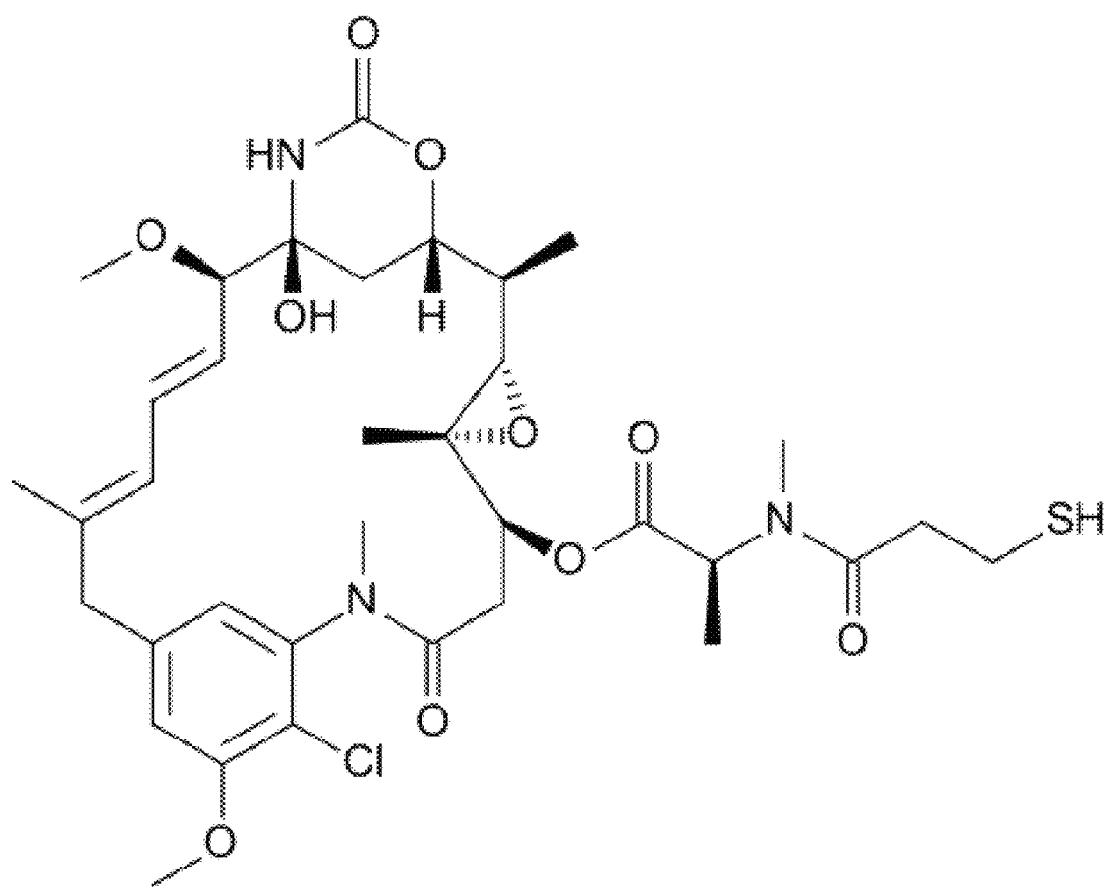
FIG. 18 demonstrates the chemical structure of mertansine, a potent microtubule inhibitor.

Mertansine is a thiolated maytansinoid with high potency binding at a rhizoxin site (FIG. 18). Mertansine disrupts microtubule formation in cells. It is the drug used in KADCYLA®—the only FDA approved ADC for solid tumors. It was investigated whether mertansine is potent in pancreatic cancer (~1 nM IC50). Thus, a dipeptide linker to connect mertansine was developed herein.

Aim #3: Mertansine is Highly Effective in PDAC Cell Lines

Figure 19:
FIG. 19 demonstrates that mertansine is highly effective in PDAC cell lines.

Cell viability was measured in response to increasing doses of mertansine in Panc1 and MIA PaCa2 cell lines to determine the IC50 compared to other chemotherapeutic agents (gemcitabine and Nab-paclitaxel) (FIG. 19). Panc1 cells are a human pancreatic cancer cell line isolated from a pancreatic carcinoma of ductal cell origin. MIA PaCa-2 cells are another type of pancreatic cancer cell line that was derived from the carcinoma of a patient. The IC50 of mertansine in Panc1 cells is 1.19 nanoMolar (nM) and 268 picoMolar (pM) in PaCa2 cells.

Aim #3: ADC Drug Linker Design

Goal: Develop a plasma stable drug linker. The linker has a central cathepsin-B cleaved dipeptide linker; includes a C-terminal "self-immolative" spacer between dipeptide and mertansine; and an N-terminal tyrosine reactive urazole. The general linker structure is shown in FIG. 20.

Aim #3: ADC Linker Functionality

The dipeptide sequence of the linker has high cathepsin B specificity (limits degradation to lyososome). Use of a self-immolative spacer allows free mertansine to release after degradation. The linker allows for a "bystander killing effect" that is shown to improve ADC efficacy (FIG. 21).

Aim #3: Synthesis of Tyrosine Reactive Urazole

Figure 22E:
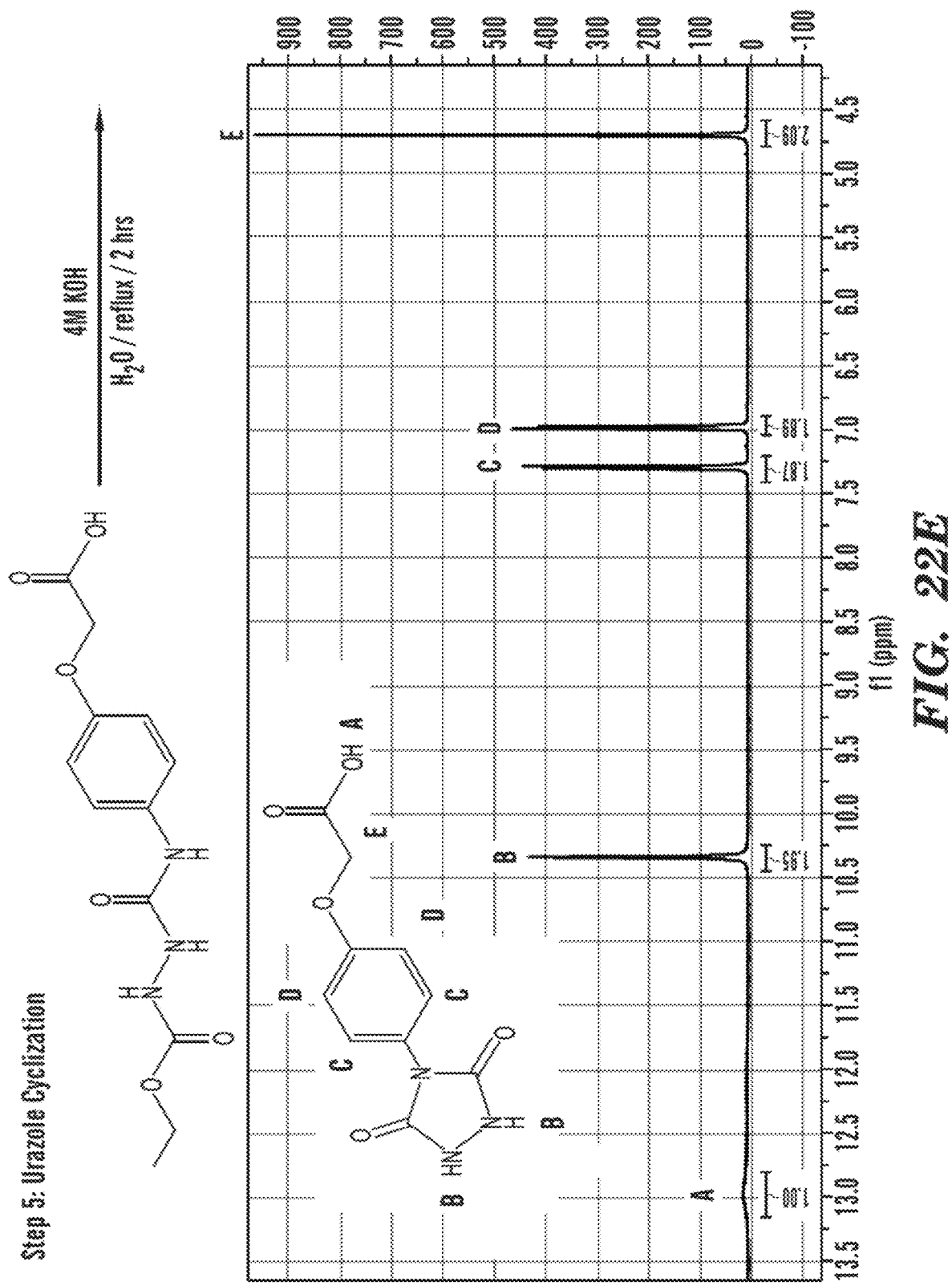
Figure 22E:
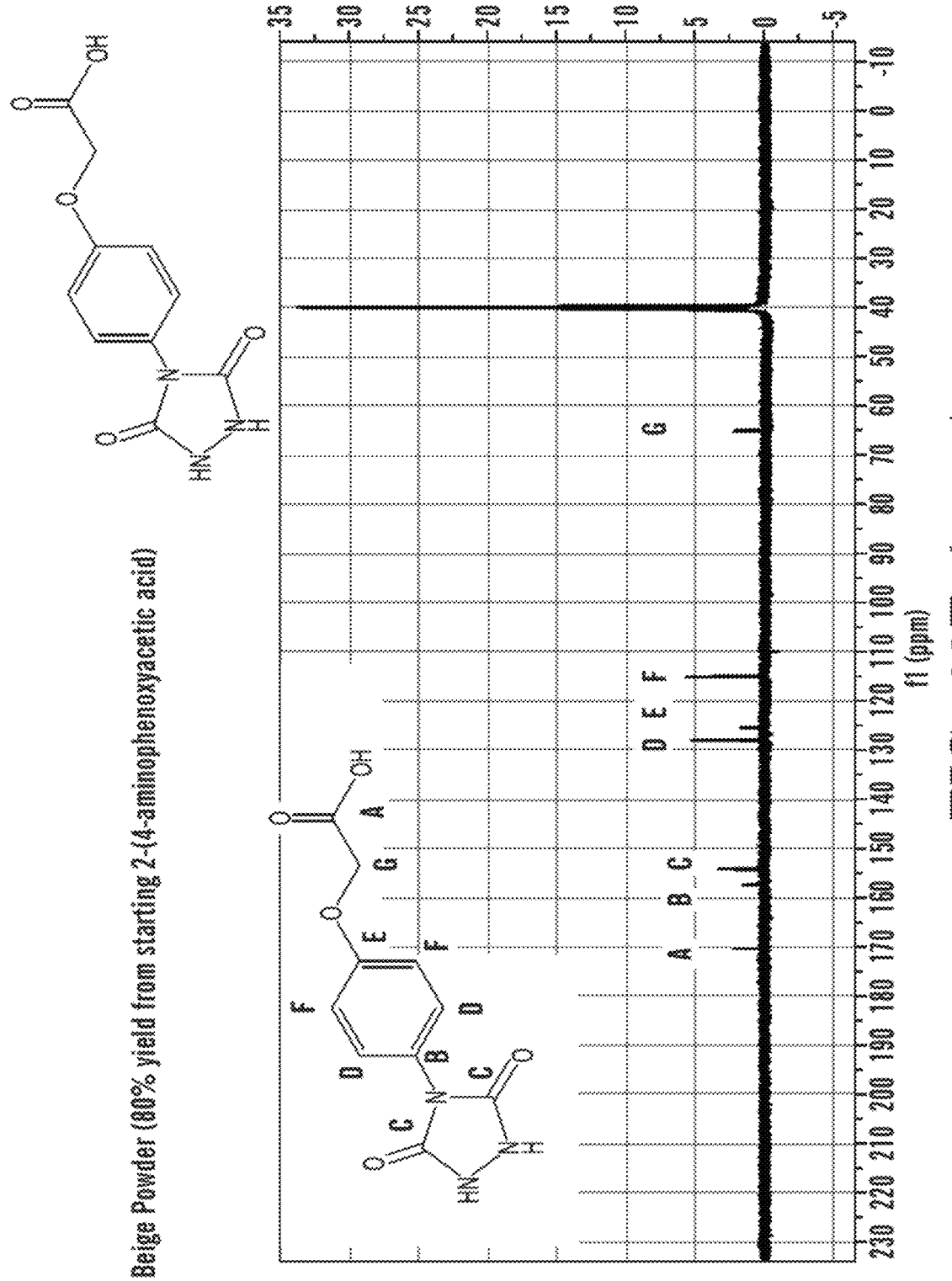
Figure 22F:
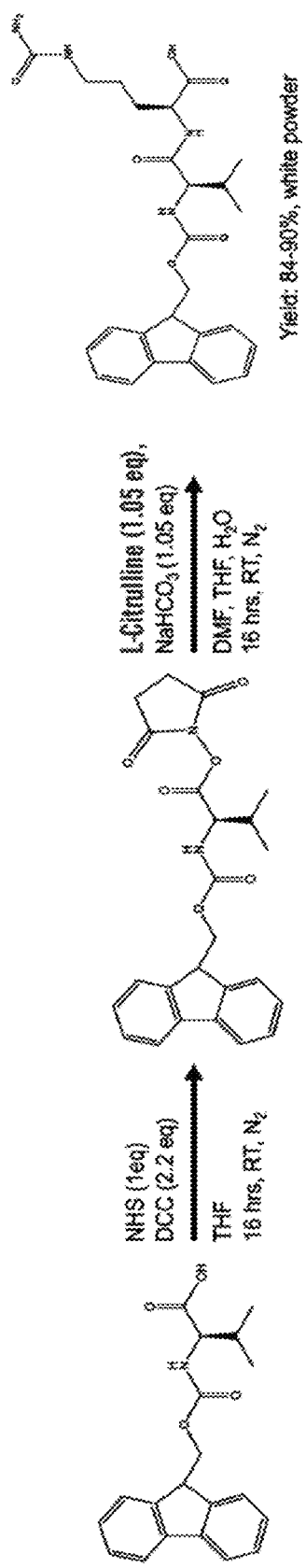
Figure 22G:
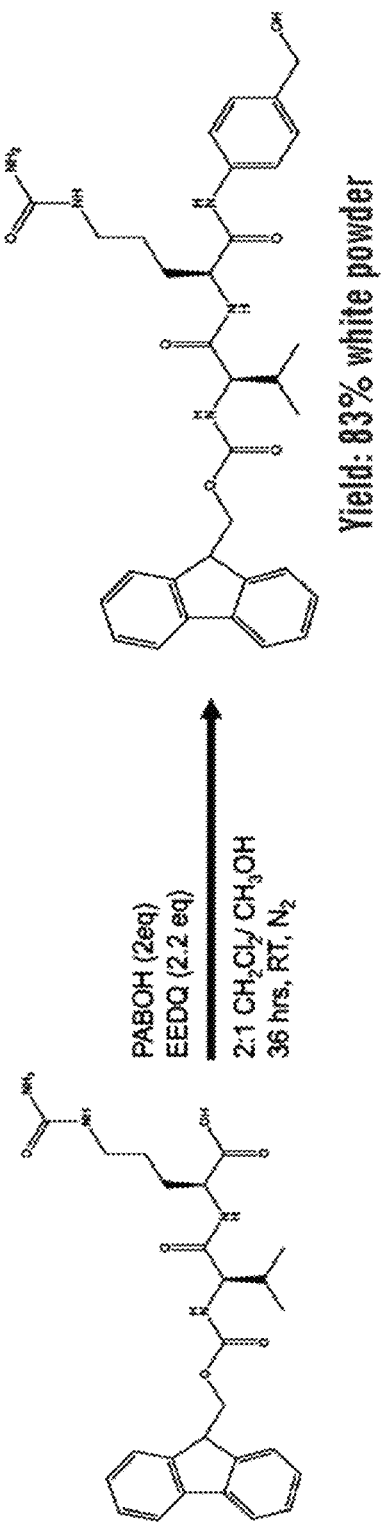
Figure 22H:
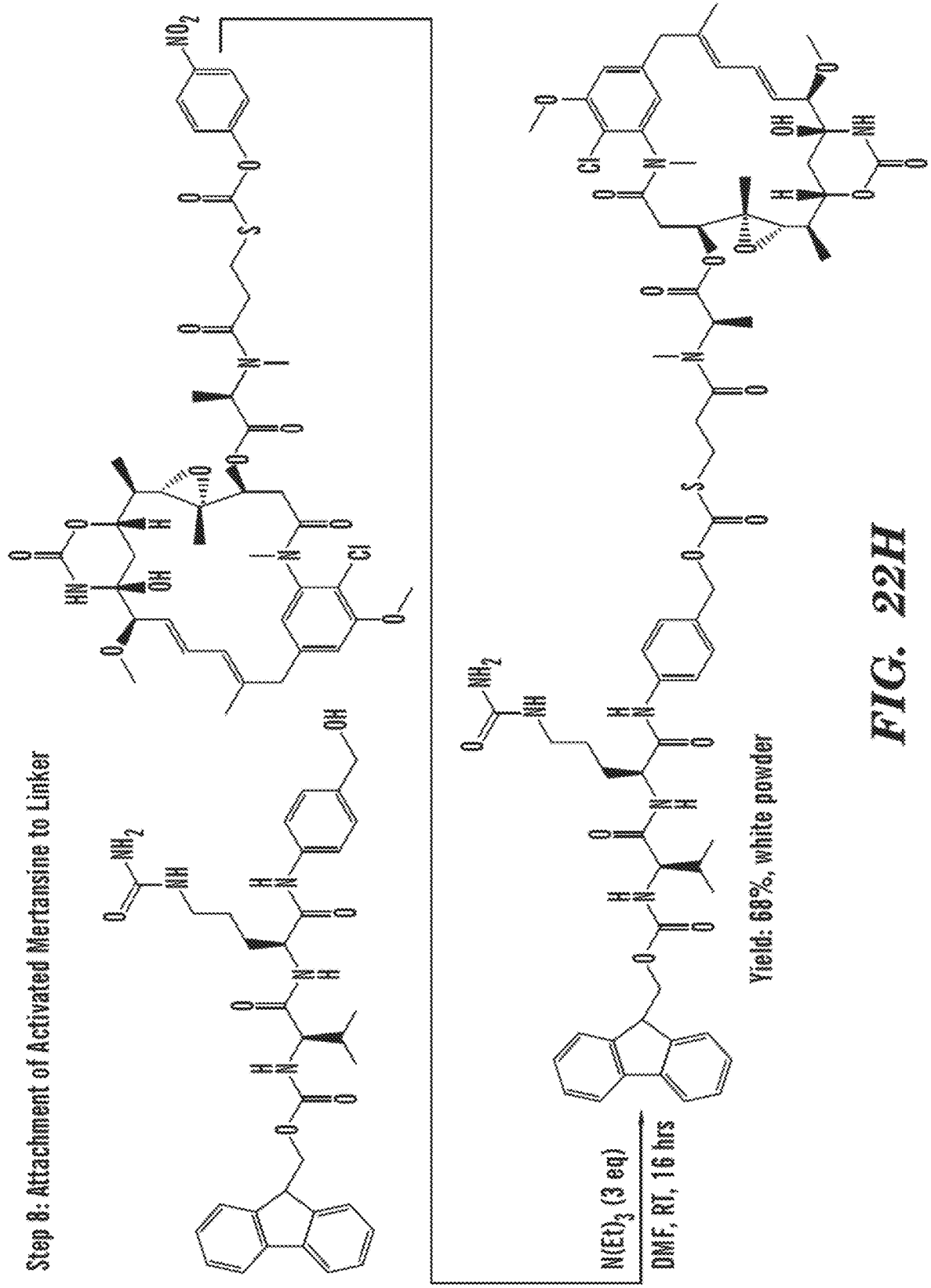
Figure 22I:
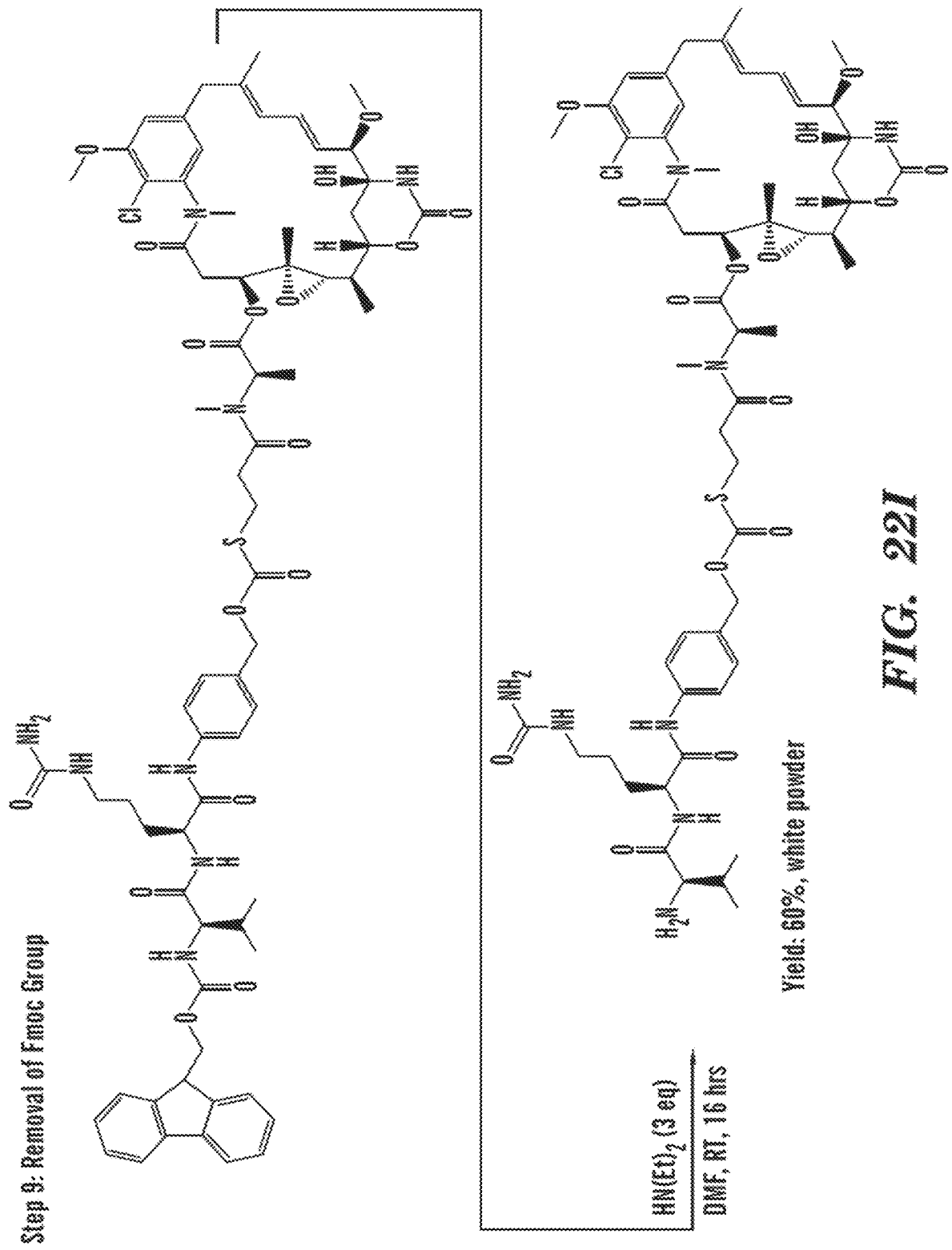
Figure 22J:
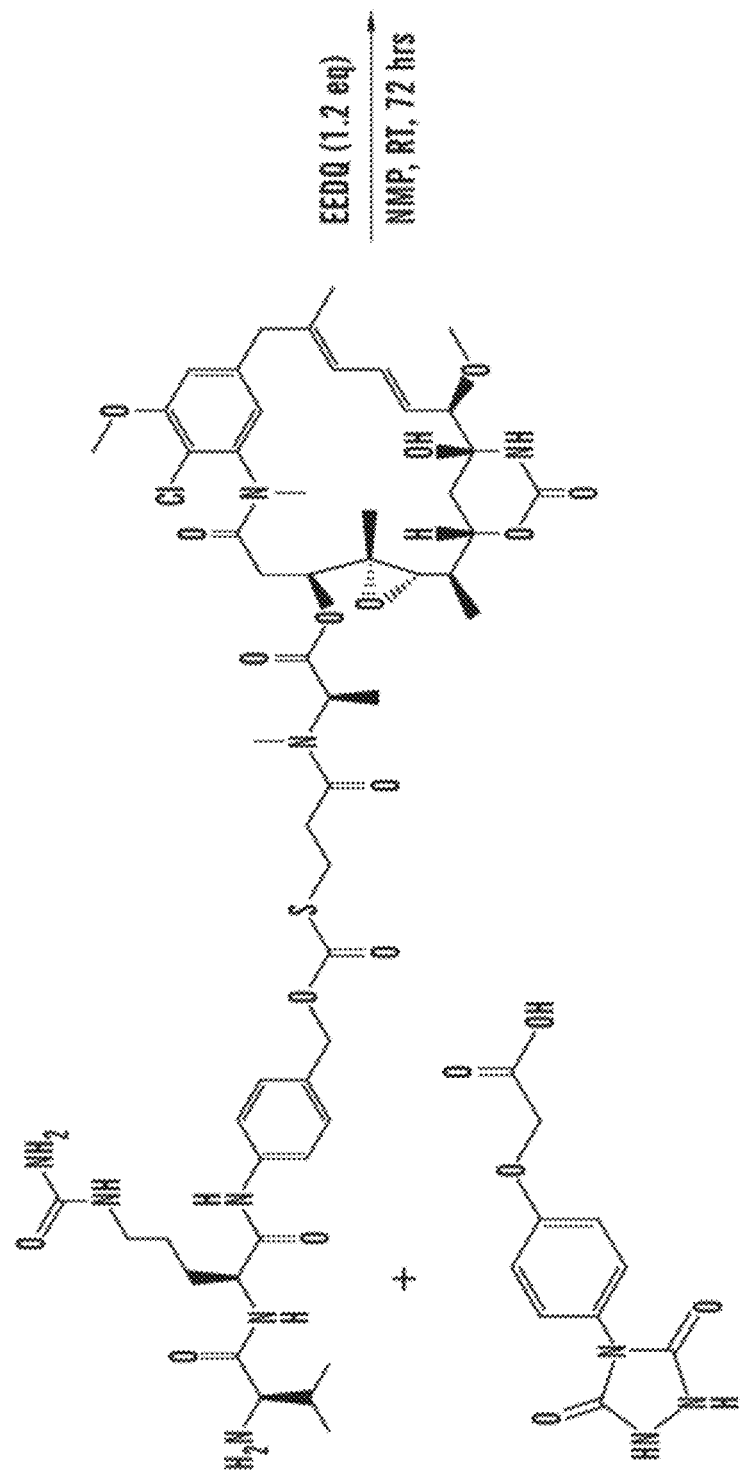
Figure 22J:
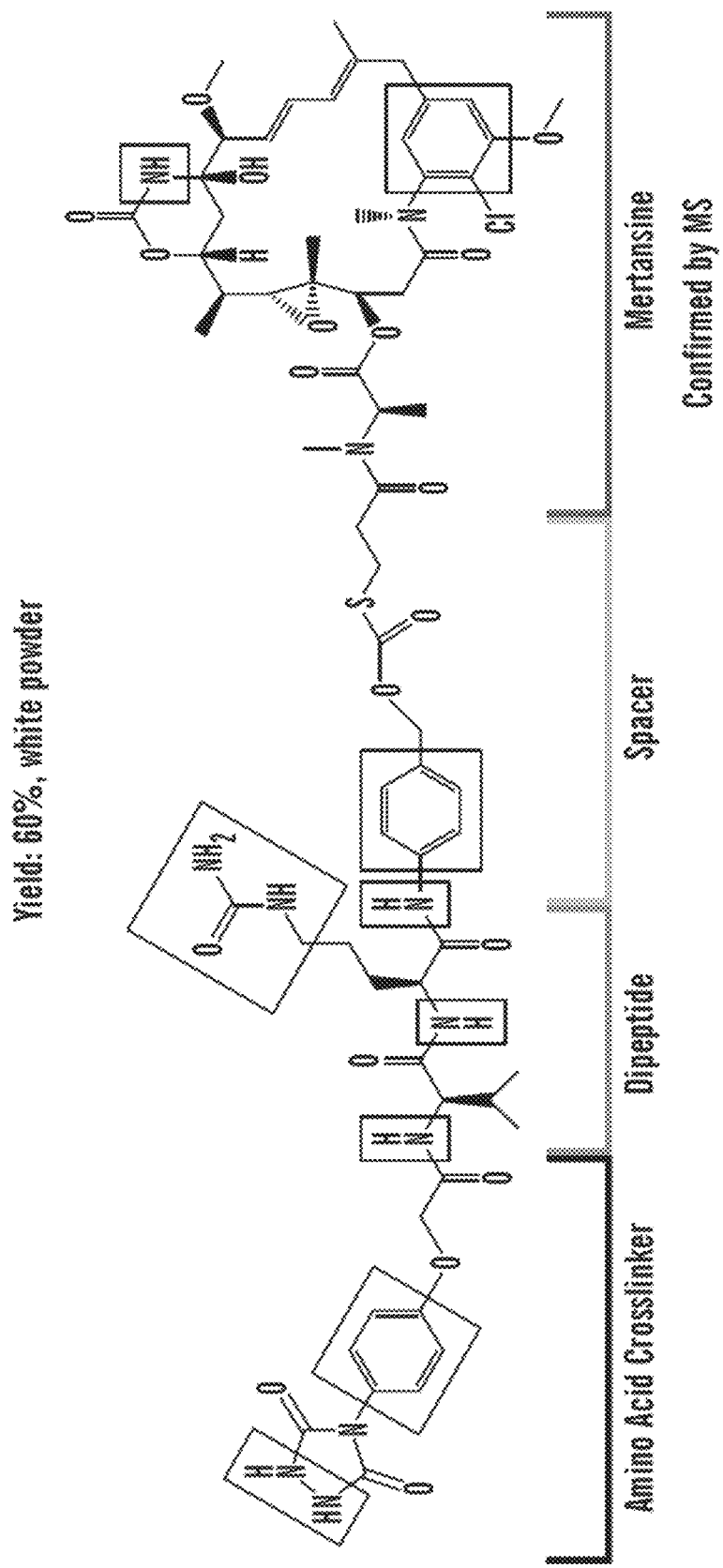
Figure 22J:
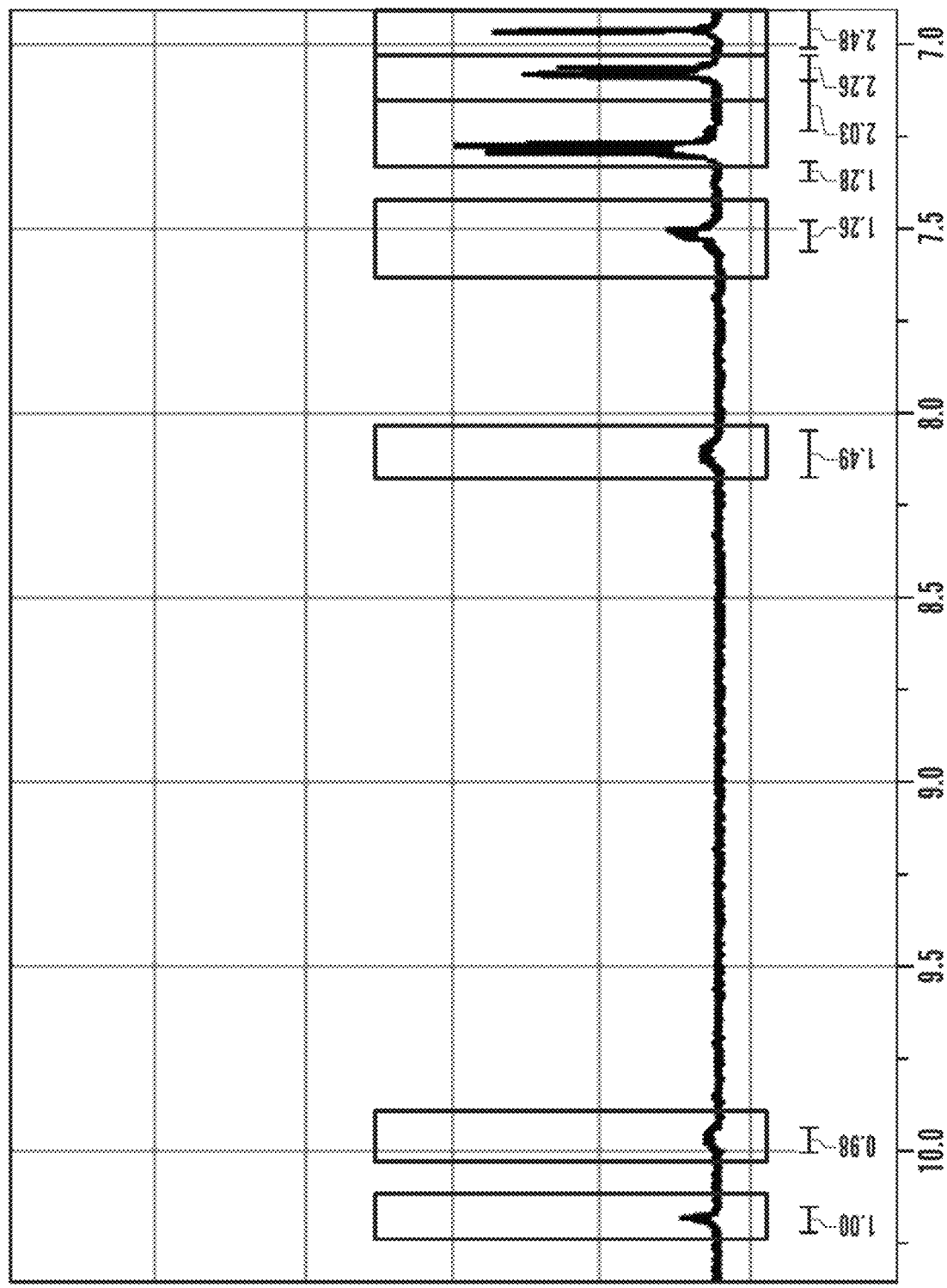
Figure 22J:
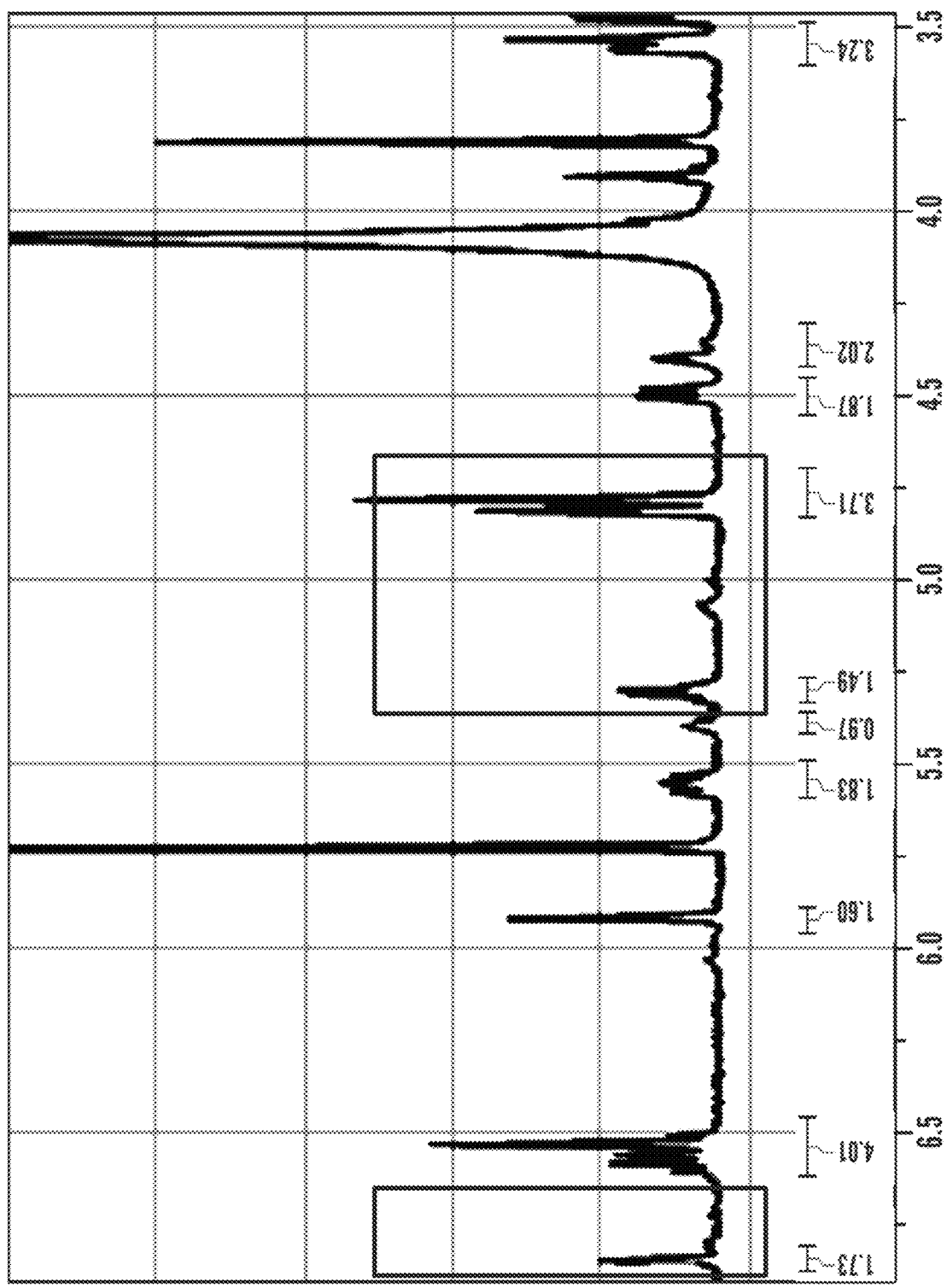
Figure 22J:
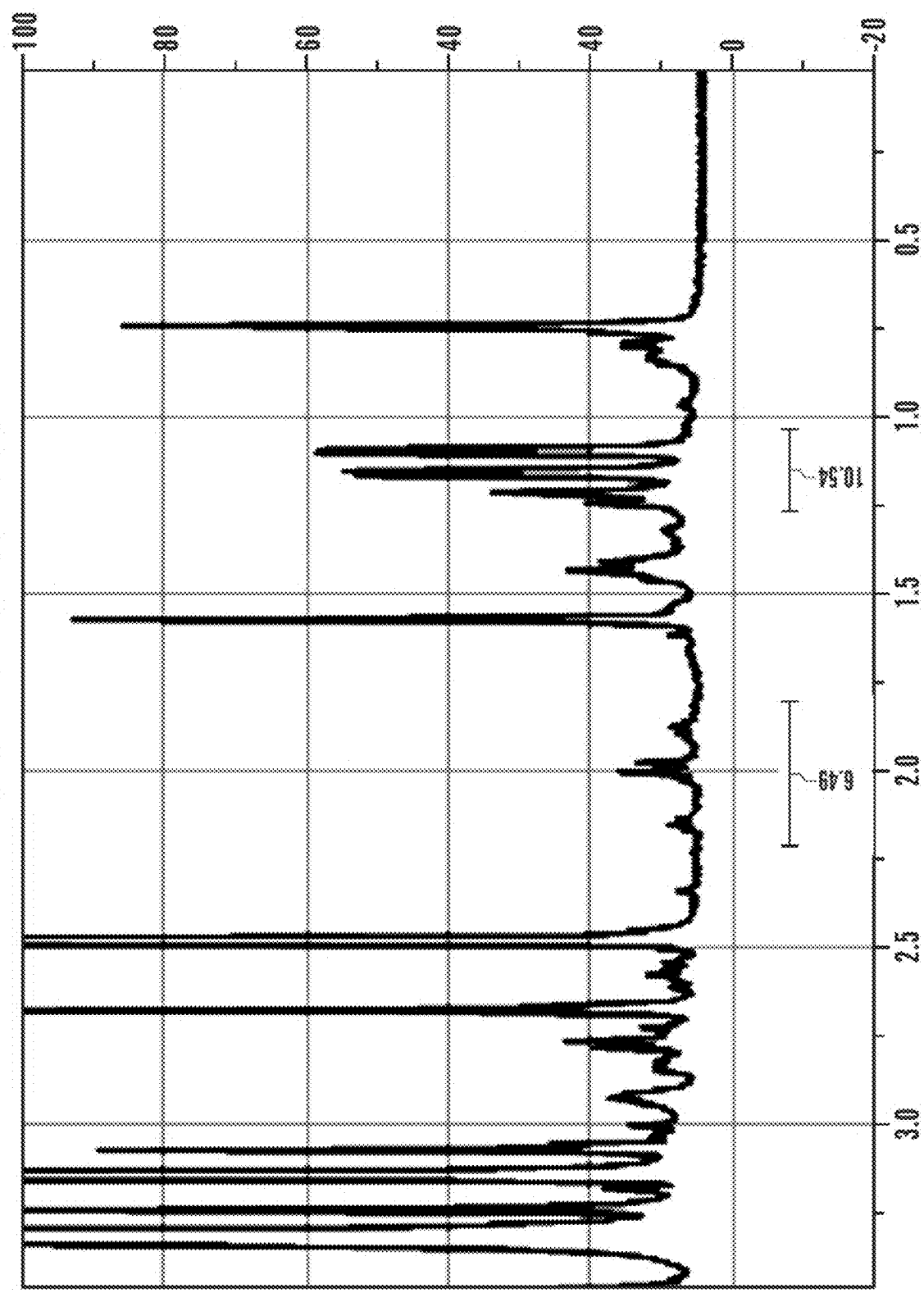

FIG. 22A-22J shows the synthesis of the tyrosine-reactive linker. FIG. 22A shows ether synthesis for the synthesis of the Tyrosine reactive urazole. FIG. 22B shows acyl deprotection for the synthesis of the Tyrosine reactive urazole. FIG. 22C shows amine-free base synthesis for the synthesis of the Tyrosine reactive urazole. FIG. 22D shows semicarbazate synthesis for the synthesis of the Tyrosine reactive urazole. FIG. 22E shows urazole cyclization for the synthesis of the Tyrosine reactive urazole. FIG. 22F shows synthesis of the Capthesin B dipeptide sequence. FIG. 22G demonstrates the addition of the "self immolative" sequence. FIG. 22H shows preparation of the ADC drug linker by attachment of activated mertansine. FIG. 22I shows removal of the Fmoc Group from the ADC drug linker. FIG. 22J shows the addition of a PTAD group to the ADC linker.

Aim #4: Synthesized ADC

Goal: To synthesize an anti-pancreatic cancer ADC. Key Features of the ADC include (1) a comparison in binding between an antibody alone and the ADC; (2) Evaluation of cytotoxicity in pancreatic cancer cell lines; and (3) Evaluation of cytotoxicity in normal cell lines.

Aim #4: ADC Development

Figure 23:
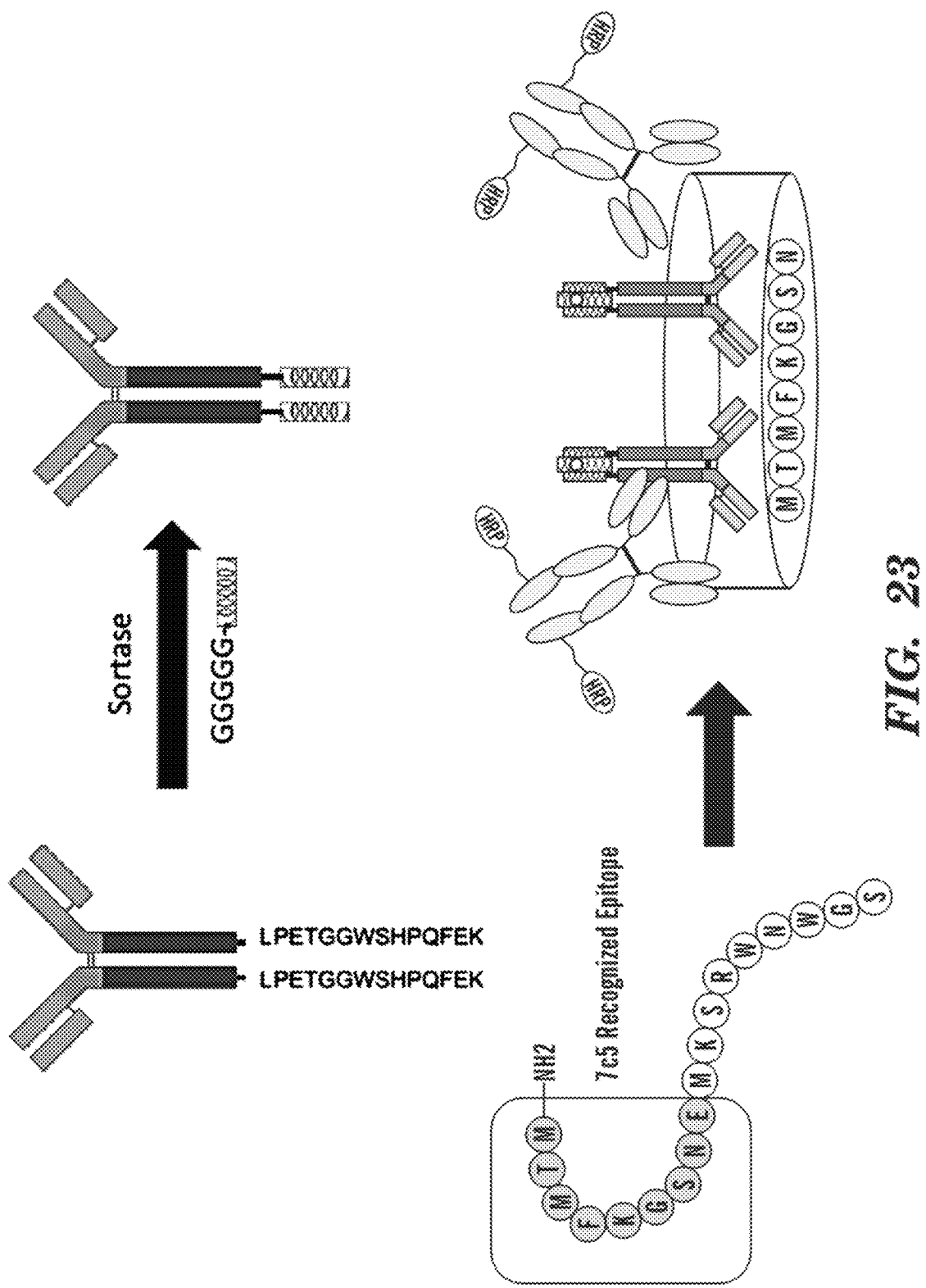
FIG. 23 shows ADC development using a C-terminal sortase A sequence (LPETGG (SEQ ID NO: 7)) and a StrepTactin sequence (WSHPQFEK (SEQ ID NO: 8)) for cleanup. This ADC allows for sortase-mediated conjugation of peptide sequences (SEQ ID NO: 5).

A monoclonal murine anti-DEspR antibody, 7c5 was used. The antibody comprised a C-terminal sortase A sequence (LPETGG (SEQ ID NO: 7)) and a StrepTactin sequence (WSHPQFEK (SEQ ID NO: 8)) for purification. Sortase-mediated the conjugation of the peptide sequence (FIG. 23).

A "Drug Loaded Peptide" was prepared with a PTAD linker. Samples were loaded with drug loaded peptide (ADC) or 488-loaded peptide (AFC). Purification was performed with rProtein Column and 100 kDA dialysis. UV-VIS analysis of ADC revealed: A280=1.74; A252=1.05; ADR: 1.99. UV-VIS analysis of AFC: A280=1.08; A494=0.69; and AFR: 1.98.

Aim #4: Binding Characterization of ADCs

Figure 24:
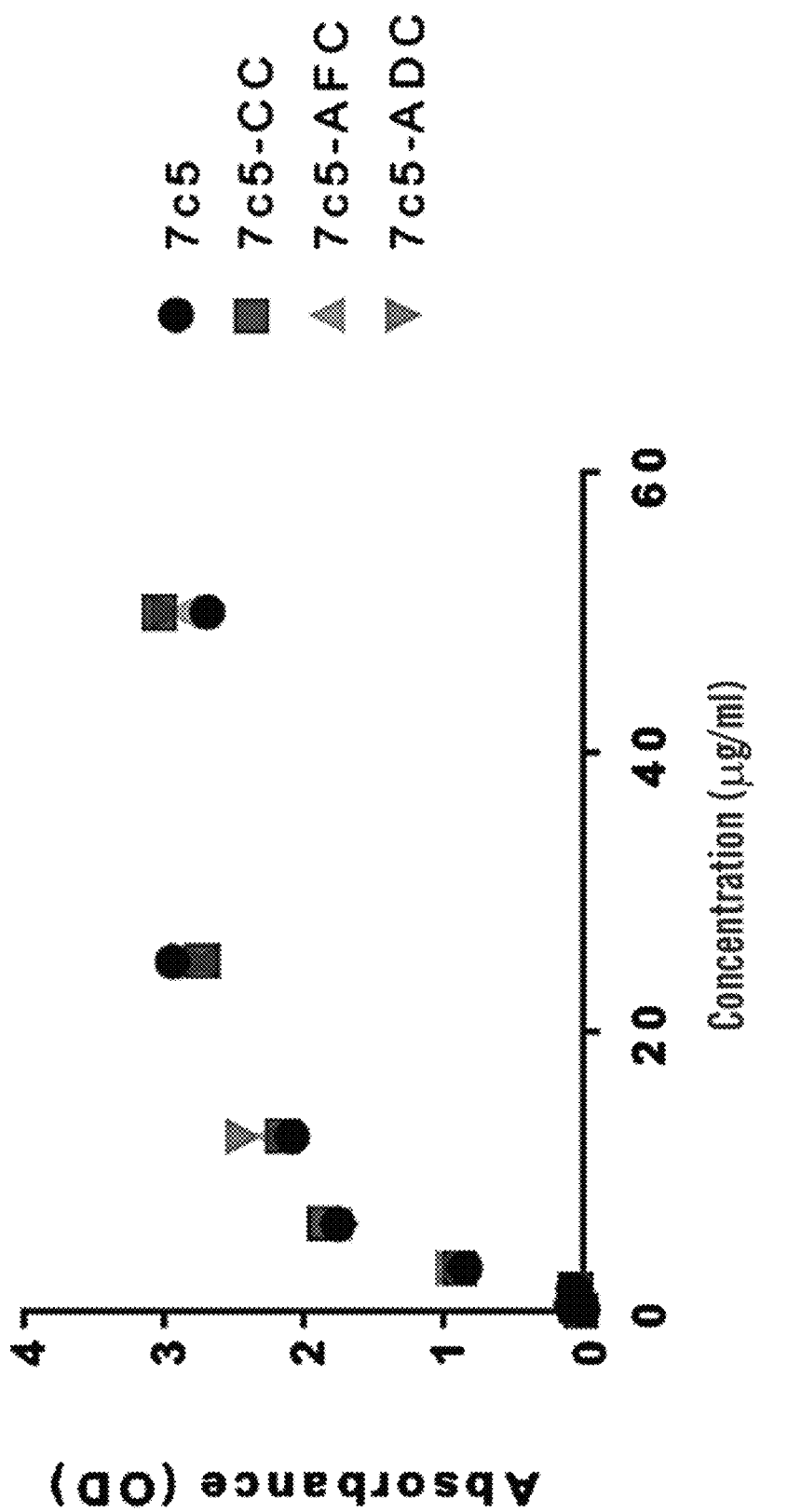
FIG. 24 shows binding characterization of ADCs, comparing the native antibody, 7c5, to 7c5 with the docking sequences included (7c5-cc), the antibody conjugated with the fluorophores via the above conjugation method (7c5-AFC), and mertansine conjugated the antibody via the above conjugation method (7c5-ADC). Binding of each species to the antigenic peptide recognized by the antigen binding region of 7c5 were equivalent, suggesting that this method of conjugation does not impact binding.

The binding of antibody (7c5) and conjugates to antigenic peptide (Epitope 1 of DEspR) were compared. The Kd was determined for the following samples: Kd 7c5: 8.68 µg/ml; Kd 7c5-CC: 9.31 µg/ml; Kd 7c5-AFC: 8.511 µg/ml; and Kd 7c5-ADC: 8.81 µg/ml. These results suggested that the conjugation and preparation steps did not impact binding of the ADC to the antigenic peptide (FIG. 24).

Aim #4: Binding Characterization of PDAC Cells

Figure 25:
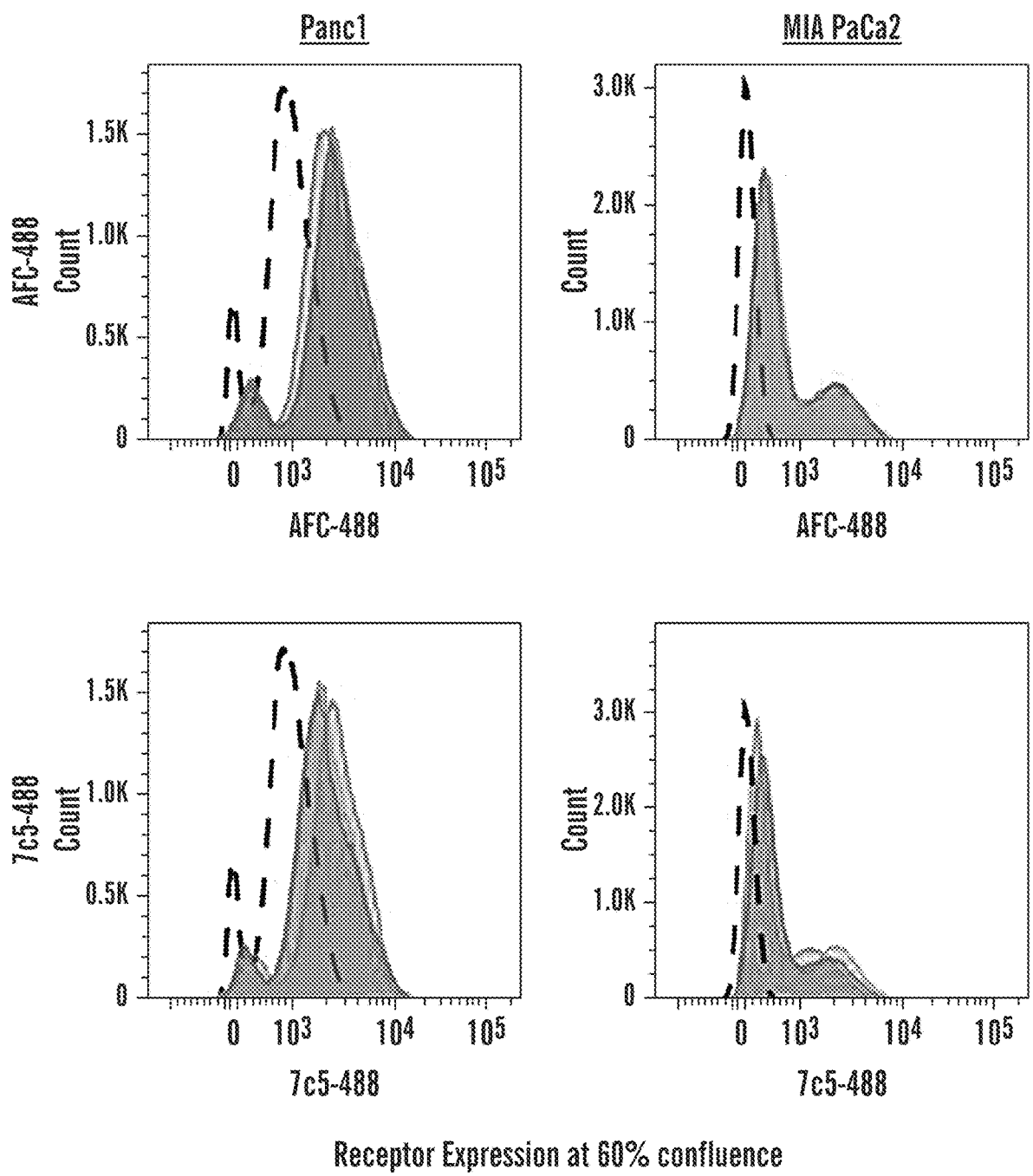
FIG. 25 shows binding characterization of PDAC cells. Panc1 Cells: 7c5-AFC: 43.2%+2.2%; 7c5-488: 40.4%+4.5%. MIA PaCa2 Cells: 7c5-AFC: 60.0%+3.5%; 7c5-488: 59.4%+7.9%. Capan-1 Cells: 7c5-AFC: 40.6%+0.5%; 7c5-488: 31.0%+1.0%. BxPC-3 Cells: 7c5-AFC: 61.9%+3.2%; 7c5-488: 60.9%+4.3%.

The binding of the AFC was tested in pancreatic ductal adenocarcinoma (PDAC) cell lines. Receptor expression was at 60% confluenece. The results were as follows: Panc1 Cells: 7c5-AFC: 43.2%+2.2%; 7c5-488: 40.4%+4.5%. MIA PaCa2 Cells: 7c5-AFC: 60.0%+3.5%; 7c5-488: 59.4%+7.9%. Capan-1 Cells: 7c5-AFC: 40.6%+0.5%; 7c5-488: 31.0%+1.0%. BxPC-3 Cells: 7c5-AFC: 61.9%+3.2%; 7c5-488: 60.9%+4.3% (FIG. 25).

Aim #4: AFC Internalization in PDAC Cells

Figure 26:
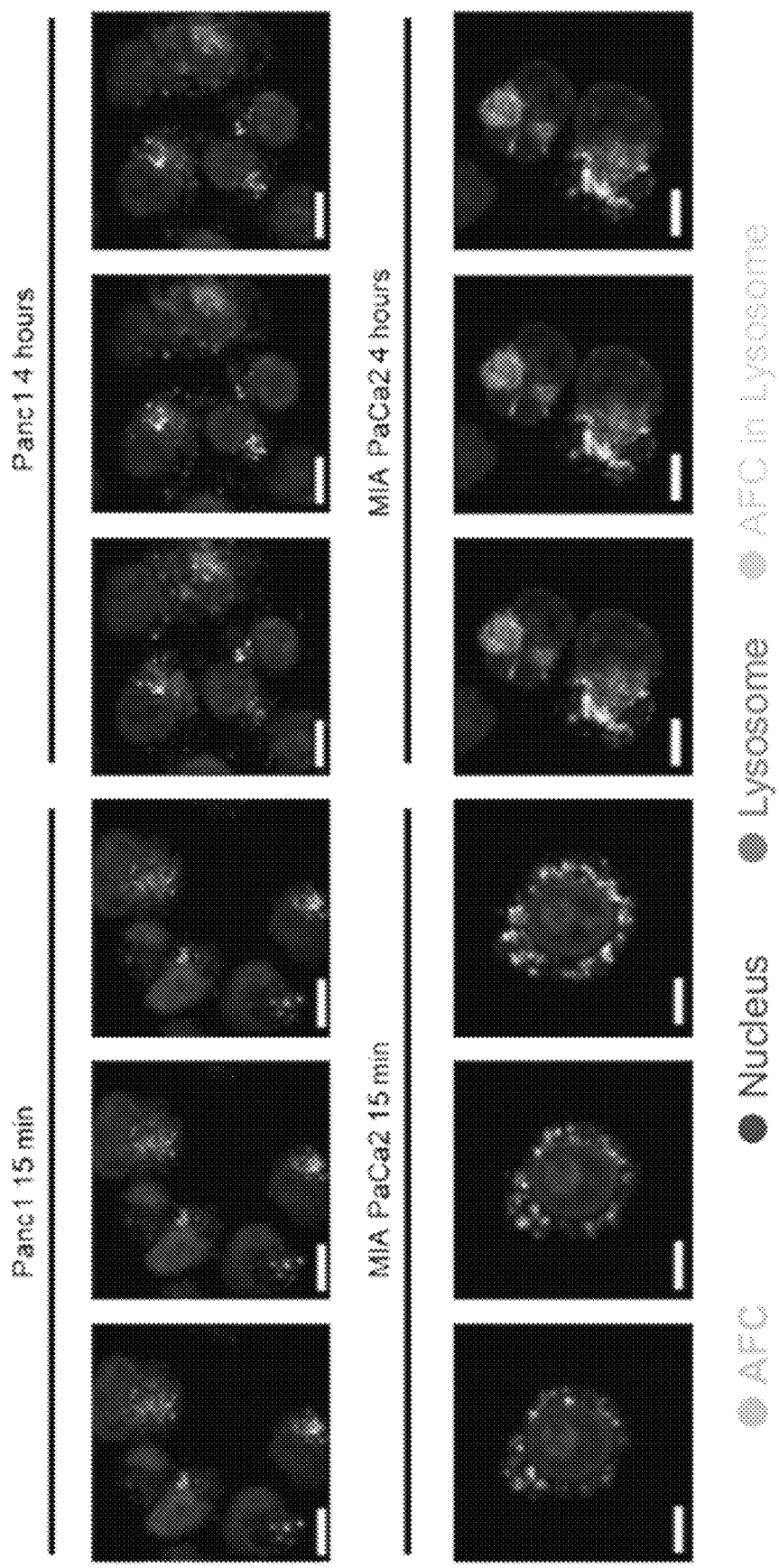
FIG. 26 shows AFC internalization in PDAC Cells at 15 minutes and 4 hours. The AFC was effectively internalized in Panc1, MIA PaCa2, BxPC3, and Capan-1 cells. Lysosomal trafficking occurred as early as 15 minutes and increases through 4 hours.
Figure 27:
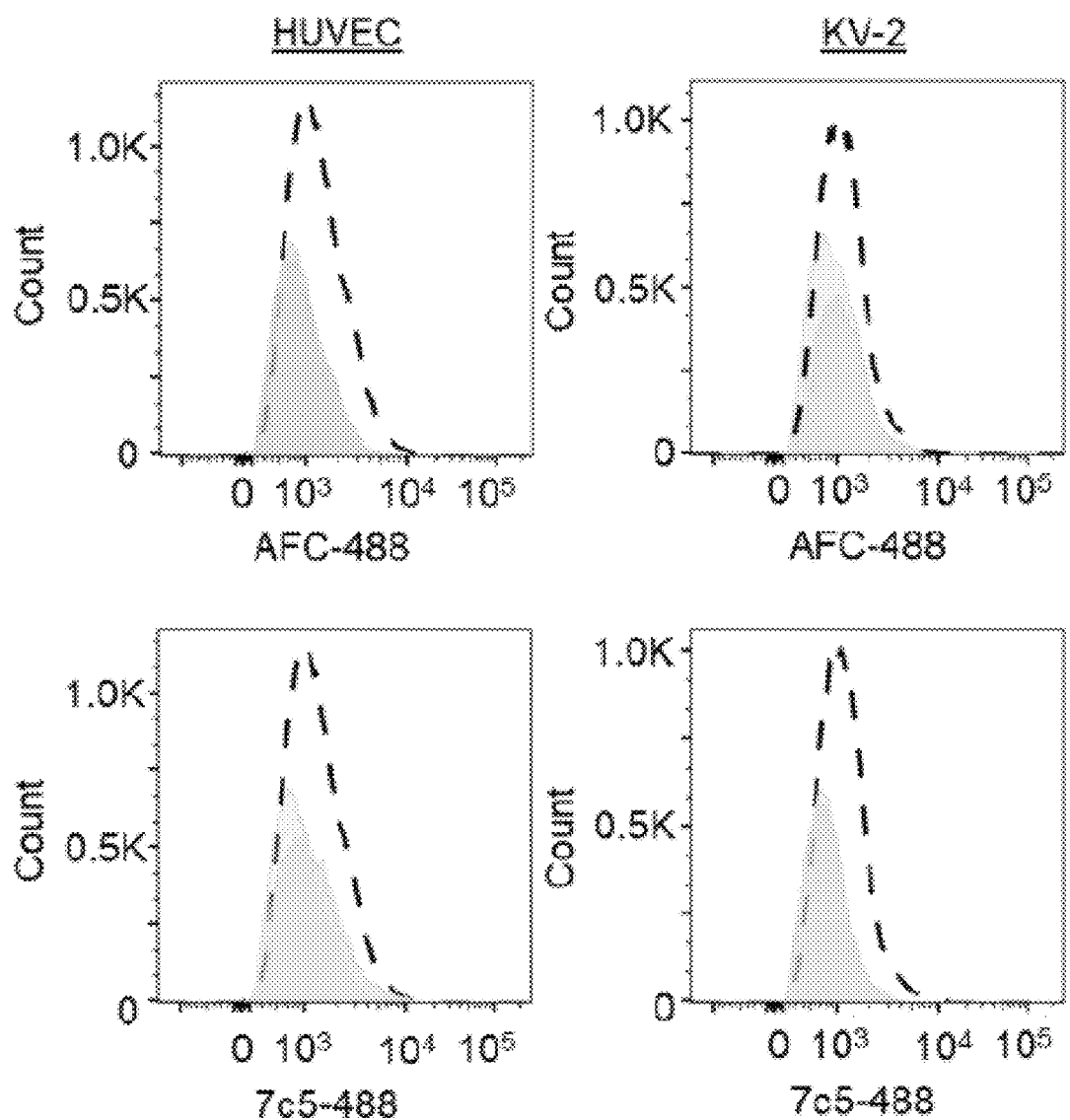
FIG. 27 discloses SEQ ID NOS 5, 5, and 20-22, respectively, in order of appearance.

AFC was effectively internalized in Panc1, MIA PaCa2, BxPC3, and Capan-1 cells. Lysosomal trafficking was detected as early as 15 minutes, increases through 4 hours by fluoresecent microscopy (FIG. 26, FIG. 27).

Aim #4: Binding Characterization of Normal Cells

The binding of the AFC was tested in normal cells. Receptor expression was at 60% confluenece. The results were as follows: H6c7: 7c5-AFC: 24.6+0.6%; 7c5-488: 52.3+1.4%. HUVEC Cells: 7c5-488: 0.0+0.0%; 7c5-AFC: 0.0+0.0%; KV-2 Cells: 7c5-488: 0.0+0.0%; 7c5-AFC: 0.0+0.0%. BJ Fibroblasts Cells: 7c5-488: 6.1%+1.5%; 7c5-AFC: 17.2%+2.9% (FIG. 27).

Aim #4: ADC Cytotoxicity in Pancreatic Cancer Cell Lines

Figure 28:
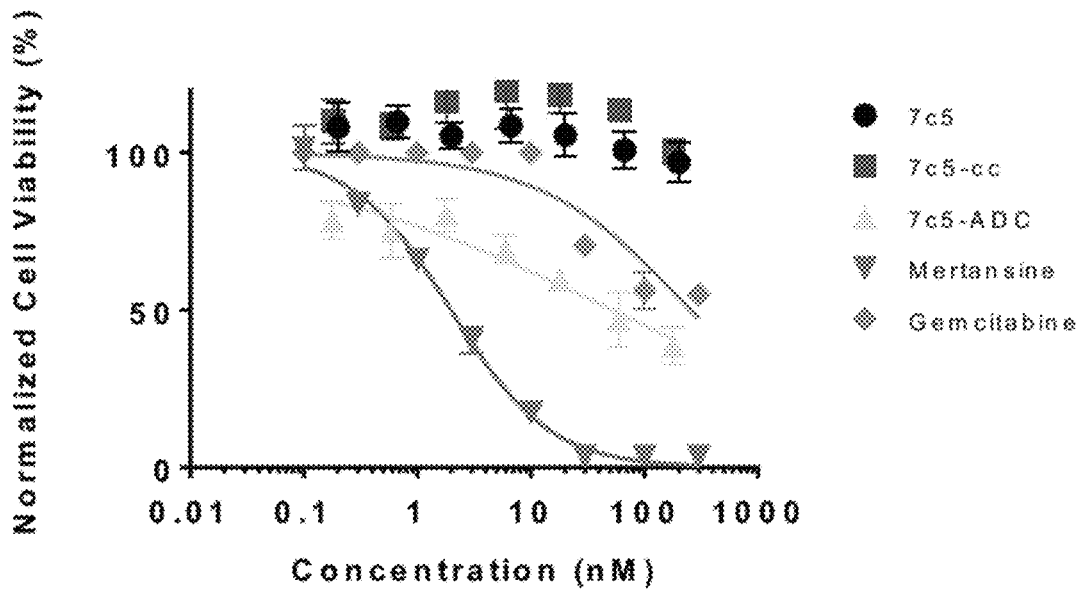
FIG. 28 demonstrates ADC cytotoxicity in Panc1 cell lines measuring cell viability of remaining proliferating cancer cells on culture dish. Comparative IC 50 in Panc1: 7c5-ADC: 52.49 nM; Mertansine: 1.98 nM; Gemcitabine: 0.7 µM. ADC demonstrates greater potency than standard of care gemcitabine and ideal sub micromolar potency.

Cell viability was assessed by an MTT assay in Panc1 cells and other cell lines at 72 hours post-treatment with increasing concentrations of the ADC and relevant controls. The assay confluence was 20% at the start and up to 60% confluence. FIG. 28 demonstrates ADC cytotoxicity in pancreatic cancer cell lines. The IC50s of the antibody (7c5), drug-loaded ADC (7c5-ADC), and drug alone (Mertansine) were determined. Panc1: 7c5-ADC: 52.49 nM; Mertansine: 1.98 nM; Gemcitabine: 0.7 µM.

Figure 29:
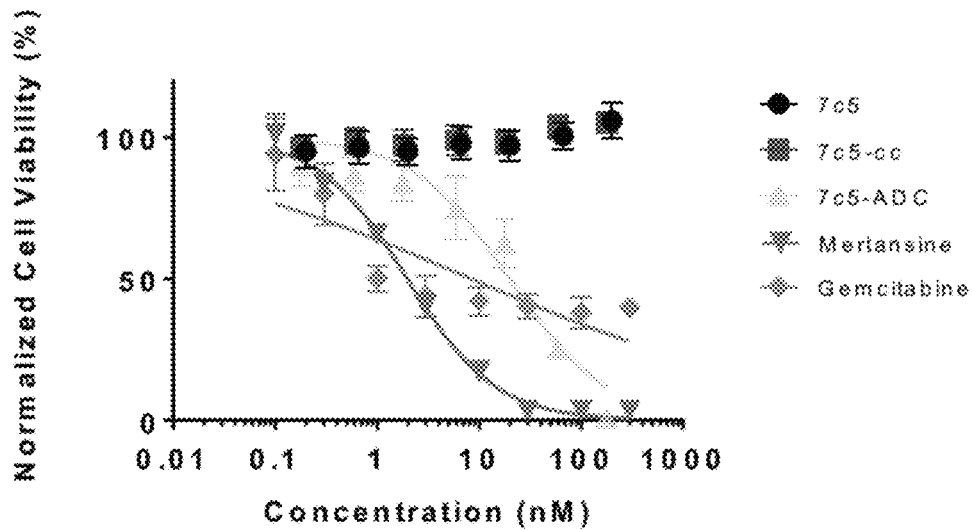
FIG. 29 demonstrates ADC cytotoxicity in MIA PaCa2 cell lines by measuring viability of remaining proliferating cells on culture dish. Panc1: 7c5-ADC: 52.49 nM. MIA PaCa2: 7c5-ADC: 19.90 nM; Mertansine: 0.31 nM; Gemcitabine: 256 nM. ADC demonstrates greater potency than standard of care gemcitabine and ideal sub micromolar potency.
Figure 30:
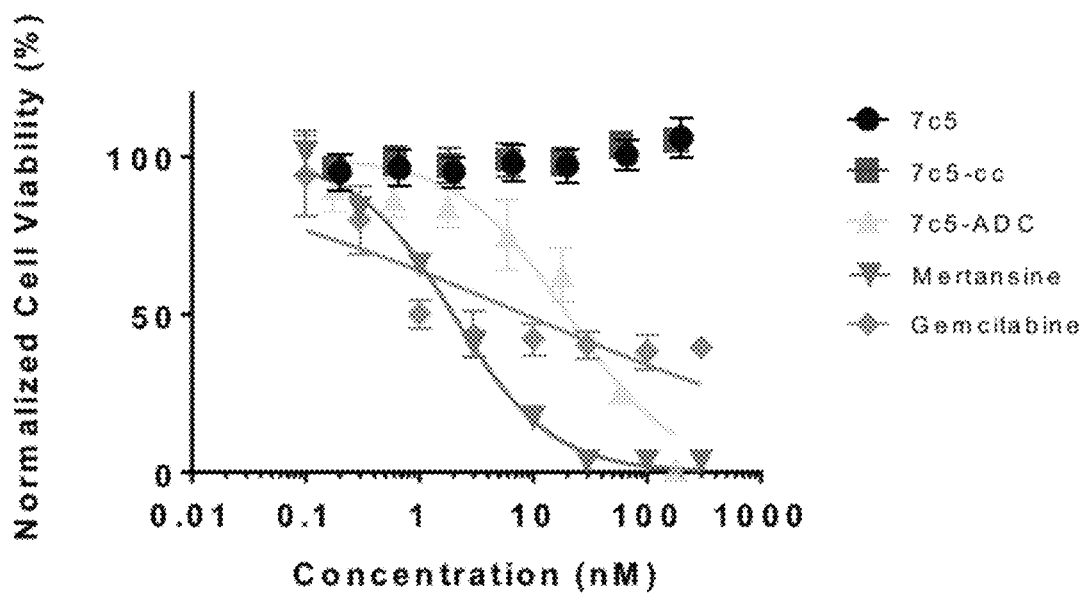
FIG. 30 demonstrates ADC cytotoxicity in pancreatic cancer cell lines by measuring viability of remaining proliferating cells on culture dish. Panc1: 7c5-ADC: 52.49 nM. MIA PaCa2: 7c5-ADC: 19.90 nM; Mertansine: 0.31 nM; Gemcitabine: 256 nM. BxPC-3: 7c5-ADC: 45.5 nM; Mertansine: 18.78 nM. Capan-1: 7c5-ADC: 82.6 nM; Mertansine: 22.06 nM. Notably, 7c5-ADC demonstrates a different $IC_{50}$ and IC profile compared to free mertansine or 7c5 alone, suggesting the ADC acts through release of mertansine following internalization. Furthermore, IC 50 of 7c5-ADC is better than Gemcitabine, the standard of care for pancreatic cancer in patients. Mertansine has greater cytotoxicity but its toxicity does not allow therapeutic use in patients, thus requiring ADC formulations.

Cell viability was assessed by an MTT assay in other pancreatic cancer cell lines. FIG. 29 demonstrates ADC cytotoxicity in pancreatic cancer cell lines. Panc1: 7c5-ADC: 52.49 nM. MIA PaCa2: 7c5-ADC: 19.90 nM; Mertansine: 0.31 nM; Gemcitabine: 256 nM FIG. 30 demonstrates ADC cytotoxicity in pancreatic cancer cell lines. Panc1: 7c5-ADC: 52.49 nM. MIA PaCa2: 7c5-ADC: 19.90 nM; Mertansine: 0.31 nM; Gemcitabine: 256 nM. BxPC-3: 7c5-ADC: 45.5 nM; Mertansine: 18.78 nM. Capan-1: 7c5-ADC: 82.6 nM; Mertansine: 22.06 nM.

Aim #4: ADC Cytotoxicity in Normal Cell Lines

Figure 31:
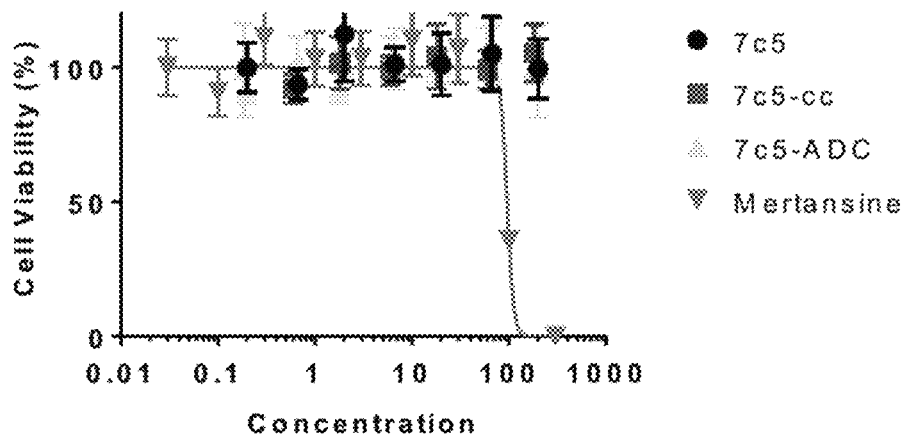
FIG. 31 demonstrates ADC non-cytotoxicity in normal cell lines compared with free mertansine. KV-2: 7c5-ADC: not significantly (NS) different from 100% viability of control non-treated cells; NS; Mertansine: 95.5 nM. Data show safety of 7c5-ADC in vitro in sparing normal cell lines.

Cell viability was assessed by an MTT assay in KV2 cells and other normal cell lines at 72 hours post-treatment with increasing concentrations of the ADC and relevant controls. FIG. 31 demonstrates ADC cytotoxicity in normal cell lines. KV-2: 7c5-ADC: NS; Mertansine: 95.5 nM.

Figure 32:
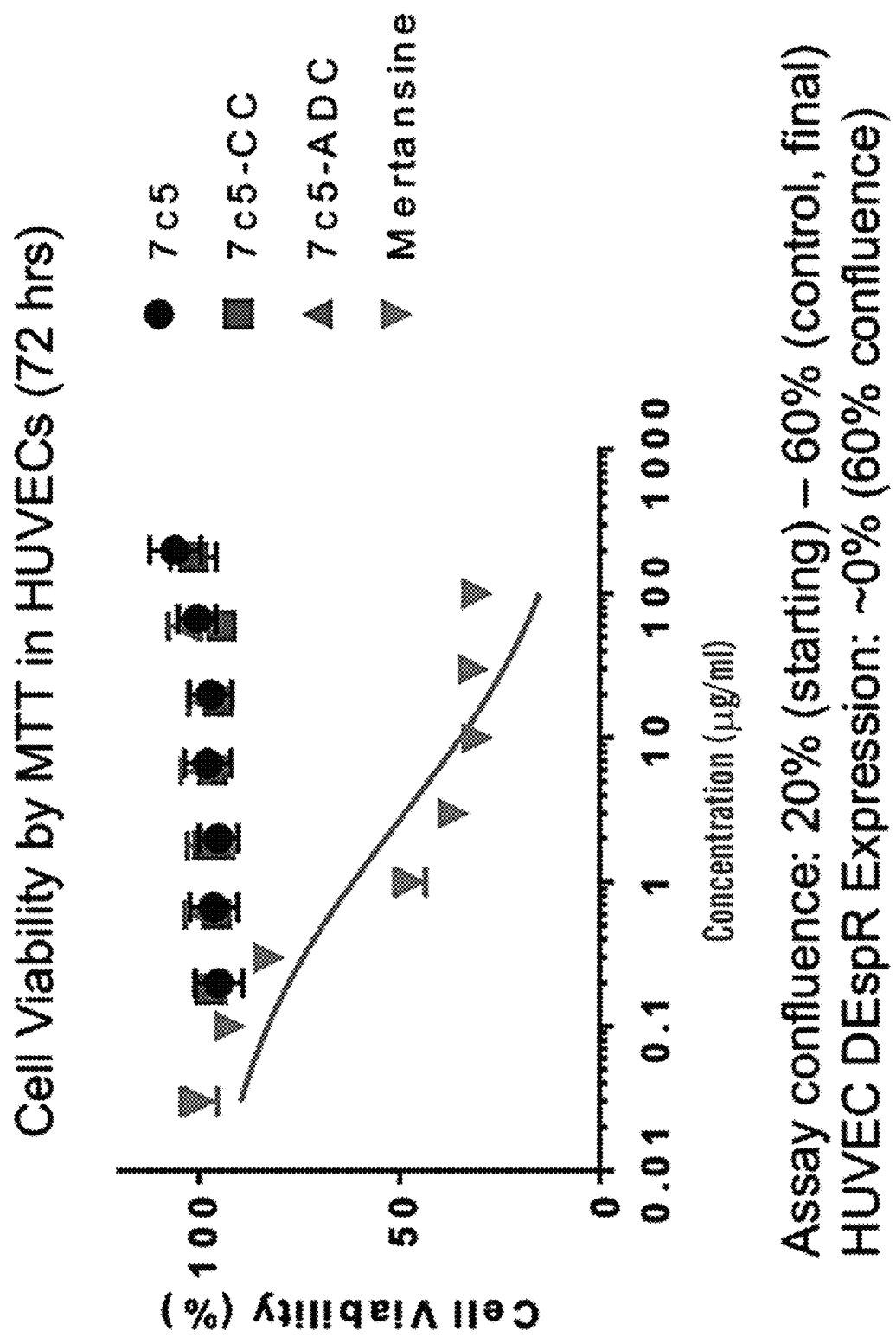
FIG. 32 demonstrates ADC non-cytotoxicity in normal cell lines. HUVECs: 7c5-ADC: NS not significantly (NS) different from 100% viability of control non-treated cells; Mertansine: 95.5 nM. HUVECs: 7c5-ADC: NS; Mertansine: 2.7 nM. mIMCD: 7c5-ADC: NS; Mertansine: 3.0 nM. BJ: 7c5-ADC: NS; Mertansine: 16.8 nM

FIG. 32 demonstrates ADC cytotoxicity in normal cell lines. KV-2: 7c5-ADC: NS; Mertansine: 95.5 nM. HUVECs: 7c5-ADC: NS; Mertansine: 2.7 nM. mIMCD: 7c5-ADC: NS; Mertansine: 3.0 nM. BJ: 7c5-ADC: NS; Mertansine: 16.8 nM.

Chemical Conjugation Does Not Affect Peptide V/E+V/K Stability

Figure 33:
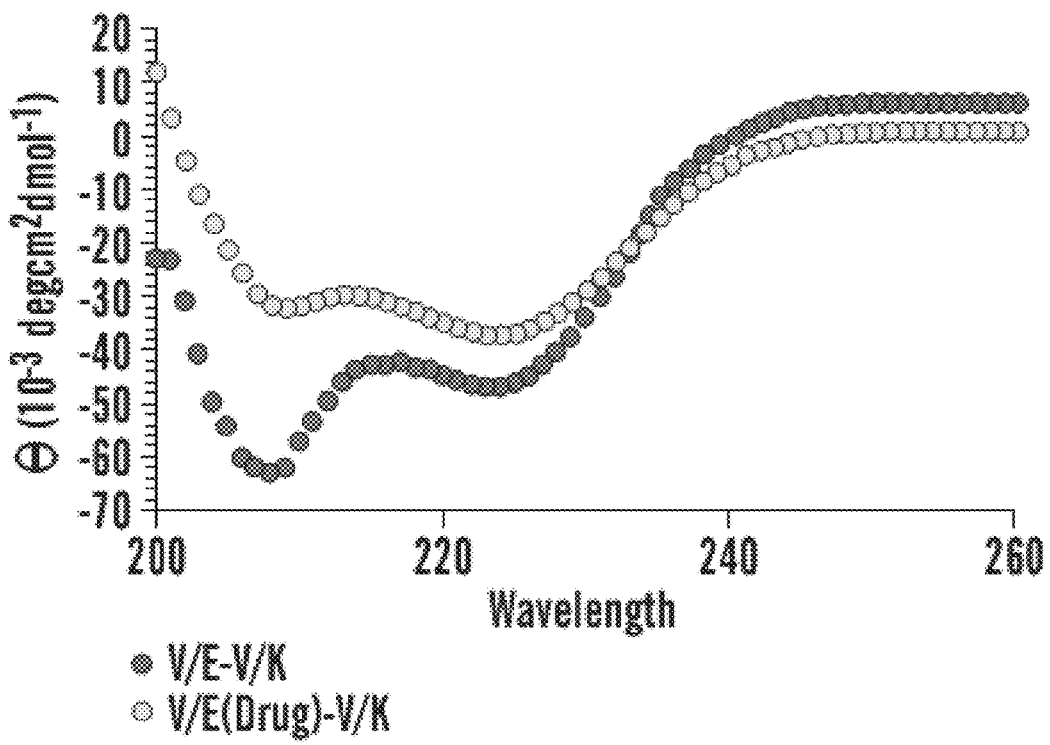
FIG. 33 shows that chemical conjugation does not affect peptide V/E+V/K stability.
Figure 33:
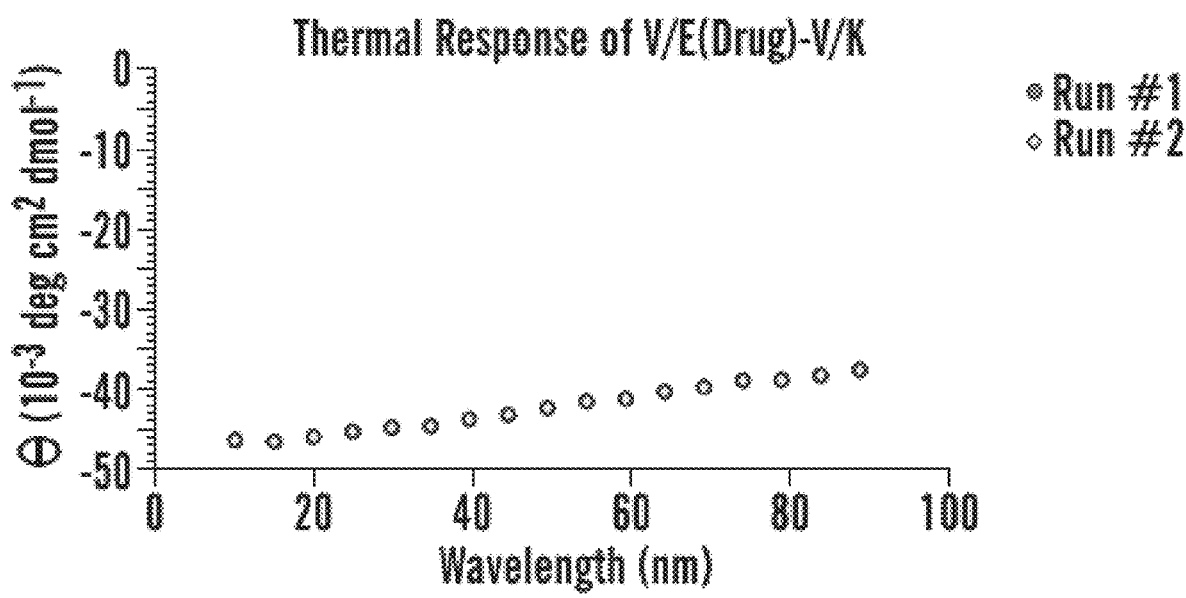

V/E-Drug-V/K forms helical structure. The greater absorption from drug occurred at 200-210 nm wavelength. Similar stability of V/E-Drug-V/K was observed (FIG. 33).

Additional Binding Characterization of PDAC Cells

Figure 34:
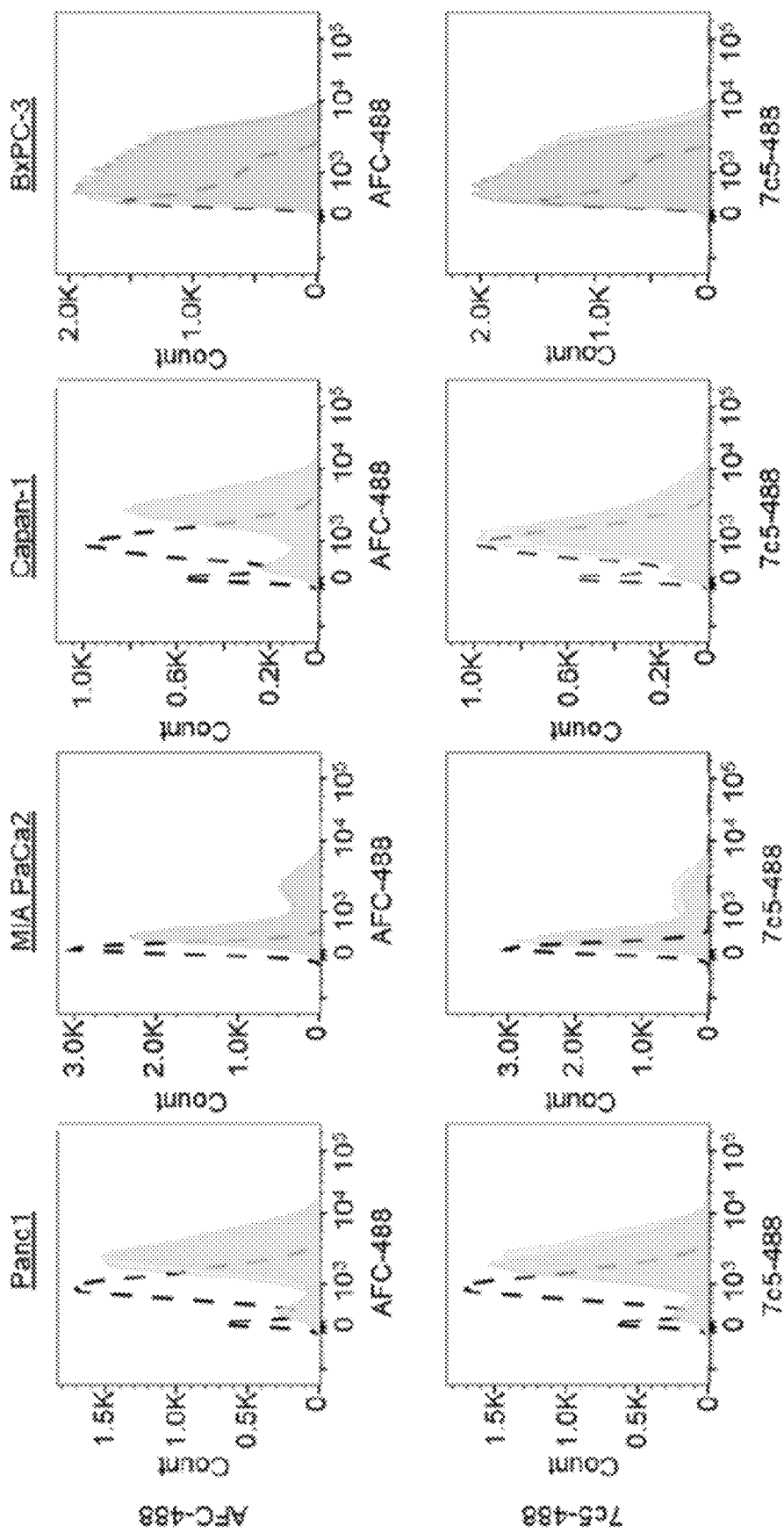
FIG. 34 shows comparative binding characterization to of PDAC cells of pertinent comparators in specific conditions used here. Panc1 Cells: 7c5-AFC: 43.2%+2.2%; 7c5-488: 40.4%+4.5%. MIA PaCa2 Cells: 7c5-AFC: 60.0%+3.5%; 7c5-488: 59.4%+7.9%. Capan-1 Cells: 7c5-AFC: 40.6%+0.5%; 7c5-488: 31.0%+1.0%. MIA PaCa2 Cells: 7c5-AFC: 61.9%+3.2%; 7c5-488: 60.9%+4.3%.

The binding of the AFC was tested in pancreatic ductal adenocarcinoma (PDAC) cell lines. The results were as follows: Panc1 Cells: 7c5-AFC: 43.2%+2.2%; 7c5-488: 40.4%+4.5%. MIA PaCa2 Cells: 7c5-AFC: 60.0%+3.5%; 7c5-488: 59.4%+7.9%; Capan-1 Cells: 7c5-AFC: 40.6%+ 0.5%: 7c5-488: 31.0%+1.0%. MIA PaCa2 Cells: 7c5-AFC: 61.9%+3.2%; 7c5-488: 60.9%+4.3% (FIG. 34).

Additional Binding Characterization of Normal Cells

Figure 35:
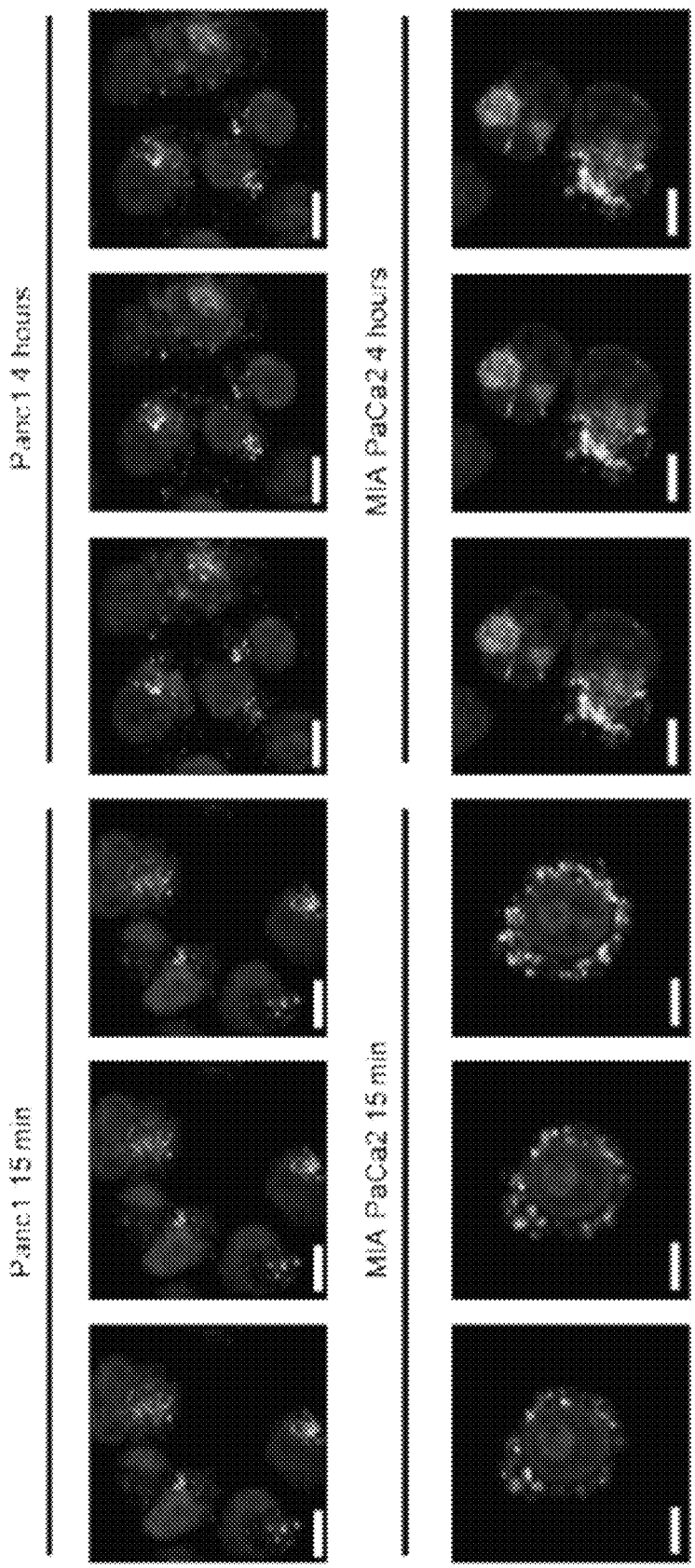
FIG. 35 shows AFC internalization in PDAC cells. AFC was effectively internalized in Panc1, MIA PaCa2, BxPC3, and Capan-1 cells. Lysosomal trafficking as early as 15 minutes, increases through 4 hours.
Figure 35:
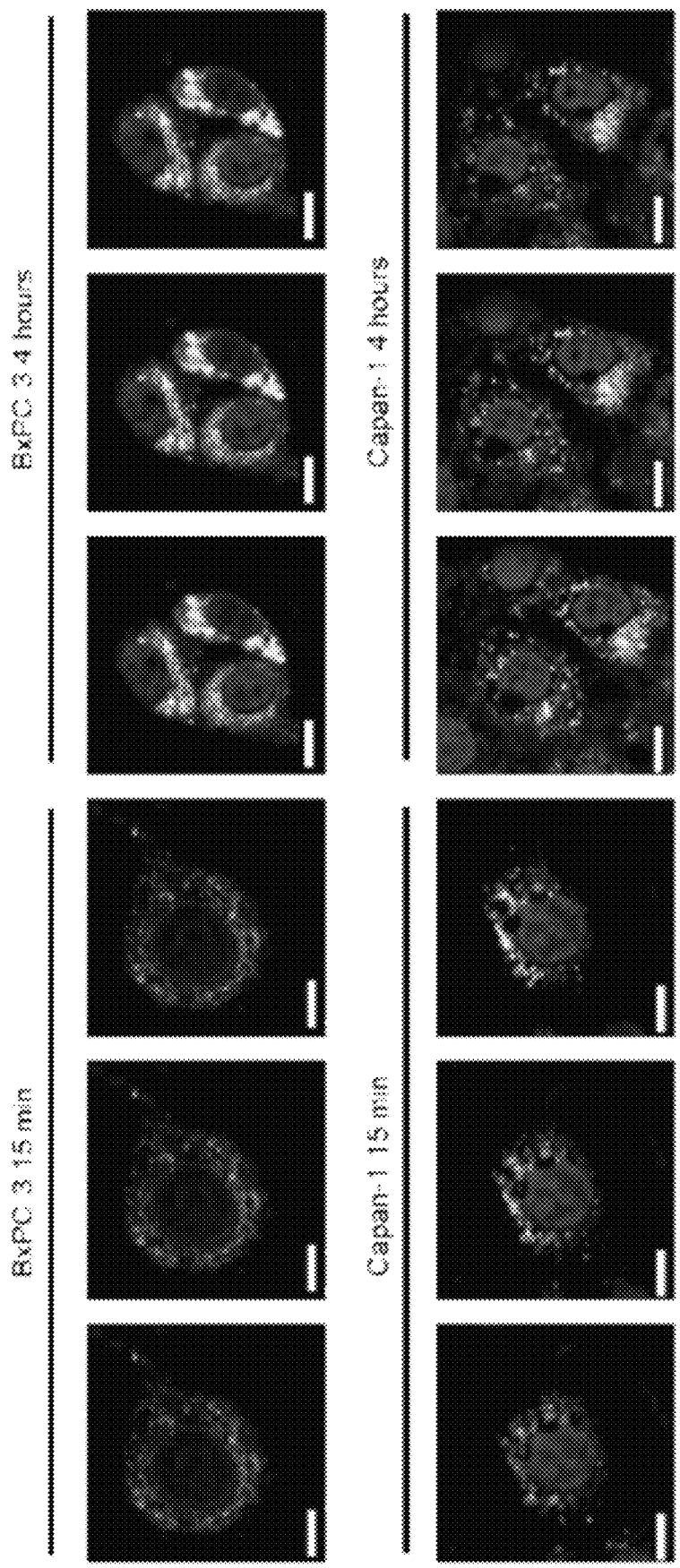
Figure 36:
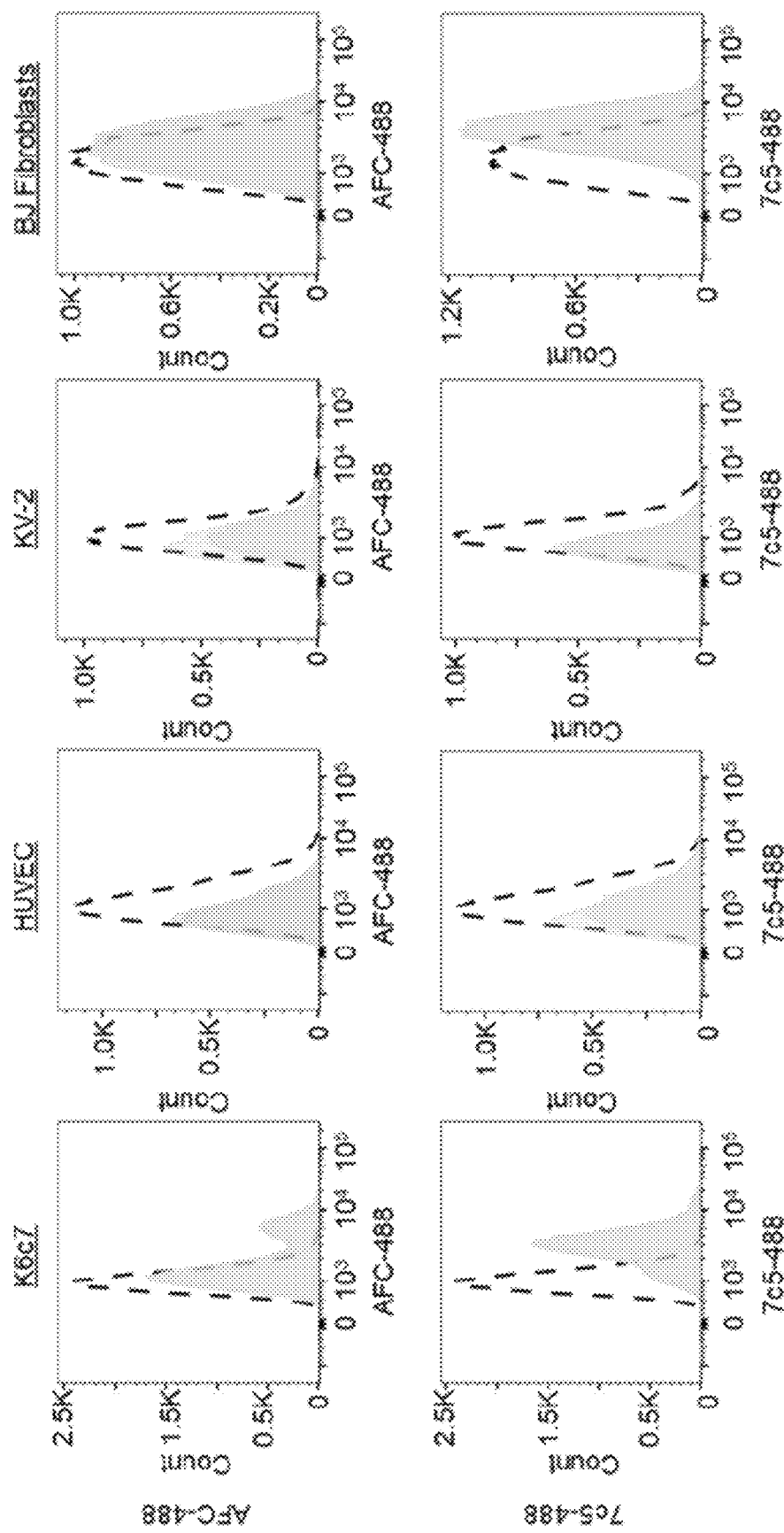
FIG. 36 demonstrates comparative binding characterization of Normal Cells of the following pertinent comparators in specific conditions used here. HH6c7: 7c5-AFC: 24.6+0.6%; 7c5-488: 52.3+1.4%. As this is discordant to IHC of normal human pancreatic tissue, immortalized H6c7 pancreatic epithelia cells do not accurately reflect normal pancreatic cells as they are immortalized. HUVEC Cells: 7c5-488: 0.0+0.0%; 7c5-AFC: 0.0+0.0%. KV-2 Cells: 7c5-488: 0.0+0.0%; 7c5-AFC: 0.0+0.0%. BJ Fibroblasts Cells: 7c5-488: 6.1%+1.5%; 7c5-AFC: 17.2%+2.9%.

The binding of the AFC was tested in normal cells. The results were as follows: H6c7: 7c5-AFC: 24.6+0.6%; 7c5-488: 52.3+1.4%. HUVEC Cells: 7c5-488: 0.0+0.0%; 7c5-AFC: 0.0+0.0%. KV-2 Cells: 7c5-488: 0.0+0.0%; 7c5-AFC: 0.0+0.0%. BJ Fibroblasts Cells: 7c5-488: 6.1%+1.5%; 7c5-AFC: 17.2%+2.9% (FIG. 35).

AFC Internalization in Normal Cells

Figure 37:
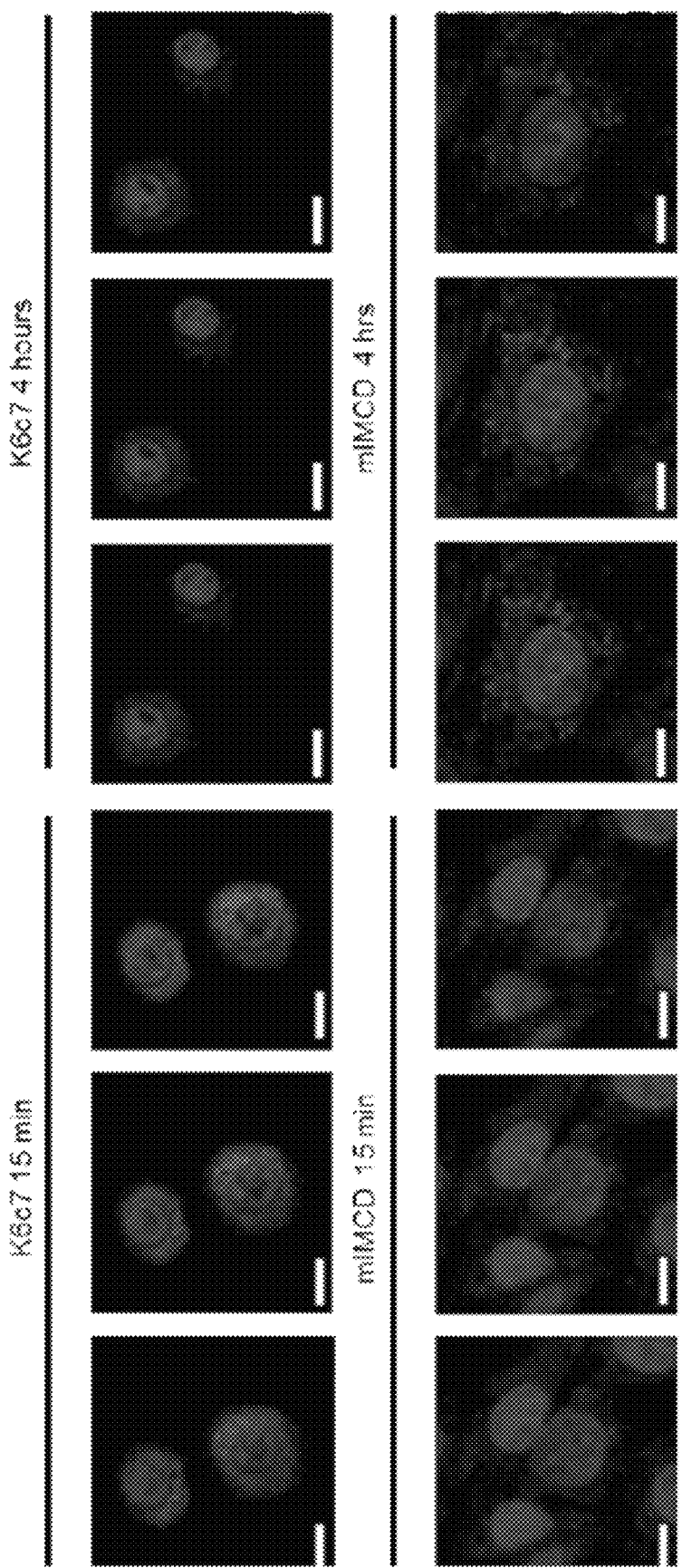
FIG. 37 demonstrates AFC non-internalization in normal cells. AFC was not internalized in H6c7 H6c7 cells (DEspR positive/immortalized non-tumor normal pancreatic duct epithelial acinar cellss). AFC was not internalized in mIMCD cells (hDEspR negative/kidney cells).

AFC was not internalized in H6c7 cells (DEspR positive/normal pancreas). AFC was not internalized in mIMCD cells (hDEspR negative/kidney cells) (FIG. 37).

Additional ADC Cytotoxicity Characterization in Pancreatic Cancer Cell Lines

Figure 38:
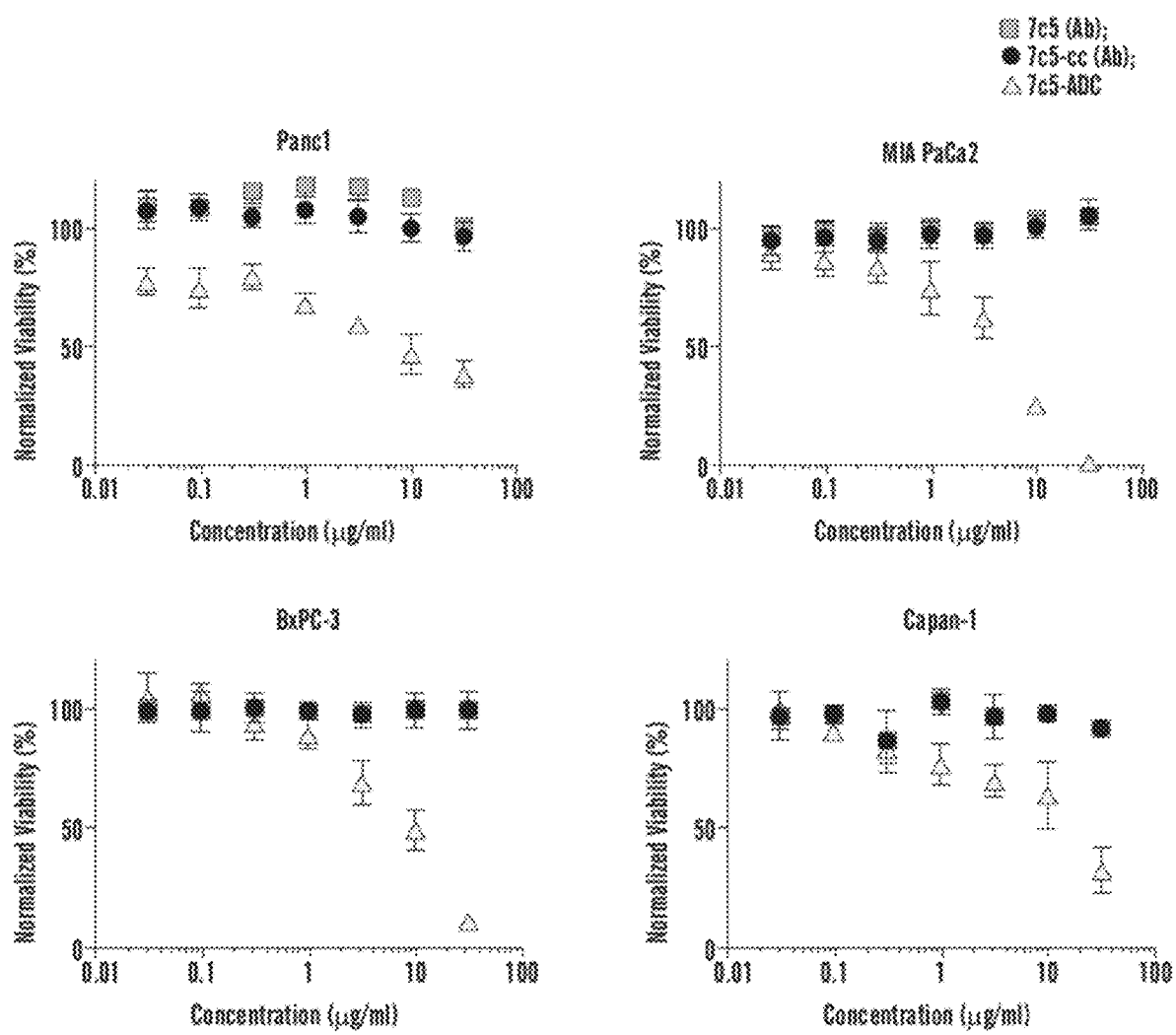
FIG. 38 demonstrates ADC cytotoxicity in pancreatic cancer cell lines in conditions used measuring cell viability of remaining tumor cells on the culture dish. Panc1: 7c5-ADC: 8.819 µg/ml; 7c5: >>30 µg/ml. MIA PaCa2: 7c5-ADC: 3.343 µg/ml; 7c5: >>30 µg/ml. BxPC-3; 7c5-ADC: 7.646 µg/ml; 7c5: >>30 µg/ml. Capan-1: 7c5-ADC: 13.88 µg/ml; 7c5: >>30 µg/ml FIG. 39 demonstrates ADC cytotoxicity in pancreatic cancer cell lines. Panc1: 7c5-ADC: 117.1 nM; Mertansine: 1.98 nM. MIA PaCa2: 7c5-ADC: 18.68 nM; Mertansine: 0.31 nM. BxPC-3: 7c5-ADC: 101.6 nM; Mertansine: 18.78 nM. Capan-1: 7c5-ADC: 187.8 nM; Mertansine: 22.06 nM.
Figure 39:
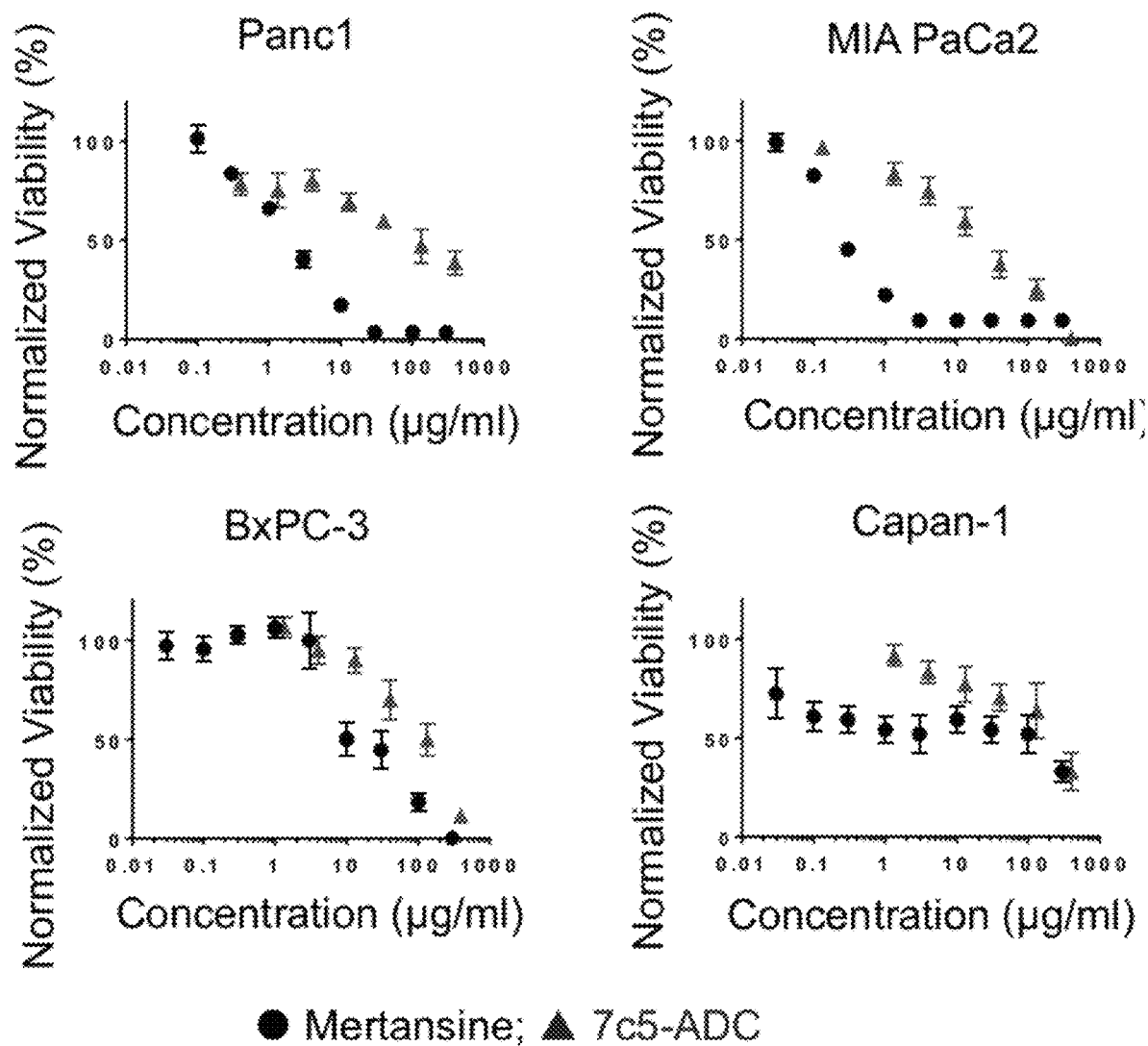

Cell viability was assessed by an MTT assay in pancreatic cancer cell lines at 72 hours post-treatment with increasing concentrations of the ADC and relevant controls. FIG. 38 demonstrates ADC cytotoxicity in pancreatic cancer cell lines. Panc1: 7c5-ADC: 8.819 µg/ml; 7c5: >>30 µg/ml. MIA PaCa2: 7c5-ADC: 3.343 µg/ml; 7c5: >>30 µg/ml. BxPC-3; 7c5-ADC: 7.646 µg/ml; 7c5: >>30 µg/ml. Capan-1: 7c5-ADC: 13.88 µg/ml; 7c5: >>30 µg/ml FIG. 39 demonstrates ADC cytotoxicity in pancreatic cancer cell lines. Panc1: 7c5-ADC: 117.1 nM; Mertansine: 1.98 nM. MIA PaCa2: 7c5-ADC: 18.68 nM; Mertansine: 0.31 nM. BxPC-3: 7c5-ADC: 101.6 nM; Mertansine: 18.78 nM. Capan-1: 7c5-ADC: 187.8 nM; Mertansine: 22.06 nM.

Additional ADC Cytotoxicity Characterization in Normal Cell Lines

Figure 40:
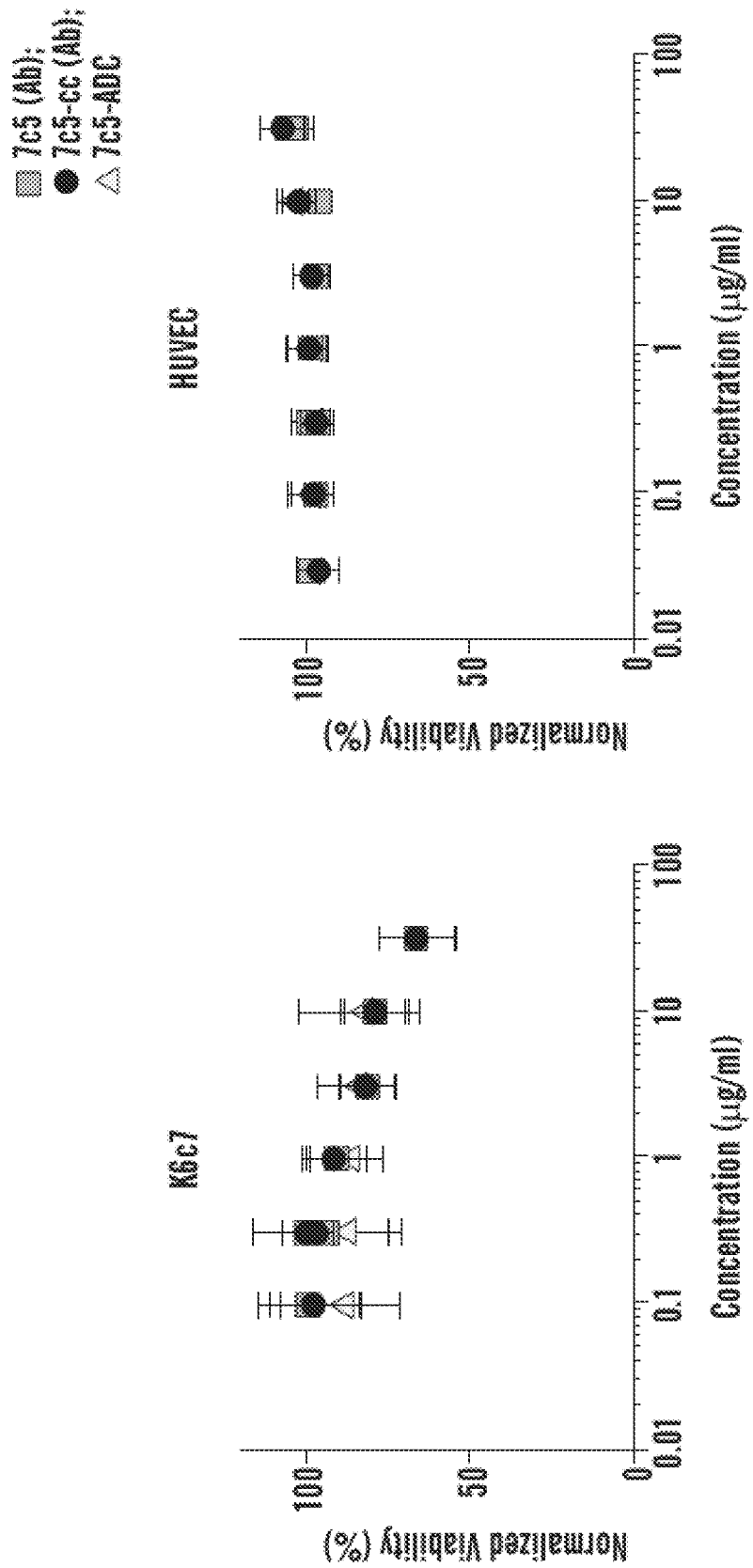
FIG. 40 demonstrates ADC non- to minimal cytotoxicity in normal cell lines. H6c7: 7c5-ADC: IC 50 106.9 µg/ml; 7c5: IC 50 110.6 µg/ml. As this cytotoxicity is discordant with non-internalization of 7c5 and 7c5-ADC in FIG. 37, the cytotoxicity is possibly due to issues with H6c7 culturing conditions. HUVEC, KV2, mIMCD, BJ: 7c5-ADC: No observed cell toxicity; 7c5: No observed cell toxicity. As toxicity is consistent from 7c5, 7c5-cc, and 7c5-ADC, toxicity most likely results from another factor in H6c7 culturing. The detected low/slight cytotoxicity in H6c7 immortalized pancreatic duct epithelial cells indicates partial release of mertansine from the 7c5-ADC due likely to effects on apoptosis and/or cytotoxicity from bicarbonate released by H6c7 cells in current culture conditions (e.g., see Shiari et al. Oxidative Medicine and Cellular Longevity Article ID 326731 (2012); and Dong et al. Exp Cell Res. 2003 Aug. 15; 288(2):301-12).
Figure 40:
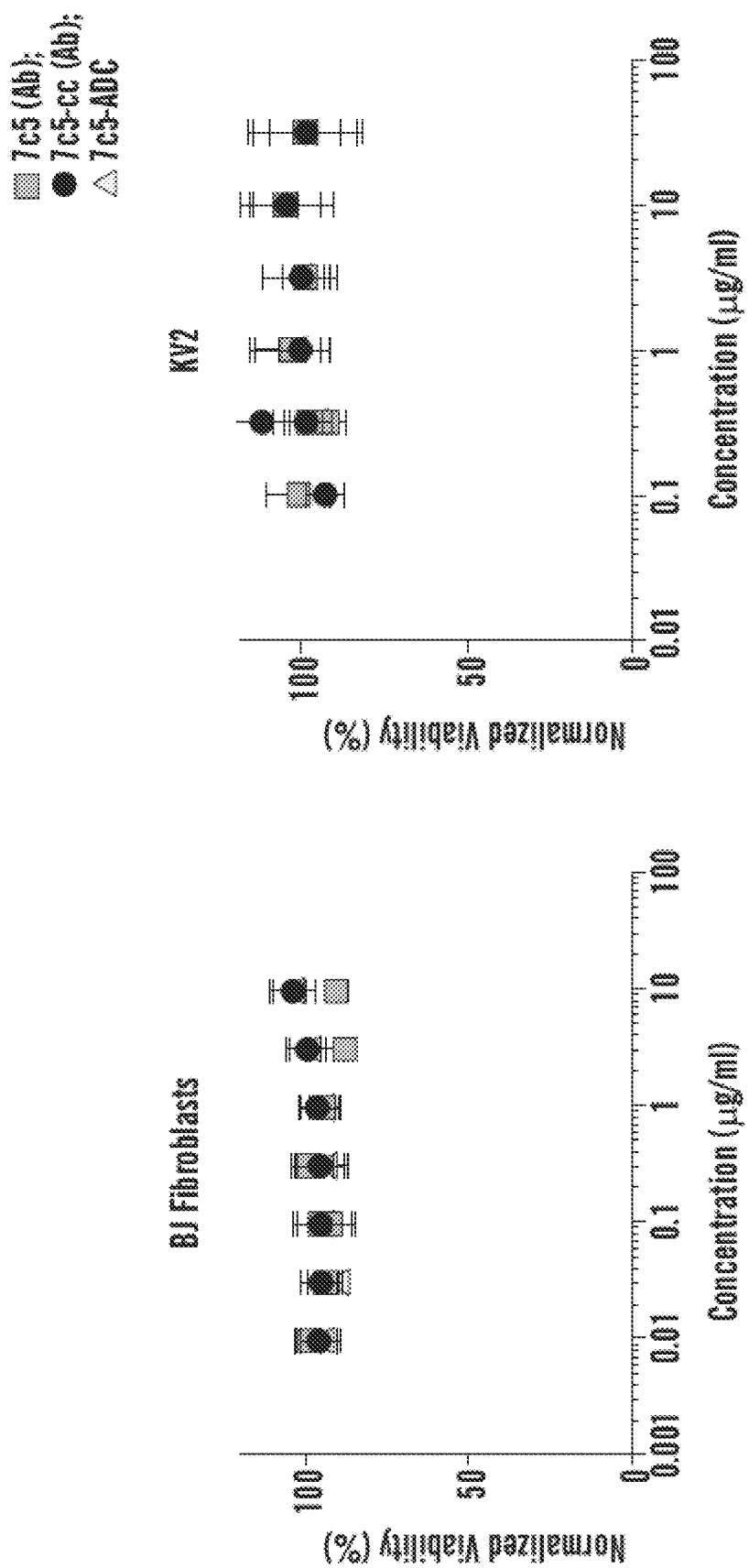
Figure 40:
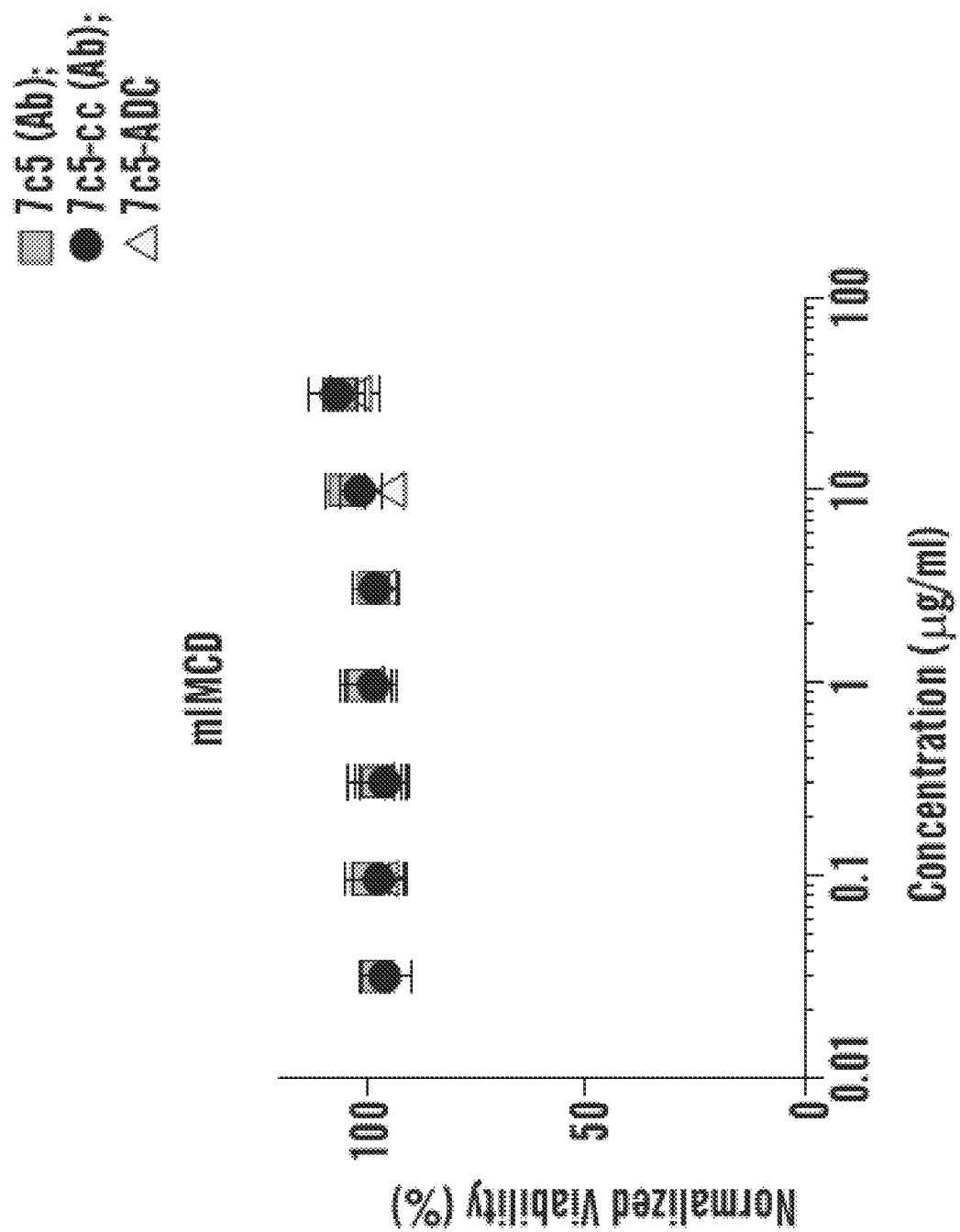
Figure 41:
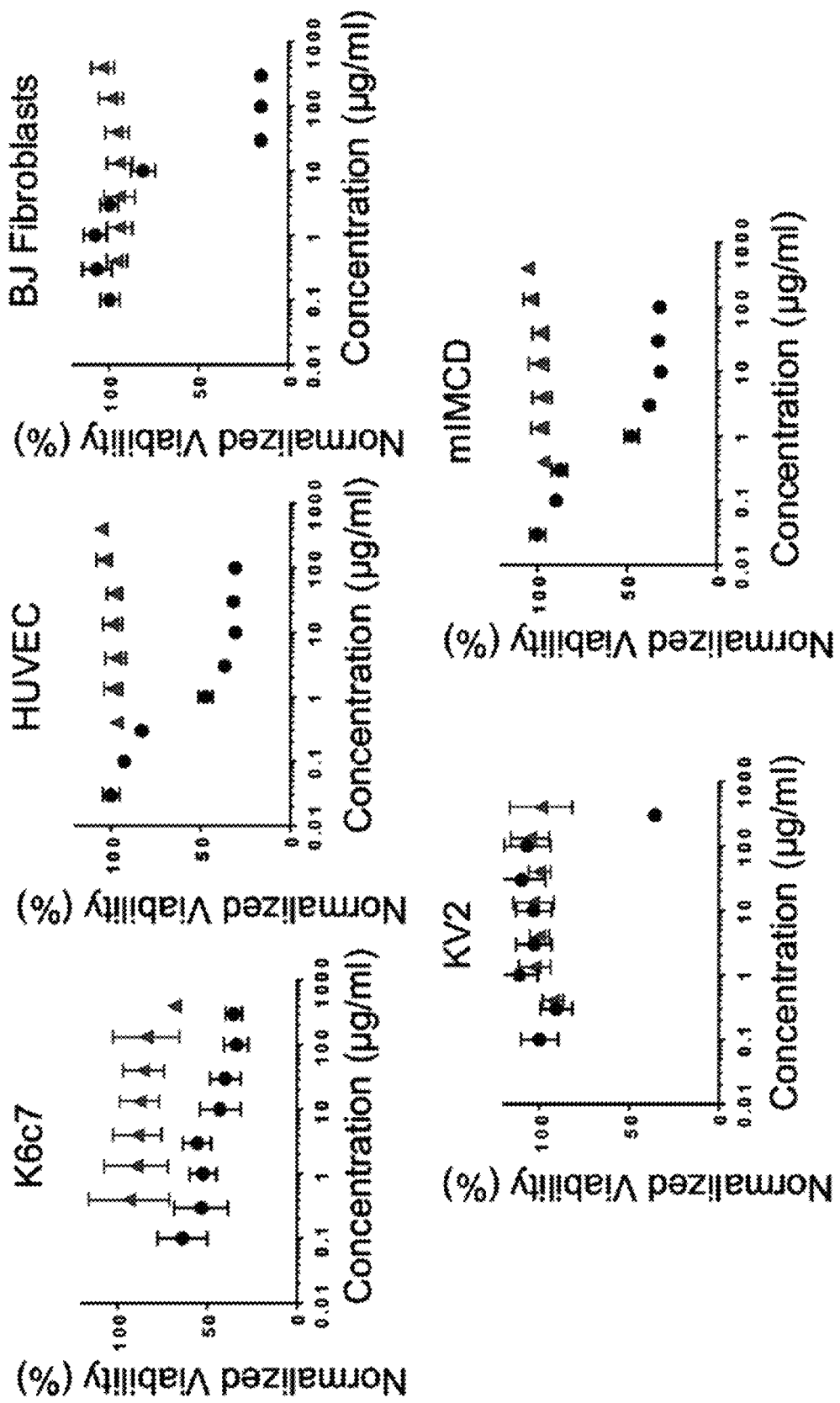
FIG. 41 demonstrates ADC non-cytotoxicity in normal cell lines. HH6c7:7c-ADC:16,878 nM; Mertansine: 2.4 nM. HUVEC vascular endothelial cells:7c5-ADC: No cytotoxicity; Mertansine: 2.7 nM. 7c5-ADKV2: 7c5-ADC: No cytotoxicity; Mertansine: 289 nM. mIMCD kidney cells: 7c5-ADC: No cytotoxicity; Mertansine: 3.0 nM. BJ fibroblasts: 7c5-ADC: No cytotoxicity; Mertansine: 16.8 nM.

Cell viability was assessed by an MTT assay in normal cell lines at 72 hours post-treatment with increasing concentrations of the ADC and relevant controls. FIG. 40 demonstrates ADC cytotoxicity in normal cell lines. H6c7: 7c5-ADC: 106.9 µg/ml; 7c5: 110.6 µg/ml. HUVEC, KV2, mIMCD, BJ: 7c5-ADC: No observed cell toxicity; 7c5: No observed cell toxicity FIG. 41 demonstrates ADC cytotoxicity in normal cell lines. H6c7:7c-ADC: 16,878 nM; Mertansine: 2.4 nM. HUVEC:7c5-ADC: No cytotoxicity; Mertansine: 2.7 nM. 7c5-ADKV2: 7c5-ADC: No cytotoxicity; Mertansine: 289 nM. mIMCD: 7c5-ADC: No cytotoxicity; Mertansine: 3.0 nM. BJ: 7c5-ADC: No cytotoxicity; Mertansine: 16.8 nM.

ADDITIONAL SEQUENCES

SEQ ID NO: 5
(Sortase)
LPETGGWSHPQFEK

What is claimed herein is:

1. A composition comprising:
   a. a first polypeptide component comprising a V/K-type docking peptide comprising:
      the sequence $(XJJXJJJ)_z$ where each X is independently a hydrophobic amino acid, each J is independently any amino acid, z is an integer greater than or equal to 1, and the $7^{th}$ position of XJJXJJJ is a valine;
   b. a second polypeptide component comprising a V/K-type docking peptide comprising:
      the sequence $(XJJXJJJ)_z$ where each X is independently a hydrophobic amino acid, each J is independently any amino acid, z is an integer greater than or equal to 1, and the $7^{th}$ position of XJJXJJJ is a valine;
   c. a third polypeptide component comprising a V/E-type docking peptide comprising:
      the sequence $(XJJXJJJ)z$ where each X is independently a hydrophobic amino acid, each J is independently any amino acid, z is an integer greater than or equal to 1, and the $5^{th}$ position of XJJXJJJ is a valine; and
   d. a fourth polypeptide component comprising a V/E-type docking peptide comprising:
      the sequence $(XJJXJJJ)z$ where each X is independently a hydrophobic amino acid, each J is independently any amino acid, z is an integer greater than or equal to 1, and the $5^{th}$ position of XJJXJJJ is a valine;
   wherein the z of at least one docking peptide is an integer greater than or equal to 3.

2. The composition of claim 1, wherein the z of each docking peptide is an integer greater than or equal to 3.

3. The composition of claim 1, wherein the z of at least one docking peptide is 3.

4. The composition of claim 1, wherein the z of at each docking peptide is 3.

5. The composition of claim 1, wherein each docking peptide comprises leucine at the $1^{st}$ position of XJJXJJJ and an isoleucine at the $4^{th}$ position of XJJXJJJ.

6. The composition of claim 1, wherein the XJJXJJJ of at least one of the V/K-type docking peptides is LKKIJJV (SEQ ID NO: 15).

7. The composition of claim 1, wherein the z of at least one of the V/E-type docking peptides is greater than 1 and at least 1 iteration of XJJXJJJ comprises tyrosine at the sixth position.

8. The composition of claim 1, wherein at least one of the V/E-type docking peptides comprises an amino acid sequence of LEEIJJJ (SEQ ID NO: 29).

9. The composition of claim 1, wherein at least one of the V/E-type docking peptides comprises an amino acid sequence of LEEIXJX (SEQ ID NO: 30).

10. The composition of claim 1, wherein at least one docking peptide comprises an amino acid sequence selected from the group consisting of SEQ ID NOs: 1-4 or 6; and any combination thereof.

11. The composition of claim 1, wherein the first, second, third, and fourth docking peptides form a tetrameric-coiled coil structure.

12. The composition of claim 1, wherein at least one of the polypeptide components further comprises a targeting domain and/or a payload domain.

13. The composition of claim 12, wherein the targeting domain comprises an aptamer, antibody reagent, or antigen-binding portion thereof, polypeptide reagent, or a small molecule.

14. The composition of claim 13, wherein each antibody reagent is a Fab, ScFv, monoclonal antibody, bispecific monoclonal antibody, or a humanized antibody.

15. The composition of claim 12, wherein the payload domain comprises a small molecule, enzyme, polypeptide, antibody reagent, or chemotherapeutic agent.

16. The composition of claim 15, wherein the chemotherapeutic agent is selected from the group consisting of: mertansine; emtansine; ravtansine; ansamitocin; soravtansine; maytansine; paclitaxel; gemcitabine; fluorouracil; irinotecan; leucovorin; oxaliplatin; capecitabine; cisplatin; and docetaxel.

17. The composition of claim 1, wherein at least one docking peptide is located at the C-terminus of the respective polypeptide component.

18. The composition of claim 12, wherein at least one polypeptide component further comprises a polypeptide linker between the docking peptide and the payload and/or targeting domain of the polypeptide component.

19. The composition of claim 18, wherein the polypeptide linker comprises at least one of:
    a. an amino acid crosslinker;
    b. a lysosomally cleaved sequence;
    c. a self-immolative sequence; or
    d. a cathepsin B cleavage site.

20. The composition of claim 18, wherein the polypeptide linker comprises an ester, a thioester, a hydrazine, a disulfide, or a protease-cleavable linker.

21. The composition of claim 18, wherein the polypeptide linker comprises a 4-phenyl-urazole; an amide; a carbamate; urea; thiourea; or a triazole linker.

22. A method of treating a disease, the method comprising: administering the composition of claim 12 to a subject in need thereof, wherein the payload domain comprises a therapeutic agent.

23. The method of claim 22, wherein the disease is cancer, infection, or trauma; and wherein at least one payload domain comprises a chemotherapeutic agent when the disease is cancer.

24. The method of claim 22, wherein the disease is selected from the group consisting of: myocardial infarction, stroke, disseminated intravascular coagulation, hyper-coagulation, atherosclerosis, acute respiratory distress syndrome, infant respiratory distress syndrome, Crohn's disease, ulcerative colitis, rheumatoid arthritis, Celiac disease, type 1 diabetes, lupus, and multiple sclerosis.

25. A method of delivering a payload domain to a cell, the method comprising: contacting a population of cells and/or a subject with a composition of claim 12, wherein at least one polypeptide component comprises a targeting domain and at least one polypeptide component comprises a payload domain;
    whereby the payload domain is delivered to a cell expressing the target of the targeting domain.

* * * * *

```
                         SEQUENCE LISTING

<160> NUMBER OF SEQ ID NOS: 31

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Leu Lys Lys Ile Lys Ser Val Leu Lys Lys Ile Lys Ser Val
1               5                   10                  15

Leu Lys Lys Ile Lys Ser Val Leu Lys Lys Ile Lys Ser Val Val Gly
            20                  25                  30

Glu Arg

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Leu Glu Glu Ile Val Ser Glu Leu Glu Glu Ile Val Ser Glu
1               5                   10                  15

Leu Glu Glu Ile Val Thr Glu Leu Glu Glu Ile Val Ser Glu Val Gly
            20                  25                  30

Glu Arg
```

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Glu Glu Ile Val Tyr Glu
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Lys Lys Ile Lys Ser Val
1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Pro Glu Thr Gly Gly Trp Ser His Pro Gln Phe Glu Lys
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Glu Glu Ile Val Ser Glu
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Pro Glu Thr Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 8

Trp Ser His Pro Gln Phe Glu Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydrophobic amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 9

Leu Lys Lys Xaa Xaa Xaa Val
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 10

Leu Lys Lys Leu Xaa Xaa Val
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydrophobic amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 11

Xaa Lys Lys Leu Xaa Xaa Val
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydrophobic amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 12

Leu Lys Lys Xaa Val Xaa Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydrophobic amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 13

Xaa Lys Lys Leu Val Xaa Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 14

Leu Lys Lys Leu Val Xaa Xaa
1               5

<210> SEQ ID NO 15
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 15

Leu Lys Lys Ile Xaa Xaa Val
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 16

Ile Lys Lys Leu Xaa Xaa Val
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 17

Leu Lys Lys Ile Val Xaa Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
```

```
<400> SEQUENCE: 18

Ile Lys Lys Leu Val Xaa Xaa
1               5

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Gly Gly Gly Ser Met Lys Leu Lys Lys Ile Lys Ser Gly Leu Lys
1               5                   10                  15

Lys Ile Lys Ser Gly Leu Lys Lys Ile Lys Ser Gly Leu Lys Lys Ile
            20                  25                  30

Lys Ser Gly Val Gly Glu Arg
        35

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Gly
1               5

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Thr Met Phe Lys Gly Ser Asn Glu Met Lys Ser Arg Trp Asn Trp
1               5                   10                  15

Gly Ser

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Thr Met Phe Lys Gly Ser Asn
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Leu Glu Glu Ile Leu Tyr Glu
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Lys Lys Ile Lys Ser Leu
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Glu Glu Ile Ile Tyr Glu
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Lys Lys Ile Lys Ser Ile
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Glu Glu Ile Val Tyr Glu
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Lys Lys Ile Lys Ser Val
1               5

<210> SEQ ID NO 29
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Any amino acid

<400> SEQUENCE: 29

Leu Glu Glu Ile Xaa Xaa Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydrophobic amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Hydrophobic amino acid

<400> SEQUENCE: 30

Leu Glu Glu Ile Xaa Xaa Xaa
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydrophobic amino acid
<220> FEATURE:
<221> NAME/KEY: MOD_RES
<222> LOCATION: (6)..(7)
<223> OTHER INFORMATION: Any amino acid

<400> SEQUENCE: 31

Leu Glu Glu Ile Xaa Xaa Xaa
1               5
```